US011859225B2

(12) United States Patent
Smolke et al.

(10) Patent No.: US 11,859,225 B2
(45) Date of Patent: Jan. 2, 2024

(54) METHODS OF PRODUCING EPIMERASES AND BENZYLISOQUINOLINE ALKALOIDS

(71) Applicant: The Board of Trustees of the Leland Stanford Junior University, Stanford, CA (US)

(72) Inventors: Christina D. Smolke, Menlo Park, CA (US); Stephanie Galanie, Palo Alto, CA (US); Isis Trenchard, Redwood City, CA (US); Catherine Thodey, Mountain View, CA (US); Yanran Li, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/567,358

(22) PCT Filed: May 9, 2016

(86) PCT No.: PCT/US2016/031506
§ 371 (c)(1),
(2) Date: Oct. 17, 2017

(87) PCT Pub. No.: WO2016/183023
PCT Pub. Date: Nov. 17, 2016

(65) Prior Publication Data
US 2018/0163241 A1 Jun. 14, 2018

Related U.S. Application Data

(60) Provisional application No. 62/174,475, filed on Jun. 11, 2015, provisional application No. 62/159,122, filed on May 8, 2015.

(51) Int. Cl.
| | | |
|---|---|---|
| C12P 17/12 | (2006.01) | |
| C12N 15/52 | (2006.01) | |
| C12P 41/00 | (2006.01) | |
| C12N 9/04 | (2006.01) | |
| C12N 9/02 | (2006.01) | |
| C12N 15/62 | (2006.01) | |

(52) U.S. Cl.
CPC ............ *C12P 17/12* (2013.01); *C12N 9/0006* (2013.01); *C12N 9/0071* (2013.01); *C12N 15/52* (2013.01); *C12N 15/62* (2013.01); *C12P 41/002* (2013.01); *C12Y 101/01247* (2013.01); *C12N 2800/22* (2013.01)

(58) Field of Classification Search
CPC ...... C12P 17/12; C12P 17/188; C12N 9/1007; C12Y 201/01075
USPC ...................... 435/122, 25, 320.1
See application file for complete search history.

(56) References Cited

U.S. PATENT DOCUMENTS

| | | |
|---|---|---|
| 3,785,927 A | 1/1974 | Schoenewaldt et al. |
| 6,204,337 B1 | 3/2001 | Corcoran et al. |
| 6,579,985 B1 | 6/2003 | Hill |
| 6,949,645 B1 | 9/2005 | Francis |
| 7,037,674 B1 | 5/2006 | Kutchan et al. |
| 7,045,290 B2 | 5/2006 | Lindquist et al. |
| 7,193,127 B1 | 3/2007 | Kutchan et al. |
| 7,390,642 B2 | 6/2008 | Kutchan et al. |
| 7,514,251 B2 | 4/2009 | Kutchan et al. |
| 7,767,428 B2 | 8/2010 | Kutchan et al. |
| 8,318,474 B1 | 11/2012 | Smolke et al. |
| 8,710,226 B2 | 4/2014 | Patel et al. |
| 8,735,111 B2 | 5/2014 | Vanhercke |
| 8,975,063 B2 | 3/2015 | Smolke et al. |
| 8,993,280 B2 | 3/2015 | Sato et al. |
| 9,200,261 B2 | 12/2015 | Winzer et al. |
| 9,322,039 B2 | 4/2016 | Smolke et al. |
| 9,376,696 B1 | 6/2016 | Smolke et al. |
| 9,447,444 B2 | 9/2016 | Winzer et al. |
| 9,458,481 B2 | 10/2016 | Winzer et al. |
| 9,534,241 B2 | 1/2017 | Smolke et al. |
| 9,725,732 B2 | 8/2017 | Winzer et al. |
| 9,862,979 B2 | 1/2018 | Winzer et al. |
| 9,926,329 B2 | 3/2018 | Huntley et al. |
| 10,006,010 B2 | 6/2018 | Winzer et al. |
| 10,017,799 B2 | 7/2018 | Smolke et al. |
| 10,190,141 B2 | 1/2019 | Facchini et al. |
| 10,519,453 B2 | 12/2019 | Smolke et al. |

(Continued)

FOREIGN PATENT DOCUMENTS

| | | |
|---|---|---|
| CA | 2728766 A1 | 12/2009 |
| CN | 102657652 A1 | 9/2012 |

(Continued)

OTHER PUBLICATIONS

Davos et al., Proteins: Structure, Function and Genetics, 2000, vol. 41: 98-107.*
Wristlock et al., Quarterly Reviews of Biophysics 2003, vol. 36 (3): 307-340.*
Kwiatkowski et al., Biochemistry 38:11643-11650, 1999.*
Kisselev L., Structure, 2002, vol. 10: 8-9.*
Mishra et al. "Wound Induced Tanscriptional Regulation of Benzylisoquinoline Pathway and Characterization of Wound Inducible PsWRKY Transcription Factor from Papaver somniferum," PLOS One, Jan. 30, 2013 (Jan. 30, 2013), vol. 8, Iss. 1, pp. 1-15.*
Mitchell et al. PNAS, 2014, 111, 17003-17010.*
Vasquez et al. ( Molecular Plant 2010, 3, pp. 678-690.*

(Continued)

*Primary Examiner* — Robert B Mondesi
*Assistant Examiner* — Mohammad Y Meah
(74) *Attorney, Agent, or Firm* — Bret E. Field; Bozicevic, Field & Francis LLP

(57) ABSTRACT

A method of epimerizing an (S)-1-benzylisoquinoline alkaloid to an (R)-1-benzylisoquinoline alkaloid is provided. The method comprises contacting the (S)-1-benzylisoquinoline alkaloid with at least one enzyme. Contacting the (S)-1-benzylisoquinoline alkaloid with the at least one enzyme converts the (S)-1-benzylisoquinoline alkaloid to an (R)-1-benzylisoquinoline alkaloid.

24 Claims, 31 Drawing Sheets

Specification includes a Sequence Listing.

(56) References Cited

U.S. PATENT DOCUMENTS

| | | | |
|---|---|---|---|
| 10,752,093 B2 | 8/2020 | Kabushiki et al. | |
| 11,124,814 B2 | 9/2021 | Siddiqui et al. | |
| 2004/0038352 A1 | 2/2004 | Maier | |
| 2005/0106588 A1 | 5/2005 | Kutchan et al. | |
| 2005/0139490 A1 | 6/2005 | Chou et al. | |
| 2005/0277179 A1 | 12/2005 | Takai et al. | |
| 2006/0185032 A1 | 8/2006 | Kutchan et al. | |
| 2007/0065910 A1 | 3/2007 | Stephanopoulos | |
| 2007/0199090 A1 | 8/2007 | Apuya et al. | |
| 2007/0298481 A1 | 12/2007 | Sato | |
| 2008/0102499 A1 | 5/2008 | Templeton et al. | |
| 2008/0176754 A1 | 7/2008 | Smolke et al. | |
| 2008/0196123 A1 | 8/2008 | Kutchan et al. | |
| 2010/0075385 A1 | 3/2010 | Kutchan et al. | |
| 2010/0184166 A1 | 7/2010 | Sato et al. | |
| 2013/0130340 A1 | 5/2013 | Yan et al. | |
| 2013/0340119 A1 | 12/2013 | Plesch et al. | |
| 2014/0013465 A1 | 1/2014 | Coombs et al. | |
| 2014/0273109 A1 | 9/2014 | Smolke et al. | |
| 2015/0267233 A1 | 9/2015 | Smolke et al. | |
| 2016/0201101 A1 | 7/2016 | Facchini et al. | |
| 2016/0251688 A1 | 9/2016 | Siddiqui et al. | |
| 2016/0304923 A1 | 10/2016 | Smolke et al. | |
| 2016/0312256 A1* | 10/2016 | Facchini et al. | C12N 9/0071 |
| 2016/0319314 A1 | 11/2016 | Smolke et al. | |
| 2016/0340704 A1 | 11/2016 | Martin et al. | |
| 2017/0058267 A1* | 3/2017 | Winzer et al. | C12P 17/12 |
| 2017/0058305 A1 | 3/2017 | Facchini | |
| 2017/0130250 A1 | 5/2017 | Facchini | |
| 2017/0198299 A1 | 7/2017 | Winzer et al. | |
| 2017/0253898 A1 | 9/2017 | Smolke et al. | |
| 2017/0267686 A1 | 9/2017 | Facchini | |
| 2017/0280647 A1 | 10/2017 | Fist et al. | |
| 2017/0306301 A1 | 10/2017 | Martin et al. | |
| 2017/0362617 A1 | 12/2017 | Peralta-Yahya et al. | |
| 2018/0163212 A1 | 6/2018 | Smolke et al. | |
| 2018/0251801 A1 | 9/2018 | Aharoni et al. | |
| 2018/0273967 A1 | 9/2018 | Hashimoto et al. | |
| 2019/0055567 A1 | 2/2019 | Smolke et al. | |
| 2019/0100781 A1 | 4/2019 | Smolke et al. | |
| 2019/0127770 A1 | 5/2019 | Siddiqui et al. | |

FOREIGN PATENT DOCUMENTS

| | | |
|---|---|---|
| EP | 1512748 A1 | 3/2007 |
| EP | 1837396 | 9/2007 |
| JP | H05504252 A | 7/1993 |
| JP | 2009/225669 | 10/2009 |
| JP | 2014525255 | 9/2014 |
| WO | WO2000058333 A1 | 10/2000 |
| WO | WO2002101052 A2 | 12/2002 |
| WO | WO2005021763 A2 | 3/2005 |
| WO | WO2006015887 A2 | 2/2006 |
| WO | WO 2008/067070 A2 | 6/2008 |
| WO | WO 2008/067070 A3 | 10/2008 |
| WO | WO 2008/153094 A1 | 12/2008 |
| WO | WO2009122436 A2 | 10/2009 |
| WO | WO 2011/058446 | 5/2011 |
| WO | WO2011058446 A1 | 5/2011 |
| WO | WO2011161431 A2 | 12/2011 |
| WO | WO 2012/039438 A1 | 3/2012 |
| WO | WO 2012/135389 A2 | 10/2012 |
| WO | WO 2013/136057 A2 | 9/2013 |
| WO | WO 2014/143744 A2 | 9/2014 |
| WO | WO 2015/021561 A1 | 2/2015 |
| WO | WO2015021561 A1 | 2/2015 |
| WO | WO2018027324 A1 | 2/2015 |
| WO | WO 2015/066642 A1 | 5/2015 |
| WO | WO 2015/081437 A1 | 6/2015 |
| WO | WO 2015/103711 A1 | 7/2015 |
| WO | WO 2014/143744 A3 | 11/2015 |
| WO | WO2015164960 A1 | 11/2015 |
| WO | WO2015173590 | 11/2015 |
| WO | WO2015173590 A1 | 11/2015 |
| WO | WO2016049364 A2 | 3/2016 |
| WO | WO 2016/081371 A1 | 5/2016 |
| WO | WO2016149821 A1 | 9/2016 |
| WO | WO 2016/179296 | 11/2016 |
| WO | WO2016179296 A1 | 11/2016 |
| WO | WO2016207643 A1 | 12/2016 |
| WO | WO2017083632 A1 | 5/2017 |
| WO | WO2017122011 A1 | 7/2017 |
| WO | WO2018000089 A1 | 1/2018 |
| WO | WO2018005553 A1 | 1/2018 |
| WO | WO2018029282 A1 | 2/2018 |
| WO | WO2018039749 A1 | 3/2018 |
| WO | WO2018136654 A1 | 7/2018 |
| WO | WO2020185626 A1 | 9/2020 |

OTHER PUBLICATIONS

Englander et al, ACS Synth Biol. 2017, 6 pp. 710-720.*

Siddique et al. FEMS yeast RES 2014, 14, pp. 1171-1185.*

Beaudoin "Characterization of Oxidative Enzymes Involved in the Biosynthesis of Benzylisoquinoline Alkaloids in Opium Poppy", Mar. 2015, University of Calgary, 409 pages.

Alcantara et al. "Sanguinarine Biosynthesis Is Associated with the Endoplasmic Reticulum in Cultured Opium Poppy Cells after Elicitor Treatment," Plant Physiology, Apr. 22, 2005, vol. 138, pp. 173-183.

Allen et al., "RNAi-Mediated Replacement of Morphine with the Nonnarcotic Alkaloid Reticuline in Opium Poppy", Nat. Biotechnol. (2004), 22:1559-1566.

Avalos et al., "Compartmentalization of Metabolic Pathways in Yeast Mitochondria Improves the Production of Branched-Chain Alcohols", Nat. Biotechnol. (2013), 31:335-341.

Backes et al., "Organization of Multiple Cytochrome P450s with NADPH-Cytochrome P450 Reductase in Membranes", Pharmacol. Ther. (2003), 98:221-233.

Bayer et al., "Synthesis of Methyl Halides from Biomass Using Engineered Microbes", J. Am. Chem. Soc. (2009), 131:6508-6515.

Beaudoin et al., "Isolation and Characterization of a cDNA Encoding (S)-cis-N-Methylstylopine 14-Hydroxylase from Opium Poppy, a Key Enzyme in Sanguinarine Biosynthesis", Biochem. Biophys. Res. Commun. (2013), 431:597-603.

Bitter, Grant A., "Heterologous Gene Expression in Yeast," Methods in Enzymology, vol. 152, pp. 673-684 (1987).

Branden et al. Introduction to Protein Structure, Garland Publishing Inc., New York, p. 247 (1991).

Bruce et al., "Microbial Degradation of the Morphine Alkaloids. Purification and Characterization of Morphine Dehydrogenase from Pseudomonas putida M10", Biochem. J. (1991), 274(3):875-880.

Cautha, Sarat C. "Model based design of a *Saccharomyces cerevisiae* platform strain with improved tyrosine production capabilities," Masters Thesis, Toronto, Canada, 72 pages (2012). Retrieved from the internet on Jan. 28, 2015 at: http://hdl.handle.net/1807/33358.

Chávez-Béjar et al. "Metabolic Engineering of *Escherichia coli* for L-Tyrosine Production by Expression of Genes Coding for the Chorismate Mutase Domain of the Native Chorismate Mutase-Prephenate Dehydratase and a Cyclohexadienyl Dehydrogenase from Zymomonas mobilis," Applied and Environmental Microbiology, American Society for Microbiology, US, vol. 74, No. 10, pp. 3284-3290 (Mar. 14, 2008).

Choi et al., "Molecular Cloning and Characterization of Coclaurine N-Methyltransferase from Cultured Cells of Coptis japonica", J. Biol. Chem. (2002), 277:830-835.

Cooper et al., "On the amine oxidases of Klebsiella aerogenes strain W70," FEMS Microbiol. Lett., 146(1):85-89 (1997).

Curran et al. "Metabolic engineering of muconic acid production in *Saccharomyces cerevisiae*," Metabolic Engineering, Academic Press, US, vol. 15, Nov. 17, 2012, pp. 55-66.

Diaz Chavez et al., "Characterization of two Methylenedioxy Bridge-Forming Cytochrome P450-Dependent Enzymes of Alkaloid Formation in the Mexican Prickly Poppy Argemone mexicana", Arch. Biochem. Biophys. (2011), 507:186-193.

Dumas et al., "11 Beta-Hydroxylase Activity in Recombinant Yeast Mitochondria. In vivo Conversion of 11-Deoxycortisol to Hydrocortisone", Eur. J. Biochem. (1996), 238:495-504.

(56) References Cited

OTHER PUBLICATIONS

Facchini et al., "Differential and Tissue-Specific Expression of a Gene Family for Tyrosine/Dopa Decarboxylase in Opium Poppy," J. Biol. Chem., 269(43):26684-26690 (1994).
Farhi et al., "Harnessing Yeast Subcellular Compartments for the Production of Plant Terpenoids", Metab. Eng. (2011), 13:474-481.
Farrow et al., "Dioxygenases Catalyze O-Demethylation and O,Odemethylenation with Widespread Roles in Benzylisoquinoline Alkaloid Metabolism in Opium Poppy", J. Biol. Chem. (2013), 288:28997-29012.
Fisinger et al., "Thebaine Synthase: a New Enzyme in the Morphine Pathway in Papaver somniferum", Natural Product Communications (2007), 2(3):249-253.
French et al., "Biological Production of Semisynthetic Opiates Using Genetically Engineered Bacteria", Biotechnology (N Y) (1995), 13:674-676.
French et al., "Purification and Characterization of Morphinone Reductase from Pseudomonas putida M10", Biochem. J. (1994), 301(1):97-103.
Fukuda et al. "Breeding of Brewing Yeast Producing a Large Amount of Beta-Phenylethyl Alcohol and Beta-Phenylethyl Acetate," Agricultural and Biological Chemistry, Tokyo, Japan, vol. 54, No. 1, pp. 269-271 (1990).
Fukuda et al. "Feedback-Insensitive Mutation of 3-Deoxy-D-Arabino-Hepturosonate-7-Phosphate Synthase Caused by a Single Nucleotide Substitution of ARO4 Structural Gene in Saccharomyces cerevisiae," Journal of Fermentation and Bioengineering, vol. 74, No. 2, pp. 117-119 (1992).
Fukuda et al. "Molecular Breeding of a Sake Yeast with a Mutated AR04 Gene Which Causes Both Resistance to o-Fluoro-DL-Phenylalanine and Increased Production of Beta-Phenethyl Alcohol," Journal of Fermentation and Bioengineering, vol. 73, No. 5, pp. 366-369 (1992).
Geissler et al., "Molecular Modeling and Site-Directed Mutagenesis Reveal the Benzylisoquinoline Binding Site of the Short-Chain Dehydrogenase/Reductase Salutaridine Reductase", Plant Physiol. (2007), 143(4):1493-503.
Gesell et al. "CVP719B1 Is Salutaridine Synthase. the C—C Phenol-coupling Enzyme of Morphine Biosynthesis in Opium Poppy", Journal of Biological Chemistry, vol. 284, No. 36, Sep. 4, 2009, pp. 24432-24442.
Gesell et al., "Heterologous Expression of Two FAD-Dependent Oxidases with (S) Tetrahydroprotoberberine Oxidase Activity from Argemone mexicana and Berberis wilsoniae in Insect Cells", Planta. (2011), 233:1185-1197.
Grothe et al., "Molecular Characterization of the Salutaridinol 7-O-Acetyltransferase Involved in Morphine Biosynthesis in Opium Poppy Papaver somniferum", J. Biol. Chem. (2001), 276:30717-30723.
Gustafsson et al. "Codon bias and heterologous protein expression," Trends in Biotechnology, vol. 22, No. 7, pp. 346-353 (Jul. 2004).
Hagel et al., "Benzylisoquinoline Alkaloid Metabolism: a Century of Discovery and a Brave New World", Plant Cell Physiol. (2013), 54:647-672.
Hagel et al., "Characterization of a Flavoprotein Oxidase from Opium Poppy Catalyzing the Final Steps in Sanguinarine and Papaverine Biosynthesis", J. Biol. Chem. (2012), 287:42972-42983.
Hagel et al., "Dioxygenases Catalyze the O-Demethylation Steps of Morphine Biosynthesis in Opium Poppy", Nat. Chem. Biol. (2010), 6:273-275.
Hartmann et al. "Evolution of feedback-inhibited beta/alpha barrel isoenzymes by gene duplication and a single mutation," PNAS, vol. 100, No. 3, pp. 862-867 (Feb. 4, 2003).
Hawkins et al. "Production of benzylisoquinoline alkaloids in Saccharomyces cerevisiae," Nature Chemical Biology, vol. 4, No. 9, pp. 564-573 (Aug. 10, 2008).
Hawkins et al. "Supplementary Text and Figures. Production of benzylisoquinoline alkaloids in Saccharomyces cerevisiae," Nature Chemical Biology, Aug. 10, 2008, 15 pages.
Hawkins, K. "Metabolic Engineering of Saccharomyces cerevisiae for the Production of Benzylisoquinoline Alkaloids," Ph.D. Thesis, California Institute of Technology, Pasadena, California, 2009, pp. 1-154.
Higashi et al., "Atomic Structure of Salutaridine Reductase from the Opium Poppy (Papaver somniferum)", J. Biol. Chem. (2011), 286:6532-6541.
Hinnen et al. "Chapter 10: Heterologous Gene Expression in Yeast," Yeast Genetic Engineering, Barr et al. eds., Butterworths, pp. 193-213 (1989).
Hiroi et al., "Dopamine Formation from Tyramine by CYP2D6," Biochemical & Biophysical Research Communications, 249:838-843 (1998).
Ikezawa et al., "Molecular Cloning and Characterization of CYP719, a Methylenedioxy Bridge-Forming Enzyme that Belongs to a Novel P450 Family, from Cultured Coptis japonica Cells", J. Biol. Chem. (2003), 278:38557-38565.
Ikezawa et al., "Molecular Cloning and Characterization of Methylenedioxy Bridge-Forming Enzymes Involved in Stylopine Biosynthesis in Eschscholzia californica", FEBS J. (2007), 274:1019-1035.
Iraqui et al., "Characterisation of *Saccharomyces cerevisiae* AR08 and AR09 genes encoding aromatic aminotransferases I and II reveals a new aminotransferase subfamily," Mol. Gen. Genet., 257(2):238-248 (1998).
Jensen et al., "Plant NADPH-Cytochrome P450 Oxidoreductases", Phytochemistry (2010). 71:132-141.
Kim et al., "Improvement of Reticuline Productivity from Dopamine by Using Engineered *Escherichia coli*", Biosci. Biotechnol. Biochem. (2013), 77(10):2166-2168.
Kocharin, Kanokarn, "Metabolic Engineering of *Saccharomyces cerevisiae* for Polyhydroxybutyrate Production" PhD Thesis, Apr. 2013, 168 pages.
Koopman et al. "De novo production of the flavonoid naringenin in engineered *Saccharomyces cerevisiae*," Microbial Cell Factories, Biomed Central, GB, vol. 11, No. 1, Dec. 8, 2012, p. 155 (15 pages).
Kushnirov, "Rapid and Reliable Protein Extraction from Yeast", Yeast (2000), 16:857-860.
Kutchan et al., "Molecular Genetics of Plant Alkaloid Biosynthesis," Alkaloids, 50:257-316 (1998).
Kutchan, Tony M. "Heterologous expression of alkaloid biosynthetic genes—a review", Gene, vol. 179, No. 1, Nov. 7, 1996, pp. 73-81.
Larkin et al., "Increasing Morphinan Alkaloid Production by Over-Expressing Codeinone Reductase in Transgenic Papaver somniferum", Plant Biotechnol. J. (2007), 5:26-37.
Lee et al. "Bacillus licheniformis APase I gene promoter: a strong well-regulated promoter in B. Subtilis," Journal of General Microbiology, vol. 137, pp. 1127-1133 (1991).
Lee et al. "Metabolic engineering of microorganisms: general strategies and drug production," Drug Discovery Today, vol. 14, No. 1/2, pp. 78-88 (Sep. 18, 2008).
Lenz et al., "Acetyl Coenzyme A:Salutaridinol-7-O Acetyltransferase from Papaver somniferum Plant Cell Cultures", J. Biol. Chem. (1995), 270:31091-31096.
Lenz et al., "Purification and Properties of Codeinone Reductase (NADPH) from Papaver somniferum Cell Cultures and Differentiated Plants", Eur. J. Biochem. (1995), 233:132-139.
Liscombe et al., "Targeted Metabolite and Transcript Profiling for Elucidating Enzyme Function: Isolation of Novel N Methyltransferases from Three Benzylisoquinoline Alkaloid-Producing Species", Plant J. (2009), 60:729-743.
Lütke-Eversloh et al. "L-Tyrosine production by deregulated strains of *Escherichia coli*," Applied Microbiology and Biotechnology, Springer, Berlin, DE, vol. 75, No. 1,Jan. 13, 2007, pp. 103-110.
Lütke-Eversloh et al. "Perspectives of biotechnological production of L-tyrosine and its applications," Applied Microbiology and Biotechnology, Springer, Berlin, DE, vol. 77, No. 4, Oct. 30, 2007, pp. 751-762.
Luttik et al. "Alleviation of feedback inhibition in Saccharomyces cerevisiae aromatic amino acid biosynthesis: Quantification of metabolic impact," Metabolic Engineering, vol. 10, pp. 141-153 (2008).

(56) References Cited

OTHER PUBLICATIONS

Lv et al. "LC-MS-MS Simultaneous Determination of L-Dopa and Its Prodrug L-Dopa n-Pentyl Hydrochloride in Rat Plasma," Chromatographia, vol. 72, No. 3/4, pp. 239-243, (2010).
Minami et al., "Microbial Production of Plant Benzylisoquinoline Alkaloids", Proc. Natl. Acad. Sci. U S A (2008), 105:7393-7398.
Minami, H. "Fermentation Production of Plant Benzylisoquinoline Alkaloids in Microbes," Bioscience, Biotechnology, and Biochemistry, vol. 77, No. 8, pp. 1617-1622 (Aug. 7, 2013).
Mishra et al. "Wound Induced Tanscriptional Regulation of Benzylisoquinoline Pathway and Characterization of Wound Inducible PsWRKY Transcription Factor from Papaver somniferum," PLOS One, Jan. 30, 2013, vol. 8, No. 1, pp. 1-15.
Mizutani et al., "Diversification of P450 Genes During Land Plant Evolution", Annu. Rev. Plant Biol. (2010), 61:291-315.
Moerner et al., "Illuminating single molecules in condensed matter," Science, 283(5408):1670-1676 (1999).
Morishige et al., "Molecular Characterization of the Sadenosyl-L-Methionine:3'-Hydroxy-N-Methylcoclaurine 4'-O-Methyltransferase Involved in Isoquinoline Alkaloid Biosynthesis in Coptis japonica", J. Biol. Chem. (2000), 275:23398-23405.
Muñoz et al. "Metabolic engineering of Escherichia coli for improving L-3,4-dihydroxyphenylalanine (L-DOPA) synthesis from glucose," Journal of Industrial Microbiology and Biotechnology; vol. 38, No. 11, pp. 1845-1852 (Apr. 22, 2011).
Nakagawa et al. "A bacterial platform for fermentative production of plant alkaloids," Nature Communications, vol. 2, Article No. 326, 8 pages (May 24, 2011).
Nakagawa et al., "Bench-Top Fermentative Production of Plant Benzylisoquinoline Alkaloids Using a Bacterial Platform", Bioeng. Bugs (2012), 3:49-53.
Ng et al. "Production of 2,3-butanediol in Saccharomyces cerevisiae by in silica aided metabolic engineering," Microbial Cell Factories, Biomed Central, GB, vol. 11, No. 1, May 28, 2012, p. 68 (14 pages).
Olson et al. "Production of tyrosine from sucrose or glucose achieved by rapid genetic changes to phenylalanine-producing Escherichia coli strains," Applied Microbiology and Biotechnology, vol. 74, No. 5, pp. 1031-1040 (Jan. 11, 2007).
Onoyovwe et al., "Morphine Biosynthesis in Opium Poppy Involves Two Cell Types: Sieve Elements and Laticifers", Plant Cell (2013), 25(10): 4110-4122.
Ounaroon et al., "(R,S)-Reticuline 7-O-Methyltransferase and (R,S)-Norcoclaurine 6-O-Methyltransferase of Papaver somniferum-cDNA Cloning and Characterization of Methyl Transfer Enzymes of Alkaloid Biosynthesis in Opium Poppy", Plant J. (2003), 36:808-819.
Rueffer et al. "(S)-Norlaudanosoline Synthase—The 1st Enzyme in the Benzylisoquinoline Biosynthetic-Pathway," FEBS Letters, vol. 129, No. 1, pp. 5-9 (Jun. 1981).
Ruohonen et al. "Modifications to the ADH1 promoter of Saccharomyces cerevisiae for efficient production of heterologous proteins," Journal of Biotechnology, vol. 39, pp. 193-203 (1995).
Samanani et al., "Molecular cloning and characterization of norcoclaurine synthase, an enzyme catalyzing the first committed step in benzylisoquinoline alkaloid biosynthesis," Plant J., 40(2):302-313 (2004).
Sandig et al., "Regulation of Endoplasmic Reticulum Biogenesis in Response to Cytochrome P450 Overproduction", Drug Metab. Rev. (1999), 31:393-410.
Sato et al., "Purification and Characterization of S-adenosyl-L-methionine: norcoclaurine 6-O-methyltransferase from Cultured Coptis japonica Cells", Eur. J. Biochem. (1994), 225:125-131.
Schmidheini et al. "A Single Point Mutation Results in a Constitutively Activated and Feedback-Resistant Chorismate Mutase of Saccharornyces cerevisiae," Journal of Bacteriology, vol. 171, No. 3, pp. 1245-1253 (Mar. 1989).
Schmidt et al. "Poppy alkaloid profiling by electrospray tandem mass spectrometry and electrospray FT-ICR mass spectrometry after [ring-13C6]-tyramine feeding," Phytochemistry, vol. 68, No. 2, pp. 189-202 (2007).
Siddiqui et al., "Advancing Secondary Metabolite Biosynthesis in Yeast with Synthetic Biology Tools", FEMS Yeast Res. (2012), 12:144-170.
Single Molecule Detection and Manipulation Workshop, Apr. 17-18, 2000, 28 pages. Retrieved from http://www.nigms.nih.gov/news/reports/single_molecules.html.
Stewart et al., "A Chemist's Perspective on the Use of Genetically Engineered Microbes as Reagents for Organic Synthesis," Biotechnology and Genetic Engineering Reviews, 14:67-143 (1997).
Takemura et al., "Molecular Cloning and Characterization of a Cytochrome P450 in Sanguinarine Biosynthesis from Eschscholzia californica Cells", Phytochemistry (2013), 91:100-108.
Trenchard et al. "De novo production of the key branch point benzylisoquinoline alkaloid reticuline in yeast," Metab. Eng., Jul. 10, 2015, vol. 31, pp. 74-83.
Unterlinner et al., "Molecular Cloning and Functional Expression of Codeinone Reductase: the Penultimate Enzyme in Morphine Biosynthesis in the Opium Poppy Papaver somniferum", Plant J. (1999), 18:465-475.
Vuralhan et al., "Identification and characterization of phenylpyruvate decarboxylase genes in Saccharomyces cerevisiae," Appl. Environ. Microbial., 69(8):4534-4541 (2003).
Vuralhan, Z. "Engineering of aromatic amino acid metabolism in Saccharomyces cerevisiae," Ph. D. Thesis. Apr. 11, 2006, pp. 1-110.
Wijekoon et al., "Systematic Knockdown of Morphine Pathway Enzymes in Opium Poppy Using Virus-Induced Gene Silencing", Plant J. (2012), 69:1052-1063.
Zenk et al., "Benzylisoquinoline Biosynthesis by Cultivated Plant Cells and Isolated Enzymes," Journal of Natural Products, 48(5):725-738 (1985).
Zhang et al., "14-Hydroxylation of Opiates: Catalytic Direct Autoxidation of Codeinone to 14-Hydroxycodeinone", J. Am. Chem. Soc. (2005), 127:7286-7287.
Ziegler et al., "Removal of Substrate Inhibition and Increase in Maximal Velocity in the Short Chain Dehydrogenase/Reductase Salutaridine Reductase Involved in Morphine Biosynthesis", J. Biol. Chem. (2009), 284:26758-26767.
Zimmer et al., "Protein Quality—a Determinant of the Intracellular Fate of Membrane-Bound Cytochromes P450 in Yeast", DNA Cell Biol. (1997), 16:501-514.
European Patent Office, Search Results under Rule 164(2)(b) EPC issued May 18, 2017 in corresponding European Patent Application No. 14802992.9, 14 pages.
PCT/US2014/063738 International Preliminary Report on Patentability dated May 10, 2016, 18 pages.
PCT/US2014/063738 International Search Report dated Apr. 9, 2015, 8 pages.
PCT/US2014/063738 Written Opinion dated Apr. 9, 2015, 10 pages.
French et al., Bacterial morphinone reductase is related to Old Yellow Enzyme, Biochem J. Dec. 15, 1995;312 ( Pt 3):671-8.
Lister et al., Transformations of codeine to important semisynthetic opiate derivatives by Pseudomonas putida m10, FEMS Microbiol Lett. Dec. 1, 1999;181(1):137-44.
Runguphan et al., Redesign of a dioxygenase in morphine biosynthesis, Chem Biol. Jun. 22, 2012;19(6):674-8.
Sharafi et al., Metabolic engineering of morphinan alkaloids by over-expression of codeinone reductase in transgenic hairy roots of Papaver bracteatum, the Iranian poppy, Biotechnol Lett. Mar. 2013,35(3):445-53.
Walker et al., Mechanistic studies of morphine dehydrogenase and stabilization against covalent inactivation, Biochem J. Feb. 1, 2000;345 Pt 3:687-92.
Willey et al., Nucleotide sequence and over-expression of morphine dehydrogenase, a plasmid-encoded gene from Pseudomonas putida M10, Biochem J. Mar. 1, 1993; 290(Pt 2): 539-544.
U.S. Office Action issued for U.S. Appl. No. 15/517,761, dated Dec. 23, 2019, 35 pages.
Dang, et al. "Cloning and characterization of canadine synthase involved in noscapine biosynthesis in opium poppy", FEBS Lett. Jan. 3, 2014;588(1):198-204.
Guo, et al. "Mini-review: In vitro Metabolic Engineering for Biomanufacturing of High-value Products", Comput Struct Biotechnol J. Jan. 19, 2017;15:161-167.

(56) References Cited

OTHER PUBLICATIONS

Liscombe, et al. "Molecular cloning and characterization of tetrahydroprotoberberine cis-N-methyltransferase, an enzyme involved in alkaloid biosynthesis in opium poppy", J Biol Chem. May 18, 2007;282(20).
Broun, et al. "Catalytic plasticity of fatty acid modification enzymes underlying chemical diversity of plant lipids", Science. Nov. 13, 1998;282(5392):1315-7.
Devos, et al. "Practical limits of function prediction", Proteins. Oct. 1, 2000;41(1):98-107.
Nakagawa, et al. "(R,S)-Tetrahydropapaveroline production by stepwise fermentation using engineered *Escherichia coli*", Scientific Reports vol. 4, Article No. 6695 (2014).
Nakagawa, et al. "Bioengineering of Isoquinoline Alkaloid Production in Microbial Systems", Advances in Botanical Research 68:183-203, 2013.
Seffernick, et al. "Melamine Deaminase and Atrazine Chlorohydrolase: 98 Percent Identical but Functionally Different", J. Bacteriol. Apr. 2001 vol. 183 No. 8 2405-2410.
Whisstock, et al. "Prediction of protein function from protein sequence and structure", Q Rev Biophys. Aug. 2003;36(3):307-40.
Winzer, et al. "A Papaver somniferum 10-gene cluster for synthesis of the anticancer alkaloid noscapine", Science. Jun. 29, 2012;336(6089):1704-8.
Witkowski, et al. "Conversion of a beta-ketoacyl synthase to a malonyl decarboxylase by replacement of the active-site cysteine with glutamine", Biochemistry. Sep. 7, 1999;38(36):11643-50.
Communication, The extended European Search Report from European patent application No. 15861129.3, dated Jul. 11, 2018, 10 pages.
Examination report No. 1 for standard patent application for Australian Application No. 2015350229, dated Jul. 19, 2018, 10 pages.
Hirata, et al. "1,2-Dehydroreticuline synthase, the branch point enzyme opening the morphinan biosynthetic pathway", Phytochemistry, vol. 65, 2004, pp. 1039-1046.
Communication pursuant to Rule 164(1) EPC for European patent application No. 16793332.4, dated Feb. 28, 2019, 11 pages.
U.S. Appl. No. 16/216,829, filed Dec. 11, 2018, Smolke et al.
European search report and search opinion dated Apr. 10, 2017 for EP Application No. 14729501.8, 12 pages.
International search report and written opinion dated Sep. 15, 2015 for PCT Application No. PCT/US2014/027833 (with publication), 131 pages.
International Search Report for PCT/US07/81974, dated Jul. 8, 2008, 3 pages.
Notice of allowance dated Oct. 14, 2016 for U.S. Appl. No. 14/211,611, 19 pages.
Notice of allowance dated Nov. 18, 2016 for U.S. Appl. No. 14/211,611, 7 pages.
Notice of allowance dated dated Nov. 7, 2014 for U.S. Appl. No. 11/875,814, 9 pages.
Office action dated Jul. 25, 2016 for U.S. Appl. No. 14/211,611, 28 pages.
Office action dated Dec. 10, 2015 for U.S. Appl. No. 14/211,611, 27 pages.
Office action dated dated Feb. 18, 2009 for U.S. Appl. No. 11/875,814, 17 pages.
Office action dated dated May 23, 2014 for U.S. Appl. No. 11/875,814, 13 pages.
Office action dated dated Dec. 3, 2013 for U.S. Appl. No. 11/875,814, 14 pages.
Office action dated dated Dec. 29, 2009 for U.S. Appl. No. 11/875,814, 12 pages.
U.S. Appl. No. 15/078,874 Office Action dated Feb. 16, 2018, 9 pages.
U.S. Appl. No. 15/139,263 Office Action dated Feb. 16, 2018, 18 pages.
U.S. Appl. No. 15/360,763 Notice of Allowance dated May 11, 2018, 10 pages.
U.S. Appl. No. 15/360,763 Office Action dated Apr. 10, 2018, 6 pages.
U.S. Appl. No. 15/360,763 Office Action dated Dec. 20, 2017, 5 pages.
U.S. Appl. No. 15/567,354 Office Action dated Jul. 19, 2018, 31 pages.
U.S. Appl. No. 16/191,247 Office Action dated Jan. 15, 2019, 34 pages.
U.S. Appl. No. 15/567,354 Office Action dated Feb. 4, 2019, 10 pages.
U.S. Appl. No. 15/517,761 Office Action dated Feb. 26, 2019, 19 pages.
Farrow, et al. "Stereochemical inversion of (S)-reticuline by a cytochrome P450 fusion in opium poppy", Nat Chem Biol. Sep. 2015;11(9):728-32.
De-Eknamkul, et al. "Purification and properties of 1,2-dehydroreticuline reductase from Papaver somniferum seedlings", vol. 31, Issue 3, Mar. 1992, pp. 813-821.
Communication, The Extended European Search Report for European patent application No. 1679333.4, dated May 29, 2019, 12 pages.
Second Office Action for China patent application No. 201480068628.3, dated Oct. 21, 2019, 8 pages.
Uni ProtKB Database. AR01, AR02, AR07 & TYR 1. revtrieved from https://www.uniprot.org/uniprot/ on Oct. 28, 2019.
U.S. Office Action issued for U.S. Appl. No. 15/031,618, dated Nov. 1, 2019, 31 pages.
Communication pursuant to Article 94(3) EPC issued for European patent application No. 14802992.9, dated Feb. 19, 2019, 8 pages.
Dang, et al. "CYP82Y1 Is N-Methylcanadine 1-Hydroxylase, a Key Noscapine Biosynthetic Enzyme in Opium Poppy", The Journal of Biological Chemistry vol. 289, No. 4, pp. 2013-2026, 2014.
Communication, The Extended European Search Report for European patent application No. 16793332.4, dated May 29, 2019, 12 pages.
Notice of Reasons for Rejection for Japanese Patent Application No. 2017-520348, dated Aug. 22, 2019, 5 pages.
Examination Report under Section 18(3) for Great Britain patent application No. GB1707059.0, dated Sep. 27, 2019, 6 pages.
Search and Examination Report under Section 17 and 18(3) for Great Britain patent application No. GB1518138.1, dated Sep. 30, 2019, 9 pages.
Examination report No. 2 for Australian patent application No. 2016261490, dated Oct. 12, 2019, 4 pages.
U.S. Appl. No. 16/224,217, filed Dec. 18, 2018, Siddiqui, et al.
U.S. Appl. No. 16/165,940, filed Oct. 19, 2018, Smolke, et al.
U.S. Appl. No. 15/031,618 Office Action dated May 16, 2019, 20 pages.
U.S. Appl. No. 15/567,354 Office Action dated May 1, 2019, 57 pages.
U.S. Appl. No. 16/165,940 Office Action dated May 15, 2019, 50 pages.
U.S. Appl. No. 15/139,263.
U.S. Appl. No. 16/165,940 Office Action dated Dec. 17, 2018, 37 pages.
International search report and written opinion dated Aug. 4, 2016 for PCT Application No. PCT/US2016/030808, 13 pages.
U.S. Appl. No. 15/078,874.
Hiromichi, et al. "Microbial production of plant benzylisoquinoline alkaloids", PNAS, May 27,2008, vol. 105, No. 21, pp. 7393-7398.
Dang, et al., "Elucidation of the noscapine biosynthetic pathway in opium poppy", Doctoral Thesis, University of Calgary, 2014, 207 pages.
Fossati, et al., "Reconstitution of a 10-gene pathway for synthesis of the plant alkaloid dihydrosanguinarine in *Saccharomyces cerevisiae*", Nat. Comm. 5:3283, 2014, 11 pages.
Lister, et al., "Transformations of codeine to important semisynthetic opiate derivatives by Pseudomonas putida m10." FEMS Microbiol Lett.; vol. 181, No. 1, pp. 137-144, 1999.
Runguphan, et al., Redesign of a dioxygenase in morphine biosynthesis. Chem Biol.; vol. 19, No. 6, pp. 674-678, 2012.

(56) References Cited

OTHER PUBLICATIONS

Sharafi, et al., Metabolic engineering of morphinan alkaloids by over-expression of codeinone reductase in transgenic hairy roots of *Papaver bracteatum*, the Iranian poppy. Biotechnol Lett.; vol. 35, No. 3, pp. 445-453, 2012.
Mitchell, et al. "Circular permutation of a synthetic eukaryotic chromosome with the telomerator", PNAS, 2014,111, pp. 17003-17010.
Vasquez, et al. "Genome Organization and Function: A View from Yeast and *Arabidopsis*" Molecular Plant 2010, 3, pp. 678-690.
Zeng, et al. "Integration of Transcriptome, Proteome and Metabolism Data Reveals the Alkaloids Biosynthesis in Macleaya cordata and Macleaya microcarpa", Plos One, vol. 8, Issue 1, pp. 1-18, 2013.
Ba et al., Semi-Rational Engineering of Cytochrome P450sca-2 in a Hybrid System for Enhanced Catalytic Activity: Insights Into the Important Role of Electron Transfer, Biotechnology and Bioengineering, Nov. 2013, vol. 110, No. 11, p. 2815-2825.
Banerjee et al., Improving Enzymes for Biomass Conversion: A Basic Research Perspective, Bioenerg. Res., Jan. 2010, vol. 3, p. 82-92.
Chica et al., Semi-rational approaches to engineering enzyme activity: combining the benefits of directed evolution and rational design, Current Opinion in Biotechnology, Jul. 2005, vol. 16, p. 378-384.
Galanie et al., Complete biosynthesis of opioids in yeast, Science, Sep. 2015, vol. 349, No. 6252, p. 1095-1100.
Guo et al., Protein tolerance to random amino acid change, PNAS, Jun. 2004, vol. 101, No. 25, p. 9205-9210.
Kimchi-Sarfaty et al., A "Silent" Polymorphism in the MDR1 Gene Changes Substrate Specificity, Science, Jan. 2007, vol. 315, No. 5811, p. 525-528.
Nackley et al., Human Catechol-O-Methyltransferase Haplotypes Modulate Protein Expression by Altering mRNA Secondary Structure, Science, Dec. 2006, vol. 314, No. 5807, p. 1930-1933.
Sauna et al., Silent Polymorphisms Speak: How They Affect Pharmacogenomics and the Treatment of Cancer, Cancer Res., Oct. 2007, vol. 67, No. 20, p. 9609-9612.
Sen et al., Developments in Directed Evolution for Improving Enzyme Functions, Appl Biochem Biotechnol, Aug. 2007, vol. 143, p. 212-223.
Braus "Aromatic amino acid biosynthesis in the yeast *Saccharomyces cerevisiae*: a model system for the regulation of a eukaryotic biosynthetic pathway", Microbiol Rev., 1991;55(3):349-70.
Fukuda, et al. "A mutated ARO4 gene for feedback-resistant DAHP synthase which causes both o-fluoro-DL-phenylalanine resistance and beta-phenethyl-alcohol overproduction in *Saccharomyces cerevisiae*", Curr Genet., Dec. 1991;20(6):453-6.
Lechner, et al. "Library of Norcoclaurine Synthases and Their Immobilization for Biocatalytic Transformations", Biotechnol J., Mar. 2018;13(3).
Lee, et al. "Norcoclaurine Synthase Is a Member of the Pathogenesis-Related 10/Bet v1 Protein Family[W]", Plant Cell. Oct. 2010; 22(10): 3489-3503.
Rodriguez, et a.. "Establishment of a yeast platform strain for production of p-coumaric acid through metabolic engineering of aromatic amino acid biosynthesis", Metab Eng., Sep. 2015;31:181-8.
U.S. Office Action dated Jan. 16, 2018 in U.S. Appl. No. 15/101,474.
U.S. Final Office Action dated Jul. 26, 2018 in U.S. Appl. No. 15/101,474.
U.S. Notice of Allowance dated Sep. 12, 2018 in U.S. Appl. No. 15/101,474.
U.S. Office Action dated Oct. 29, 2020 in U.S. Appl. No. 16/213,037.
Pauli, H.H. et al., T.M., The Plant Journal; 1998, vol. 13, No. 6; pp. 793-801.
Millgate, A.G. et al. Nature; Sep. 2004, vol. 431, pp. 413-414.
De-Eknannkul, W. et al., Tetrahedron Letters, vol. 31, No. 34; pp. 4855-4858.
Salis, H.M. et al., "Automated Design of Synthetic Ribosome Binding Sites to Precisely Control Protein Expression," Nat Biotechnol. Oct. 2009; 27(10):946-950.
Altschul, S.F. et al., "Basic Local Alignment Search Tool", J. Molec. Biol. 215:403-410 (1990).
Carillo, H. et. al., "The Multiple Sequence Alignment Problem in Biology", SIAM J. Applied Math., 48(5)1078-1083 (1988).
Desgagne-Penix, I. et al., "Integration of deep transcriptome and proteome analyses reveals the components of alkaloid metabolism in opium poppy cell cultures", BMC Plant Biology, 10(1):1-17 (2010).
Devereaux, J. et al., "A comprehensive set of sequence analysis programs for the VAX", Nucleic Acids Res., 12 (1):387-395 (1984).
Henikoff, S. et al., "Amino acid substitution matrices from protein blocks", Proc. Natl. Acad. Sci. USA, 89:10915-10919 (1992).
Needleman, S.B. et al., "A General Method Applicable to the Search for Similarities in the Amino Acid Sequence of Two Proteins", J. Mol. Biol., 48:443-453 (1970).
Niedz, R. P. et al., "Green fluorescent protein: an in vivo reporter of plant gene expression", Plant Cell Rep., 14:403-406 (1995).
Jez et al., Biochem. Pharmacol., 54:639-647 (1997).
Yoshida et al., Chemistry: An Organism, 36: 393-398 (1998).
Imai, Chemistry: An Organism, 36: 530-533 (1998).
Morris et al., "Plug-and-Play Benzylisoquinoline Alkaloid Biosynthetic Gene Discovery in Engineered Yeast" in Methods in Enzymology, 144-178 (Elsevier 2016).
Facchini, P. J., GenBank Accession No. FE967184, Mar. 31, 2008 (Mar. 31, 2008), [online] [retrieved on Sep. 19, 2017].
Plant Molecular Biology: A Laboratory Manual, Chapter 7, Clark, Ed., Springer.
Paterson, A. H., The DNA Revolution, Chapter 2 in: Genome Mapping in Plants; Academic Press/R.G. Landis Company, Austin, TX (1996).
Smith, T.F. et al., "Comparison of Biosequences", Adv. Appl. Math., 2:482-489 (1981).
Teitel, S. et al., "An Improved Synthesis of Various Racemic Polyphenolic Tetrahydroisoquinoline alkaloids", Journal of Heterocyclic Chemistry 5:825-829 (1968).
Thompson, J.D. et al., "Clustal W: Improving the Sensitivity of Progressive Multiple Sequence Alignment through sequence weighting, position-specific gap penalties and weight matrix choice", Nucleic Acid Res., 22(22):4673-4680 (1994).
U.S. Office Action dated Jan. 29, 2019 in U.S. Appl. No. 16/149,025.
U.S. Office Action dated Jun. 4, 2020 in U.S. Appl. No. 16/541,078.
U.S. Notice of Allowance dated Jun. 5, 2019 in U.S. Appl. No. 16/149,025.
U.S. Notice of Allowance dated Aug. 27, 2019 in U.S. Appl. No. 16/149,025.
U.S. Office Action dated Aug. 14, 2019 in U.S. Appl. No. 16/541,078.
Sato, et al. "Microbial production of isoquinoline alkaloids as plant secondary metabolites based on metabolic engineering research", Proc Jpn Acad Ser B Phys Biol Sci, 2013;89(5):165-82.
Cravens, et al. "Synthetic biology strategies for microbial biosynthesis of plant natural products", Nature Communications vol. 10, Article No. 2142 (2019).
Li, et al. "Strategies for microbial synthesis of high-value phytochemicals", Nat Chem, Apr. 2018;10(4):395-404.
CAS Registry No. 86709-01-5 (Neomorphine) Nov. 16, 1984, (Modify Date: Apr. 9, 2021), 3 pages.
CAS Registry No. 466-99-9 (Hydromorphone) Nov. 16, 1984, (Modify Date: Jun. 10, 2019), 3 pages.
CAS Registry No. 57-27-2 (Morphine) Nov. 16, 1984, (Modify Date: Jun. 10, 2019), 19 pages.
Clinical trials.gov, "Morphine vs. Oxycodone for Postoperative Pain Management", ClinicalTrials.gov, https://clinicaltrials.gov/ct2/show/NCT00528177, 2011, 4 pages.
Clinical trials.gov, "Fasting Study of Hydromorphone Hydrochloride 8 mg Tablets and Dilaudid 8 mg Tablets", ClinicalTrials.gov, https://web.archive.org/web/20121216193456/https://clinicaltrails.gov/ct2/show/NCT00853554, Dec. 16, 2012.
Babiskin, et al. "A synthetic library of RNA control modules for predictable tuning of gene expression in yeast", Mol. Syst Biol., 2011;7:471.

(56) References Cited

OTHER PUBLICATIONS

Enyzyme, https://www.expasy.org/cgi-bin/enzyme-search-de, 2000, 1 page.
Gold, et al. "Metabolic engineering of a tyrosine overproducing yeast platform using targeted metabolomics". Microbial Cell Factories, vol. 14, Article No. 73 (2015).
Neviogt, et al. "Engineering promoter regulation", Biotechnol Bioeng, . Feb. 15, 2007,96(3):550-8.
Enyzyme, Nucleic Acids Research, vol. 28, Issue 1, Jan. 1, 2000, pp. 304-305.
Li, et al. "Engineering biosynthesis of the anticancer alkaloid noscapine in yeast", Nature Communications, vol. 7, Article No. 12137 (2016).
KEGG Compound C06172, Neopinone, https://web.archive.org/web/20130117233034/https://www.genome.jp/dbget-bin/www_bget?C06172, Downloaded on Jul. 8, 2021, 1 page.
Non-Final Office Action for U.S. Appl. No. 16/541,078, dated Apr. 23, 2021, 43 pages.
Final Office Action for U.S. Appl. No. 16/213,037, dated Jul. 9, 2021, 12 pages.
Daubner, et al., "Tyrosine Hydroxylase and Regulation of Dopamine Synthesis", Arch Biochem Biophys, 508(1), 1-12.
Shi, et al., "Regulation of Tetrahydrobiopterin Synthesis and Bioavailability in Endothelial Cells", Cell Biochemistry and Biophysics, 41, 415-433.
Axelsson et al., Cell separation, centrifugation. Enc. Indust. Biotechnol: Bioprocess, Bioseparation and Cell Technol.,. 2010, pp. 1-20; Ed., Flickinger M.C., John Wiley & Sons, Inc.
Dastmalchi et al., Neopinone isomerase is involved in codeine and morphine biosynthesis in opium poppy, Nat Chem Biol. Apr. 2019; 15(4):384-390.
Julien et al., Isolation and Characterization of the epothilone biosynthetic gene cluster from Sorangium cellulosm, Gene, 2000, 249:153-160.
Sariyar et al., Six Alkaloids from Papaver Species, Phytochemistry, 1986, 25(10):2403-2406.
Smirnova et al., Optical isomerism and biological activity of pharmaceutical preparations. Moscow Univ. Chem. Bull., 2012, 67(3): 95-102.
Soares, Flocculation in Saccharomyces cerevisiae: a review. J. Appl. Microbial., 2010, 110: 1-18.
Sadowski et al., The sequence-structure relationship and protein function prediction, Curr Opin Struct Biol, Jun. 2009;19(3):357-62.
Tang et al., Identification of Dehalobacter reductive dehalogenases that catalyse dechlorination of chloroform, 1,1,1-trichloroethane and 1,1-dichloroethane, Phil Trans R Soc B 368: 20120318.
Pasternak et al., Preclinical Pharmacology and Opioid Combinations, Pain Med. Mar. 1, 2012; 13(s1): S4-S11.
Cardillo et al., Expression of Brugmansia candida Hyoscyamine 6beta-Hydroxylase gene in *Saccharomyces cerevisiae* and its potential use as biocatalyst, Microb Cell Fact 7, 17 (May 27, 2008).
Kohnen-Johannsen et al., Tropane Alkaloids: Chemistry, Pharmacology, Biosynthesis and Production, Molecules, 24(4), 796 (Feb. 22, 2019).
Ping et al., Building Microbial Hosts for Heterologous Production of N-Methylpyrrolinium, ACS Synth. Biol., 8, 2, 257-263 (Jan. 29, 2019).
Srinivasan et al., Engineering a microbial biosynthesis platform for de novo production of tropane alkaloids, Nat Commun 10, 3634 (Aug. 12, 2019 ).
Srinivasan et al., Biosynthesis of medicinal tropane alkaloids in yeast, Nature 585, 614-619 (Sep. 2, 2020).
Srinivasan et al., Engineering cellular metabolite transport for biosynthesis of computationally predicted tropane alkaloid derivatives in yeast, PNAS, vol. 118, No. 25 (Jun. 17, 2021).

\* cited by examiner

>RQNK-2062398
MELQYISYFQPTSSVVALLLALVSILSSVVVLRKTFLNNYSSSPASSTKTAVLSH
QRQQSCALPISGLLHIFMNKNGLIHVTLGNMADKYGPIFSFPTGSHRTLVVSS
WEMVKECFTGNNDTAFSNRPIPLAFKTIFYACGGIDSYGLSSVPYGKYWREL
RKVCVHNLLSNQQLLKFRHLIISQVDTSFNKLYELCKNSEDNHGNYTTTTTA
AGMVRIDDWLAELSFNVIGRIVCGFQSGPKTGAPSRVEQFKEAINEASYFMS
TSPVSDNVPMLGWIDQLTGLTRNMKHCGKKLDLVVESIINDHRQKRRFSRTK
GGDEKDDEQDDFIDICLSIMEQPQLPGNNNPSQIPIKSIVLDMIGGGTDTTKLT
TIWTLSLLLNNPHVLDKAKQEVDAHFRTKRRSTNDAAAAVVDFDDIRNLVYIQ
AIIKESMRLYPASPVVERLSGEDCVVGGFHVPAGTRLWANVWKMQRDPKVW
DDPLVFRPDRFLSDEQKMVDVRGQNYELLPFGAGRRVCPGVSFSLDLMQLV
LTRLILEFEMKSPSGKVDMTATPGLMSYKVIPLDILLTHRRIKPCVQSAASERD
MESSGVPVITLGSGKVMPVLGMGTFEKVGKGSERERLAILKAIEVGYRYFDT
AAAYETEEVLGEAIAEALQLGLVKSRDELFISSMLWCTDAHADRVLLALQNSL
RNLKLEYVDLYMLPFPASLKPGKITMDIPEEDICRMDYRSVWAAMEECQNLG
FTKSIGVSNFSCKKLQELMATANIPPAVNQVEMSPAFQQKKLREYCNANNILV
SAISVLGSNGTPWGSNAVLGSEVLKKIAMAKGKSVAQVSMRWVYEQGASLV
VKSFSEERLRENLNIFDWELTKEDHEKIGEIPQCRILSAYFLVSPNGPFKSQEE
LWDDEA*

FIG. 4

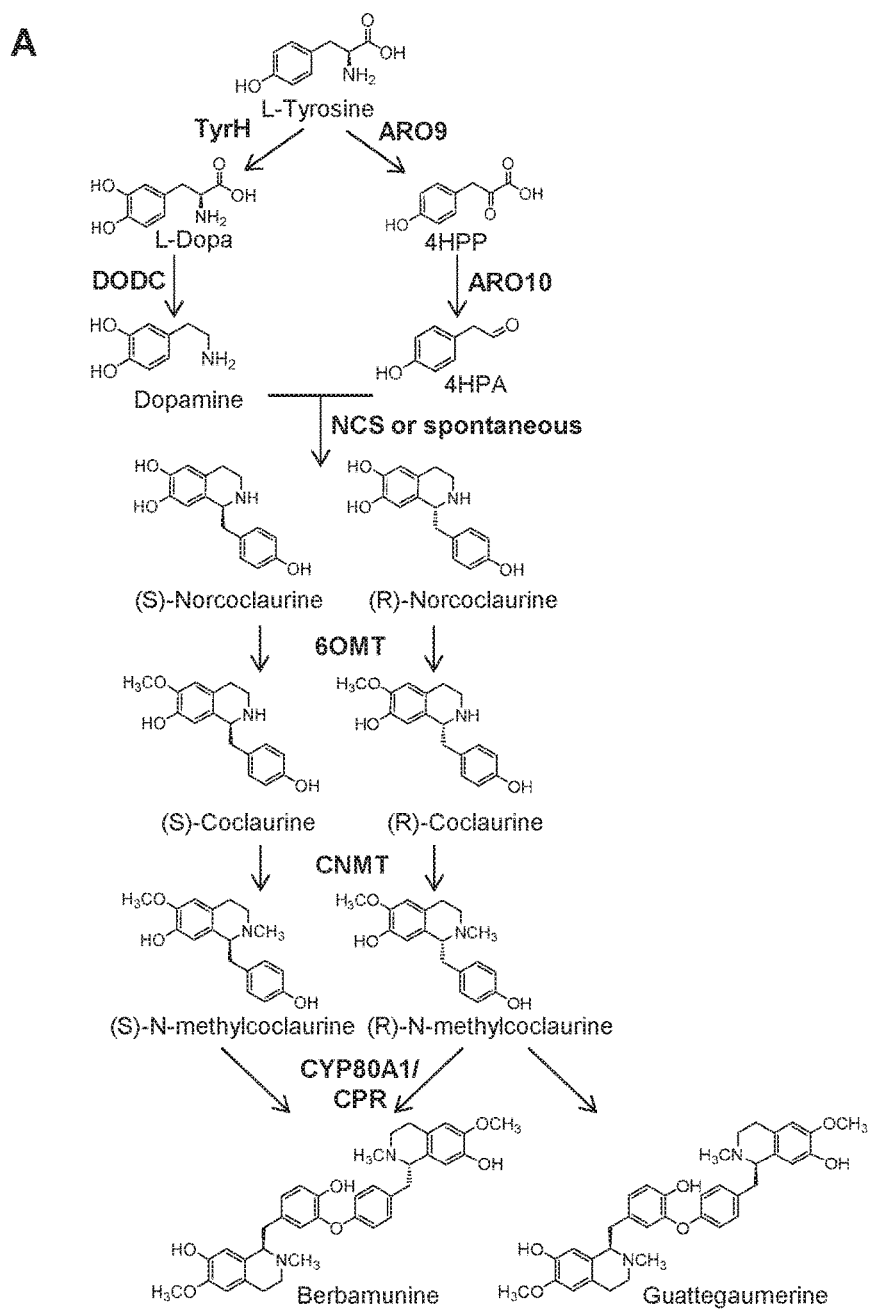
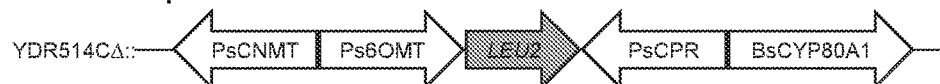
FIG. 16

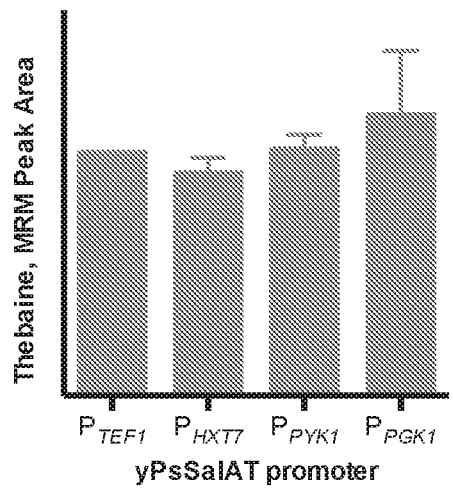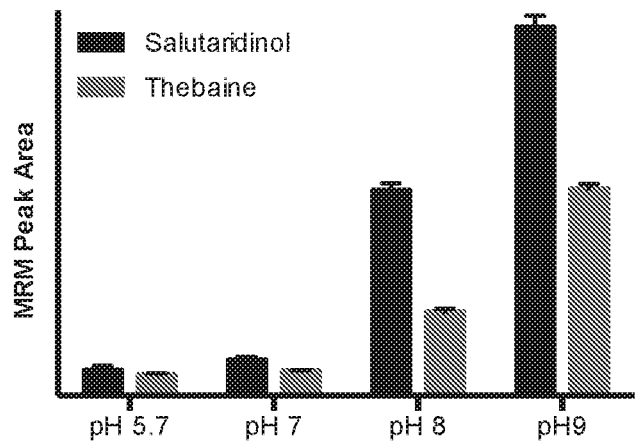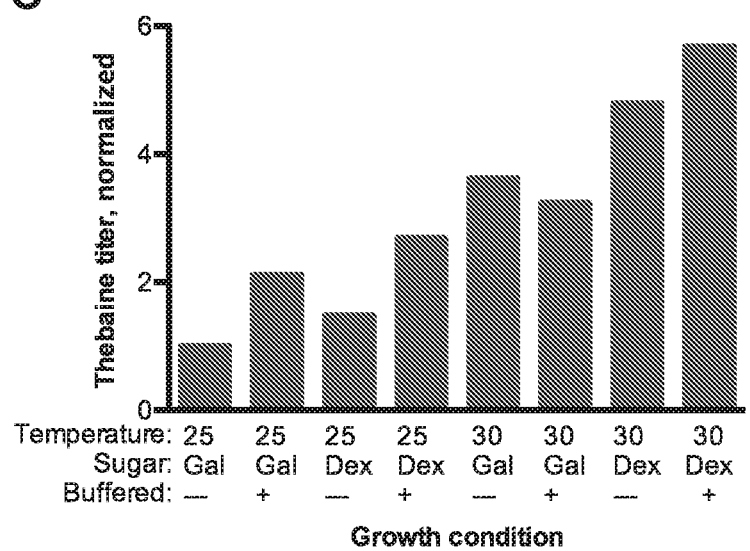
FIG. 25

Four genetic constructs integrated into the yeast genome:
1. YBR197CΔ::P$_{TPI1}$-RnSepR-T$_{STE2}$, P$_{TEF1}$-RnPTPS-T$_{CYC1}$, *KanMX marker*, P$_{GPD}$-RnQDHPR-T$_{ADH1}$, P$_{PGK1}$-RnPCD-T$_{PHO5}$
2. HIS3 Δ ::P$_{GPD}$-RnTyrH-T$_{ADH1}$, P$_{TPI1}$-PpDODC-T$_{STE2}$, *HIS5 marker*, P$_{TEF1}$-RnDHFR-T$_{CYC1}$, P$_{PGK1}$-CjNCS-T$_{PHO5}$
3. YDR514CΔ::P$_{PYK1}$-PsCNMT-T$_{MFa1}$, P$_{PGK1}$-Ps6OMT-T$_{PHO5}$, P$_{GPD}$-EcCYP80B1-T$_{ADH1}$, *LEU2 marker*, P$_{TEF1}$-PsCPR-T$_{CYC1}$, P$_{TPI1}$-Ps4'OMT-T$_{STE2}$
4. ARO4Δ::P$_{TEF1}$-ARO4$^{FBR}$-T$_{CYC1}$, P$_{GPD}$-ARO7$^{FBR}$-T$_{ADH1}$, *HygR marker*, P$_{PGK1}$-TKL1-T$_{PHO5}$, P$_{TPI1}$-ARO10-T$_{STE2}$

Schematic of the integrated constructs indicating the orientation of each expression cassette:

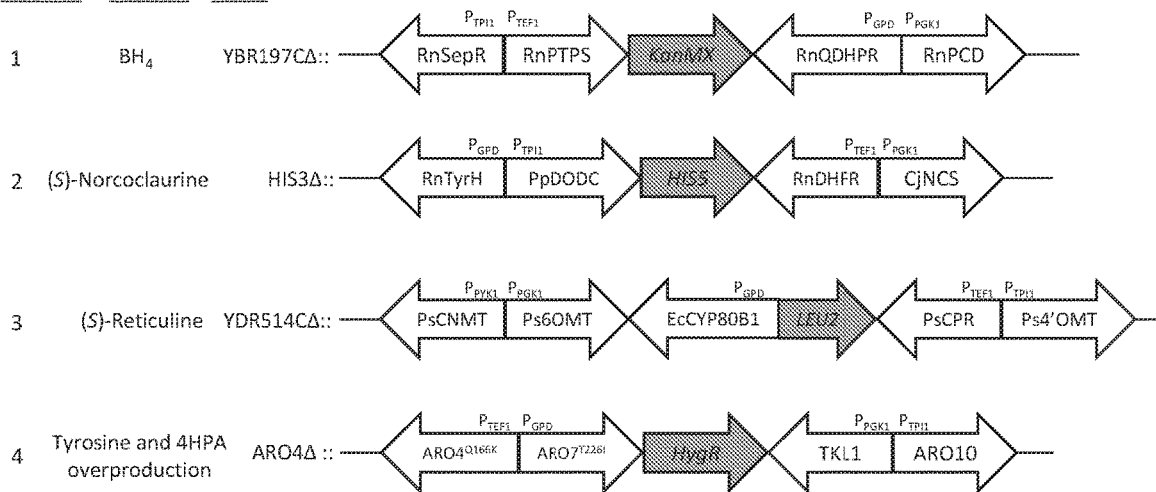

FIG. 26

A
Example genetic constructs:
5. YPL250CΔ::$P_{GPD}$-RnTyrH-$T_{ADH1}$, $P_{TEF1}$-Ps4OMT-$T_{CYC1}$, $P_{PGK1}$-CjNCS-$T_{PHO5}$, bleR marker
6. TRP1::$P_{PGK1}$-PsSalAT-$T_{PHO5}$, $P_{TPI1}$-PbSalR-$T_{STE2}$, URA3 marker, $P_{GPD}$-EcCFS$^{1-83}$-PbSalSyn$^{92-504}$-$T_{ADH1}$, $P_{HXT7}$-PbCYP-COR-$T_{CYC1}$
7. YAC::$P_{GPD}$-PsT6ODM-$T_{ADH1}$, $P_{PGK1}$-PbmorB-$T_{PHO5}$
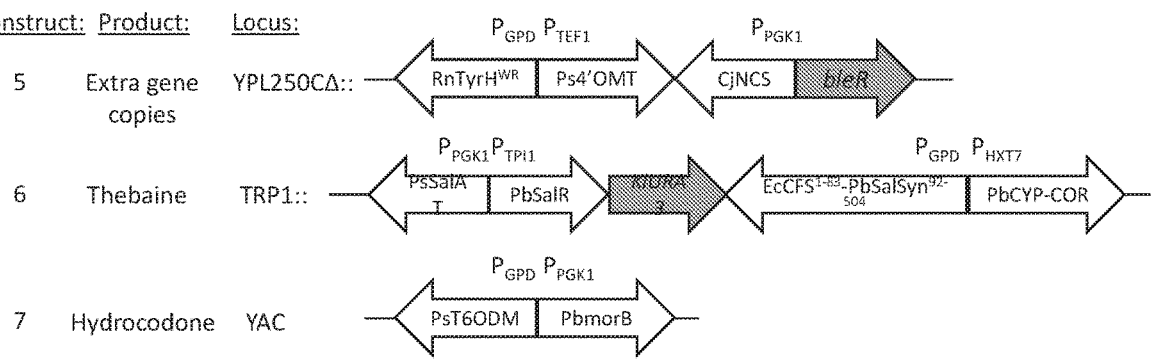
B
*Integration of Multi-Gene Construct 5:*
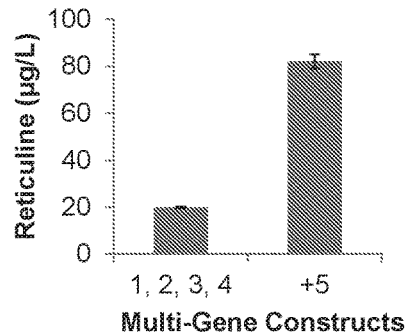
FIG 27

C *Integration of Multi-Gene Construct 6:*
Thebaine Biosynthesis
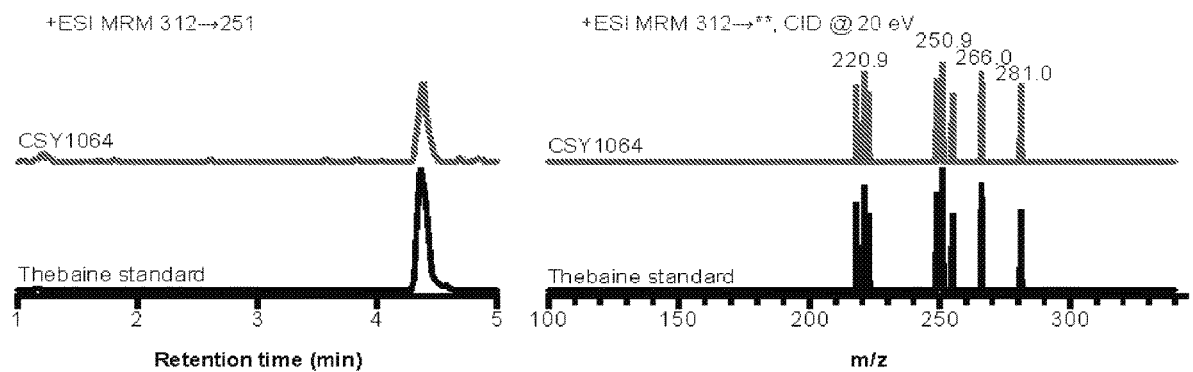
D *Integration of Multi-Gene Construct 7:*
Hydrocodone Biosynthesis
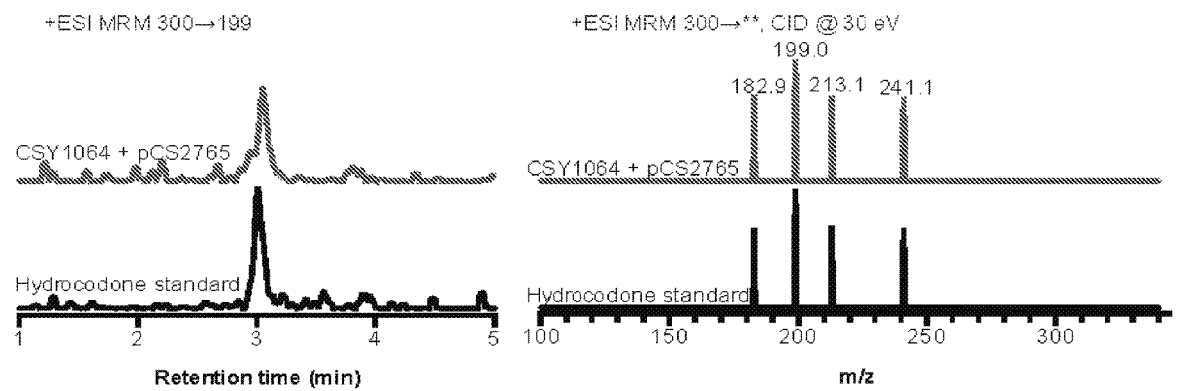
FIG 27

METHODS OF PRODUCING EPIMERASES AND BENZYLISOQUINOLINE ALKALOIDS

CROSS-REFERENCE

Pursuant to 35 U.S.C. § 119(e), this application claims priority to the filing date of U.S. Provisional Patent Application Ser. No. 62/159,122 filed on May 8, 2015 and U.S. Provisional Patent Application Ser. No. 62/174,475 filed on Jun. 11, 2015; the disclosures of which applications are herein incorporated by reference.

Additionally, this application is related to: U.S. patent application Ser. No. 14/211,611 now published as US 2014-0273109, which application was filed on Mar. 14, 2014; PCT Application Serial No. PCT/US2014/027833 now published as WO 2014/143744, which application was filed on Mar. 14, 2014; U.S. patent application Ser. No. 15/031,618, which application was filed on Apr. 22, 2016; Application Serial No. PCT/US2014/063738 now published as WO 2015/066642, which application was filed on Nov. 3, 2014; U.S. Provisional Patent Application Ser. No. 62/080,610, which was filed Nov. 17, 2014; U.S. Provisional Patent Application Ser. No. 62/107,238, which was filed Jan. 23, 2015; Application Serial No. PCT/US2015/060891 which application was filed on Nov. 16, 2015; U.S. Provisional Patent Application Ser. No. 62/156,701, which was filed May 4, 2015; and Application Serial No. PCT/US2016/030808 which application was filed on May 4, 2016; the disclosures of which applications are herein incorporated by reference.

STATEMENT AS TO FEDERALLY SPONSORED RESEARCH

This invention was made with Government support under contract AT007886 awarded by the National Institutes of Health. The Government has certain rights in the invention.

SUMMARY OF THE INVENTION

The present disclosure provides methods for the production of diverse benzylisoquinoline alkaloids (BIAs) in engineered host cells. The present disclosure further provides compositions of diverse alkaloids produced in engineered host cells. Additionally, the present disclosure provides methods for the production of an epimerase in engineered host cells. In particular cases, the disclosure provides methods for producing diverse alkaloid products through the epimerization of a (S)-1-benzylisoquinoline alkaloid to a (R)-1-benyzlisoquinoline alkaloid in an engineered host cell. In further particular cases, the present disclosure provides methods for producing diverse alkaloid products through the epimerization of (S)-reticuline to (R)-reticuline.

An aspect of the invention provides an engineered non-plant cell having increased tyrosine hydroxylase activity relative to a non-engineered cell. Another aspect of the invention provides an engineered non-plant cell having increased tyrosine hydroxylase activity relative to a cell that expresses wild-type TyrH. An additional aspect of the invention provides an engineered non-plant cell having increased tyrosine hydroxylase activity relative to a cell that expresses wild-type TyrH without mutations that increase tyrosine hydroxylase activity as provided herein. In particular, the engineered non-plant cell has at least one modification selected from a group consisting of: a substrate inhibition alleviating mutation; a product inhibition alleviating mutation; and a cofactor recovery promoting mechanism.

An additional aspect of the invention provides a method of epimerizing an (S)-1-benzylisoquinoline alkaloid to an (R)-1-benzylisoquinoline alkaloid. The method comprises contacting the (S)-1-benzylisoquinoline alkaloid with at least one enzyme. Contacting the (S)-1-benzylisoquinoline alkaloid with the at least one enzyme converts the (S)-1-benzylisoquinoline alkaloid to an (R)-1-benzylisoquinoline alkaloid.

Another aspect of the invention provides an engineered non-plant cell that produces an epimerase that converts (S)-1-benzylisoquinoline alkaloid to (R)-1-benzylisoquinoline alkaloid. The epimerase comprises an amino acid sequence selected from the group consisting of: SEQ ID NOs: 1, 2, 3, 4, 5, 6, 7, 8, 9, 10, 11, 12, 13, 14, and 15, as listed in Table 1.

A further aspect of the invention provides a process for converting an (S)-1-benzylisoquinoline alkaloid to an (R)-1-benzylisoquinoline alkaloid comprising contacting the (S)-1-benzylisoquinoline alkaloid with an epimerase in an amount sufficient to convert the (S)-1-benzylisoquinoline alkaloid to (R)-1-benzylisoquinoline alkaloid.

In another aspect of the invention, a method of epimerizing a stereocenter of a 1-benzylisoquinoline alkaloid is provided. The method comprises contacting the 1-benzylisoquinoline alkaloid with at least one enzyme. Contacting the 1-benzylisoquinoline alkaloid with the at least one enzyme inverts the stereochemistry of the stereocenter of the 1-benzylisoquinoline alkaloid to the opposite stereochemistry of the stereocenter of the 1-benzylisoquinoline alkaloid.

In some examples, an engineered non-plant cell comprises a plurality of coding sequences each encoding an enzyme that is selected from the group of enzymes listed in Table 2. In some examples, the heterologous coding sequences may be operably connected. Heterologous coding sequences that are operably connected may be within the same pathway of producing a particular benzylisoquinoline alkaloid product and/or epimerase product.

In an additional aspect of the invention, an engineered non-plant cell that produces a bisbenzylisoquinoline alkaloid is provided. The bisbenzylisoquinoline alkaloid is produced using a coupling enzyme that is present within the engineered non-plant cell. Additionally, the engineered non-plant cell comprises at least one heterologous coding sequence encoding at least one enzyme used in the production of at least one benzylisoquinoline alkaloid monomer within the engineered non-plant cell. Further, the at least one coupling enzyme dimerizes two benzylisoquinoline alkaloid monomers within the engineered non-plant cell, thereby forming the bisbenzylisoquinoline alkaloid.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the invention will be obtained by reference to the following detailed description that sets forth illustrative embodiments, in which the principles of the invention are utilized, and the accompanying drawings of which:

FIG. 4 illustrates an amino acid sequence of a CYP-COR enzyme, in accordance with embodiments of the invention.

FIG. 16 illustrates (A) a biosynthetic scheme for conversion of L-tyrosine to bisBIAs and (B) yeast strains engineered to biosynthesize bisBIAs, in accordance with embodiments of the invention.

FIGS. 25(A), 25(B) and 25(C) illustrate fermentation optimization for conversion of (R)-reticuline to thebaine by engineered yeast, in accordance with embodiments of the invention.

FIG. 26 illustrates yeast platform strains for the production of the key branchpoint intermediate reticuline from L-tyrosine, in accordance with embodiments of the invention.

FIGS. 27(A), 27(B), 27(C) and 27(D) illustrate thebaine and hydrocodone production in engineered yeast strains, in accordance with embodiments of the invention.

DETAILED DESCRIPTION OF THE INVENTION

Figure 1:
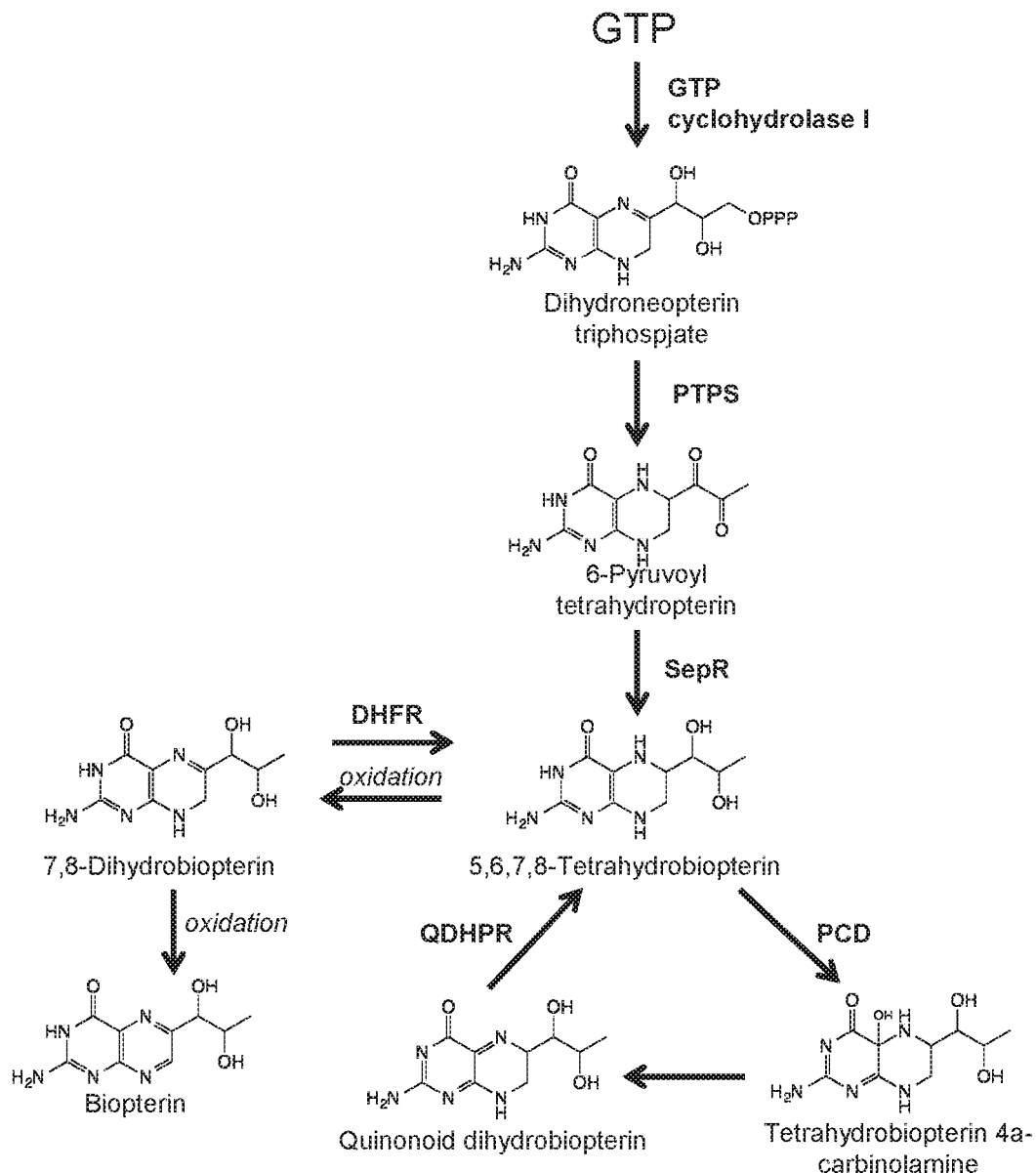
FIG. 1 illustrates examples of synthesis, recycling, and salvage pathways of tetrahydrobiopterin, in accordance with embodiments of the invention.

The present disclosure provides methods for the production of diverse benzylisoquinoline alkaloids (BIAs) in engineered host cells. The present disclosure further provides compositions of diverse alkaloids produced in engineered host cells. Additionally, the present disclosure provides methods for the production of an epimerase in engineered host cells. In particular cases, the disclosure provides methods for producing diverse alkaloid products through the epimerization of a (S)-1-benzylisoquinoline alkaloid to a (R)-1-benyzlisoquinoline alkaloid in an engineered host cell. In further particular cases, the present disclosure provides methods for producing diverse alkaloid products through the epimerization of (S)-reticuline to (R)-reticuline.

Benzylisoquinoline Alkaloids (BIAs) of Interest

Host cells which produce BIAs of interest are provided. In some examples, engineered strains of host cells such as the engineered strains of the invention provide a platform for producing benzylisoquinoline alkaloids of interest and modifications thereof across several structural classes including, but not limited to, precursor BIAs, benzylisoquinolines, protoberberines, protopines, benzophenanthridines, promorphinans, morphinans, secoberberines, phthalideisoquinolines, aporphines, bisbenzylisoquinolines, and others.

Each of these classes is meant to include biosynthetic precursors, intermediates, and metabolites thereof, of any convenient member of an engineered host cell biosynthetic pathway that may lead to a member of the class. Non-limiting examples of compounds are given below for each of these structural classes. In some cases, the structure of a given example may or may not be characterized itself as a benzylisoquinoline alkaloid. The present chemical entities are meant to include all possible isomers, including single enantiomers, racemic mixtures, optically pure forms, mixtures of diastereomers, and intermediate mixtures.

BIA precursors may include, but are not limited to, norcoclaurine (NC) and norlaudanosoline (NL), as well as NC and NL precursors, such as tyrosine, tyramine, 4-hydroxyphenylacetaldehyde (4-HPA), 4-hydroxyphenylpyruvic acid (4-HPPA), L-3,4-dihydroxyphenylalanine (L-DOPA), 3,4-dihydroxyphenylacetaldehyde (3,4-DHPA), and dopamine. In some embodiments, the one or more BIA precursors are 3,4-dihydroxyphenylacetaldehyde (3,4-DHPA) and dopamine. In certain instances, the one or more BIA precursors are 4-hydroxyphenylacetaldehyde (4-HPA) and dopamine. In particular, NL and NC may be synthesized, respectively, from precursor molecules via a Pictet-Spengler condensation reaction, where the reaction may occur spontaneously or may by catalyzed by any convenient enzymes.

Benzylisoquinolines may include, but are not limited to, norcoclaurine, norlaudanosoline, coclaurine, 3'-hydroxycoclaurine, 4'-O-methylnorlaudanosoline, 4'-O-methyl-laudanosoline, N-methylnorcoclaurine, laudanosoline, N-methylcoclaurine, 3'-hydroxy-N-methylcoclaurine, reticuline, norreticuline, papaverine, laudanine, laudanosine, tetrahydropapaverine, 1,2-dihydropapaverine, and orientaline.

Protoberberines may include, but are not limited to, scoulerine, cheilanthifoline, stylopine, nandinine, jatrorrhizine, stepholidine, discretamine, cis-N-methylstylopine, tetrahydrocolumbamine, palmatine, tetrahydropalmatine, columbamine, canadine, N-methylcanadine, 1-hydroxycanadine, berberine, N-methyl-ophiocarpine, 1,13-dihydroxy-N-methylcanadine, and 1-hydroxy-10-O-acetyl-N-methylcanadine.

Protopines may include, but are not limited to, protopine, 6-hydroxyprotopine, allocryptopine, cryptopine, muramine, and thalictricine.

Benzophenanthridines may include, but are not limited to, dihydrosanguinarine, sanguinarine, dihydrocheilirubine, cheilirubine, dihydromarcapine, marcapine, and chelerythrine.

Promorphinans may include, but are not limited to, salutaridine, salutaridinol, and salutaridinol-7-O-acetate.

Morphinans may include, but are not limited to, thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydroetorphine, ethylmorphine, etorphine, metopon, buprenorphine, pholcodine, heterocodeine, and oxymorphone.

Secoberberines may include, but are not limited to, 4'-O-desmethylmacrantaldehyde, 4'-O-desmethylpapaveroxine, 4'-O-desmethyl-3-O-acetylpapaveroxine, papaveroxine, and 3-O-aceteylpapaveroxine.

Phthalideisoquinolines may include, but are not limited to, narcotolinehemiacetal, narcotinehemiacetal, narcotoline, noscapine, adlumidine, adlumine, (+) or (−)-bicuculline, capnoidine, carlumine, corledine, corlumidine, decumbenine, 5'-O-demethylnarcotine, (+) or (−)-α or β-hydrastine, and hypecoumine.

Aporphines may include, but are not limited to, magnoflorine, corytuberine, apomorphine, boldine, isoboldine, isothebaine, isocorytuberine, and glaufine.

Bisbenzylisoquinolines may include, but are not limited to, berbamunine, guattgaumerine, dauricine, and liensinine.

Other compounds that may be produced by the engineered strains of the invention may include, but are not limited to, rhoeadine, pavine, isopavine, and cularine.

In certain embodiments, the engineered strains of the invention may provide a platform for producing compounds related to tetrahydrobiopterin synthesis including, but not limited to, dihydroneopterin triphosphate, 6-pyruvoyl tetrahydropterin, 5,6,7,8-tetrahydrobiopterin, 7,8-dihydrobiopterin, tetrahydrobiopterin 4a-carbinolamine, quinonoid dihydrobiopterin, and biopterin.

Host Cells

Any convenient cells may be utilized in the subject host cells and methods. In some cases, the host cells are non-plant cells. In some instances, the host cells may be characterized as microbial cells. In certain cases, the host cells are insect cells, mammalian cells, bacterial cells, or yeast cells. Any convenient type of host cell may be utilized in producing the subject BIA-producing cells, see, e.g., US2008/0176754, and US2014/0273109 the disclosures of which are incorporated by reference in their entirety. Host cells of interest include, but are not limited to, bacterial cells, such as *Bacillus subtilis, Escherichia coli, Streptomyces*, and *Salmonella typhimuium* cells, insect cells such as *Drosophila melanogaster* S2 and *Spodoptera frugiperda* Sf9 cells, and yeast cells such as *Saccharomyces cerevisiae, Schizosaccharomyces pombe*, and *Pichia pastoris* cells. In some examples, the host cells are yeast cells or *E. coli* cells. In some cases, the host cell is a yeast cell. In some instances, the host cell is from a strain of yeast engineered to produce a BIA of interest, such as an (R)-1-benzylisoquinoline alkaloid. In some instances, the host cell is from a strain of yeast engineered to produce an enzyme of interest. In some instances, the host cell is from a strain of yeast engineered to produce an epimerase. The epimerase may have an oxidase and a reductase. Additionally, the epimerase may be able to convert an (S)-1-benzylisoquinoline alkaloid to an (R)-1-benzylisoquinoline alkaloid. Further, the epimerase may be separated into smaller enzymes that retain oxidase or reductase activity so as to be used to convert an (S)-1-benzylisoquinoline alkaloid to an (R)-1-benzylisoquinoline alkaloid.

Any of the host cells described in US2008/0176754 and US2014/0273109 by Smolke et al. may be adapted for use in the subject cells and methods. In certain embodiments, the yeast cells may be of the species *Saccharomyces cerevisiae* (*S. cerevisiae*). In certain embodiments, the yeast cells may be of the species *Schizosaccharomyces pombe*. In certain embodiments, the yeast cells may be of the species *Pichia pastoris*. Yeast is of interest as a host cell because cytochrome P450 proteins are able to fold properly into the endoplasmic reticulum membrane so that their activity is maintained. In examples, cytochrome P450 proteins are involved in some biosynthetic pathways of interest. In additional examples, cytochrome P450 proteins are involved in the production of BIAs of interest. In further examples, cytochrome P450 proteins are involved in the production of an enzyme of interest, such as an epimerase having an oxidase and a reductase.

Yeast strains of interest that find use in the invention include, but are not limited to, CEN.PK (Genotype: MATa/α ura3-52/ura3-52 trp1-289/trp1-289 leu2-3_112/leu2-3_112 his3 ΔI/his3 Δ1 MAL2-8C/MAL2-8C SUC2/SUC2), S288C, W303, D273-10B, X2180, A364A, Σ1278B, AB972, SK1, and FL100. In certain cases, the yeast strain is any of S288C (MATα; SUC2 mal mel gal2 CUP1 flo1 flo8-1 hap1), BY4741 (MATα; his3Δ1; leu2Δ0; met15Δ0; ura3Δ0), BY4742 (MATα; his3Δ1; leu2Δ0; lys2Δ0; ura3Δ0), BY4743 (MATα/MATα; his3Δ1/his3Δ1; leu2Δ0/leu2Δ0; met15Δ0/MET15; LYS2/lys2Δ0; ura3Δ0/ura3Δ0), and WAT11 or W(R), derivatives of the W303-B strain (MATα; ade2-1; his3-11, -15; leu2-3, -112; ura3-1; canR; cyr+) which express the Arabidopsis thaliana NADPH-P450 reductase ATR1 and the yeast NADPH-P450 reductase CPR1, respectively. In another embodiment, the yeast cell is W303alpha (MATα; his3-11,15 trp1-1 leu2-3 ura3-1 ade2-1). The identity and genotype of additional yeast strains of interest may be found at EUROSCARF (web.uni-frankfurt.de/fb15/mikro/euroscarf/col_index.html).

Genetic Modifications to Host Cells

The host cells may be engineered to include one or more modifications (such as two or more, three or more, four or more, five or more, or even more modifications) that provide for the production of BIAs of interest. Additionally or alternatively, the host cells may be engineered to include one or more modifications (such as two or more, three or more, four or more, five or more, or even more modifications) that provide for the production of enzymes of interest. In some cases, a modification is a genetic modification, such as a mutation, addition, or deletion of a gene or fragment thereof, or transcription regulation of a gene or fragment thereof. As used herein, the term "mutation" refers to a deletion, insertion, or substitution of an amino acid(s) residue or nucleotide(s) residue relative to a reference sequence or motif. The mutation may be incorporated as a directed mutation to the native gene at the original locus. In some cases, the mutation may be incorporated as an additional copy of the gene introduced as a genetic integration at a separate locus, or as an additional copy on an episomal vector such as a 2μ or centromeric plasmid. In certain instances, the substrate inhibited copy of the enzyme is under the native cell transcriptional regulation. In some instances, the substrate inhibited copy of the enzyme is introduced with engineered constitutive or dynamic regulation of protein expression by placing it under the control of a synthetic promoter. In some examples, the object of one or more modifications may be a native gene. In some examples, the object of one or more modifications may be a non-native gene. In some examples, a non-native gene may be inserted into a host cell. In further examples, a non-native gene may be altered by one or more modifications prior to being inserted into a host cell.

An engineered host cell may overproduce one or more BIAs of interest. By overproduce is meant that the cell has an improved or increased production of a BIA molecule of interest relative to a control cell (e.g., an unmodified cell). By improved or increased production is meant both the production of some amount of the BIA of interest where the control has no BIA of interest production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some BIA of interest production.

An engineered host cell may overproduce one or more (S)-1-benzylisoquinoline alkaloids. In some cases, the engineered host cell may produce some amount of the (S)-1-benzylisoquinoline alkaloid of interest where the control has no (S)-1-benzylisoquinoline alkaloid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some (S)-1-benzylisoquinoline alkaloid of interest production.

An engineered host cell may further overproduce one or more (R)-1-benzylisoquinoline alkaloids. In some cases, the engineered host cell may produce some amount of the (R)-1-benzylisoquinoline alkaloid of interest where the control has no (R)-1-benzylisoquinoline alkaloid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some (R)-1-benzylisoquinoline alkaloid of interest production. An engineered host cell may further overproduce one or more of morphinan, protoberberine, noscapinoid, and benzophenanthridine alkaloids.

In some cases, the engineered host cell is capable of producing an increased amount of (R)-reticuline relative to a control host cell that lacks the one or more modifications (e.g., as described herein). In certain instances, the increased amount of (R)-reticuline is about 10% or more relative to the control host cell, such as about 20% or more, about 30% or more, about 40% or more, about 50% or more, about 60% or more, about 80% or more, about 100% or more, about 2-fold or more, about 5-fold or more, or even about 10-fold or more relative to the control host cell. In some cases, (R)-reticuline is the product of an epimerization reaction within an engineered host cell. In these cases, (S)-reticuline may be the substrate of the epimerization reaction.

Additionally, an engineered host cell may overproduce one or more enzymes of interest. By overproduce is meant that the cell has an improved or increased production of an enzyme of interest relative to a control cell (e.g., an unmodified cell). By improved or increased production is meant both the production of some amount of the enzyme of interest where the control has no production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some enzyme of interest production.

An engineered host cell may overproduce one or more CYP-COR enzyme. In some cases, the engineered host cell may produce some amount of the CYP-COR enzyme where the control has no CYP-COR enzyme production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some CYP-COR enzyme production.

An engineered host cell may further overproduce one or more enzymes that are derived from the CYP-COR enzyme. In some cases, the engineered host cell may produce some amount of the enzymes that are derived from the CYP-COR enzyme, where the control has no production of enzymes that are derived from the CYP-COR enzyme, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some production of enzymes that are derived from the CYP-COR enzyme.

Additionally, an engineered host cell may overproduce one or more bisbenzylisoquinoline alkaloids (bisBIAs). In particular, an engineered host cell is capable of producing an increased amount of bisbenzylisoquinoline alkaloids (bisBIAs) relative to a control host cell that lacks the one or more modifications (e.g., as described herein). In certain instances, the increased amount of bisBIAs is about 10% or more relative to the control host cell, such as about 20% or more, about 30% or more, about 40% or more, about 50% or more, about 60% or more, about 80% or more, about 100% or more, about 2-fold or more, about 5-fold or more, or even about 10-fold or more relative to the control host cell. In some cases, the bisBIA is formed from at least one BIA monomer that is the product, or derivative thereof, of an epimerization reaction within an engineered host cell. An engineered host cell may further overproduce one or more of cepharanthine, fangchinoline, liensinine, neferine, tubocurarine, dauricine, tetrandrine, curine, berbamunine, guattegaumerine, 2'-norberbamunine, and berbamine.

In some cases, the one or more (such as two or more, three or more, or four or more) modifications may be selected from: a substrate inhibition alleviating mutation in a biosynthetic enzyme gene; a product inhibition alleviating mutation in a biosynthetic enzyme gene; a cofactor recovery promoting mechanism; a feedback inhibition alleviating mutation in a biosynthetic enzyme gene; a transcriptional modulation modification of a biosynthetic enzyme gene; an inactivating mutation in an enzyme gene; an epimerization modification; a bisBIA generating modification; and a heterologous coding sequence that encodes an enzyme. A cell that includes one or more modifications may be referred to as an engineered cell.

Substrate Inhibition Alleviating Mutations

In some instances, the engineered host cells are cells that include one or more substrate inhibition alleviating mutations (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "substrate inhibition alleviating mutation" refers to a mutation that alleviates a substrate inhibition control mechanism of the cell.

A mutation that alleviates substrate inhibition reduces the inhibition of a regulated enzyme in the cell of interest relative to a control cell and provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the engineered host cell or a downstream product thereof.

A variety of substrate inhibition control mechanisms and biosynthetic enzymes in the engineered host cell that are directed to regulation of levels of BIAs of interest, or precursors thereof, may be targeted for substrate inhibition alleviation. The engineered host cell may include one or more substrate inhibition alleviating mutations in one or more biosynthetic enzyme genes. The one or more mutations may be located in any convenient biosynthetic enzyme genes where the biosynthetic enzyme is subject to regulatory control. In some embodiments, the one or more biosynthetic enzyme genes encode one or more tyrosine hydroxylase enzymes. In certain instances, the one or more substrate inhibition alleviating mutations are present in a biosynthetic enzyme gene that is TyrH. In some embodiments, the engineered host cell may include one or more substrate inhibition alleviating mutations in one or more biosynthetic enzyme genes such as one of those genes described in Table 2.

In certain embodiments, the one or more substrate inhibition alleviating mutations are present in the TyrH gene. The TyrH gene encodes tyrosine hydroxylase, which is an enzyme that converts tyrosine to L-DOPA. However, TyrH is inhibited by its substrate, tyrosine. Mammalian tyrosine hydroxylase activity, such as that seen in humans or rats, can be improved through mutations to the TyrH gene that relieve substrate inhibition. In particular, substrate inhibition from tyrosine can be relieved by a point mutation W166Y in the TyrH gene. The point mutation W166Y in the TyrH gene may also improve the binding of the cosubstrate of tyrosine hydroxylase, $BH_4$, to catalyze the reaction of tyrosine to L-DOPA. The mutants of TyrH, when expressed in yeast strains to produce BIAs from sugar (such as those described in U.S. Provisional Patent Application Ser. No. 61/899,496) can significantly improve the production of BIAs.

Any convenient numbers and types of mutations may be utilized to alleviate a substrate inhibition control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more substrate inhibition alleviating mutations, such as 1, 2, 3, 4, 5, 6, 7, 8, 9, 10, 11, 12, 13, 14 or 15 substrate inhibition alleviating mutations in one or more biosynthetic enzyme genes within the engineered host cell.

Cofactor Recovery Promoting Mechanisms

In some instances, the engineered host cells are cells that include one or more cofactor recovery promoting mechanisms (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "cofactor recovery promoting mechanism" refers to a mechanism that promotes a cofactor recovery control mechanism of the cell.

A variety of cofactor recovery control mechanisms and biosynthetic enzymes in the engineered host cell that are directed to regulation of levels of BIAs of interest, or precursors thereof, may be targeted for cofactor recovery promotion. The engineered host cell may include one or more cofactor recovery promoting mechanism in one or more biosynthetic enzyme genes. In examples, the engineered host cell may include a heterologous coding sequence that encodes dihydrofolate reductase (DHFR). When DHFR is expressed, it may convert 7,8-dihydrobiopterin ($BH_2$) to the tetrahydrobiopterin ($BH_4$), thereby recovering $BH_4$ as a TyrH cosubstrate. In some examples, the engineered host cell may include one or more cofactor recovery promoting mechanisms in one or more biosynthetic enzyme genes such as one of those genes described in Table 2.

Any convenient numbers and types of mechanisms may be utilized to promote a cofactor recovery control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more cofactor recovery promoting mechanisms such as 1, 2, 3, 4, 5, 6, 7, 8, 9, 10, 11, 12, 13, 14 or 15 cofactor recovery promoting mechanisms in one or more biosynthetic enzyme genes within the engineered host cell.

Product Inhibition Alleviating Mutations

In some instances, the engineered host cells are cells that include one or more product inhibition alleviating mutations (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "product inhibition alleviating mutation" refers to a mutation that alleviates a short term and/or long term product inhibition control mechanism of an engineered host cell. Short term product inhibition is a control mechanism of the cell in which there is competitive binding at a cosubstrate binding site. Long term product inhibition is a control mechanism of the cell in which there is irreversible binding of a compound away from a desired pathway.

A mutation that alleviates product inhibition reduces the inhibition of a regulated enzyme in the cell of interest relative to a control cell and provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the engineered host cell or a downstream product thereof.

A variety of product inhibition control mechanisms and biosynthetic enzymes in the engineered host cell that are directed to regulation of levels of BIAs of interest may be targeted for product inhibition alleviation. The engineered host cell may include one or more product inhibition alleviating mutations in one or more biosynthetic enzyme genes. The mutation may be located in any convenient biosynthetic enzyme genes where the biosynthetic enzyme is subject to regulatory control. In some embodiments, the one or more biosynthetic enzyme genes encode one or more tyrosine hydroxylase enzymes. In certain instances, the one or more product inhibition alleviating mutations are present in a biosynthetic enzyme gene that is TyrH. In some embodiments, the engineered host cell includes one or more product inhibition alleviating mutations in one or more biosynthetic enzyme genes such as one of those genes described in Table 2.

In certain embodiments, the one or more product inhibition alleviating mutations are present in the TyrH gene. The TyrH gene encodes tyrosine hydroxylase, which is an enzyme that converts tyrosine to L-DOPA. TyrH requires tetrahydrobiopterin ($BH_4$) as a cosubstrate to catalyze the hydroxylation reaction. Some microbial strains, such as *Saccharomyces cerevisiae*, do not naturally produce $BH_4$, but can be engineered to produce this substrate through a four-enzyme synthesis and recycling pathway, as illustrated in FIG. 1. FIG. 1 illustrates examples of synthesis, recycling, and salvage pathways of tetrahydrobiopterin, in accordance with embodiments of the invention. FIG. 1 provides the use of the enzymes PTPS, pyruvoyl tetrahydropterin synthase; SepR, sepiapterin reductase; PCD, pterin 4a-carbinolamine dehydratase; QDHPR, dihydropteridine reductase; and DHFR, dihydrofolate reductase. Of the enzymes that are illustrated in FIG. 1, yeast synthesizes an endogenous GTP cyclohydrolase I. GTP and dihydroneopterin triphosphate are naturally synthesized in yeast. Additionally, other metabolites in FIG. 1 are not naturally produced in yeast.

TyrH is inhibited by its product L-DOPA, as well as other catecholamines, particularly dopamine Mammalian tyrosine hydroxylase activity, such as from humans or rats, can be improved through mutations that relieve product inhibition. For example, short term product inhibition, such as competitive binding at the cosubstrate binding site, can be relieved by a point mutation W166Y on the TyrH gene. In particular, the point mutation W166Y on the TyrH gene may improve binding of the cosubstrate. Additionally, short term product inhibition to relieve competitive binding at the cosubstrate binding site may be improved by a point mutation S40D on the TyrH gene. Short term product inhibition may also be improved by the joint mutations of R37E, R38E on the TyrH gene. In particular, R37E, R38E mutations may together specifically improve tyrosine hydroxylase activity in the presence of dopamine.

Additionally, long term product inhibition may be relieved by point mutations on the TyrH gene. Long term product inhibition relief may include the irreversible binding of catecholamine to iron in the active site such that there is less catecholamine present to act as a product inhibitor of tyrosine hydroxylase activity. Long term product inhibition can be relieved by the mutations E332D and Y371F, respectively, in the TyrH gene.

Combinations of the mutations can be made (such as two or three or more mutations at once) to relieve multiple types of substrate and product inhibition to further improve the activity of TyrH. The mutants of TyrH, when expressed in yeast strains to produce BIAs from sugar (such as those described in U.S. Provisional Patent Application Ser. No. 61/899,496) can significantly improve the production of BIAs.

Any convenient numbers and types of mutations may be utilized to alleviate a product inhibition control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more product inhibition alleviating mutations, such as 1, 2, 3, 4, 5, 6, 7, 8, 9, 10, 11, 12, 13, 14 or 15 product inhibition alleviating mutations in one or more biosynthetic enzyme genes within the engineered host cell.

Feedback Inhibition Alleviating Mutations

In some instances, the engineered host cells are cells that include one or more feedback inhibition alleviating mutations (such as two or more, three or more, four or more, five or more, or even more) in one or more biosynthetic enzyme genes of the cell. In some cases, the one or more biosynthetic enzyme genes are native to the cell (e.g., is present in an unmodified cell). Additionally or alternatively, in some examples the one or more biosynthetic enzyme genes are non-native to the cell. As used herein, the term "feedback inhibition alleviating mutation" refers to a mutation that alleviates a feedback inhibition control mechanism of an engineered host cell. Feedback inhibition is a control mechanism of the cell in which an enzyme in the synthetic pathway of a regulated compound is inhibited when that compound has accumulated to a certain level, thereby balancing the amount of the compound in the cell. A mutation that alleviates feedback inhibition reduces the inhibition of a regulated enzyme in the engineered host cell relative to a control cell. In this way, engineered host cell provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the host cell or a downstream product thereof.

A variety of feedback inhibition control mechanisms and biosynthetic enzymes that are directed to regulation of levels of BIAs of interest may be targeted for alleviation in the host cell. The host cell may include one or more feedback inhibition alleviating mutations in one or more biosynthetic enzyme genes native to the cell. The one or more mutations may be located in any convenient biosynthetic enzyme genes where the biosynthetic enzyme is subject to regulatory control. In some embodiments, the one or more biosynthetic enzyme genes may encode one or more enzymes selected from a 3-deoxy-d-arabinose-heptulosonate-7-phosphate (DAHP) synthase and a chorismate mutase. In some embodiments, the one or more biosynthetic enzyme genes encode a 3-deoxy-d-arabinose-heptulosonate-7-phosphate (DAHP) synthase. In some instances, the one or more biosynthetic enzyme genes may encode a chorismate mutase. In certain instances, the one or more feedback inhibition alleviating mutations may be present in a biosynthetic enzyme gene selected from ARO4 and ARO7. In certain instances, the one or more feedback inhibition alleviating mutations may be present in a biosynthetic enzyme gene that is ARO4. In certain instances, the one or more feedback inhibition alleviating mutations are present in a biosynthetic enzyme gene that is ARO7. In some embodiments, the engineered host cell may include one or more feedback inhibition alleviating mutations in one or more biosynthetic enzyme genes such as one of those genes described in Table 2.

Any convenient numbers and types of mutations may be utilized to alleviate a feedback inhibition control mechanism. As used herein, the term "mutation" refers to a deletion, insertion, or substitution of an amino acid(s) residue or nucleotide(s) residue relative to a reference sequence or motif. The mutation may be incorporated as a directed mutation to the native gene at the original locus. In some cases, the mutation may be incorporated as an additional copy of the gene introduced as a genetic integration at a separate locus, or as an additional copy on an episomal vector such as a 2μ or centromeric plasmid. In certain instances, the feedback inhibited copy of the enzyme is under the native cell transcriptional regulation. In some instances, the feedback inhibited copy of the enzyme is introduced with engineered constitutive or dynamic regulation of protein expression by placing it under the control of a synthetic promoter.

In certain embodiments, the one or more feedback inhibition alleviating mutations may be present in the ARO4 gene. ARO4 mutations of interest may include, but are not limited to, substitution of the lysine residue at position 229 with a leucine, a substitution of the glutamine residue at position 166 with a lysine residue, or a mutation as described by Hartmann M, et al. ((2003) Proc Natl Acad Sci USA 100(3):862-867) or Fukuda et al. ((1992) J Ferment Bioeng 74(2):117-119). In some instances, mutations for conferring feedback inhibition may be selected from a mutagenized library of enzyme mutants. Examples of such selections may include rescue of growth of o-fluoro-D,L-phenylalanine or growth of aro3 mutant yeast strains in media with excess tyrosine as described by Fukuda et al. ((1990) Breeding of Brewing Yeast Producing a Large Amount of Beta-Phenylethyl Alcohol and Beta-Phenylethyl Acetate. Agr Biol Chem Tokyo 54(1):269-271).

In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more feedback inhibition alleviating mutations, such as 1, 2, 3, 4, 5, 6, 7, 8, 9, 10, 11, 12, 13, 14 or 15 feedback inhibition alleviating mutations in one or more biosynthetic enzyme genes within the engineered host cell.

Transcriptional Modulation Modifications

The host cells may include one or more transcriptional modulation modifications (such as two or more, three or more, four or more, five or more, or even more modifications) of one or more biosynthetic enzyme genes of the cell. In some examples, the one or more biosynthetic enzyme genes are native to the cell. In some examples, the one or more biosynthetic enzyme genes are non-native to the cell. Any convenient biosynthetic enzyme genes of the cell may be targeted for transcription modulation. By transcription modulation is meant that the expression of a gene of interest in a modified cell is modulated, e.g., increased or decreased, enhanced or repressed, relative to a control cell (e.g., an unmodified cell). In some cases, transcriptional modulation of the gene of interest includes increasing or enhancing expression. By increasing or enhancing expression is meant that the expression level of the gene of interest is increased by 2-fold or more, such as by 5-fold or more and sometimes by 25-, 50-, or 100-fold or more and in certain embodiments 300-fold or more or higher, as compared to a control, i.e., expression in the same cell not modified (e.g., by using any convenient gene expression assay). Alternatively, in cases where expression of the gene of interest in a cell is so low that it is undetectable, the expression level of the gene of interest is considered to be increased if expression is increased to a level that is easily detectable. In certain instances, transcriptional modulation of the gene of interest includes decreasing or repressing expression. By decreasing or repressing expression is meant that the expression level of the gene of interest is decreased by 2-fold or more, such as by 5-fold or more and sometimes by 25-, 50-, or 100-fold or more and in certain embodiments 300-fold or more or higher, as compared to a control. In some cases, expression is decreased to a level that is undetectable. Modifications of host cell processes of interest that may be adapted for use in the subject host cells are described in U.S. Publication No. 20140273109 (Ser. No. 14/211,611) by Smolke et al., the disclosure of which is herein incorporated by reference in its entirety.

Figure 2:
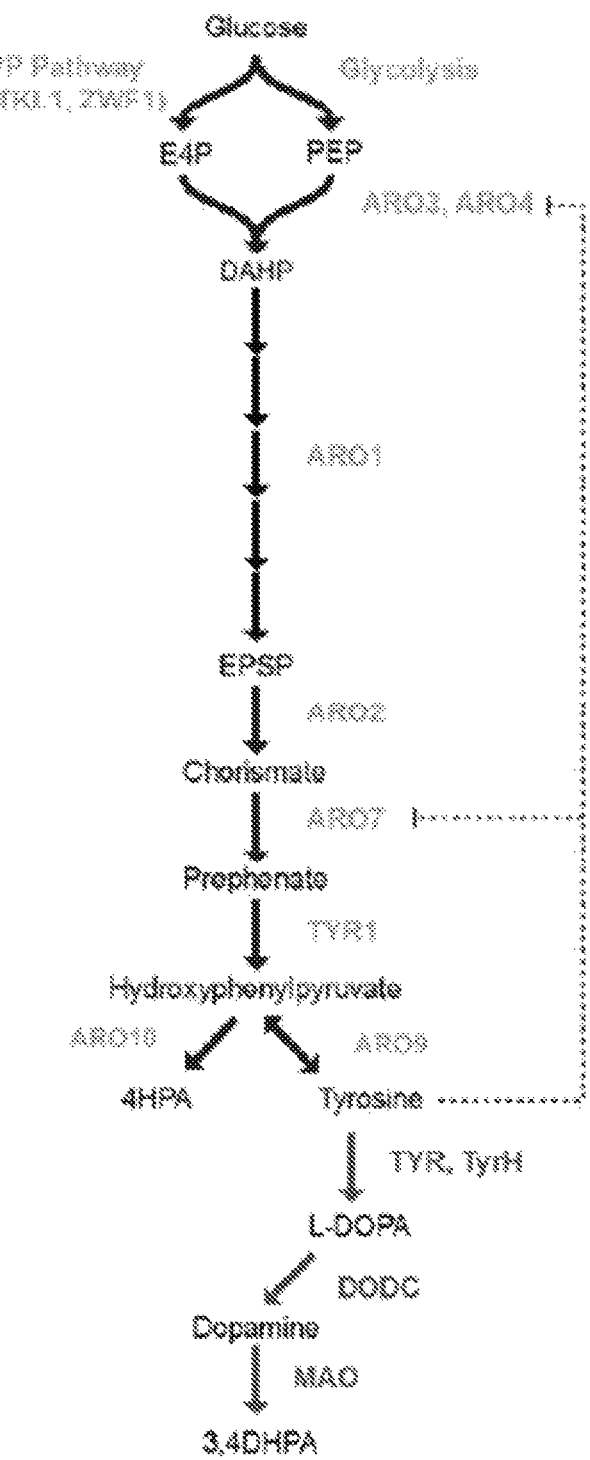
FIG. 2 illustrates a biosynthetic scheme for conversion of glucose to 4-HPA, dopamine, and 3,4-DHPA, in accordance with embodiments of the invention.

Any convenient biosynthetic enzyme genes may be transcriptionally modulated, and include but are not limited to, those biosynthetic enzymes described in FIG. 2. In particular, FIG. 2 illustrates a biosynthetic scheme for conversion of glucose to 4-HPA, dopamine, and 3,4-DHPA, in accordance with embodiments of the invention. Examples of enzymes described in FIG. 2 include ARO3, ARO4, ARO1, ARO7, TYR1, TYR, TyrH, DODC, MAO, ARO10, ARO9, and TKL. In some instances, the one or more biosynthetic enzyme genes may be selected from ARO10, ARO9, and TKL. In some cases, the one or more biosynthetic enzyme genes may be ARO10. In certain instances, the one or more biosynthetic enzyme genes may be ARO9. In some embodiments, the one or more biosynthetic enzyme genes may be TKL. In some embodiments, the host cell includes one or more transcriptional modulation modifications to one or more genes such as one of those genes described in Table 2.

In some embodiments, the transcriptional modulation modification may include a substitution of a strong promoter for a native promoter of the one or more biosynthetic enzyme genes or the expression of an additional copy(ies) of the gene or genes under the control of a strong promoter. The promoters driving expression of the genes of interest may be constitutive promoters or inducible promoters, provided that the promoters may be active in the host cells. The genes of interest may be expressed from their native promoters. Additionally or alternatively, the genes of interest may be expressed from non-native promoters. Although not a requirement, such promoters may be medium to high strength in the host in which they are used. Promoters may be regulated or constitutive. In some embodiments, promoters that are not glucose repressed, or repressed only mildly by the presence of glucose in the culture medium, may be used. There are numerous suitable promoters, examples of which include promoters of glycolytic genes such as the promoter of the *B. subtilis* tsr gene (encoding fructose biphosphate aldolase) or GAPDH promoter from yeast *S. cerevisiae* (coding for glyceraldehyde-phosphate dehydrogenase) (Bitter G. A., *Meth. Enzymol.* 152:673 684 (1987)). Other strong promoters of interest include, but are not limited to, the ADHI promoter of baker's yeast (Ruohonen L., et al, *J. Biotechnol.* 39:193 203 (1995)), the phosphate-starvation induced promoters such as the PHOS promoter of yeast (Hinnen, A., et al, in *Yeast Genetic Engineering*, Barr, P. J., et al. eds, Butterworths (1989), the alkaline phosphatase promoter from *B. licheniformis* (Lee. J. W. K., et al., *J. Gen. Microbiol.* 137:1127 1133 (1991)), GPD1, and TEF1. Yeast promoters of interest include, but are not limited to, inducible promoters such as Gal1-10, Gal1, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), MRP7 promoter, etc. In some instances, the strong promoter is GPD1. In certain instances, the strong promoter is TEF1. Autonomously replicating yeast expression vectors containing promoters inducible by hormones such as glucocorticoids, steroids, and thyroid hormones are also known and include, but are not limited to, the glucorticoid responsive element (GRE) and thyroid hormone responsive element (TRE), see e.g., those promoters described in U.S. Pat. No. 7,045,290. Vectors containing constitutive or inducible promoters such as alpha factor, alcohol oxidase, and PGH may be used. Additionally any promoter/enhancer combination (as per the Eukaryotic Promoter Data Base EPDB) could also be used to drive expression of genes of interest. It is understood that any convenient promoters specific to the host cell may be selected, e.g., *E. coli*. In some cases, promoter selection may be used to optimize transcription, and hence, enzyme levels to maximize production while minimizing energy resources.

Inactivating Mutations

The engineered host cells may include one or more inactivating mutations to an enzyme of the cell (such as two or more, three or more, four or more, five or more, or even more). The inclusion of one or more inactivating mutations may modify the flux of a synthetic pathway of an engineered host cell to increase the levels of a BIA of interest or a desirable enzyme or precursor leading to the same. In some examples, the one or more inactivating mutations are to an enzyme native to the cell. Additionally or alternatively, the one or more inactivating mutations are to an enzyme non-native to the cell. As used herein, by "inactivating mutation" is meant one or more mutations to a gene or regulatory DNA sequence of the cell, where the mutation(s) inactivates a biological activity of the protein expressed by that gene of interest. In some cases, the gene is native to the cell. In some instances, the gene encodes an enzyme that is inactivated and is part of or connected to the synthetic pathway of a BIA of interest produced by the host cell. In some instances, an inactivating mutation is located in a regulatory DNA sequence that controls a gene of interest. In certain cases, the inactivating mutation is to a promoter of a gene. Any convenient mutations (e.g., as described herein) may be utilized to inactivate a gene or regulatory DNA sequence of interest. By "inactivated" or "inactivates" is meant that a biological activity of the protein expressed by the mutated gene is reduced by 10% or more, such as by 20% or more, 30% or more, 40% or more, 50% or more, 60% or more, 70% or more, 80% or more, 90% or more, 95% or more, 97% or more, or 99% or more, relative to a control protein expressed by a non-mutated control gene. In some cases, the protein is an enzyme and the inactivating mutation reduces the activity of the enzyme.

In some examples, the engineered host cell includes an inactivating mutation in an enzyme native to the cell. Any convenient enzymes may be targeted for inactivation. Enzymes of interest may include, but are not limited to those enzymes, described in Table 2 whose action in the synthetic pathway of the engineered host cell tends to reduce the levels of a BIA of interest. In some cases, the enzyme has glucose-6-phosphate dehydrogenase activity. In certain embodiments, the enzyme that includes an inactivating mutation is ZWF1. In some cases, the enzyme has alcohol dehydrogenase activity. In some embodiments, the enzyme that includes an inactivating mutation is selected from ADH2, ADH3, ADH4, ADH5, ADH6, ADH7, and SFA1. In certain embodiments, the enzyme that includes an inactivating mutation(s) is ADH2. In certain embodiments, the enzyme that includes an inactivating mutation(s) is ADH3. In certain embodiments, the enzyme that includes an inactivating mutation(s) is ADH4. In certain embodiments, the enzyme that includes an inactivating mutation(s) is ADH5. In certain embodiments, the enzyme that includes an inactivating mutation(s) is ADH6. In certain embodiments, the enzyme that includes an inactivating mutation(s) is ADH7. In some cases, the enzyme has aldehyde oxidoreductase activity. In certain embodiments, the enzyme that includes an inactivating mutation is selected from ALD2, ALD3, ALD4, ALD5, and ALD6. In certain embodiments, the enzyme that includes an inactivating mutation(s) is ALD2. In certain embodiments, the enzyme that includes an inactivating mutation(s) is ALD3. In certain embodiments, the enzyme that includes an inactivating mutation(s) is ALD4. In certain embodiments, the enzyme that includes an inactivating mutation(s) is ALD5. In certain embodiments, the enzyme that includes an inactivating mutation(s) is ALD6. In some embodiments, the host cell includes one or more inactivating mutations to one or more genes described in Table 2.

Epimerization Modifications

Figure 3:
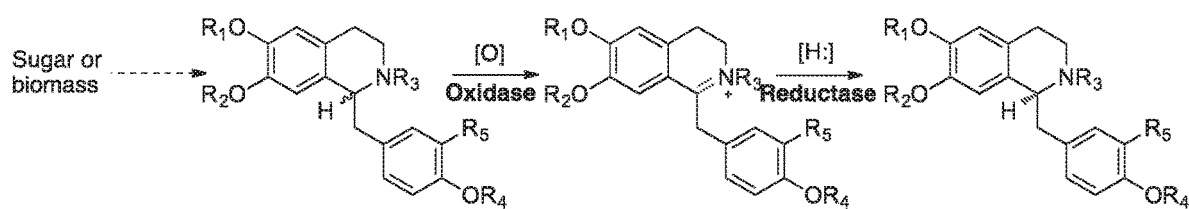
FIG. 3 illustrates a schematic example of (R)-1-benzylisoquinoline alkaloid formation, in accordance with embodiments of the invention.

Some methods, processes, and systems provided herein describe the conversion of (S)-1-benzylisoquinoline alkaloids to (R)-1-benzylisoquinoline alkaloids. Some of these methods, processes, and systems may comprise an engineered host cell. In some examples, the conversion of (S)-1-benzylisoquinoline alkaloids to (R)-1-benzylisoquinoline alkaloids is a key step in the conversion of a substrate to a diverse range of alkaloids. In some examples, the conversion of (S)-1-benzylisoquinoline alkaloids to (R)-1-benzylisoquinoline alkaloids comprises an epimerization reaction. In some cases, epimerization of a substrate alkaloid may be performed by oxidizing an (S)-substrate to the corresponding Schiff base or imine intermediate, then stereospecifically reducing this intermediate to an (R)-product as provided in FIG. 3 and as represented generally in Scheme 1. As provided in Scheme 1, $R_1$, $R_2$, $R_3$, and $R_4$ may be H or $CH_3$. $R_5$ may be H, OH, or $OCH_3$.

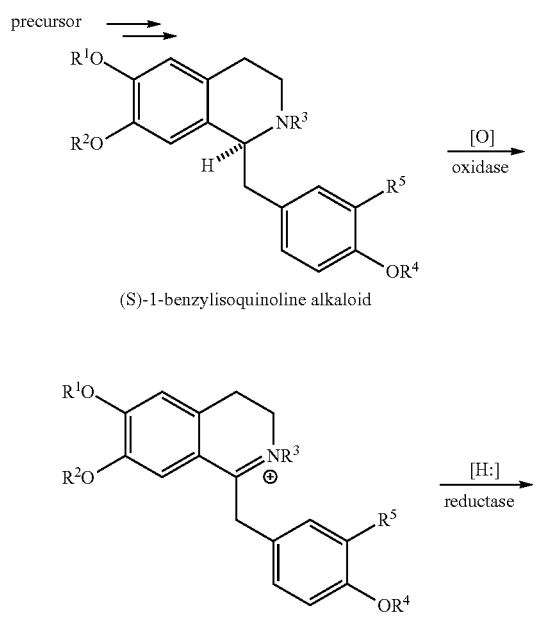

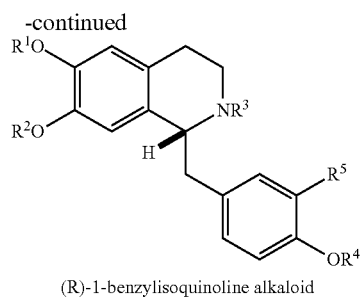

(R)-1-benzylisoquinoline alkaloid

In some examples, the conversion of the (S)-substrate to the (R)-product may involve at least one oxidation reaction and at least one reduction reaction. In some cases, an oxidation reaction is optionally followed by a reduction reaction. In some cases, at least one of the oxidation and reduction reactions is carried out in the presence of an enzyme. In some cases, at least one of the oxidation and reduction reactions is catalyzed by an enzyme. In some cases, the oxidation and reduction reactions are both carried out in the presence of at least one enzyme. In some cases, at least one enzyme is useful to catalyze the oxidation and reduction reactions. The oxidation and reduction reactions may be catalyzed by the same enzyme.

In some methods, processes and systems described herein, an oxidation reaction may be performed in the presence of an enzyme. In some examples, the enzyme may be an oxidase. The oxidase may use an (S)-1-benzylisoquinoline as a substrate. The oxidase may convert the (S)-substrate to a corresponding imine or Schiff base derivative. The oxidase may be referred to as 1,2-dehydroreticuline synthase (DRS). Non-limiting examples of enzymes suitable for oxidation of (S)-1-benzylisoquinoline alkaloids in this disclosure include a cytochrome P450 oxidase, a 2-oxoglutarate-dependent oxidase, and a flavoprotein oxidase. For example, (S)-tetrahydroprotoberberine oxidase (STOX, E.C1.3.3.8) may oxidize (S)-norreticuline and other (S)-1-benzylisoquinoline alkaloids to 1,2-dehydronorreticuline and other corresponding 1,2-dehydro products. In some examples, a protein that comprises an oxidase domain of any one of the preceding examples may perform the oxidation. In some examples, the oxidase may catalyze the oxidation reaction within a host cell, such as an engineered host cell, as described herein.

In some examples, a reduction reaction may follow the oxidation reaction. The reduction reaction may be performed by an enzyme. In some examples, the reductase may use an imine or Schiff base derived from a 1-benzylisoquinoline as a substrate. The reductase may convert the imine or Schiff base derivative to an (R)-1-benzylisoquinoline. The reductase may be referred to as 1,2-dehydroreticuline reductase (DRR). Non-limiting examples of enzymes suitable for reduction of an imine or Schiff base derived from an (S)-1-benzylisoquinoline alkaloid include an aldo-keto reductase (e.g., a codeinone reductase-like enzyme (EC 1.1.1.247)) and a short chain dehydrogenase (e.g., a salutaridine reductase-like enzyme (EC 1.1.1.248)). In some examples, a protein that comprises a reductase domain of any one of the preceding examples may perform the reduction. In a further embodiment, the reduction is stereospecific. In some examples, the reductase may catalyze the reduction reaction within a host cell, such as an engineered host cell, as described herein.

An example of an enzyme that can perform an epimerization reaction that converts (S)-1-benzylisoquinoline alkaloids to (R)-1-benzylisoquinoline alkaloids includes an epimerase having an oxidase domain and a reductase domain. In particular, the epimerase may have a cytochrome P450 oxidase 82Y2-like domain Additionally, the epimerase may have a codeinone reductase-like domain. Further, an epimerase having a cytochrome P450 oxidase 82Y2-like domain and also having a codeinone reductase-like domain may be referred to as a CYP-COR enzyme. In particular, a CYP-COR enzyme may be a fusion enzyme.

An example of an amino acid sequence of a CYP-COR enzyme that may be used to perform the conversion of (S)-1-benzylisoquinoline alkaloids to (R)-1-benzylisoquinoline alkaloids is provided in FIG. 4. In particular, FIG. 4 illustrates an amino acid sequence of a CYP-COR enzyme, in accordance with embodiments of the invention. As seen in FIG. 4, underlined text denotes the cytochrome P450 CYP82Y2-like domain (59% identity to AFB74617.1). The dotted underlined text denotes the aldo-keto reductase NADPH-dependent codeinone reductase-like domain (75% identity to ACM44066.1). Additional amino acid sequences of a CYP-COR enzyme are set forth in Table 1. An amino acid sequence for an epimerase that is utilized in converting an (S)-1-benzylisoquinoline alkaloid to an (R)-1-benzylisoquinoline alkaloid may be 75% or more identical to a given amino acid sequence as listed in Table 1. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an epimerase that converts (S)-1-benzylisoquinoline alkaloid to (R)-1-benzylisoquinoline alkaloid, wherein the epimerase comprises an amino acid sequence selected from the group consisting of: SEQ ID NOs: 1, 2, 3, 4, 5, 6, 7, 8, 9, 10, 11, 12, 13, 14, and 15. The epimerase that is produced within the engineered host cell may be recovered and purified so as to form a biocatalyst. In some cases, the epimerase may be split into one or more enzymes. Additionally, one or more enzymes that are produced by splitting the epimerase may be recovered from the engineered host cell. These one or more enzymes that result from splitting the epimerase may also be used to catalyze the conversion of (S)-1-benzylisoquinoline alkaloids to (R)-1-benzylisoquinoline alkaloids. In particular, the one or more enzymes that are recovered from the engineered host cell that produces the epimerase may be used in a process for converting an (S)-1-benzylisoquinoline alkaloid to an (R)-1-benzylisoquinoline alkaloid. The process may include contacting the (S)-1-benzylisoquinoline alkaloid with an epimerase in an amount sufficient to convert said (S)-1-benzylisoquinoline alkaloid to (R)-1-benzylisoquinoline alkaloid. In examples, the (S)-1-benzylisoquinoline alkaloid may be contacted with a sufficient amount of the one or more enzymes such that at least 5% of said (S)-1-benzylisoquinoline alkaloid is converted to (R)-1-benzylisoquinoline alkaloid. In further examples, the (S)-1-benzylisoquinoline alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said (S)-1-benzylisoquinoline alkaloid is converted to (R)-1-benzylisoquinoline alkaloid.

The one or more enzymes that may be used to convert an (S)-1-benzylisoquinoline alkaloid to an (R)-1-benzylisoquinoline alkaloid may contact the (S)-1-benzylisoquinoline alkaloid in vitro. Additionally, or alternatively, the one or more enzymes that may be used to convert an (S)-1-benzylisoquinoline alkaloid to an (R)-1-benzylisoquinoline alkaloid may contact the (S)-1-benzylisoquinoline alkaloid in vivo. Additionally, the one or more enzymes that may be used to convert an (S)-1-benzylisoquinoline alkaloid to an (R)-1-benzylisoquinoline alkaloid may be provided to a cell having the (S)-1-benzylisoquinoline alkaloid within, or may be produced within an engineered host cell.

In some examples, the methods provide for engineered host cells that produce an alkaloid product, wherein the epimerization of an (S)-substrate to an (R)-product may comprise a key step in the production of an alkaloid product. In some examples, the alkaloid produced is an (R)-1-benzylisoquinoline alkaloid. In still other embodiments, the alkaloid produced is derived from an (R)-1-benzylisoquinoline alkaloid, including, for example, 4-ring promorphinan and 5-ring morphinan alkaloids. In another embodiment, an (S)-1-benzylisoquinoline alkaloid is an intermediate toward the product of the engineered host cell. In still other embodiments, the alkaloid product is selected from the group consisting of morphinan, protoberberine, noscapinoid, and benzophenanthridine alkaloids.

In some examples, the (S)-substrate is an (S)-1-benzylisoquinoline alkaloid selected from the group consisting of (S)-norreticuline, (S)-reticuline, (S)-tetrahydropapaverine, (S)-norcoclaurine, (S)-coclaurine, (S)—N-methylcoclaurine, (S)-3'-hydroxy-N-methylcoclaurine, (S)-norisoorientaline, (S)-orientaline, (S)-isoorientaline, (S)-norprotosinomenine, (S)-protosinomenine, (S)-norlaudanosoline, (S)-laudanosoline, (S)-4'-O-methyllaudanosoline, (S)-6-O-methylnorlaudanosoline, (S)-4'-O-methylnorlaudanosoline.

In some examples, the (S)-substrate is a compound of Formula I:

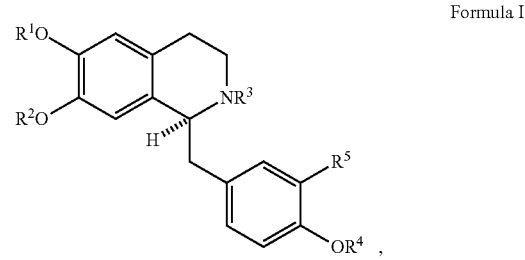

Formula I or a salt thereof, wherein:
$R^1$, $R^2$, $R^3$, and $R^4$ are independently selected from hydrogen and methyl; and
$R^5$ is selected from hydrogen, hydroxy, and methoxy.

In some other examples, at least one of $R^1$, $R^2$, $R^3$, $R^4$, and $R^5$ is hydrogen.

In still other examples, the (S)-substrate is a compound of Formula II:

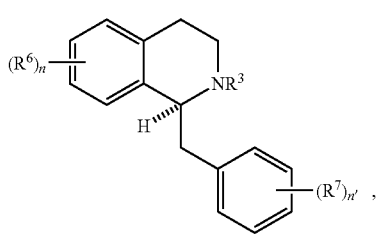

Formula II or a salt thereof, wherein:
$R^3$ is selected from hydrogen and $C_1$-$C_4$ alkyl;
$R^6$ and $R^7$ are independently selected at each occurrence from hydroxy, fluoro, chloro, bromo, carboxaldehyde, $C_1$-$C_4$ acyl, $C_1$-$C_4$ alkyl, and $C_1$-$C_4$ alkoxy;
n is 0, 1, 2, 3, or 4; and
n' is 0, 1, 2, 3, 4 or 5.

When a bond is drawn across a ring, it means substitution may occur at a non-specific ring atom or position. For example, in Formula II shown above, the hydrogen of any —CH— in the 6-membered ring may be replaced with $R^7$ to form —$CR^7$—.

In some examples, $R^6$ and $R^7$ are independently methyl or methoxy. In some other examples, n and n' are independently 1 or 2. In still other embodiments, $R^3$ is hydrogen or methyl.

In some other examples, the (S)-substrate is a compound of Formula III:

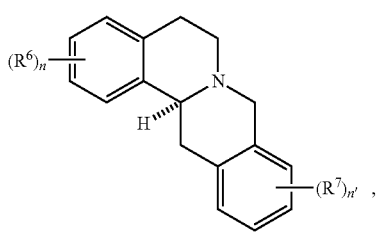

Formula III or a salt thereof, wherein:
$R^6$ and $R^7$ are independently selected at each occurrence from hydroxy, fluoro, chloro, bromo, carboxaldehyde, $C_1$-$C_4$ acyl, $C_1$-$C_4$ alkyl, and $C_1$-$C_4$ alkoxy; and
n and n' are independently 0, 1, 2, 3, or 4.

In some examples, $R^6$ and $R^7$ are independently hydroxy, methyl, or methoxy. In some other examples, n and n' are independently 1 or 2. In still further embodiments, $R^6$ and $R^7$ are independently fluoro, hydroxy, methyl, or methoxy.

In some examples, the methods provide for engineered host cells that produce alkaloid products from (S)-reticuline. The epimerization of (S)-reticuline to (R)-reticuline may comprise a key step in the production of diverse alkaloid products from a precursor. In some examples, the precursor is L-tyrosine or a sugar (e.g., glucose). The diverse alkaloid products can include, without limitation, morphinan, protoberberine, noscapinoid, and benzophenanthridine alkaloids.

Any suitable carbon source may be used as a precursor toward an epimerized 1-benzylisoquinoline alkaloid. Suitable precursors can include, without limitation, monosaccharides (e.g., glucose, fructose, galactose, xylose), oligosaccharides (e.g., lactose, sucrose, raffinose), polysaccharides (e.g., starch, cellulose), or a combination thereof. In some examples, unpurified mixtures from renewable feedstocks can be used (e.g., cornsteep liquor, sugar beet molasses, barley malt, biomass hydrolysate). In still other embodiments, the carbon precursor can be a one-carbon compound (e.g., methanol, carbon dioxide) or a two-carbon compound (e.g., ethanol). In yet other embodiments, other carbon-containing compounds can be utilized, for example, methylamine, glucosamine, and amino acids (e.g., L-tyrosine). In some examples, a 1-benzylisoquinoline alkaloid may be added directly to an engineered host cell of the invention, including, for example, norlaudanosoline, laudanosoline, norreticuline, and reticuline. In still further embodiments, a 1-benzylisoquinoline alkaloid may be added to the engineered host cell as a single enantiomer (e.g., an (S)-1-benzylisoquinoline alkaloid), or a mixture of enantiomers, including, for example, a racemic mixture.

In some examples, the methods provide for the epimerization of a stereocenter of a 1-benzylisoquinoline alkaloid, or a derivative thereof. In a further embodiment, the method comprises contacting the 1-benzylisoquinoline alkaloid with at least one enzyme. The at least one enzyme may invert the stereochemistry of a stereocenter of a 1-benzylisoquinoline alkaloid, or derivative thereof, to the opposite stereochemistry. In some examples, the at least one enzyme converts an (S)-1-benzylisoquinoline alkaloid to an (R)-1-benzylisoquinoline alkaloid. In some examples of this conversion of an (S)-1-benzylisoquinoline alkaloid to an (R)-1-benzylisoquinoline alkaloid utilizing the at least one enzyme, the (S)-1-benzylisoquinoline alkaloid is selected from the group consisting of (S)-norreticuline, (S)-reticuline, (S)-tetrahydropapaverine, (S)-norcoclaurine, (S)-coclaurine, (S)—N-methylcoclaurine, (S)-3'-hydroxy-N-methylcoclaurine, (S)-norisoorientaline, (S)-orientaline, (S)-isoorientaline, (S)-norprotosinomenine, (S)-protosinomenine, (S)-norlaudanosoline, (S)-laudanosoline, (S)-4'-O-methyllaudanosoline, (S)-6-O-methylnorlaudanosoline, and (S)-4'-O-methylnorlaudanosoline.

In some other examples, the at least one enzyme converts an 5'R-phthalideisoquinoline alkaloid to an 5'S-phthalideisoquinoline alkaloid. In some examples of this conversion of an 5'R-phthalideisoquinoline alkaloid to an S'S-phthalideisoquinoline alkaloid utilizing the at least one enzyme, the 5'R-phthalideisoquinoline alkaloid is selected from the group consisting of 5'R-narcotolinehemiacetal, 5'R-narcotoline, 5'R-narcotinehemiacetal, and 5'R-noscapine.

In some examples, the 3S, 5'R-phthalideisoquinoline alkaloid is a compound of Formula IV:

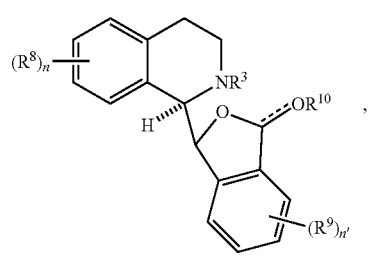

Formula IV or a salt thereof, wherein:

$R^3$ is selected from hydrogen and $C_1$-$C_4$ alkyl;

$R^8$ and $R^9$ are independently selected at each occurrence from hydroxy, fluoro, chloro, bromo, carboxaldehyde, $C_1$-$C_4$ acyl, $C_1$-$C_4$ alkyl, and $C_1$-$C_4$ alkoxy;

$R^{10}$ is absent, hydrogen, or $C_1$-$C_4$ alkyl;

two $R^8$s and the carbon atoms to which they are attached optionally form a 5- to 8-membered cycloalkyl or heterocycloalkyl moiety;

two $R^9$s and the carbon atoms to which they are attached optionally form a 5- to 8-membered cycloalkyl or heterocycloalkyl moiety; and n and n' are independently 0, 1, 2, 3, or 4.

In some other examples, the at least one enzyme converts an 5'R-secoberberine alkaloid to an 5'S-secoberberine alkaloid. In some examples of this conversion of an 5'R-secoberberine alkaloid to an 5'S-secoberberine alkaloid utilizing the at least one enzyme, the 5'R-secoberberine alkaloid is selected from the group consisting of 5'R-4'-O-desmethyl-3-O-acetylpapaveroxine, 5'R-3-O-acetylpapaveroxine, and 5'R-papaveroxine In some examples, the 5'R-secoberberine alkaloid is a compound of Formula V:

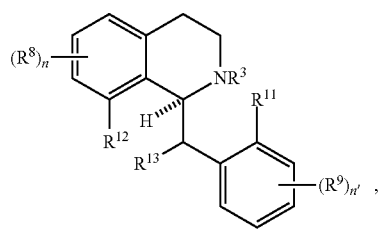

Formula V or a salt thereof, wherein:

$R^3$ is selected from hydrogen and $C_1$-$C_4$ alkyl;

$R^8$ and $R^9$ are independently selected at each occurrence from hydroxy, fluoro, chloro, bromo, carboxaldehyde, $C_1$-$C_4$ acyl, $C_1$-$C_4$ alkyl, and $C_1$-$C_4$ alkoxy;

$R^{11}$ is selected from hydrogen and aldehyde;

$R^{12}$ is selected from hydrogen, hydroxyl, and O-methyl;

$R^{13}$ is selected from hydroxyl and O-methyl;

two $R^8$s and the carbon atoms to which they are attached optionally form a 5- to 8-membered cycloalkyl or heterocycloalkyl moiety;

two $R^9$s and the carbon atoms to which they are attached optionally form a 5- to 8-membered cycloalkyl or heterocycloalkyl moiety; and n and n' are independently 0, 1, 2, 3, or 4.

In still other embodiments, the 1-benzylisoquinoline alkaloid that is epimerized may comprise two or more stereocenters, wherein only one of the two or more stereocenters is inverted to produce a diastereomer of the substrate (e.g., (S, R)-1-benzylisoquinoline alkaloid converted to (R, R)-1-benzylisoquinoline alkaloid). In examples where only one stereocenter of a 1-benzylisoquinoline alkaloid is inverted when contacted with the at least one enzyme, the product is referred to as an epimer of the 1-benzylisoquinoline alkaloid.

In some examples, the 1-benzylisoquinoline alkaloid is presented to the enzyme as a single stereoisomer. In some other examples, the 1-benzylisoquinoline alkaloid is presented to the enzyme as a mixture of stereoisomers. In still further embodiments, the mixture of stereoisomers may be a racemic mixture. In some other examples, the mixture of stereoisomers may be enriched in one stereoisomer as compared to another stereoisomer.

In some examples, an 1-benzylisoquinoline alkaloid, or a derivative thereof, is recovered. In some examples, the 1-benzylisoquinoline alkaloid is recovered from a cell culture. In still further embodiments, the recovered 1-benzylisoquinoline alkaloid is enantiomerically enriched in one stereoisomer as compared to the original mixture of 1-benzylisoquinoline alkaloids presented to the enzyme. In still further embodiments, the recovered 1-benzylisoquinoline alkaloid has an enantiomeric excess of at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100%.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. "Diastereoisomers" or "diastereomers" are stereoisomers that have at least two asymmetric atoms but are not mirror images of each other. The term "epimer" as used herein refers to a compound having the identical chemical formula but a different optical configuration at a particular position. For example, the (R, S) and (S, S) stereoisomers of a compound are epimers of one another. In some examples, a 1-benzylisoquinoline alkaloid is converted to its epimer (e.g., epi-1-benzylisoquinoline alkaloid). The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms that can be defined, in terms of absolute stereochemistry, as (R)- or (S)-.

TABLE 1

Example partial and full-length amino acid sequences of CYP-COR fusion enzymes.

| Sequence | Description | SEQ. ID NO. |
|---|---|---|
| MELQYISYFQPTSSVVALLLALVSILSSVVVLRKTFLNNYSSSPASSTKTA VLSHQRQQSCALPISGLLHIFMNKNGLIHVTLGNMADKYGPIFSFPTGSH RTLVVSSWEMVKECFTGNNDTAFSNRPIPLAFKTIFYACGGIDSYGLSSV PYGKYWRELRKVCVHNLLSNQQLLKFRHLIISQVDTSFNKLYELCKNSE DNHGNYTTTTTTAAGMVRIDDWLAELSFNVIGRIVCGFQSGPKTGAPSR VEQFKEAINEASYFMSTSPVSDNVPMLGWIDQLTGLTRNMKHCGKKLD | P. somniferum plant source; full-length amino acid sequence | SEQ. ID NO. 1 |

TABLE 1-continued

Example partial and full-length amino acid sequences of CYP-COR fusion enzymes.

| Sequence | Description | SEQ. ID NO. |
|---|---|---|
| LVVESIINDHRQKRRFSRTKGGDEKDDEQDDFIDICLSIMEQPQLPGNNN PSQIPIKSIVLDMIGGGTDTTKLTTIWTLSLLLNNPHVLDKAKQEVDAHF RTKRRSTNDAAAAVVDFDDIRNLVYIQAIIKESMRLYPASPVVERLSGE DCVVGGFHVPAGTRLWANVWKMQRDPKVWDDPLVFRPDRFLSDEQK MVDVRGQNYELLPFGAGRRVCPGVSFSLDLMQLVLTRLILEFEMKSPSG KVDMTATPGLMSYKVIPLDILLTHRRIKPCVQSAASERDMESSGVPVITL GSGKVMPVLGMGTFEKVGKGSERERLAILKAIEVGYRYFDTAAAYETE EVLGEMAEALQLGLVKSRDELFISSMLWCTDAHADRVLLALQNSLRNL KLEYVDLYMLPFPASLKPGKITMDIPEEDICRMDYRSVWAAMEECQNL GFTKSIGVSNFSCKKLQELMATANIPPAVNQVEMSPAFQQKKLREYCNA NNILVSAISVLGSNGTPWGSNAVLGSEVLKKIAMAKGKSVAQVSMRWV YEQGASLVVKSFSEERLRENLNIFDWELTKEDHEKIGEIPQCRILSAYFL VSPNGPFKSQEELWDDEA* | >RQNK-2062398 (also FPYZ-2037562. BMRX-2007040. and MLPX-2016197) | |
| MELQYISYFQPTSSVVALLLALVSILSSVVVLRKTFLNNYSSSPASSTKTA VLSHQRQQSCALPISGLLHIFMNKNGLIHVTLGNMADKYGPIFSFPTGSH RTLVVSSWEMVKECFTGNNDTAFSNRPIPLAFKTIFYACGGIDSYGLSSV PYGKYWRELRKVCVHNLLSNQQLLKFRHLIISQVDTSFNKLYELCKNSE DNHGNYTTXLLLPQLAWRQPWKLYYXTTTTAAGMVRIDDWLAELSFN VIGRIVCGFQSGPKTGAPSRVEQFKEAINEASYFMSTSPVSDNVPMLGWI DQLTGLTRNMKHCGKKLDLVVESIINDHRQKRRFSRTKGGDEKDDEQD DFIDICLSIMEQPQLPGNNNPSQIPIKSIVLDMIGGGTDTTKLTTIWTLSLL LNNPHVLDKAKQEVDAHFRTKRRSTNDAAAAVVDFDDIRNLVYIQAII KESMRLYPASPVVERLSGEDCVVGGFHVPAGTRLWANVWKMQRDPK VWDDPLVFRPDRFLSDEQKMVDVRGQNYELLPFGAGRRVCPGVSFSLD LMQLVLTRLILEFEMKSPSGKVDMTATPGLMSYKVIPLDILLTHRRIKPC VQSAASERDMESSGVPVITLGSGKVMPVLGMGTFEKVGKGSERERLAIL KAIEVGYRYFDTAAAYETEEVLGEMAEALQLGLVKSRDELFISSMLWC TDAHADRVLLALQNSLRNLKLEYVDLYMLPFPASLKPGKITMDIPEEDI CRMDYRSVWAAMEECQNLGFTKSIGVSNFSCKKLQELMATANIPPAVN QVEMSPAFQQKKLREYCNANNILVSAISVLGSNGTPWGSNAVLGSEVL KKIAMAKGKSVAQVSMRWVYEQGASLVVKSFSEERLRENLNIFDWELT KEDHEKIGEIPQCRILSAYFLVSPNGPFKSQEELWDDEA* | P. somniferum plant source; full-length amino acid sequence >KKCW-2026866 (also FPYZ-2037562. MLPX-2016197) | SEQ. ID NO. 2 |
| MELQYISYFQPTSSVVALLLALVSILSSVVVLRKTFLNNYSSSPASSTKTA VLSHQRQQSCALPISGLLHIFMNKNGLIHVTLGNMADKYGPIFSFPTGSH RTLVVSSWEMVKECFTGNNDTAFSNRPIPLAFKTIFYACGGIDSYGLSSV PYGKYWRELRKVCVHNLLSNQQLLKFRHLIISQVDTSFNKLYELCKNSE DNHGNYTTTTTTAAGMVRIDDWLAELSFNVIGRIVCGFQSGPKTGAPSR VEQFKEAINEASYFMSTSPVSDNVPMLGWIDQLTGLTRNMKHCGKKLD LVVESIINDHRQKRRFSRTKGGDEKDDEQDDFIDICLSIMEQPQLPGNNN PSQIPIKSIVLDMIGGGTDTTKLTTIWTLSLLLNNPHVLDKAKQEVDAHF RTKRRSTNDAAAAVVDFDDIRNLVYIQAIIKESMRLYPASPVVERLSGE DCVVGGFHVPAGTRLWANVWKMQRDPKVWDDPLVFRPDRFLSDEQK MVDVRGQNYELLPFGAGRRVCPGVSFSLDLMQLVLTRLILEFEMKSPSG KVDMTATPGLMSYKVIPLDILLTHRRIKPCVQSAASERDMESSGVPVITL GSGKVMPVLGMGTFEKVGKGSERERLAILKAIEVGYRYFDTAAAYETE EVLGEAIAEALQLGLVKSRDELFISSMLWCTDAHADRVLLALQNSLRNL KLEYVDLYMLPFPASLKPGKITMDIPEEDICRMDYRXVSKPWLH* | P. somniferum plant source; partial-length amino acid sequence >SUFP-2025636 | SEQ. ID NO. 3 |
| MRWHRXIDSYGLSSVPYGKYWRELRKVCVHNLLSNQQLLKFRHLIISQ VDTSFNKLYELCKNSEDNQGNYPTTTTAAGMVRIDDWLAELSFNVIGRI VCGFQSGPKTGAPSRVEQFKEAINEASYFMSTSPVSDNVPMLGWIDQLT GLTRNMKHCGKKLDLVVESIINDHRQKRRFSRTKGGDEKDDEQDDFIDI CLSIMEQPQLPGNNNPSQIPIKSIVLDMIGGGTDTTKLTTIWTLSLLLNNP HVLDKAKQEVDAHFRTKRRSTNDAAAAVVDFDDIRNLVYIQAIIKESM RLYPASPVVERLSGEDCVVGGFHVPAGTRLWANVWKMQRDPKVWDD PLVFRPDRFLSDEQKMVDVRGQNYELLPFGAGRRVCPGVSFSLDLMQL VLTRLILEFEMKSPSGKVDMTATPGLMSYKVIPLDILLTHRRIKPCVQSA ASERDMESSGVPVITLGSGKVMPVLGMGTFEKVGKGSERERLAILKAIE VGYRYFDTAAAYETEEVLGEAIAEALQLGLVKSRDELFISSMLWCTDA HADRVLLALQNSLRNLKLEYVDLYMLPFPASLKPGKITMDIPEEDICRM DYRSVWAAMEECQNLGFTKSIGVSNFSCKKLQELMATANIPPAVNQVE MSPAFQQKKLREYCNANNILVSAISVLGSNGTPWGSNAVLGSEVLKKIA MAKGKSVAQVSMRWVYEQGASLVVKSFSEERLRENLNIFDWELTKED HEKIGEIPQCRILSAYFLVSPNGPFKSQEELWDDEA* | P. somniferum plant source; partial-length amino acid sequence >MIKW-2013651 | SEQ. ID NO. 4 |
| MELQYISYFQPTSSVVALLLALVSILSSVVVLRKTFLNNYSSSPASSTKTA VLSHQRQQSCALPISGLLHIFMNKNGLIHVTLGNMADKYGPIFSFPTGSH RTLVVSSWEMVKECFTGNNDTAFSNRPIPLAFKTIFYACGGIDSYGLSSV PYGKYWRELRKVCVHNLLSNQQLLKFRHLIISQVDTSFNKLYELCKNSE DNQGNYTTTTTAAGMVRIDDWLAELSFNVIGRIVCGFQSGPKTGAPSRV EQFKEAINEASYFMSTSPVSDNVPMLGWIDQLTGLTRNMKHCGKKLDL VVESIINDHRQKRRFSRTKGGDEKDDEQDDFIDICLSIMEQPQLPGNNNP SQIPIKSIVLDMIGGGTDTTKLTTIWTLSLLLNNPHVLDKAKQEVDAHFR | P. setigerum plant source; full-length amino acid sequence >EPRK-2027940 (also FPYZ- | SEQ. ID NO. 5 |

TABLE 1-continued

Example partial and full-length amino acid sequences of CYP-COR fusion enzymes.

| Sequence | Description | SEQ. ID NO. |
|---|---|---|
| TKRRSTNDAAAAVVDFDDIRNLVYIQAIIKESMRLYPASPVVERLSGED CVVGGFHVPAGTRLWANVWKMQRDPKVWDDPLVFRPDRFLSDEQKM VDVRGQNYELLPFGAGRRVCPGVSFSLDLMQLVLTRLILEFEMKSPSGK VDMTATPGLMSYKVIPLDILLTHRRIKPCVQSAASERDMESSGVPVITLG SGKVMPVLGMGTFEKVGKGSERERLAILKAIEVGYRYFDTAAAYETEE VLGEAIAEALQLGLVKSRDELFISSMLWCTDAHADRVLLALQNSLRNL KLEYVDLYMLPFPASLKPGKITMDIPEEDICRMDYRSVWAAMEECQNL GFTKSIGVSNFSCKKLQELMATANIPPAVNQVEMSPAFQQKKLREYCNA NNILVSAISVLGSNGTPWGSNAVLGSEVLKKIAMAKGKSVAQVSMRWV YEQGASLVVKSFSEERLRENLNIFDWELTKEDHEKIGEIPQCRILSAYFL VSPNGPFKSQEELWDDEA* | 2037562. STDO-2019715. FNXH-2029312, MLPX-2016196, MLPX-2016197) | |
| MELQYISYFQPTSSVVALLLALVSILSSVVVLRKTFLNNYSSSPASSTKTA VLSHQRQQSCALPISGLLHIFMNKNGLIHVTLGNMADKYGPIFSFPTGSH RTLVVSSWEMVKECFTGNNDTAFSNRPIPLAFKTIFYACGGIDSYGLSSV PYGKYWRELRKVCVHNLLSNQQLLKFRHLIISQVDTSFNKLYELCKNSE DNQGNYTTTTTAAGMVRIDDWLAELSFNVIGRIVCGFQSGPKTGAPSRV EQFKEAINEASYFMSTSPVSDNVPMLGWIDQLTGLTRNMKHCGKKLDL VVESIINDHRQKRRFSRTKGGDEKDDEQDDFIDICLSIMEQPQLPGNNNP SQIPIKSIVLDMIGGGTDTTKLTTIWTLSLLLNNPHVLDKAKQEVDAHFR TKRRSTNDAAAAVVDFDDIRNLVYIQALYPASPVVERLSGEDCVVGGF HVPAGTRLWANVWKMQRDPKVWDDPLVFRPDRFLSDEQKMVDVRGQ NYELLPFGAGRRVCPGVSFSLDLMQLVLTRLILEFEMKSPSGKVDMTAT PGLMSYKVIPLDILLTHRRIKPCVQSAASERDMESSGVPVITLGSGKVMP VLGMGTFEKVGKGSERERLAILKAIEVGYRYFDTAAAYETEEVLGEAIA EALQLGLVKSRDELFISSMLWCTDAHADRVLLALQNSLRNLKLEYVDL YMLPFPASLKPGKITMDIPEEDICRMDYRSVWAAMEE | P. setigerum plant source; partial-length amino acid sequence >QCOU-2000833 | SEQ. ID NO. 6 |
| MELQYFSYFQPTSSVVALLLALVSILFSVVVLRKTFSNNYSSPASSTETA VLCHQRQQSCALPISGLLHVFMNKNGLIHVTLGNMADKYGPIFSFPTGS HRTLVVSSWEMVKECFTGNNDTAFSNRPIPLAFQTIFYACGGIDSYGLSS VPYGKYWRELRKVCVHNLLSNQQLLKFRHLIISQVDTSFNKLYELCKNS EDNQGMVRMDDWLAQLSFNVIGRIVCGFQSDPKTGAPSRVEQFKEVIN EASYFMSTSPVSDNVPMLGWIDQLTGLTRNMKHCGKKLDLVVESIIKD HRQKRRFSRTKGGDEKDDEQDDFIDICLSIMEQPQLPGNNSPPQIPIKSIV LDMIGGGTDTTKLTTIWTLSLLLNNPHVLDKAKQEVDAHFRKKRRSTD DAAAAVVDFDDIRNLVYIQAIIKESMRLYPASPVVERLSGEDCVVGGFH VPAGTRLWANVWKMQRDPKVWDDPLVFRPERFLSDEQKMVDVRGQN YELLPFGAGRRICPGVSFSLDLMQLVLTRLILEFEMKSPSGKVDMTATPG LMSYKVVPLDILLTHRRIKSCVQLASSERDMESSGVPVITLSSGKVMPVL GMGTFEKVGKGSERERLAILKAIEVGYRYFDTAAAYETEEVLGEAIAEA LQLGLIESRDELFISSMLWCTDAHPDRVLLALQNSLRNLKLEYLDLYML PFPASLKPGKITMDIPEEDICRMDYRSVWSAMEECQNLGFTKSIGVSNFS SKKLQELMATANIPPAVNQVEMSPAFQQKKLREYCNANNILVSAVSILG SNGTPWGSNAVLGSEVLKQIAMAKGKSVAQVSMRWVYEQGASLVVK SFSEERLRENLNIFDWELTKEDNEKIGEIPQCRILTAYFLVSPNGPFKSQE ELWDDKA* | P. bracteatum plant source; full-length amino acid sequence >SSDU-2015634 (also SSDU-2015636. ZSNV-2027701, RRID-2004435) | SEQ. ID NO. 7 |
| MELQYFSYFQPTSSVVALLLALVSILFSVVVLRKTFSNNYSSPASSTETA VLCHQRQQSCALPISGLLHVFMNKNGLIHVTLGNMADKYGPIFSFPTGS HRTLVVSSWEMVKECFTGNNDTAFSNRPIPLAFQTIFYACGGIDSYGLSS VPYGKYWRELRKVCVHNLLSNQQLLKFRHLIISQVDTSFNKLYELCKNS EDNQGMVRMDDWLAQLSFNVIGRIVCGFQSDPKTGAPSRVEQFKEVIN EASYFMSTSPVSDNVPMLGWIDQLTGLTRNMKHCGKKLDLVVESIIKD HRQKRRFSRTKGGDEKDDEQDDFIDICLSIMEQPQLPGNNSPPQIPIKSIV LDMIGGGTDTTKLTTIWTLSLLLNNPHVLDKAKQEVDAHFRKKRRSTD DAAAAVVDFDDIRNLVYIQAIIKESMRLYPASPVVERLSGEDCVVGGFH VPAGTRLWANVWKMQRDPKVWDDPLVFRPERFLSDEQKMVDVRGQN YELLPFGAGRRICPGVSFSLDLMQLVLTRLILEFEMKSPSGKVDMTATPG LMSYKVVPLDILLTHRRIKSCVQLASSERDMESSGVPVITLSSGKVMPVL GMGTFEKVGKGSERERLAILKAIEVGYRYFDTAAAYETEEVLGEAIAEA LQLGLIESRDELFISSMLWCTDAHPDRVLLALQNSLRNLKLEYLDLYML PFPASLKPGKITMDIPEEDICRMDYRSVWSAMEECQNLGFTKSIGVSNFS CKKLQELMATANIPPAVNQVEMSPAFQQKKLREYCNANNILVSAVSILG SNGTPWGSNAVLGSEVLKQIAMAKGKSVAQVSMRWVYEQGASLVVK SFSEERLRENLNIFDWELTKEDNEKIGEIPQCRILTAYFLVSPNGPFKSQE ELWDDKA* | P. bracteatum plant source; full-length amino acid sequence >TMWO-2027322 (also RRID-2004435) | SEQ. ID NO. 8 |
| SSPASSTETAVLCHQRQQSCALPISGLLHIFMNKNGLIHVTLGNMADKY GPIFSFPTGSHRILVVSSWEMVKECFTGNNDTAFSNRPIPLAFKTIFYACR GIDSYGLSSVPYGKYWRELRKVCVHNLLSNQQLLKFRHLIISQVDTSFN KLYELCKNSEDNQGMVRMDDWLAQLSFSVIGRIVCGFQSDPKTGAPSR VEQFKEAINEASYFMSTSPVSDNVPMLGWIDQLTGLTRNMTHCGKKLD LVVESIINDHRQKRRFSRTKGGDEKDDEQDDFIDICLSIMEQPQLPGNNN PPKIPIKSIVLDMIGAGTDTTKLTIIWTLSLLLNNPNVLAKAKQEVDAHFE | P. bracteatum plant source; partial-length amino acid sequence | SEQ. ID NO. 9 |

TABLE 1-continued

Example partial and full-length amino acid sequences of CYP-COR fusion enzymes.

| Sequence | Description | SEQ. ID NO. |
|---|---|---|
| TKKRSTNEASVVVDFDDIGNLVYIQAIIKESMRLYPVSPVVERLSSEDCV VGGFHVPAGTRLWANVWKMQRDPKVWDDPLVFRPERFLSDEQKMVD VRGQNYELLPFGAGRRICPGVSFSLDLMQLVLTRLILEFEMKSPSGKVD MTATPGLMSYKVVPLDILLTHRRIKSCVQLASSERDMESSGVPITLRSG KVMPVLGMGTFEKAGKGSERERLAILKAIEVGYRYFDTAAAYETEEVL GEAIAEALQLGLIKSRDELFISSMLWCTDAHPDRVLLALQNSLRNLKLE YVDLYMLPFPASLKPGKITMDIPEEDICPMDYRSVWSAMEECQNLGLTK SIGVSNFSCKKLEELMATANIPPAVNQVEMSPAFQQKKLREYCNANNIL VSAVSILGSNGTPWGSNAVLGSEVLKKIAMAKGKSVAQVSMRWVYEQ GASLVVKSFSEERLRENLNIFDWQLTKEDNEKIGEIPQCRILSAYFLVSPK GPFKSQEELWDDKA* | >pbr.PBRS T1PF_89405 | |
| SSPASSTETAVLCHQRQQSCALPISGLLHIFMNKNGLIHVTLGNMADKY GPIFSFPTGSHRILVVSSWEMVKECFTGNNDTFFSNRPIPLAFKIIFYAGG VDSYGLALVPYGKYWRELRKICVHNLLSNQQLLKFRHLIISQVDTSFNK LYELCKNSEDNQGMVRMDDWLAQLSFSVIGRIVCGFQSDPTGAPSRV EQFKEAINEASYFMSTSPVSDNVPMLGWIDQLTGLTRNMTHCGKKLDL VVESIINDHRQKRRFSRTKGGDEKDDEQDDFIDICLSIMEQPQLPGNNNP PKIPIKSIVLDMIGGGTDTTKLTTIWTLSLLLNNPHVLDKAKQEVDAHFL TKRRSTNDAAVVDFDDIRNLVYIQAIIKESMRLYPASPVVERLSGEDCV VGGFHVPAGTRLWVNVWKMQRDPNVWADPMVFRPERFLSHGQKKM VDVRGKNYELLPFGAGRRICPGISFSLDLMQLVLTRLILEFEMKSPSGKV DMTATPGLMSYKVVPLDILLTHRRIKSCVQLASSERDMESSGVPITLRS GKVMPVLGMGTFEKAGKGSERERLAILKAIEVGYRYFDTAAAYETEEV LGEAIAEALQLGLIKSRDELFISSMLWCTDAHPDRVLLALQNSLRNLKLE YVDLYMLPFPASLKPGKITMDIPEEDICPMDYRSVWSAMEECQNLGLTK SIGVSNFSCKKLEELMATANIPPAVNQVEMSPAFQQKKLREYCNANNIL VSAVSILGSNGTPWGSNAVLGSEVLKKIAMAKGKSVAQVSMRWVYEQ GASLVVKSFSEERLRENLNIFDWQLTKEDNEKIGEIPQCRILSAYFLVSPK GPFKSQEELWDDKA* | *P. bracteatum* plant source; partial-length amino acid sequence >pbr.PBRS T1PF_4328 | SEQ. ID NO. 10 |
| SSPASSTETAVLCHQRQQSCALPISGLLHIFMNKNGLIHVTLGNMADKY GPIFSFPTGSHRILVVSSWEMVKECFTGNNDTFFSNRPIPLAFKIIFYAGG VDSYGLALVPYGKYWRELRKICVHNLLSNQQLLKFRHLIISQVDTSFNK LYDLSNKKKNTTTDSGTVRMDDWLAQLSFNVIGRIVCGFQTHTETSATS SVERFTEAIDEASRFMSIATVSDTFPWLGWIDQLTGLTRKMKHYGKKLD LVVESIIEDHRQNRRISGTKQGDDFIDICLSIMEQPQIIPGNDPPRQIPIKS IVLDMIGGGTDTTKLTTTWTLSLLLNNPHVLEKAREEVDAHFGTKRRPT NDDAVMVEFDDIRNLVYIQAIIKESMRLYPASPVVERLSGEDCVVGGFH VPAGTRLWVNVWKMQRDPNVWADPMVFRPERFLSDEQKMVDVRGQ NYELLPFGAGRRICPGVSFSLDLMQLVLTRLILEFEMKSPSGKVDMTATP GLMSYKVVPLDILLTHRRIKSCVQLASSERDMESSGVPITLRSGKVMP VLGMGTFEKAGKGSERERLAILKAIEVGYRYFDTAAAYETEEVLGEAIA EALQLGLIKSRDELFISSMLWCTDAHPDRVLLALQNSLRNLKLEYVDLY MLPFPASLKPGKITMDIPEEDICPMDYRSVWSAMEECQNLGLTKSIGVS NFSCKKLEELMATANIPPAVNQVEMSPAFQQKKLREYCNANNILVSAV SILGSNGTPWGSNAVLGSEVLKKIAMAKGKSVAQVSMRWVYEQGASL VVKSFSEERLRENLNIFDWQLTKEDNEKIGEIPQCRILSAYFLVSPKGPFK SQEELWDDKA* | *P. bracteatum* plant source; partial-length amino acid sequence >pbr.PBRS T1PF_12180 | SEQ. ID NO. 11 |
| VALRKKILKNYYSSSSSTATAVSHQWPKASRALPLIDLLHVFFNKTDLM HVTLGNMADKFGPIFSFPTGSHRTLVVSSWEKAKECFTGNNDIVFSGRP LPLAFKLIFYAGGIDSYGISQVPYGKKWRELRNICVHNILSNQQLLKFRH LMISQVDNSFNKLYEVCNSNKDEGDSATSTTAAGIVRMDDWLGKLAFD VIARIVCGFQSQTETSTTSSMERFTEAMDEASRFMSVTAVSDTVPWLGW IDQLTGLKRNMKHCGKKLNLVVKSIIEDHRQKRRLSSTKKGDENIIDED EQDDFIDICLSIMEQPQLPGNNNPPKIPIKSIVLDMIGGGTDTTKLTTIWTL SLLLNNPHVLDKAKQEVDAHFLTKRRSTNDAAVVDFDDIRNLVYIQAII KESMRLYPASPVVERLSGEDCVVGGFHVPAGTRLWVNVWKMQRDPN VWADPMVFRPERFLSDEQKMVDVRGQNYELLPFGAGRRICPGVSFSLD LMQLVLTRLILEFEMKSPSGKVDMTATPGLMSYKVVPLDILLTHRRIKS CVQLASSERDMESSGVPITLRSGKVMPVLGMGTFEKAGKGSERERLAI LKAIEVGYRYFDTAAAYETEEVLGEAIAEALQLGLIKSRDELFISSMLWC TDAHPDRVLLALQNSLRNLKLEYVDLYMLPFPASLKPGKITMDIPEEDIC PMDYRSVWSAMEECQNLGLTKSIGVSNFSCKKLEELMATANIPPAVNQ VEMSPAFQQKKLREYCNANNILVSAVSILGSNGTPWGSNAVLGSEVLK KIAMAKGKSVAQVSMRWVYEQGASLVVKSFSEERLRENLNIFDWQLT KEDNEKIGEIPQCRILSAYFLVSPKGPFKSQEELWDDKA* | *P. bracteatum* plant source; partial-length amino acid sequence >pbr.PBRS T1PF_4329 | SEQ. ID NO. 12 |
| MELQYFSYFQPTSSVVALLLALVSILFSVVVLRKTFSNNYSSPASSTETA VLCHQRQQSCALPISGLLHVFMNKNGLIHVTLGNMADKYGPIFSFPTGS HRTLVVSSWEMVKECFTGNNDTAFSNRPIPLAFQTIFYACGIDSYGLSS VPYGKYWRELRKVCVHNLLSNQQLLKFRHLIISQVDTSFNKLYELCKNS EDNQGMVRMDDWLAQLSFNVIGRIVCGFQSDPKTGAPSRVEQFKEVIN EASYFMSTSPVSDNVPMLGWIDQLTGLTRNMKHCGKKLDLVVESIIKD | *P. bracteatum* plant source; partial-length amino acid | SEQ. ID NO. 13 |

TABLE 1-continued

Example partial and full-length amino acid sequences of CYP-COR fusion enzymes.

| Sequence | Description | SEQ. ID NO. |
|---|---|---|
| HRQKRRFSRTKGGDEKDDEQDDFIDICLSIMEQPQLPGNNSPPQIPIKSIV LDMIGGGTDTTKLTTIWTLSLLLNNPHVLDKAKQEVDAHFRKKRRSTD DAAAAVVDFDDIRNLVYIQAIIKESMRLYPASPVVERLSGEDCVVGGFH VPAGTRLWANVWKMQRDPKVWDDPLVFRPERFLSDEQKMVDVRGQN YELLPFGAGRRICPGVSFSLDLMQLVLTRLILEFEMKSPSGKVDMTATPG LMSYKVVPLDILLTHRRIKSCVQLASSERDMESSGVPVITLSSGKVMPVL GMGTFEKVGKGSERERLAILKAIEVGYRYFDTAAAYETEEVLGEAIAEA LQLGLIESRDELFISSMLWCTDAHPDRVLLALQNSLRNLKLEYLDLYML PFPASLKPGKITMDIPEEDICRMDYRSVWSAMEECQNLGFTKSIGVSNFS SKKLQELMATANIPPAVNQVEMSPAFQQKKLREYCNANNILVSAVSILG SNGTPWGSNAVLGSEVLKQIAMAKGKSVAQVSMRWVXKFSAYAIVWS LFFGHRICITLYSFLIRNVAYICITY* | sequence | >SSDU-2015635 |
| MELQYFSYFQPTSSVVALLLALVSILFSVVVLRKTFSNNYSSPASSTETA VLCHQRQQSCALPISGLLHVFMNKNGLIHVTLGNMADKYGPIFSFPTGS HRTLVVSSWEMVKECFTGNNDTAFSNRPIPLAFQTIFYACGGIDSYGLSS VPYGKYWRELRKVCVHNLLSNQQLLKFRHLIISQVDTSFNKLYELCKNS EDNQGMVRMDDWLAQLSFNVIGRIVCGFQSDPKTGAPSRVEQFKEVIN EASYFMSTSPVSDNVPMLGWIDQLTGLTRNMKHCGKKLDLVVESIIKD HRQKRRFSRTKGGDEKDDEQDDFIDICLSIMEQPQLPGNNSPPQIPIKSIV LDMIGGGTDTTKLTTIWTLSLLLNNPHVLDKAKQEVDAHFRKKRRSTD DAAAAVVDFDDIRNLVYIQAIIKESMRLYPASPVVERLSGEDCVVGGFH VPAGTRLWANVWKMQRDPKVWDDPLVFRPERFLSDEQKMVDVRGQN YELLPFGAGRRICPGVSFSLDLMQLVLTRLILEFEMKSPSGKVDMTATPG LMSYKVVPLDILLTHRRIKSCVQLASSERDMESSGVPVITLSSGKVMPVL GMGTFEKVGKGSERERLAILKAIEVGYRYFDTAAAYETEEVLGEAIAEA LQLGLIESRDELFISSMLWCTDAHPDRVLLALQNSLRQVFLMQIRLIYIC TYQQVHLNIYFQINEFVLCDMYRNLKLEY | P. bracteatum plant source; partial-length amino acid sequence >SSDU-2015637 | SEQ. ID NO. 14 |
| LNNYSSSPASSTKTAVLSHQRQQSCALPISGLLHIFMNKNGLIHVTLGNM ADKYGPIFSFPTGSHRTLVVSSWEMVKECFTGNNDTAFSNRPIPLAFKTI FYACGGIDSYGLSSVPYGKYWRELRKVCVHNLLSNQQLLKFRHLIISQV DTSFNKLYELCKNSEDNQGNYPTTTTAAGMVRIDDWLAELSFNVIGRIV CGFQSGPKTGAPSRVEQFKEAINEASYFMSTSPVSDNVPMLGWIDQLTG LTRNMKHCGKKLDLVVESIINDHRQKRRFSRTKGGDEKDDEQDDFIDIC LSIMEQPQLPGNNPSQIPIKSIVLDMIGGGTDTTKLTTIWTLSLLLNNPH VLDKAKQEVDAHFRTKRRSTNDAAAAVVDFDDIRNLVYIQAIIKESMR LYPASPVVERLSGEDCVVGGFHVPAGTRLWANVWKMQRDPKVWDDP LVFRPDRFLSDEQKMVDVRGQNYELLPFGAGRRVCPGVSFSLDLMQLV LTRLILEFEMKSPSGKVDMTATPGLMSYKVIPLDILLTHRRIKPCVQSAA SERDMESSGVPVITLGSGKVMPVLGMGTFEKVGKGSERERLAFLKAIEV GYRYFDTAAAYETEEFLGEAIAEALQLGLIKSRDELFITSKLWPCDAHPD LVVPALQNSLRNLKLEYVDLYMLPFPASLKPGKITMDIPEEDICRMDYR SVWAAMEECQNLGFTKSIGVSNFSCKKLQELMATANIPPAVNQVEMSP AFQQKKLREYCNANNILVSAISVLGSNGTPWGSNAVLGSEVLKKIAMA KGKSVAQVSMRWVYEQGASLVVKSFSEERLRENLNIFDWELTKEDHEK IGEIPQCRILSAYFLVSPNGPFKSQEELWDDEA* | C. majus plant source; partial-length amino acid sequence >chm.CMAST2PF_14984 | SEQ. ID NO. 15 |

BisBIA Generating Modifications

Some methods, processes, and systems provided herein describe the production of bisbenzylisoquinoline alkaloids (bisBIAs). BisBIAs are dimeric molecules that may be formed by coupling reactions between two BIA monomers. In examples, bisBIAs may be formed by carbon-oxygen coupling reactions. In other examples, bisBIAs may be formed by carbon-carbon coupling reactions. In some examples, the bisBIA dimeric molecule is a homodimer, comprising two identical BIA monomers. In examples, an engineered host cell may produce one BIA monomer. In these examples, the BIA monomers may form homodimers when contacted with one or more coupling enzymes. In other examples, the bisBIA dimeric molecule is a heterodimer, comprising two different BIA monomers. For example, a bisBIA may be a heterodimer that comprises BIA monomers that are enantiomers of each other. In some examples, an engineered host cell may produce two or more BIA monomers. In these examples, the BIA monomers may form homodimers and heterodimers when contacted with one or more coupling enzymes.

Some of these methods, processes, and systems that describe the production of bisBIAs may comprise an engineered host cell. In some examples, the engineered host cell may be engineered to produce BIA monomers which, in turn, may be used as building block molecules for forming bisBIAs. Examples of BIA monomers that may be used to form bisBIAs include coclaurine, N-methylcoclaurine, laudanine, norcoclaurine, norlaudanosoline, 6-O-methyl-norlaudanosoline, 3'-hydroxy-N-methylcoclaurine, 3'-hydroxycoclaurine, reticuline, norreticuline, norlaudanine, laudanosine, and papaverine. In particular, engineered host cells may synthesize BIA monomers from norcoclaurine or norlaudanosoline by expression of heterologous enzymes including O-methyltransferases, N-methyltransferases, and 3'-hydroxylases. Examples of O-methyltransferases may include norcoclaurine 6-O-methyltransferase (6 OMT) from *Thalicrum flavum, Nelumbo nucifera, Populus euphratica*, or another species. Further examples of O-methyltransferases may include catechol O-methyltransferase (COMT) from *Homo sapiens, Mus musculus, Rattus norvegicus, Gorilla gorilla*, or another species. Further examples of N-methyltransferases may include coclaurine N-methyltransferase (CNMT) from *T. flavum, N. nucifera, Aristolochia fimbriata*, or another species. Examples of 3'hydroxylases may include N-methylcoclaurine 3'-hydroxylase (CYP80B1) from *Eschscholzia californica, T. flavum, N. nucifera*, or another species.

The engineered host cells may produce either (S) or (R) enantiomers of any given BIA monomer. Additionally or alternatively, the engineered host cells may produce a mixture of both enantiomers. The ratio of (S) and (R) enantiomers may be determined by the substrate and product specificities of the one or more enzymes that synthesize the BIA monomers. Alternatively, the amount of each enantiomer present may be modified by the expression of an additional enzyme or enzymes that perform the epimerization of one stereoisomer into another, as discussed above.

These BIA monomers may be fused into a dimeric bisBIA scaffold. In particular, the BIA monomers may be fused into a dimeric bisBIA scaffold utilizing one or more enzymes that are produced by the engineered host cell. Additionally or alternatively, the BIA monomers may be fused into a dimeric bisBIA scaffold utilizing one or more enzymes that are provided to the BIA monomers from a source that is external to the engineered host cell. The one or more enzymes may be used to form carbon-oxygen and/or carbon-carbon coupling reactions to fuse two BIA monomers at one, two, or three positions. In some examples, two BIA monomers may be linked by an ether bridge. In some examples, a direct carbon-carbon bond may be used to connect the two BIA monomers. In some examples, a bisBIA that is formed by fusing two BIA monomers may comprise one diphenyl ether linkage. In some examples, two BIA monomers may be fused to form a bisBIA that comprises two diphenyl ether linkages. In some examples, a bisBIA that is formed from two BIA monomers may comprise three diphenyl ether linkages. In some examples, the bisBIA may comprise one diphenyl ether linkage and one benzyl phenyl ether linkage. In some cases, the bisBIA may comprise one benzyl phenyl ether linkage and two diphenyl ether linkages.

In examples, the BIA monomers may be contacted with a sufficient amount of the one or more enzymes that may be used to form coupling reactions to fuse two BIA monomers such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said BIA monomers are converted to bisBIAs. The one or more enzymes that may be used to dimerize the BIA monomers into bisBIAs may contact the BIA monomers in vitro. Additionally, or alternatively, the one or more enzymes that may be used to dimerize the BIA monomers into bisBIAs may contact the BIA monomers in vivo. Additionally, the one or more bisBIA dimerizing enzyme may be expressed in a host cell that produces BIA monomers. Alternatively, the BIA monomers may be provided to the engineered host cell that expresses the bisBIA dimerizing enzyme. Alternatively, the one or more bisBIA dimerizing enzymes may be provided to a cell having BIA monomers within.

In some examples, the bisbenzylisoquinoline alkaloid is a compound of any one of Formulas Va-Vu:

Formula Va
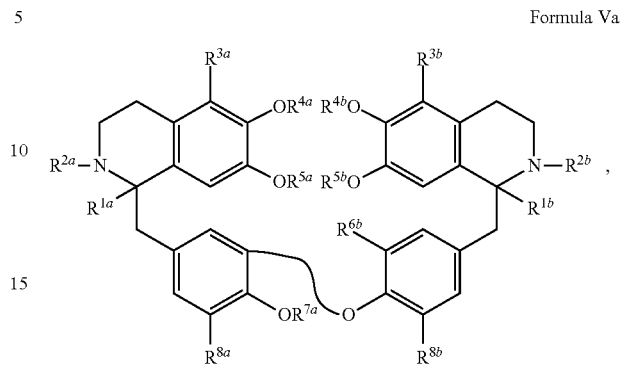

Formula Vb
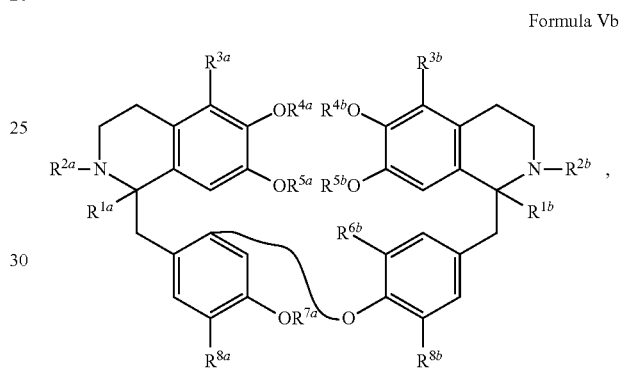

Formula Vc
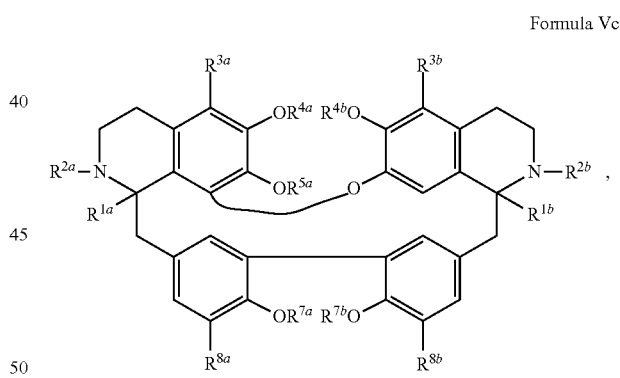

Formula Vd
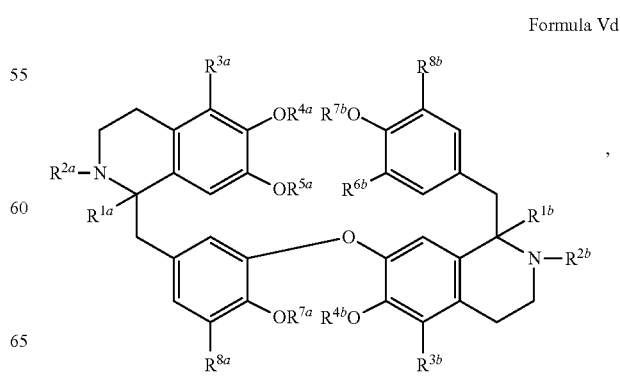

-continued
Formula Ve
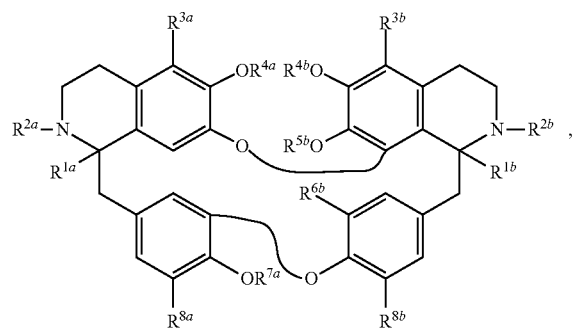
Formula Vf
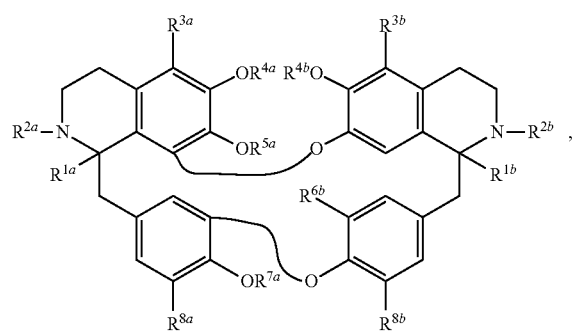
Formula Vg
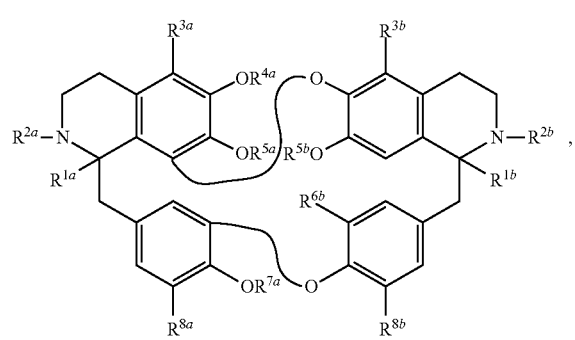
Formula Vh
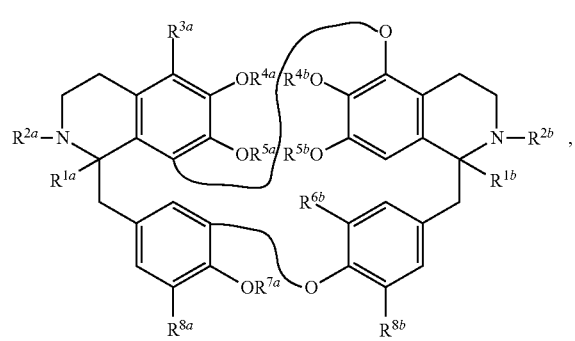
Formula Vi
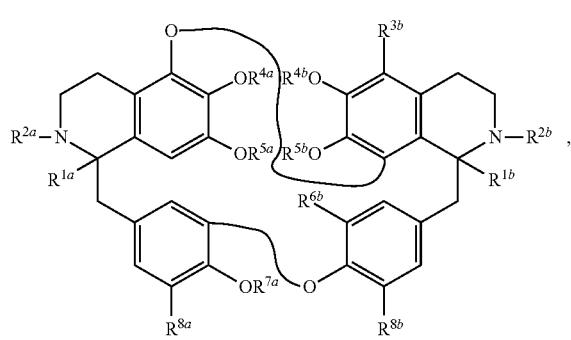
Formula Vj
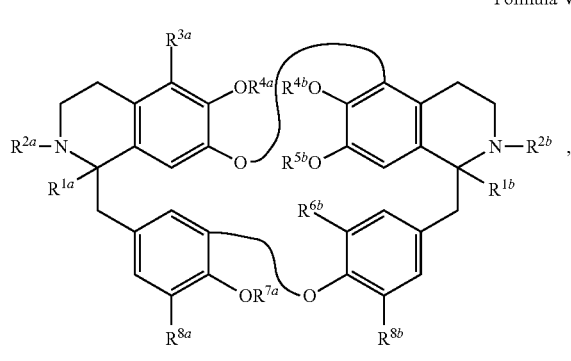
Formula Vk
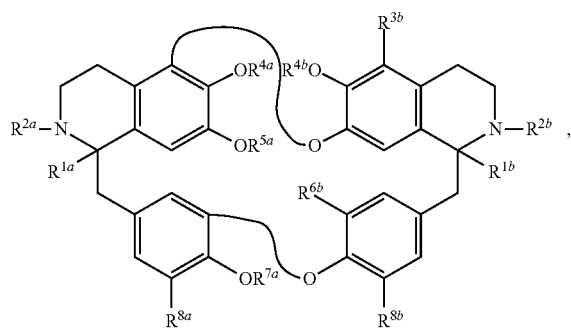
Formula Vl
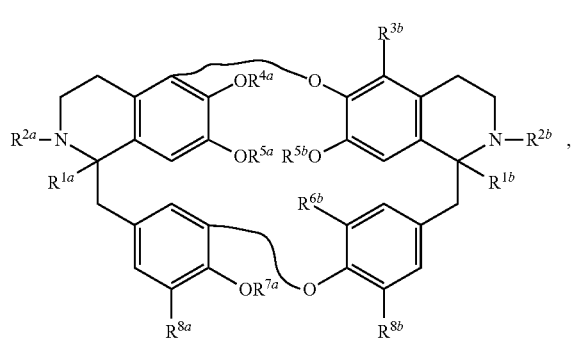

-continued
Formula Vm
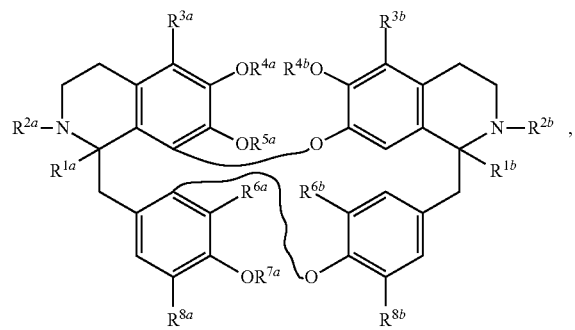
Formula Vn
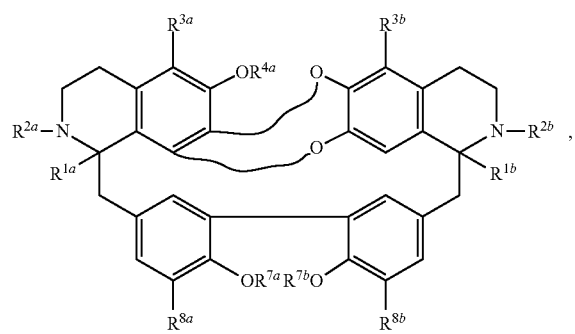
Formula Vo
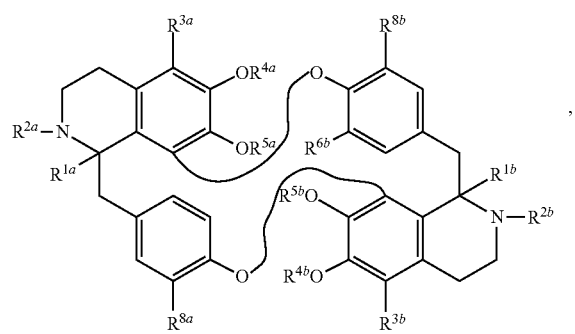
Formula Vp
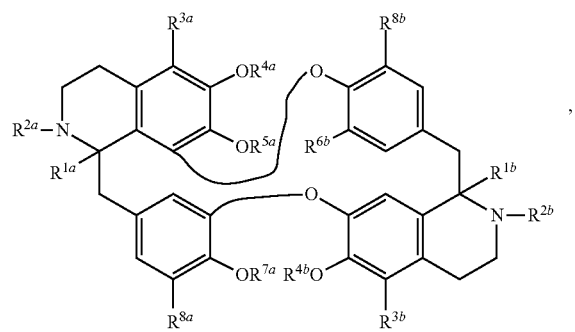
Formula Vq
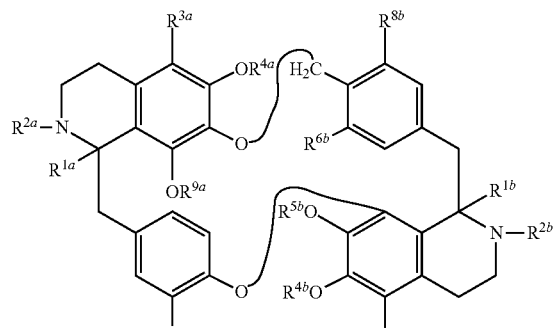
Formula Vr
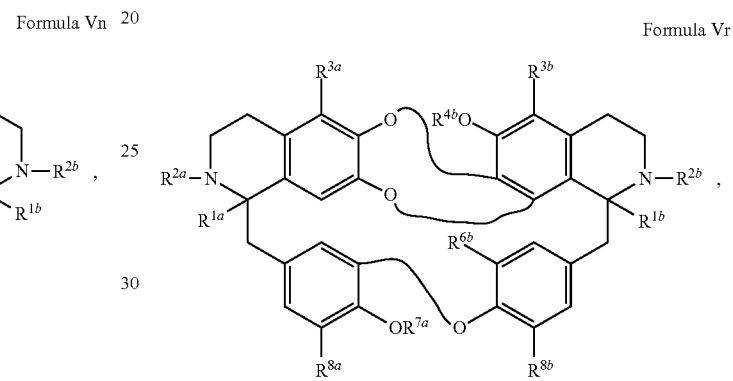
Formula Vs
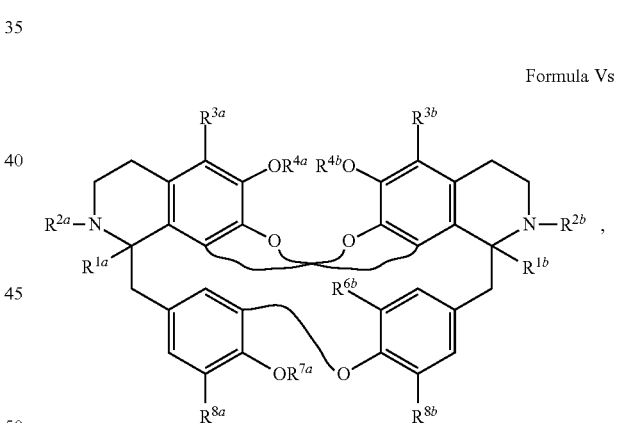
Formula Vt
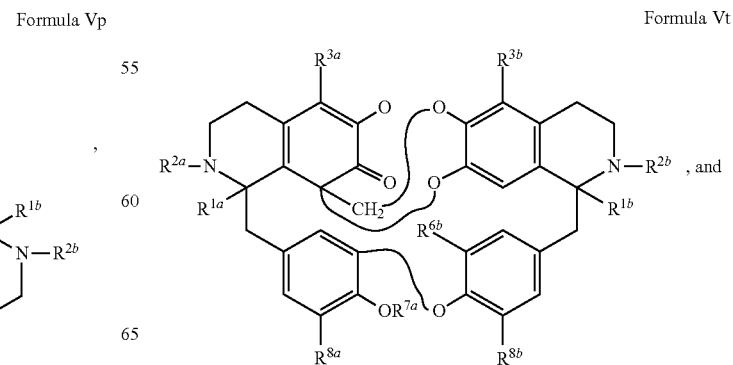
, and -continued Formula Vu

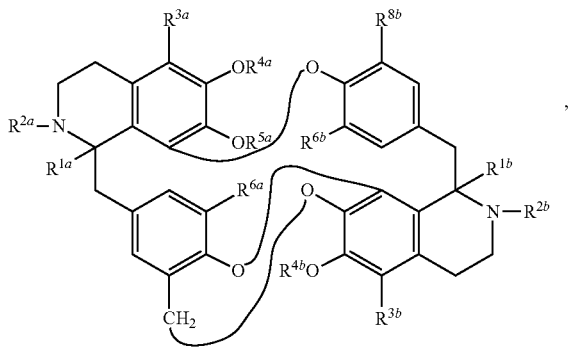

or a salt thereof, wherein:
$R^{1a}$, $R^{1b}$, $R^{2a}$, and $R^{2b}$ are independently selected from hydrogen and $C_1$-$C_4$ alkyl;
$R^3$, $R^{3b}$, $R^{6a}$, $R^{6b}$, $R^{8a}$, and $R^{8b}$ are independently selected from hydrogen, hydroxy, fluoro, chloro, bromo, carboxaldehyde, $C_1$-$C_4$ acyl, $C_1$-$C_4$ alkyl, and $C_1$-$C_4$ alkoxy;
$R^{4a}$ and $R^{5a}$ are independently selected from hydrogen and $C_1$-$C_4$ alkyl, or $R^{4a}$ and $R^{5a}$ together form a methylene bridge;
$R^{4b}$ and $R^{5b}$ are independently selected from hydrogen and $C_1$-$C_4$ alkyl, or $R^{4b}$ and $R^{5b}$ together form a methylene bridge; and
$R^{7a}$, $R^{7b}$, and $R^{9a}$ are independently selected from hydrogen and $C_1$-$C_4$ alkyl.

In some examples, $R^{1a}$ and $R^{1b}$ are each hydrogen; $R^{2a}$ and $R^{2b}$ are each methyl; $R^{3a}$ and $R^{3b}$ are each hydrogen; $R^{4a}$ and $R^{5a}$ are independently hydrogen or methyl; $R^{4b}$ and $R^{5b}$ are independently hydrogen or methyl, or $R^{4b}$ and $R^{5b}$ together form a methylene bridge; $R^{6a}$, $R^{6b}$, $R^{8a}$, and $R^{8b}$ are each hydrogen; and $R^{7a}$, $R^{7b}$, and $R^{9a}$ are independently hydrogen or methyl.

As illustrated above, the bisBIA compounds of Formulas Va, Vb, and Vd are formed by fusing two BIA monomers using a carbon-oxygen coupling reaction. Additionally, the bisBIA compounds of Formulas Vc, Vf, and Vh are formed by fusing two BIA monomers using both a carbon-oxygen coupling reaction and a carbon-carbon coupling reaction. Further, the bisBIA compounds of Formulas Ve, Vg, Vi, Vj, Vk, Vl, Vm, Vo, Vp, and Vq are formed by fusing two BIA monomers using two carbon-oxygen coupling reactions. The bisBIA compound of Formula Vn is formed by fusing two BIA monomers using two carbon-oxygen coupling reactions and a carbon-carbon coupling reaction. Additionally, the bisBIA compound of Formula Vr is formed by fusing two BIA monomers using three carbon-oxygen coupling reactions.

The one or more enzymes that may be used to form the coupling reactions may include known cytochrome P450s such as *Berberis stolonifera* CYP80A1 or similar cytochrome P450 enzymes from other plants that naturally synthesize these compounds. Alternatively, the coupling reaction may be performed by an enzyme that is not a cytochrome P450. The one or more enzymes that may be used to form the coupling reactions may be engineered to accept non-native substrates. Accordingly, the one or more enzymes that may be used to form the coupling reactions may be used to generate non-natural bisBIA molecules. In examples, the one or more enzymes may fuse a natural BIA monomer with a non-natural BIA monomer to produce a non-natural bisBIA molecule. In other examples, the one or more enzymes may fuse two non-natural BIA monomers to produce a non-natural bisBIA molecule. Enzyme engineered strategies may be used to identify one or more enzymes that may be used to form the coupling reactions that fuse BIA monomers to produce bisBIAs. In examples, enzyme engineering strategies may include site directed mutagenesis, random mutagenesis and screening, DNA shuffling, and screening.

Once bisBIAs are formed, the bisBIAs may be further derivatized or modified. The bisBIAs may be derivatized or modified utilizing one or more enzymes that are produced by the engineered host cell. In particular, the bisBIAs may be derivatized or modified by contacting the bisBIAs with one or more enzymes that are produced by the engineered host cell. Additionally or alternatively, the bisBIAs may be derivatized or modified by contacting the bisBIAs with one or more enzymes that are provided to the bisBIAs from a source that is external to the engineered host cell. The one or more enzymes that may be used to derivatize or modify the bisBIAs may be used to perform tailoring reactions. Examples of tailoring reactions include oxidation, reduction, O-methylation, N-methylation, O-demethylation, acetylation, methylenedioxybridge formation, and O,O-demethylenation. A bisBIA may be derivatized or modified using one or more tailoring reactions.

Examples of tailoring reactions are provided in Table 3. In some examples, tailoring enzymes may be used to catalyze carbon-carbon coupling reactions performed on a bisBIA, or a derivative thereof. Examples of tailoring enzymes that may be used to catalyze carbon-carbon coupling reactions include a Berberine bridge enzyme (BBE) from *Papaver somniferum, Eschscholzia californica, Coptis japonica, Berberis stolonifer, Thalictrum flavum*, or another species; Salutaridine synthase (SalSyn) from *Papaver somniferum* or another species; and Corytuberine synthase (CorSyn) from *Coptis japonica* or another species. Non-limiting examples of reactions that can be catalyzed by tailoring enzymes are shown in Scheme 2, wherein $R^a$, $R^b$, $R^c$, and $R^d$ are independently selected from hydrogen, hydroxy, fluoro, chloro, bromo, carboxaldehyde, $C_1$-$C_4$ acyl, $C_1$-$C_4$ alkyl, and $C_1$-$C_4$ alkoxy. In some examples, $R^a$, $R^b$, and the carbon atoms to which they are attached optionally form a carbocycle or heterocycle. In some examples, $R^c$, $R_d$, and the carbon atoms to which they are attached optionally form a carbocycle or heterocycle.

Scheme 2

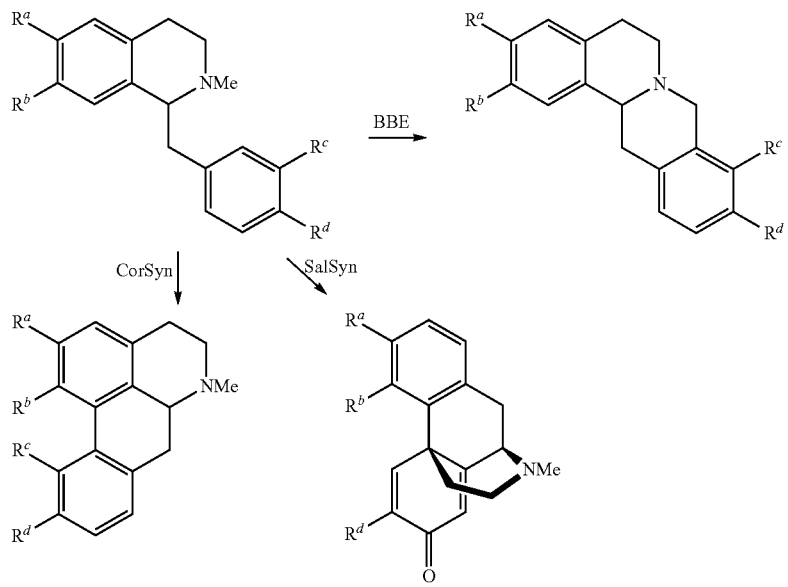

In some examples, tailoring enzymes may be used to catalyze oxidation reactions performed on a bisBIA, or a derivative thereof. Examples of tailoring enzymes that may be used to catalyze oxidation reactions include a Tetrahydroprotoberberine oxidase (STOX) from *Coptis japonica, Argemone mexicana, Berberis wilsonae*, or another species; Dihydrobenzophenanthridine oxidase (DBOX) from *Papaver somniferum* or another species; Methylstylopine hydroxylase (MSH) from *Papaver somniferum* or another species; and Protopine 6-hydroxylase (P6H) from *Papaver somniferum, Eschscholzia californica*, or another species.

Tailoring enzymes may also be used to catalyze methylenedioxy bridge formation reactions performed on a bisBIA, or a derivative thereof. Examples of tailoring enzymes that may be used to catalyze methylenedioxy bridge formation reactions include a Stylopine synthase (StySyn) from *Papaver somniferum, Eschscholzia californica, Argemone mexicana*, or another species; Cheilanthifoline synthase (CheSyn) from *Papaver somniferum, Eschscholzia californica, Argemone mexicana*, or another species; and Canadine synthase (CAS) from *Thalictrum flavum, Coptis chinensis*, or another species.

In other examples, tailoring enzymes may be used to catalyze O-methylation reactions performed on a bisBIA, or a derivative thereof. Examples of tailoring enzymes that may be used to catalyze O-methylation reactions include a Norcoclaurine 6-O-methyltransferase (6OMT) from *Papaver somniferum, Thalictrum flavum, Coptis japonica, Papaver bracteatum*, or another species; 3'hydroxy-N-methylcoclaurine 4'-O-methyltransferase (4'OMT) from *Papaver somniferum, Thalictrum flavum, Coptis japonica, Coptis chinensis*, or another species; Reticuline 7-O-methyltransferase (7OMT) from *Papaver somniferum, Eschscholzia californica*, or another species; and Scoulerine 9-O-methyltransferase (9OMT) from *Papaver somniferum, Thalictrum flavum, Coptis japonica, Coptis chinensis*, or another species.

Additionally, tailoring enzymes may be used to catalyze N-methylation reactions performed on a bisBIA, or a derivative thereof. Examples of tailoring enzymes that may be used to catalyze N-methylation reactions include Coclaurine N-methyltransferase (CNMT) from *Papaver somniferum, Thalictrum flavum, Coptis japonica*, or another species; Tetrahydroprotoberberine N-methyltransferase (TNMT) from *Papaver somniferum, Eschscholzia californica, Papaver bracteatum*, or another species.

Further, tailoring enzymes may be used to catalyze O-demethylation reactions performed on a bisBIA, or a derivative thereof. Examples of tailoring enzymes that may be used to catalyze O-demethylation reactions include Thebaine demethylase (T6ODM) from *Papaver somniferum* or another species; and Codeine demethylase (CODM) from *Papaver somniferum*, or another species.

Tailoring enzymes may also be used to catalyze reduction reactions performed on a bisBIA, or a derivative thereof. Examples of tailoring enzymes that may be used to catalyze reduction reactions include Salutaridine reductase (SalR) from *Papaver somniferum, Papaver bracteatum*, or another species; Codeinone reductase (COR) from *Papaver somniferum* or another species; and Sanguinarine reductase (SanR) from *Eschscholzia californica* or another species. In other examples, tailoring enzymes may be used to catalyze acetylation reactions performed on a bisBIA, or a derivative thereof. An example of a tailoring enzyme that may be used to catalyze acetylation reactions includes Salutaridine acetyltransferase (SalAT) from *Papaver somniferum* or another species.

Heterologous Coding Sequences

In some instances, the engineered host cells harbor one or more heterologous coding sequences (such as two or more, three or more, four or more, five or more) which encode activity(ies) that enable the engineered host cells to produce desired enzymes of interest and/or BIAs of interest, e.g., as described herein. As used herein, the term "heterologous coding sequence" is used to indicate any polynucleotide that codes for, or ultimately codes for, a peptide or protein or its equivalent amino acid sequence, e.g., an enzyme, that is not normally present in the host organism and may be expressed in the host cell under proper conditions. As such, "heterologous coding sequences" includes multiple copies of coding sequences that are normally present in the host cell, such that the cell is expressing additional copies of a coding sequence that are not normally present in the cells. The heterologous coding sequences may be RNA or any type thereof, e.g., mRNA, DNA or any type thereof, e.g., cDNA, or a hybrid of RNA/DNA. Coding sequences of interest include, but are not limited to, full-length transcription units that include such features as the coding sequence, introns, promoter regions, 3'-UTRs, and enhancer regions.

In examples, the engineered host cells may comprise a plurality of heterologous coding sequences each encoding an enzyme, such as an enzyme listed in Table 2. In some examples, the plurality of enzymes encoded by the plurality of heterologous coding sequences may be distinct from each other. In some examples, some of the plurality of enzymes encoded by the plurality of heterologous coding sequences may be distinct from each other and some of the plurality of enzymes encoded by the plurality of heterologous coding sequences may be duplicate copies.

In some examples, the heterologous coding sequences may be operably connected. Heterologous coding sequences that are operably connected may be within the same pathway of producing a particular benzylisoquinoline alkaloid product and/or epimerase product. In some examples, the operably connected heterologous coding sequences may be directly sequential along the pathway of producing a particular benzylisoquinoline alkaloid product and/or epimerase product. In some examples, the operably connected heterologous coding sequences may have one or more native enzymes between one or more of the enzymes encoded by the plurality of heterologous coding sequences. In some examples, the heterologous coding sequences may have one or more heterologous enzymes between one or more of the enzymes encoded by the plurality of heterologous coding sequences. In some examples, the heterologous coding sequences may have one or more non-native enzymes between one or more of the enzymes encoded by the plurality of heterologous coding sequences.

The engineered host cells may also be modified to possess one or more genetic alterations to accommodate the heterologous coding sequences. Alterations of the native host genome include, but are not limited to, modifying the genome to reduce or ablate expression of a specific protein that may interfere with the desired pathway. The presence of such native proteins may rapidly convert one of the intermediates or final products of the pathway into a metabolite or other compound that is not usable in the desired pathway. Thus, if the activity of the native enzyme were reduced or altogether absent, the produced intermediates would be more readily available for incorporation into the desired product.

Heterologous coding sequences include but are not limited to sequences that encode enzymes, either wild-type or equivalent sequences, that are normally responsible for the production of BIAs of interest in plants. In some cases, the enzymes for which the heterologous sequences code may be any of the enzymes in the 1-BIA pathway, and may be from any convenient source. The choice and number of enzymes encoded by the heterologous coding sequences for the particular synthetic pathway may be selected based upon the desired product. In certain embodiments, the host cells of the invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more heterologous coding sequences, such as 1, 2, 3, 4, 5, 6, 7, 8, 9, 10, 11, 12, 13, 14, or 15 heterologous coding sequences.

As used herein, the term "heterologous coding sequences" also includes the coding portion of the peptide or enzyme, i.e., the cDNA or mRNA sequence, of the peptide or enzyme, as well as the coding portion of the full-length transcriptional unit, i.e., the gene including introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences may have a deletion of one or more amino acids, with the deletion being N-terminal, C-terminal, or internal. Truncated forms are envisioned as long as they have the catalytic capability indicated herein. Fusions of two or more enzymes are also envisioned to facilitate the transfer of metabolites in the pathway, provided that catalytic activities are maintained.

Operable fragments, mutants, or truncated forms may be identified by modeling and/or screening. In some cases, this is achieved by deletion of, for example, N-terminal, C-terminal, or internal regions of the protein in a step-wise fashion, followed by analysis of the resulting derivative with regard to its activity for the desired reaction compared to the original sequence. If the derivative in question operates in this capacity, it is considered to constitute an equivalent derivative of the enzyme proper.

In examples, some heterologous proteins may show occurrences where they are incorrectly processed when expressed in a recombinant host. For example, plant proteins such as cytochrome P450 enzymes expressed in microbial production hosts may have occurrences of incorrect processing. In particular, salutaridine synthase may undergo N-linked glycosylation when heterologously expressed in yeast. This N-linked glycosylation may not be observed in plants, which may be indicative of incorrect N-terminal sorting of the nascent SalSyn transcript so as to reduce the activity of the enzyme in the heterologous microbial host. In such examples, protein engineering directed at correcting N-terminal sorting of the nascent transcript so as to remove the N-linked glycosylation pattern may result in improved activity of the salutaridine synthase enzyme in the recombinant production host. This is explained further in Example 10 below.

Aspects of the invention also relate to heterologous coding sequences that code for amino acid sequences that are equivalent to the native amino acid sequences for the various enzymes. An amino acid sequence that is "equivalent" is defined as an amino acid sequence that is not identical to the specific amino acid sequence, but rather contains at least some amino acid changes (deletions, substitutions, inversions, insertions, etc.) that do not essentially affect the biological activity of the protein as compared to a similar activity of the specific amino acid sequence, when used for a desired purpose. The biological activity refers to, in the example of an epimerase, its catalytic activity. Equivalent sequences are also meant to include those which have been engineered and/or evolved to have properties different from the original amino acid sequence. Mutable properties of interest include catalytic activity, substrate specificity, selectivity, stability, solubility, localization, etc.

In some instances, the expression of each type of enzyme is increased through additional gene copies (i.e., multiple copies), which increases intermediate accumulation and/or BIA of interest production. Embodiments of the invention include increased BIA of interest production in a host cell through simultaneous expression of multiple species variants of a single or multiple enzymes. In some cases, additional gene copies of a single or multiple enzymes are included in the host cell. Any convenient methods may be utilized including multiple copies of a heterologous coding sequence for an enzyme in the host cell.

Figure 28:
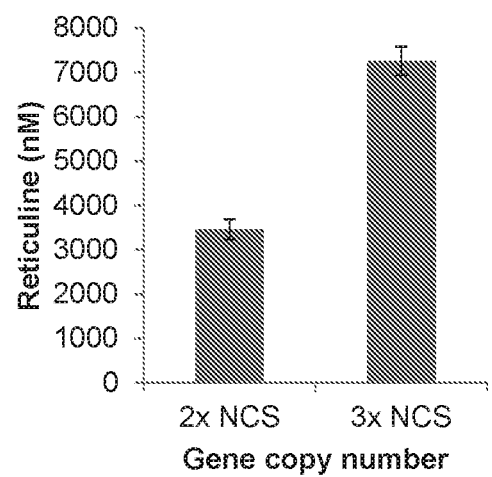
FIG. 28 illustrates increased production of the benzylisoquinoline alkaloid reticuline by increasing the copy number of the NCS gene from two copies to three copies in an engineered yeast strain, in accordance with embodiments of the invention.

In some examples, the engineered host cell includes multiple copies of a heterologous coding sequence for an enzyme, such as 2 or more, 3 or more, 4 or more, 5 or more, or even 10 or more copies. An example of this is described in FIG. 28. In particular, FIG. 28 illustrates increased production of the benzylisoquinoline alkaloid reticuline by increasing the copy number of the NCS gene from two copies to three copies in an engineered yeast strain.

In certain embodiments, the engineered host cell includes multiple copies of heterologous coding sequences for one or more enzymes, such as multiple copies of two or more, three or more, four or more, etc. In some cases, the multiple copies of the heterologous coding sequence for an enzyme are derived from two or more different source organisms as compared to the host cell. For example, the engineered host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

The engineered host cell medium may be sampled and monitored for the production of BIAs of interest. The BIAs of interest may be observed and measured using any convenient methods. Methods of interest include, but are not limited to, LC-MS methods (e.g., as described herein) where a sample of interest is analyzed by comparison with a known amount of a standard compound. Additionally, there are other ways that BIAs of interest may be observed and/or measured. Examples of alternative ways of observing and/or measuring BIAs include GC-MS, UV-vis spectroscopy, NMR, LC-NMR, LC-UV, TLC, capillary electrophoresis, among others. Identity may be confirmed, e.g., by m/z and MS/MS fragmentation patterns, and quantitation or measurement of the compound may be achieved via LC trace peaks of know retention time and/or EIC MS peak analysis by reference to corresponding LC-MS analysis of a known amount of a standard of the compound.

Additionally, a culture of the engineered host cell may be sampled and monitored for the production of enzymes of interest, such as a CYP-COR enzyme. The enzymes of interest may be observed and measured using any convenient methods. Methods of interest include enzyme activity assays, polyacrylamide gel electrophoresis, carbon monoxide spectroscopy, and western blot analysis.

Methods
Process Steps

As summarized above, aspects of the invention include methods of preparing benzylisoquinoline alkaloids (BIAs) of interest. Additionally, aspects of the invention include methods of preparing enzymes of interest. As such, aspects of the invention include culturing an engineered host cell under conditions in which the one or more host cell modifications (e.g., as described herein) are functionally expressed such that the cell converts starting compounds of interest into product enzymes and/or BIAs of interest. Also provided are methods that include culturing an engineered host cell under conditions suitable for protein production such that one or more heterologous coding sequences are functionally expressed and convert starting compounds of interest into product enzymes or BIAs of interest. In examples, the method is a method of preparing a benzylisoquinoline alkaloid (BIA) that includes culturing an engineered host cell (e.g., as described herein); adding a starting compound to the cell culture; and recovering the BIA from the cell culture. In some examples, the method is a method of preparing an enzyme that includes culturing an engineered host cell (e.g., as described herein); adding a starting compound to the cell culture; and recovering the enzyme from the cell culture.

Fermentation media may contain suitable carbon substrates. The source of carbon suitable to perform the methods of this disclosure may encompass a wide variety of carbon containing substrates. Suitable substrates may include, without limitation, monosaccharides (e.g., glucose, fructose, galactose, xylose), oligosaccharides (e.g., lactose, sucrose, raffinose), polysaccharides (e.g., starch, cellulose), or a combination thereof. In some cases, unpurified mixtures from renewable feedstocks may be used (e.g., cornsteep liquor, sugar beet molasses, barley malt). In some cases, the carbon substrate may be a one-carbon substrate (e.g., methanol, carbon dioxide) or a two-carbon substrate (e.g., ethanol). In other cases, other carbon containing compounds may be utilized, for example, methylamine, glucosamine, and amino acids.

Any convenient methods of culturing engineered host cells may be employed for producing the enzymes and/or BIAs of interest. The particular protocol that is employed may vary, e.g., depending on the engineered host cell, the heterologous coding sequences, the enzymes of interest, the BIAs of interest, etc. The cells may be present in any convenient environment, such as an environment in which the cells are capable of expressing one or more functional heterologous enzymes. In some embodiments, the cells are cultured under conditions that are conducive to enzyme expression and with appropriate substrates available to allow production of enzymes and/or BIAs of interest in vivo. In some embodiments, the functional enzymes are extracted from the engineered host for production of enzymes and/or BIAs of interest under in vitro conditions. In some instances, the engineered host cells are placed back into a multicellular host organism. The engineered host cells are in any phase of growth, including, but not limited to, stationary phase and log-growth phase, etc. In addition, the cultures themselves may be continuous cultures or they may be batch cultures.

Cells may be grown in an appropriate fermentation medium at a temperature between 14-40° C. Cells may be grown with shaking at any convenient speed (e.g., 200 rpm). Cells may be grown at a suitable pH. Suitable pH ranges for the fermentation may be between pH 5-9. Fermentations may be performed under aerobic, anaerobic, or microaerobic conditions. Any suitable growth medium may be used. Suitable growth media may include, without limitation, common commercially prepared media such as synthetic defined (SD) minimal media or yeast extract peptone dextrose (YEPD) rich media. Any other rich, defined, or synthetic growth media appropriate to the microorganism may be used.

Cells may be cultured in a vessel of essentially any size and shape. Examples of vessels suitable to perform the methods of this disclosure may include, without limitation, multi-well shake plates, test tubes, flasks (baffled and non-baffled), and bioreactors. The volume of the culture may range from 10 microliters to greater than 10,000 liters.

The addition of agents to the growth media that are known to modulate metabolism in a manner desirable for the production of alkaloids may be included. In a non-limiting example, cyclic adenosine 2'3'-monophosphate may be added to the growth media to modulate catabolite repression.

Any convenient cell culture conditions for a particular cell type may be utilized. In certain embodiments, the host cells that include one or more modifications are cultured under standard or readily optimized conditions, with standard cell culture media and supplements. As one example, standard growth media when selective pressure for plasmid maintenance is not required may contain 20 g/L yeast extract, 10 g/L peptone, and 20 g/L dextrose (YPD). Host cells containing plasmids are grown in synthetic complete (SC) media containing 1.7 g/L yeast nitrogen base, 5 g/L ammonium sulfate, and 20 g/L dextrose supplemented with the appropriate amino acids required for growth and selection. Alternative carbon sources which may be useful for inducible enzyme expression include, but are not limited to, sucrose, raffinose, and galactose. Cells are grown at any convenient temperature (e.g., 30° C.) with shaking at any convenient rate (e.g., 200 rpm) in a vessel, e.g., in test tubes or flasks in volumes ranging from 1-1000 mL, or larger, in the laboratory.

Culture volumes may be scaled up for growth in larger fermentation vessels, for example, as part of an industrial process. The industrial fermentation process may be carried out under closed-batch, fed-batch, or continuous chemostat conditions, or any suitable mode of fermentation. In some cases, the cells may be immobilized on a substrate as whole cell catalysts and subjected to fermentation conditions for alkaloid production.

A batch fermentation is a closed system, in which the composition of the medium is set at the beginning of the fermentation and not altered during the fermentation process. The desired organism(s) are inoculated into the medium at the beginning of the fermentation. In some instances, the batch fermentation is run with alterations made to the system to control factors such as pH and oxygen concentration (but not carbon). In this type of fermentation system, the biomass and metabolite compositions of the system change continuously over the course of the fermentation. Cells typically proceed through a lag phase, then to a log phase (high growth rate), then to a stationary phase (growth rate reduced or halted), and eventually to a death phase (if left untreated).

A continuous fermentation is an open system, in which a defined fermentation medium is added continuously to the bioreactor and an equal amount of fermentation media is continuously removed from the vessel for processing. Continuous fermentation systems are generally operated to maintain steady state growth conditions, such that cell loss due to medium being removed must be balanced by the growth rate in the fermentation. Continuous fermentations are generally operated at conditions where cells are at a constant high cell density. Continuous fermentations allow for the modulation of one or more factors that affect target product concentration and/or cell growth.

The liquid medium may include, but is not limited to, a rich or synthetic defined medium having an additive component described above. Media components may be dissolved in water and sterilized by heat, pressure, filtration, radiation, chemicals, or any combination thereof. Several media components may be prepared separately and sterilized, and then combined in the fermentation vessel. The culture medium may be buffered to aid in maintaining a constant pH throughout the fermentation.

Process parameters including temperature, dissolved oxygen, pH, stirring, aeration rate, and cell density may be monitored or controlled over the course of the fermentation. For example, temperature of a fermentation process may be monitored by a temperature probe immersed in the culture medium. The culture temperature may be controlled at the set point by regulating the jacket temperature. Water may be cooled in an external chiller and then flowed into the bioreactor control tower and circulated to the jacket at the temperature required to maintain the set point temperature in the vessel.

Additionally, a gas flow parameter may be monitored in a fermentation process. For example, gases may be flowed into the medium through a sparger. Gases suitable for the methods of this disclosure may include compressed air, oxygen, and nitrogen. Gas flow may be at a fixed rate or regulated to maintain a dissolved oxygen set point.

The pH of a culture medium may also be monitored. In examples, the pH may be monitored by a pH probe that is immersed in the culture medium inside the vessel. If pH control is in effect, the pH may be adjusted by acid and base pumps which add each solution to the medium at the required rate. The acid solutions used to control pH may be sulfuric acid or hydrochloric acid. The base solutions used to control pH may be sodium hydroxide, potassium hydroxide, or ammonium hydroxide.

Further, dissolved oxygen may be monitored in a culture medium by a dissolved oxygen probe immersed in the culture medium. If dissolved oxygen regulation is in effect, the oxygen level may be adjusted by increasing or decreasing the stirring speed. The dissolved oxygen level may also be adjusted by increasing or decreasing the gas flow rate. The gas may be compressed air, oxygen, or nitrogen.

Stir speed may also be monitored in a fermentation process. In examples, the stirrer motor may drive an agitator. The stirrer speed may be set at a consistent rpm throughout the fermentation or may be regulated dynamically to maintain a set dissolved oxygen level.

Additionally, turbidity may be monitored in a fermentation process. In examples, cell density may be measured using a turbidity probe. Alternatively, cell density may be measured by taking samples from the bioreactor and analyzing them in a spectrophotometer. Further, samples may be removed from the bioreactor at time intervals through a sterile sampling apparatus. The samples may be analyzed for alkaloids produced by the host cells. The samples may also be analyzed for other metabolites and sugars, the depletion of culture medium components, or the density of cells.

In another example, a feed stock parameter may be monitored during a fermentation process. In particular, feed stocks including sugars and other carbon sources, nutrients, and cofactors that may be added into the fermentation using an external pump. Other components may also be added during the fermentation including, without limitation, antifoam, salts, chelating agents, surfactants, and organic liquids.

Any convenient codon optimization techniques for optimizing the expression of heterologous polynucleotides in host cells may be adapted for use in the subject host cells and methods, see e.g., Gustafsson, C. et al. (2004) *Trends Biotechnol*, 22, 346-353, which is incorporated by reference in its entirety.

The subject method may also include adding a starting compound to the cell culture. Any convenient methods of addition may be adapted for use in the subject methods. The cell culture may be supplemented with a sufficient amount of the starting materials of interest (e.g., as described herein), e.g., a mM to μM amount such as between about 1-5 mM of a starting compound. It is understood that the amount of starting material added, the timing and rate of addition, the form of material added, etc., may vary according to a variety of factors. The starting material may be added neat or pre-dissolved in a suitable solvent (e.g., cell culture media, water, or an organic solvent). The starting material may be added in concentrated form (e.g., 10× over desired concentration) to minimize dilution of the cell culture medium upon addition. The starting material may be added in one or more batches, or by continuous addition over an extended period of time (e.g., hours or days).

Methods for Isolating Products from the Fermentation Medium

The subject methods may also include recovering the enzymes and/or BIAs of interest from the cell culture. Any convenient methods of separation and isolation (e.g., chromatography methods or precipitation methods) may be adapted for use in the subject methods to recover the enzymes and/or BIAs of interest from the cell culture. Filtration methods may be used to separate soluble from insoluble fractions of the cell culture. In some cases, liquid chromatography methods (e.g., reverse phase HPLC, size exclusion, normal phase chromatography) may be used to separate the BIA of interest from other soluble components of the cell culture. In some cases, extraction methods (e.g., liquid extraction, pH based purification, solid phase extraction, affinity chromatography, ion exchange, etc.) may be used to separate the enzymes and/or BIAs of interest from other components of the cell culture.

The produced alkaloids may be isolated from the fermentation medium using methods known in the art. A number of recovery steps may be performed immediately after (or in some instances, during) the fermentation for initial recovery of the desired product. Through these steps, the alkaloids (e.g., BIAs) may be separated from the cells, cellular debris and waste, and other nutrients, sugars, and organic molecules may remain in the spent culture medium. This process may be used to yield a BIA-enriched product.

In an example, a product stream having a benzylisoquinoline alkaloid (BIA) product is formed by providing engineered yeast cells and a feedstock including nutrients and water to a batch reactor. In particular, the engineered yeast cells may be subjected to fermentation by incubating the engineered yeast cells for a time period of at least about 5 minutes to produce a solution comprising the BIA product and cellular material. Once the engineered yeast cells have been subjected to fermentation, at least one separation unit may be used to separate the BIA product from the cellular material to provide the product stream comprising the BIA product. In particular, the product stream may include the BIA product as well as additional components, such as a clarified yeast culture medium. Additionally, a BIA product may comprise one or more BIAs of interest, such as one or more BIA compounds.

Different methods may be used to remove cells from a bioreactor medium that include an enzyme and/or BIA of interest. In examples, cells may be removed by sedimentation over time. This process of sedimentation may be accelerated by chilling or by the addition of fining agents such as silica. The spent culture medium may then be siphoned from the top of the reactor or the cells may be decanted from the base of the reactor. Alternatively, cells may be removed by filtration through a filter, a membrane, or other porous material. Cells may also be removed by centrifugation, for example, by continuous flow centrifugation or by using a continuous extractor.

If some valuable enzymes and/or BIAs of interest are present inside the cells, the cells may be permeabilized or lysed and the cell debris may be removed by any of the methods described above. Agents used to permeabilize the cells may include, without limitation, organic solvents (e.g., DMSO) or salts (e.g., lithium acetate). Methods to lyse the cells may include the addition of surfactants such as sodium dodecyl sulfate, or mechanical disruption by bead milling or sonication.

Enzymes and/or BIAs of interest may be extracted from the clarified spent culture medium through liquid-liquid extraction by the addition of an organic liquid that is immiscible with the aqueous culture medium. In examples, the use of liquid-liquid extraction may be used in addition to other processing steps. Examples of suitable organic liquids include, but are not limited to, isopropyl myristate, ethyl acetate, chloroform, butyl acetate, methylisobutyl ketone, methyl oleate, toluene, oleyl alcohol, ethyl butyrate. The organic liquid may be added to as little as 10% or as much as 100% of the volume of aqueous medium.

In some cases, the organic liquid may be added at the start of the fermentation or at any time during the fermentation. This process of extractive fermentation may increase the yield of enzymes and/or BIAs of interest from the host cells by continuously removing enzymes and/or BIAs to the organic phase.

Agitation may cause the organic phase to form an emulsion with the aqueous culture medium. Methods to encourage the separation of the two phases into distinct layers may include, without limitation, the addition of a demulsifier or a nucleating agent, or an adjustment of the pH. The emulsion may also be centrifuged to separate the two phases, for example, by continuous conical plate centrifugation.

Alternatively, the organic phase may be isolated from the aqueous culture medium so that it may be physically removed after extraction. For example, the solvent may be encapsulated in a membrane.

In examples, enzymes and/or BIAs of interest may be extracted from a fermentation medium using adsorption methods. In examples, BIAs of interest may be extracted from clarified spent culture medium by the addition of a resin such as Amberlite® XAD4 or another agent that removes BIAs by adsorption. The BIAs of interest may then be released from the resin using an organic solvent. Examples of suitable organic solvents include, but are not limited to, methanol, ethanol, ethyl acetate, or acetone.

BIAs of interest may also be extracted from a fermentation medium using filtration. At high pH, the BIAs of interest may form a crystalline-like precipitate in the bioreactor. This precipitate may be removed directly by filtration through a filter, membrane, or other porous material. The precipitate may also be collected by centrifugation and/or decantation.

The extraction methods described above may be carried out either in situ (in the bioreactor) or ex situ (e.g., in an external loop through which media flows out of the bioreactor and contacts the extraction agent, then is recirculated back into the vessel). Alternatively, the extraction methods may be performed after the fermentation is terminated using the clarified medium removed from the bioreactor vessel.

Methods for Purifying Products from Alkaloid-Enriched Solutions

Subsequent purification steps may involve treating the post-fermentation solution enriched with BIA product(s) of interest using methods known in the art to recover individual product species of interest to high purity.

In one example, BIAs of interest extracted in an organic phase may be transferred to an aqueous solution. In some cases, the organic solvent may be evaporated by heat and/or vacuum, and the resulting powder may be dissolved in an aqueous solution of suitable pH. In a further example, the BIAs of interest may be extracted from the organic phase by addition of an aqueous solution at a suitable pH that promotes extraction of the BIAs of interest into the aqueous phase. The aqueous phase may then be removed by decantation, centrifugation, or another method.

The BIA-containing solution may be further treated to remove metals, for example, by treating with a suitable chelating agent. The BIA of interest-containing solution may be further treated to remove other impurities, such as proteins and DNA, by precipitation. In one example, the BIA of interest-containing solution is treated with an appropriate precipitation agent such as ethanol, methanol, acetone, or isopropanol. In an alternative example, DNA and protein may be removed by dialysis or by other methods of size exclusion that separate the smaller alkaloids from contaminating biological macromolecules.

In further examples, the solution containing BIAs of interest may be extracted to high purity by continuous cross-flow filtration using methods known in the art.

If the solution contains a mixture of BIAs of interest, it may be subjected to acid-base treatment to yield individual BIA of interest species using methods known in the art. In this process, the pH of the aqueous solution is adjusted to precipitate individual BIAs.

For high purity, small-scale preparations, the BIAs may be purified in a single step by liquid chromatography.

Yeast-Derived Alkaloid APIs Versus Plant-Derived APIs

The clarified yeast culture medium (CYCM) may contain a plurality of impurities. The clarified yeast culture medium may be dehydrated by vacuum and/or heat to yield an alkaloid-rich powder. This product is analogous to the concentrate of poppy straw (CPS) or opium, which is exported from poppy-growing countries and purchased by API manufacturers. For the purposes of this invention, CPS is a representative example of any type of purified plant extract from which the desired alkaloids product(s) may ultimately be further purified. Table 4 and Table 5 highlight the impurities in these two products that may be specific to either CYCM or CPS or may be present in both. While some BIAs may have a pigment as an impurity, other BIAs may be categorized as pigments themselves. Accordingly, these BIAs may be assessed for impurities based on non-pigment impurities. By analyzing a product of unknown origin for a subset of these impurities, a person of skill in the art could determine whether the product originated from a yeast or plant production host.

API-grade pharmaceutical ingredients are highly purified molecules. As such, impurities that could indicate the plant- or yeast-origin of an API (such as those listed in Table 4 and Table 5) may not be present at the API stage of the product. Indeed, many of the API products derived from yeast strains of the present invention may be largely indistinguishable from the traditional plant-derived APIs. In some cases, however, conventional alkaloid compounds may be subjected to chemical modification using chemical synthesis approaches, which may show up as chemical impurities in plant-based products that require such chemical modifications. For example, chemical derivatization may often result in a set of impurities related to the chemical synthesis processes. In certain situations, these modifications may be performed biologically in the yeast production platform, thereby avoiding some of the impurities associated with chemical derivation from being present in the yeast-derived product. In particular, these impurities from the chemical derivation product may be present in an API product that is produced using chemical synthesis processes but may be absent from an API product that is produced using a yeast-derived product. Alternatively, if a yeast-derived product is mixed with a chemically-derived product, the resulting impurities may be present but in a lesser amount than would be expected in an API that only or primarily contains chemically-derived products. In this example, by analyzing the API product for a subset of these impurities, a person of skill in the art could determine whether the product originated from a yeast production host or the traditional chemical derivatization route.

Non-limiting examples of impurities that may be present in chemically-derivatized morphinan APIs but not in biosynthesized APIs include a codeine-O(6)-methyl ether impurity in API codeine; 8,14-dihydroxy-7,8-dihydrocodeinone in API oxycodone; and tetrahydrothebaine in API hydrocodone. The codeine-O(6)-methyl ether may be formed by chemical over-methylation of morphine. The 8,14-dihydroxy-7,8-dihydrocodeinone in API oxycodone may be formed by chemical over-oxidation of thebaine. Additionally, the tetrahydrothebaine in API hydrocodone may be formed by chemical over-reduction of thebaine.

However, in the case where the yeast-derived compound and the plant-derived compound are both subjected to chemical modification through chemical synthesis approaches, the same impurities associated with the chemical synthesis process may be expected in the products. In such a situation, the starting material (e.g., CYCM or CPS) may be analyzed as described above.

Methods of Engineering Host Cells

Also included are methods of engineering host cells for the purpose of producing enzymes and/or BIAs of interest. Inserting DNA into host cells may be achieved using any convenient methods. The methods are used to insert the heterologous coding sequences into the engineered host cells such that the host cells functionally express the enzymes and convert starting compounds of interest into product enzymes and/or BIAs of interest.

Any convenient promoters may be utilized in the subject engineered host cells and methods. The promoters driving expression of the heterologous coding sequences may be constitutive promoters or inducible promoters, provided that the promoters are active in the engineered host cells. The heterologous coding sequences may be expressed from their native promoters, or non-native promoters may be used. Such promoters may be low to high strength in the host in which they are used. Promoters may be regulated or constitutive. In certain embodiments, promoters that are not glucose repressed, or repressed only mildly by the presence of glucose in the culture medium, are used. Promoters of interest include but are not limited to, promoters of glycolytic genes such as the promoter of the *B. subtilis* tsr gene (encoding the promoter region of the fructose bisphosphate aldolase gene) or the promoter from yeast *S. cerevisiae* gene coding for glyceraldehyde 3-phosphate dehydrogenase (GPD, GAPDH, or TDH3), the ADH1 promoter of baker's yeast, the phosphate-starvation induced promoters such as the PHO5 promoter of yeast, the alkaline phosphatase promoter from *B. licheniformis*, yeast inducible promoters such as Gal1-10, Gal1, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-α promoter (TEF), cytochrome c-oxidase promoter (CYC1), MRP7 promoter, etc. Autonomously replicating yeast expression vectors containing promoters inducible by hormones such as glucocorticoids, steroids, and thyroid hormones may also be used and include, but are not limited to, the glucorticoid responsive element (GRE) and thyroid hormone responsive element (TRE). These and other examples are described U.S. Pat. No. 7,045,290, which is incorporated by reference, including the references cited therein. Additional vectors containing constitutive or inducible promoters such as α factor, alcohol oxidase, and PGH may be used. Additionally any promoter/enhancer combination (as per the Eukaryotic Promoter Data Base EPDB) could also be used to drive expression of genes. Any convenient appropriate promoters may be selected for the host cell, e.g., *E. coli*. One may also use promoter selection to optimize transcript, and hence, enzyme levels to maximize production while minimizing energy resources.

Any convenient vectors may be utilized in the subject engineered host cells and methods. Vectors of interest include vectors for use in yeast and other cells. The types of yeast vectors may be broken up into 4 general categories: integrative vectors (YIp), autonomously replicating high copy-number vectors (YEp or 2μ plasmids), autonomously replicating low copy-number vectors (YCp or centromeric plasmids) and vectors for cloning large fragments (YACs). Vector DNA is introduced into prokaryotic or eukaryotic cells via any convenient transformation or transfection techniques. DNA of another source (e.g. PCR-generated double stranded DNA product, or synthesized double stranded or single stranded oligonucleotides) may be used to engineer the yeast by integration into the genome. Any single transformation event may include one or several nucleic acids (vectors, double stranded or single stranded DNA fragments) to genetically modify the host cell.

Utility

The engineered host cells and methods of the invention, e.g., as described above, find use in a variety of applications. Applications of interest include, but are not limited to: research applications and therapeutic applications. Methods of the invention find use in a variety of different applications including any convenient application where the production of enzymes and/or BIAs is of interest.

The subject engineered host cells and methods find use in a variety of therapeutic applications. Therapeutic applications of interest include those applications in which the preparation of pharmaceutical products that include BIAs is of interest. The engineered host cells described herein produce BIAs of interest and enzymes of interest. Reticuline is a major branch point intermediate of interest in the synthesis of BIAs including engineering efforts to produce end products such as opioid products. The subject host cells may be utilized to produce BIAs of interest from simple and inexpensive starting materials that may find use in the production of BIAs of interest, including reticuline, and BIA end products. As such, the subject host cells find use in the supply of therapeutically active BIAs of interest.

In some instances, the engineered host cells and methods find use in the production of commercial scale amounts of BIAs thereof where chemical synthesis of these compounds is low yielding and not a viable means for large-scale production. In certain cases, the host cells and methods are utilized in a fermentation facility that would include bioreactors (fermenters) of e.g., 5,000-200,000 liter capacity allowing for rapid production of BIAs of interest thereof for therapeutic products. Such applications may include the industrial-scale production of BIAs of interest from fermentable carbon sources such as cellulose, starch, and free sugars.

The subject engineered host cells and methods find use in a variety of research applications. The subject host cells and methods may be used to analyze the effects of a variety of enzymes on the biosynthetic pathways of a variety of enzymes and/or BIAs of interest. In addition, the engineered host cells may be engineered to produce enzymes and/or BIAs of interest that find use in testing for bioactivity of interest in as yet unproven therapeutic functions. In some cases, the engineering of host cells to include a variety of heterologous coding sequences that encode for a variety of enzymes elucidates the high yielding biosynthetic pathways towards enzymes and/or BIAs of interest. In certain cases, research applications include the production of enzymes and/or BIAs of interest for therapeutic molecules of interest that may then be further chemically modified or derivatized to desired products or for screening for increased therapeutic activities of interest. In some instances, host cell strains are used to screen for enzyme activities that are of interest in such pathways, which may lead to enzyme discovery via conversion of BIA metabolites produced in these strains.

The subject engineered host cells and methods may be used as a production platform for plant specialized metabolites. The subject host cells and methods may be used as a platform for drug library development as well as plant enzyme discovery. For example, the subject engineered host cells and methods may find use in the development of natural product based drug libraries by taking yeast strains producing interesting scaffold molecules, such as protopine, and further functionalizing the compound structure through combinatorial biosynthesis or by chemical means. By producing drug libraries in this way, any potential drug hits are already associated with a production host that is amenable to large-scale culture and production. As another example, these subject engineered host cells and methods may find use in plant enzyme discovery. The subject host cells provide a clean background of defined metabolites to express plant EST libraries to identify new enzyme activities. The subject host cells and methods provide expression methods and culture conditions for the functional expression and increased activity of plant enzymes in yeast.

Kits and Systems

Aspects of the invention further include kits and systems, where the kits and systems may include one or more components employed in methods of the invention, e.g., engineered host cells, starting compounds, heterologous coding sequences, vectors, culture medium, etc., as described herein. In some embodiments, the subject kit includes an engineered host cell (e.g., as described herein), and one or more components selected from the following: starting compounds, a heterologous coding sequence and/or a vector including the same, vectors, growth feedstock, components suitable for use in expression systems (e.g., cells, cloning vectors, multiple cloning sites (MCS), bi-directional promoters, an internal ribosome entry site (IRES), etc.), and a culture medium.

Any of the components described herein may be provided in the kits, e.g., host cells including one or more modifications, starting compounds, culture medium, etc. A variety of components suitable for use in making and using heterologous coding sequences, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

Also provided are systems for producing enzymes and/or BIAs of interest, where the systems may include engineered host cells including one or more modifications (e.g., as described herein), starting compounds, culture medium, a fermenter and fermentation equipment, e.g., an apparatus suitable for maintaining growth conditions for the host cells, sampling and monitoring equipment and components, and the like. A variety of components suitable for use in large scale fermentation of yeast cells may find use in the subject systems.

In some cases, the system includes components for the large scale fermentation of engineered host cells, and the monitoring and purification of enzymes and/or BIA compounds produced by the fermented host cells. In certain embodiments, one or more starting compounds (e.g., as described herein) are added to the system, under conditions by which the engineered host cells in the fermenter produce one or more desired BIA products of interest. In some instances, the host cells produce a BIA of interest (e.g., as described herein). In certain cases, the BIA products of interest are opioid products, such as thebaine, codeine, neopine, morphine, neomorphine, hydrocodone, oxycodone, hydromorphone, dihydrocodeine, 14-hydroxycodeine, dihydromorphine, or oxymorphone.

In some cases, the system includes processes for monitoring and or analyzing one or more enzymes and/or BIAs of interest compounds produced by the subject host cells. For example, a LC-MS analysis system as described herein, a chromatography system, or any convenient system where the sample may be analyzed and compared to a standard, e.g., as described herein. The fermentation medium may be monitored at any convenient times before and during fermentation by sampling and analysis. When the conversion of starting compounds to enzymes and/or BIA products of interest is complete, the fermentation may be halted and purification of the BIA products may be done. As such, in some cases, the subject system includes a purification component suitable for purifying the enzymes and/or BIA products of interest from the host cell medium into which it is produced. The purification component may include any convenient means that may be used to purify the enzymes and/or BIA products of interest produced by fermentation, including but not limited to, silica chromatography, reverse-phase chromatography, ion exchange chromatography, HIC chromatography, size exclusion chromatography, liquid extraction, and pH extraction methods. In some cases, the subject system provides for the production and isolation of enzyme and/or BIA fermentation products of interest following the input of one or more starting compounds to the system.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Discussion of Enzyme List

The host cells may be engineered to include one or more modifications (such as two or more, three or more, four or more, five or more, or even more modifications) that provide for the production of BIAs of interest and/or enzymes of interest. Table 2 provides a list of exemplary genes that may be acted upon by one or more modifications so as to provide for the production of BIAs of interest and/or enzymes of interest in an engineered host cell.

Modifications of genes as provided in Table 2 may be used to produce BIAs of interest from engineered host cells that are supplied with a medium containing the minimal nutrients required for growth. This minimal medium may contain a carbon source, a nitrogen source, amino acids, vitamins, and salts. For example, modifications of genes as provided in Table 2 may be used to produce BIAs of interest from engineered host cells that are fed sugar. Additionally, modifications of one or more genes as provided in Table 2 may be used to augment the biosynthetic processes of host cells that may be engineered for drug production.

Additionally, the use of these modifications to provide for the production of BIAs of interest and/or enzymes of interest in engineered host cells is not readily apparent from the mere identification of enzymes that may be produced by the genes. In particular, synthetic pathways that have been reconstructed in host cells, such as yeast cells, as described herein comprise a variety of enzymes that do not act together in nature within a single organism. Additionally, some of the enzymes discussed herein do not act for BIA biosynthesis in their natural context. Further, some of the enzymes described herein are not evolved to function in particular host cells, such as yeast cells, and are not evolved to function together. In these cases, it would not be obvious that the enzymes would exhibit sufficient activity in the context of the synthetic BIA pathway in a host cell, such as yeast, to have sufficient flux through the pathway to produce downstream BIA end products.

For example, plant enzymes are often difficult to functionally express in heterologous microbial hosts, such as yeast. In many cases the enzymes may be misfolded, not correctly localized within the host cell, and/or incorrectly processed. The differences in protein translation and processing between yeast and plants can lead to these enzymes exhibiting substantially reduced to no detectable activities in the yeast host. These challenges arise commonly for endo-membrane localized enzymes, such as cytochrome P450s, which are strongly represented in the BIA pathways. Even reduced enzyme activities may pose a substantial challenge to engineering yeast to produce complex BIAs, which requires sufficient activity at each step to ensure high-level accumulation of the desired BIA products.

Additionally, there are endogenous enzymes/pathways in some host cells, such as yeast, that may act on many of the early precursors in the BIA pathway (i.e., intermediates from tyrosine to norcoclaurine), and thus it may not be readily apparent that there would be sufficient flux through the heterologous pathway to achieve substantial BIA production given these competing endogenous pathways. For example, the Erlich pathway (Hazelwood, et al. 2008. Appl. Environ. Microbiol. 74: 2259-66; Larroy, et al. 2003. Chem. Biol. Interact. 143-144: 229-38; Larroy, et al. 2002. Eur. J. Biochem. 269: 5738-45) in yeast is the main endogenous pathway that would act to convert many of the intermediates in the early BIA pathway to undesired products and divert flux from the synthetic pathway.

Further, many of the enzymes as discussed herein, and as provided in Table 2, may function under very specific regulation strategies, including spatial regulation, in the native plant hosts, which may be lost upon transfer to the heterologous yeast host. In addition, plants present very different biochemical environments than yeast cells under which the enzymes are evolved to function, including pH, redox state, and substrate, cosubstrate, coenzyme, and cofactor availabilities. Given the differences in biochemical environments and regulatory strategies between the native hosts and the heterologous yeast hosts, it is not obvious that the enzymes would exhibit substantial activities when in the context of the yeast environment and further not obvious that they would work together to direct simple precursors such as sugar to complex BIA compounds. Maintaining the activities of the enzymes in the yeast host is particularly important as many of the pathways have many reaction steps (>10), such that if these steps are not efficient then one would not expect accumulation of desired downstream products.

In addition, in the native plant hosts, the associated metabolites in these pathways may be localized across different cell and tissue types. In several examples, there are cell types that may be specialized for biosynthesis and cell types that may be synthesized for metabolite accumulation. This type of cell specialization may be lost when expressing the pathways within a heterologous yeast host, and may play an important role in controlling the toxicity of these metabolites on the cells. Thus, it is not obvious that yeast could be successfully engineered to biosynthesize and accumulate these metabolites without being harmed by the toxicity of these compounds.

As one example, in the native plant hosts, the enzyme BBE is reported to have dynamic subcellular localization. In particular, the enzyme BBE initially starts in the ER and then is sorted to the vacuole (Bird and Facchini. 2001. Planta. 213: 888-97). It has been suggested that the ER-association of BBE in plants (Alcantara, et al. 2005. Plant Physiol. 138: 173-83) provides the optimal basic pH (pH ~8.8) for BBE activity (Ziegler and Facchini. 2008. Annu. Rev. Plant Biol. 59: 735-69). As another example, there is evidence that sanguinarine biosynthesis occurs in specialized vesicles within plant cells (Amann, et al. 1986. Planta. 167: 310-20), but only some of the intermediates accumulate in the vesicles. This may occur so as to sequester them from other enzyme activities and/or toxic effects.

As another example, the biosynthetic enzymes in the morphinan pathway branch are all localized to the phloem, which is part of the vascular tissue in plants. In the phloem, the pathway enzymes may be further divided between two cell types: the sieve elements common to all plants, and the laticifer which is a specialized cell type present only in certain plants which make specialized secondary metabolites. The upstream enzymes (i.e., from NCS through to SalAT) are predominantly in the sieve elements, and the downstream enzymes (i.e., T6ODM, COR, CODM) are mostly in the laticifer (Onoyovwe, et al. 2013. Plant Cell. 25: 4110-22). Additionally, it was discovered that the final steps in the noscapine biosynthetic pathway take place in the laticifer (Chen and Facchini. 2014. Plant J. 77: 173-84). This compartmentalization is thought to be highly important for regulating biosynthesis by isolating or trafficking intermediates, providing optimal pH, enhancing supply of cofactors, although the nature of the poppy laticifer microenvironment is still under investigation (Ziegler and Facchini. 2008. Annu. Rev. Plant Biol. 59: 735-69). Further, it is predicted that several of the enzymes may function as multi-enzyme complexes or metabolic channels common to plant secondary metabolism (Kempe, et al. 2009. Phytochemistry. 70: 579-89; Allen, et al. 2004. Nat. Biotechnol. 22: 1559-66). When biosynthetic enzymes are combined from different hosts and/or expressed recombinantly in a heterologous yeast cell it is not clear that these complexes or channels will form as they would in the native host. In an additional example, in *Coptis japonica*, berberine is biosynthesized in root tissues and then accumulated within the rhizome via the action of specialized ATP-binding cassette transport proteins (shitan, et al. 2013. Phytochemistry. 91: 109-16). In opium poppy, morphinan alkaloids are accumulated within the latex (cytoplasm of laticifer cells) (Martin, et al. 1967. Biochemistry. 6: 2355-63).

Further, even without these considerations, it is also the case that the plant enzymes for several of the steps in the pathways described herein have not yet been characterized. For example, the conversion of tyrosine to the early benzylisoquinoline alkaloid scaffold norcoclaurine has not yet been characterized. Additionally, the conversion of (S)-reticuline to (R)-reticuline has only recently been characterized as described herein. Thus, for several of the steps in the pathways described herein, alternative biosynthetic scheme were produced by bringing together enzyme activities that do not normally occur together in nature for the biosynthesis of BIAs or identifying new enzyme activities from genome sequence information to use in the reconstructed pathways.

For example, the two-step conversion of tyrosine to dopamine may be achieved by combining at least 5 mammalian enzymes and 1 bacterial enzyme, which do not naturally occur together and were not evolved to function in the context of this pathway or with plant enzymes. In these instances, it may not be obvious to utilize these enzymes for the biosynthesis of compounds they were not evolved for in nature and that they would function effectively in the context of a heterologous microbial host and this pathway. As another example, the enzyme responsible for the conversion of (S)-reticuline to (R)-reticuline was unknown. Novel enzymes as discussed herein may perform this epimerization reaction in yeast and in the context of the synthetic BIA pathway. As this represents new enzyme discovery, it would not have been obvious to use this enzyme in the context of this pathway for the synthesis of those BIA compounds.

Examples of the genes that are the object of modifications so as to produce BIAs of interest and/or enzymes of interest are discussed below. Additionally, the genes are discussed in the context of a series of Figures that illustrate pathways that are used in generating BIAs of interest and/or enzymes of interest.

[TLK1] In some examples, the engineered host cell may modify the expression of the enzyme transketolase. Transketolase is encoded by the TKL1 gene. In examples, transketolase catalyzes the reaction of fructose-6-phosphate+glyceraldehyde-3-phosphate⇔xylulose-5-phosphate+erythrose-4-phosphate, as referenced in FIG. 2. An engineered host cell may be modified to include constitutive overexpression of the TKL1 gene in the engineered host cell. Additionally or alternatively, the engineered host cell may be modified to synthetically regulate the expression of the TKL1 gene in the engineered host cell. In examples, the engineered host cell may be modified to incorporate a copy, copies, or additional copies, of the TKL1 gene. Additionally or alternatively, the engineered host cell may be modified to incorporate the introduction of a strong promoter element for the overexpression of the TKL1 gene within the engineered host cell. The TKL1 gene may be derived from *Saccharomyces cerevisiae* or another species. In some examples, the TKL1 gene may be 100% similar to the naturally occurring gene.

[ZWF1] In some examples, the engineered host cell may modify the expression of the enzyme glucose-6-phosphate dehydrogenase. Glucose-6-phosphate dehydrogenase is encoded by the ZWF1 gene. In examples, glucose-6-phosphate dehydrogenase catalyzes the reaction of glucose-6-phosphate→6-phosphogluconolactone, as referenced in FIG. 2. An engineered host cell may be modified to delete the coding region of the ZWF1 gene in the engineered host cell. Alternatively, the engineered host cell may be modified to disable the functionality of the ZWF1 gene, such as by introducing an inactivating mutation.

[ARO4] In some examples, the engineered host cell may modify the expression of the enzyme 3-deoxy-D-arabino-heptulosonate-7-phosphate (DAHP) synthase. DAHP synthase is encoded by the ARO4 gene. In examples, DAHP synthase catalyzes the reaction of erythrose-4-phosphate+phosphoenolpyruvic acid→4 DAHP, as referenced in FIG. 2. An engineered host cell may modify the ARO4 gene to incorporate one or more feedback inhibition alleviating mutations. In particular, a feedback inhibition alleviating mutation (e.g., ARO4$^{FBR}$) may be incorporated as a directed mutation to a native ARO4 gene at the original locus; as an additional copy introduced as a genetic integration at a separate locus; or as an additional copy on an episomal vector such as a 2-μm or centromeric plasmid. The identifier "FBR" in the mutation ARO4$^{FBR}$ refers to feedback resistant mutants and mutations. The feedback inhibited copy of the DAHP synthase enzyme may be under a native yeast transcriptional regulation, such as when the engineered host cell is a yeast cell. Alternatively, the feedback inhibited copy of the DAHP synthase enzyme may be introduced to the engineered host cell with engineered constitutive or dynamic regulation of protein expression by placing it under the control of a synthetic promoter. In some cases, the ARO4 gene may be derived from *Saccharomyces cerevisiae*. In some cases, the ARO4 gene may be 100% similar to the naturally occurring gene. Examples of modifications to the ARO4 gene include a feedback inhibition resistant mutation, K229L, or Q166K.

[ARO7] In some examples, the engineered host cell may modify the expression of the enzyme chorismate mutase. Chorismate mutase is encoded by the ARO7 gene. In examples, chorismate mutase catalyzes the reaction of chorismate→4 prephenate, as referenced in FIG. 2. An engineered host cell may modify the ARO7 gene to incorporate one or more feedback inhibition alleviating mutations. In particular, a feedback inhibition alleviating mutation (e.g., ARO7$^{FBR}$) may be incorporated as a directed mutation to a native ARO7 gene at the original locus; as an additional copy introduced as a genetic integration at a separate locus; or as an additional copy on an episomal vector such as a 2-μm or centromeric plasmid. The identifier "FBR" in the mutation ARO7$^{FBR}$ refers to feedback resistant mutants and mutations. The feedback inhibited copy of the chorismate mutase enzyme may be under a native yeast transcriptional regulation, such as when the engineered host cell is a yeast cell. Alternatively, the feedback inhibited copy of the chorismate mutase enzyme may be introduced to the engineered host cell with engineered constitutive or dynamic regulation of protein expression by placing it under the control of a synthetic promoter. In some cases, the ARO7 gene may be derived from *Saccharomyces cerevisiae*. In some cases, the ARO7 gene may be 100% similar to the naturally occurring gene. Examples of modifications to the ARO7 gene include a feedback inhibition resistant mutation or T226I.

[ARO10] In some examples, the engineered host cell may modify the expression of the enzyme phenylpyruvate decarboxylase. Phenylpyruvate decarboxylase is encoded by the ARO10 gene. In examples, phenylpyruvate decarboxylase catalyzes the reaction of hydroxyphenylpyruvate 4-hydroxyphenylacetate (4HPA), as referenced in FIG. 2. An engineered host cell may be modified to include constitutive overexpression of the ARO10 gene in the engineered host cell. Additionally or alternatively, the engineered host cell may be modified to synthetically regulate the expression of the ARO10 gene in the engineered host cell. In examples, the engineered host cell may be modified to incorporate a copy, copies, or additional copies, of the ARO10 gene. Additionally or alternatively, the engineered host cell may be modified to incorporate the introduction of a strong promoter element for the overexpression of the ARO10 gene within the engineered host cell. The ARO10 gene may be derived from *Saccharomyces cerevisiae* or another species. In some examples, the ARO10 gene may be 100% similar to the naturally occurring gene.

[ADH2-7, SFA1] In some examples, the engineered host cell may modify the expression of alcohol dehydrogenase enzymes. Alcohol dehydrogenase enzymes may be encoded by one or more of the ADH2, ADH3, ADH4, ADH5, ADH6, ADH7, and SFA1 genes. In examples, alcohol dehydrogenase catalyzes the reaction of 4HPA→tyrosol. An engineered host cell may be modified to delete the coding region of one or more of the ADH2, ADH3, ADH4, ADH5, ADH6, ADH7, and SFA1 genes in the engineered host cell. Alternatively, the engineered host cell may be modified to disable the functionality of one or more of the ADH2, ADH3, ADH4, ADH5, ADH6, ADH7, and SFA1 genes, such as by introducing an inactivating mutation.

[ALD2-6] In some examples, the engineered host cell may modify the expression of aldehyde oxidase enzymes. Aldehyde oxidase enzymes may be encoded by one or more of the ALD2, ALD3, ALD4, ALD5, and ALD6 genes. In examples, aldehyde oxidase catalyzes the reaction of 4HPA→hydroxyphenylacetic acid. An engineered host cell may be modified to delete the coding region of one or more of the ALD2, ALD3, ALD4, ALD5, and ALD6 genes in the engineered host cell. Alternatively, the engineered host cell may be modified to disable the functionality of one or more of the ALD2, ALD3, ALD4, ALD5, and ALD6 genes, such as by introducing an inactivating mutation.

[ARO9] In some examples, the engineered host cell may modify the expression of the enzyme aromatic aminotransferase. Aromatic aminotransferase is encoded by the ARO9 gene. In examples, aromatic aminotransferase catalyzes the reaction of hydroxyphenylpyruvate+glutamate→tyrosine+alpha-ketogluterate, as referenced in FIG. 2. An engineered host cell may be modified to include constitutive overexpression of the ARO9 gene in the engineered host cell. Additionally or alternatively, the engineered host cell may be modified to synthetically regulate the expression of the ARO9 gene in the engineered host cell. In examples, the engineered host cell may be modified to incorporate a copy, copies, or additional copies, of the ARO9 gene. Additionally or alternatively, the engineered host cell may be modified to incorporate the introduction of a strong promoter element for the overexpression of the ARO9 gene within the engineered host cell. The ARO9 gene may be derived from *Saccharomyces cerevisiae* or another species. In some examples, the ARO9 gene may be 100% similar to the naturally occurring gene.

[TYR] In some examples, the engineered host cell may modify the expression of the enzyme tyrosinase. Tyrosinase is encoded by the TYR gene. In examples, tyrosinase catalyzes the reaction of tyrosine→L-DOPA, as referenced in FIG. 2. In other examples, tyrosinase catalyzes the reaction of L-DOPA→dopaquinone. An engineered host cell may be modified to include constitutive expression of the TYR gene in the engineered host cell. Additionally or alternatively, the engineered host cell may be modified to synthetically regulate the expression of the TYR gene in the engineered host cell. In examples, the engineered host cell may be modified to incorporate a copy, copies, or additional copies, of the TYR gene. Additionally or alternatively, the engineered host cell may be modified to incorporate the introduction of a strong promoter element for the overexpression of the TYR gene within the engineered host cell. The TYR gene may be derived from *Ralstonia solanacearum, Agaricus bisporus*, or another species. In some examples, the TYR gene may be 100% similar to the naturally occurring gene.

[TyrH] In some examples, the engineered host cell may modify the expression of the enzyme tyrosine hydroxylase. Tyrosine hydroxylase is encoded by the TyrH gene. In examples, tyrosine hydroxylase catalyzes the reaction of tyrosine→L-DOPA, as referenced in FIGS. 2 and 5. An engineered host cell may be modified to include constitutive expression of the TyrH gene in the engineered host cell. Additionally or alternatively, the engineered host cell may be modified to synthetically regulate the expression of the TyrH gene in the engineered host cell. In examples, the engineered host cell may be modified to incorporate a copy, copies, or additional copies, of the TyrH gene. Additionally or alternatively, the engineered host cell may be modified to incorporate the introduction of a strong promoter element for the overexpression of the TyrH gene within the engineered host cell. The TyrH gene may be derived from *Homo sapiens, Rattus norvegicus, Mus musculus*, or another species. In some examples, the TyrH gene may be 100% similar to the naturally occurring gene.

[DODC] In some examples, the engineered host cell may modify the expression of the enzyme L-DOPA decarboxylase. L-DOPA decarboxylase is encoded by the DODC gene. In examples, L-DOPA decarboxylase catalyzes the reaction of L-DOPA dopamine, as referenced in FIGS. 2 and 5. An engineered host cell may be modified to include constitutive expression of the DODC gene in the engineered host cell. Additionally or alternatively, the engineered host cell may be modified to synthetically regulate the expression of the DODC gene in the engineered host cell. In examples, the engineered host cell may be modified to incorporate a copy, copies, or additional copies, of the DODC gene. Additionally or alternatively, the engineered host cell may be modified to incorporate the introduction of a strong promoter element for the overexpression of the DODC gene within the engineered host cell. The DODC gene may be derived from *Pseudomonas putida, Rattus norvegicus*, or another species. In some examples, the DODC gene may be 100% similar to the naturally occurring gene.

[TYDC] In some examples, the engineered host cell may modify the expression of the enzyme tyrosine/DOPA decarboxylase. Tyrosine/DOPA decarboxylase is encoded by the TYDC gene. In examples, tyrosine/DOPA decarboxylase catalyzes the reaction of L-DOPA→dopamine, as referenced in FIG. 2. An engineered host cell may be modified to include constitutive expression of the TYDC gene in the engineered host cell. Additionally or alternatively, the engineered host cell may be modified to synthetically regulate the expression of the TYDC gene in the engineered host cell. In examples, the engineered host cell may be modified to incorporate a copy, copies, or additional copies, of the TYDC gene. Additionally or alternatively, the engineered host cell may be modified to incorporate the introduction of a strong promoter element for the overexpression of the TYDC gene within the engineered host cell. The TYDC gene may be derived from *Papaver somniferum* or another species. In some examples, the TYDC gene may be 100% similar to the naturally occurring gene.

[MAO] In some examples, the engineered host cell may modify the expression of the enzyme monoamine oxidase. Monoamine oxidase is encoded by the MAO gene. In examples, monoamine oxidase catalyzes the reaction of dopamine→3,4-DHPA, as referenced in FIG. 2. An engineered host cell may be modified to include constitutive expression of the MAO gene in the engineered host cell. Additionally or alternatively, the engineered host cell may be modified to synthetically regulate the expression of the MAO gene in the engineered host cell. In examples, the engineered host cell may be modified to incorporate a copy, copies, or additional copies, of the MAO gene. Additionally or alternatively, the engineered host cell may be modified to incorporate the introduction of a strong promoter element for the overexpression of the MAO gene within the engineered host cell. In some cases, the MAO gene may be codon optimized for expression in *Saccharomyces cerevisiae*. The MAO gene may be derived from *Escherichia coli, Homo sapiens, Micrococcus luteus*, or another species. In some examples, the MAO gene may be 77% similar to the naturally occurring gene.

Figure 5:
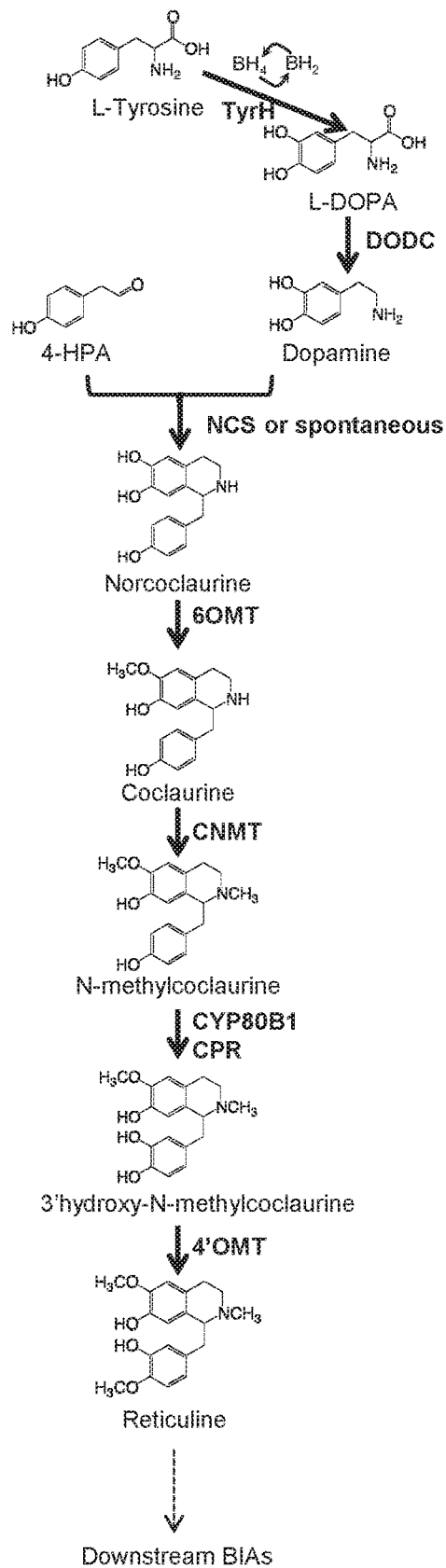
FIG. 5 illustrates a biosynthetic scheme for conversion of L-tyrosine to reticuline via norcoclaurine, in accordance with embodiments of the invention.

[NCS] In some examples, the engineered host cell may modify the expression of the enzyme norcoclaurine synthase. Norcoclaurine synthase is encoded by the NCS gene. In examples, norcoclaurine synthase catalyzes the reaction of 4HPA+dopamine→(S)-norcoclaurine, as referenced in FIG. 5. In particular, FIG. 5 illustrates a biosynthetic scheme for conversion of L-tyrosine to reticuline via norcoclaurine, in accordance with embodiments of the invention. FIG. 5 provides the use of the enzymes TyrH, tyrosine hydroxylase; DODC, DOPA decarboxylase; NCS, norcoclaurine synthase, as discussed herein; 6OMT, 6-O-methyltransferase; CNMT, coclaurine N-methyltransferase; CYP80B1, cytochrome P450 80B1; CPR, cytochrome P450 NADPH reductase; 4'OMT, 3'hydroxy-N-methylcoclaurine 4'-O-methyltransferase. L-DOPA, L-3,4-dihydroxyphenylalanine; and 4-HPA, 4-hydroxyphenylacetylaldehyde. Of the enzymes that are illustrated in FIG. 5, 4-HPA and L-tyrosine are naturally synthesized in yeast. All other metabolites shown are not naturally produced in yeast. Additionally, although TyrH is depicted as catalyzing the conversion of L-tyrosine to L-DOPA, other enzymes may also be used to perform this step as described in the specification. For example, tyrosinases may also be used to perform the conversion of L-tyrosine to L-DOPA. In addition, other enzymes such as cytochrome P450 oxidases may also be used to perform the conversion of L-tyrosine to L-DOPA. Such enzymes may exhibit oxidase activity on related BIA precursor compounds including L-DOPA and L-tyrosine.

Figure 6:
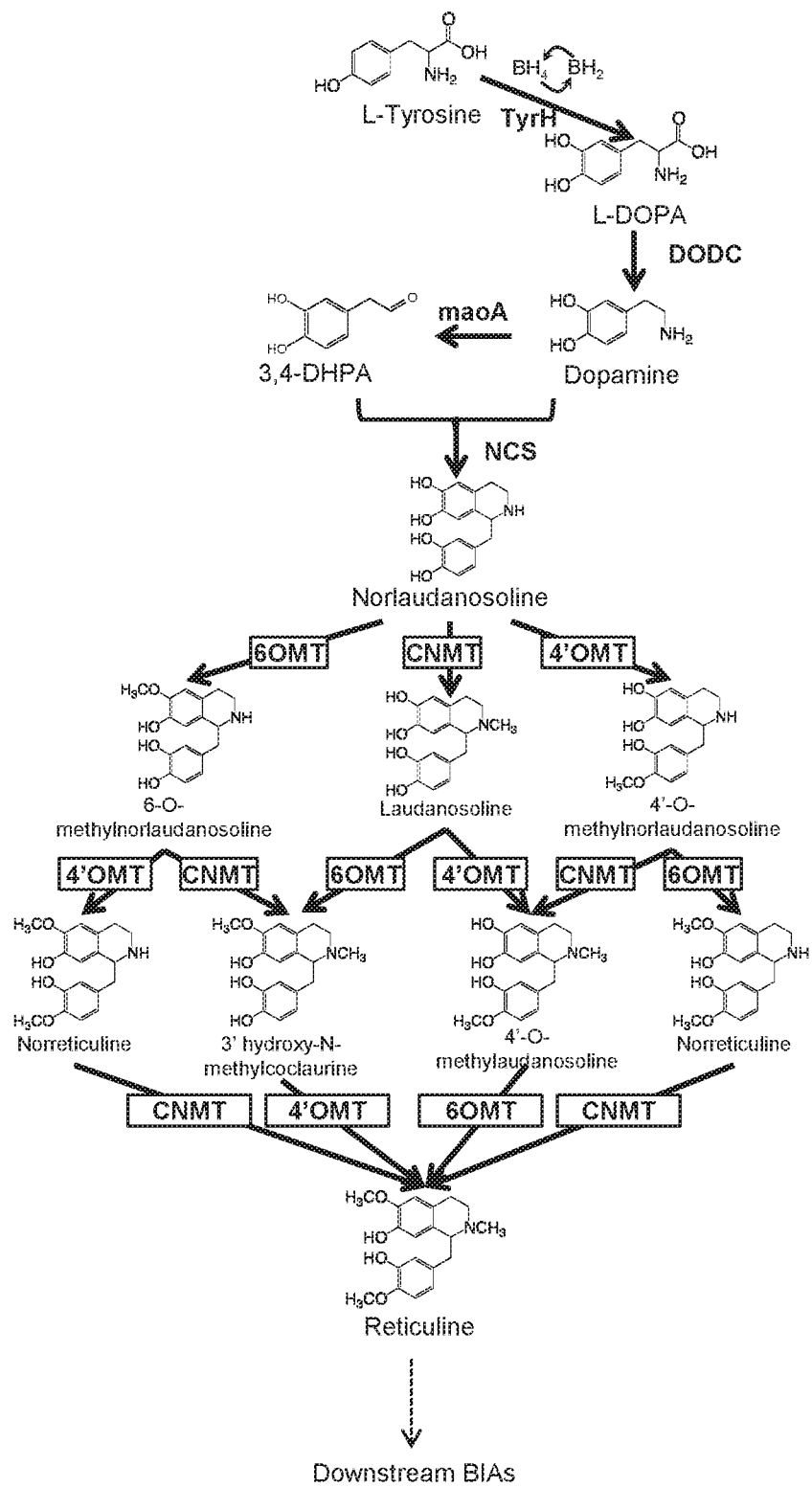
FIG. 6 illustrates a biosynthetic scheme for conversion of L-tyrosine to reticuline via norlaudanosoline, in accordance with embodiments of the invention.

Additionally, norcoclaurine synthase catalyzes the reaction of 3,4-DHPA+dopamine→(S)-norlaudanosoline, as referenced in FIG. 6. In particular, FIG. 6 illustrates a biosynthetic scheme for conversion of L-tyrosine to reticuline via norlaudanosoline, in accordance with embodiments of the invention. FIG. 6 provides the use of the enzymes TyrH, tyrosine hydroxylase; DODC, DOPA decarboxylase; maoA, monoamine oxidase; NCS, norcoclaurine synthase; 6OMT, 6-O-methyltransferase; CNMT, coclaurine N-methyltransferase; 4'OMT, 3'hydroxy-N-methylcoclaurine 4'-O-methyltransferase. L-DOPA, L-3,4-dihydroxyphenylalanine; and 3,4-DHPA, 3,4-dihydroxyphenylacetaldehyde. Of the enzymes that are illustrated in FIG. 6, L-tyrosine is naturally synthesized in yeast. Other metabolites that are shown in FIG. 6 are not naturally produced in yeast.

An engineered host cell may be modified to include constitutive expression of the NCS gene in the engineered host cell. Additionally or alternatively, the engineered host cell may be modified to synthetically regulate the expression of the NCS gene in the engineered host cell. In examples, the engineered host cell may be modified to incorporate a copy, copies, or additional copies, of the NCS gene. Additionally or alternatively, the engineered host cell may be modified to incorporate the introduction of a strong promoter element for the overexpression of the NCS gene within the engineered host cell. Additionally, the norcoclaurine synthase may have an N-terminal truncation. In some cases, the NCS gene may be codon optimized for expression in *Saccharomyces cerevisiae*. The NCS gene may be derived from *Coptis japonica, Papaver somniferum, Papver bracteatum, Thalichum flavum, Corydalis saxicola*, or another species. In some examples, the NCS gene may be 80% similar to the naturally occurring gene.

[6OMT] In some examples, the engineered host cell may modify the expression of the enzyme norcoclaurine 6-O-methyltransferase. Norcoclaurine 6-O-methyltransferase is encoded by the 6OMT gene. In some examples, norcoclaurine 6-O-methyltransferase catalyzes the reaction of norcoclaurine→coclaurine, as referenced in FIG. 5. In other examples, norcoclaurine 6-O-methyltransferase catalyzes the reaction of norlaudanosoline→3'hydroxycoclaurine, as well as other reactions detailed herein, such as those provided in FIG. 6. Additionally, the engineered host cell may be modified to include constitutive expression of the 6OMT gene in the engineered host cell. Additionally or alternatively, the engineered host cell may be modified to synthetically regulate the expression of the 6OMT gene in the engineered host cell. In examples, the engineered host cell may be modified to incorporate a copy, copies, or additional copies, of the 6OMT gene. Additionally or alternatively, the engineered host cell may be modified to incorporate the introduction of a strong promoter element for the overexpression of the 6OMT gene within the engineered host cell. The 6OMT gene may be derived from *P. somniferum, T. flavum, Coptis japonica*, or another species. In some examples, the 6OMT gene may be 100% similar to the naturally occurring gene.

[CNMT] In some examples, the engineered host cell may modify the expression of the enzyme coclaurine-N-methyltransferase. Coclaurine-N-methyltransferase is encoded by the CNMT gene. In some examples, coclaurine-N-methyltransferase catalyzes the reaction of coclaurine→N-methylcoclaurine, as referenced in FIG. 5. In other examples, the coclaurine-N-methyltransferase enzyme may catalyze the reaction of 3'hydroxycoclaurine→3'hydroxy-N-methylcoclaurine. In other examples, coclaurine-N-methyltransferase may catalyze other reactions detailed herein, such as those provided in FIG. 6. Additionally, the engineered host cell may be modified to include constitutive expression of the CNMT gene in the engineered host cell. Additionally or alternatively, the engineered host cell may be modified to synthetically regulate the expression of the CNMT gene in the engineered host cell. In examples, the engineered host cell may be modified to incorporate a copy, copies, or additional copies, of the CNMT gene. Additionally or alternatively, the engineered host cell may be modified to incorporate the introduction of a strong promoter element for the overexpression of the CNMT gene within the engineered host cell. The CNMT gene may be derived from *P. somniferum, T. flavum, Coptis japonica*, or another species. In some examples, the CNMT gene may be 100% similar to the naturally occurring gene.

[4'OMT] In some examples, the engineered host cell may modify the expression of the enzyme 4'-O-methyltransferase. 4'-O-methyltransferase is encoded by the 4'OMT gene. In some examples, 4'-O-methyltransferase catalyzes the reaction of 3'-hydroxy-N-methylcoclaurine→reticuline, as referenced in FIG. 5. In other examples, 4'-O-methyltransferase catalyzes other reactions detailed herein, such as those provided in FIG. 6. Additionally, the engineered host cell may be modified to include constitutive expression of the 4'OMT gene in the engineered host cell. Additionally or alternatively, the engineered host cell may be modified to synthetically regulate the expression of the 4'OMT gene in the engineered host cell. In examples, the engineered host cell may be modified to incorporate a copy, copies, or additional copies, of the 4'OMT gene. Additionally or alternatively, the engineered host cell may be modified to incorporate the introduction of a strong promoter element for the overexpression of the 4'OMT gene within the engineered host cell. The 4'OMT gene may be derived from *P. somniferum, T. flavum, Coptis japonica*, or another species. In some examples, the 4'OMT gene may be 100% similar to the naturally occurring gene.

[CYP80B1] In some examples, the engineered host cell may modify the expression of the enzyme cytochrome P450 80B1. Cytochrome P450 80B1 is encoded by the CYP80B1 gene. In examples, cytochrome P450 80B1 catalyzes the reaction of N-methylcoclaurine→3'-hydroxy-N-methylcoclaurine, as referenced in FIG. 5. An engineered host cell may be modified to include constitutive expression of the cytochrome P450 80B1 gene in the engineered host cell. Additionally or alternatively, the engineered host cell may be modified to synthetically regulate the expression of the cytochrome P450 80B1 gene in the engineered host cell. In examples, the engineered host cell may be modified to incorporate a copy, copies, or additional copies, of the cytochrome P450 80B1 gene. Additionally or alternatively, the engineered host cell may be modified to incorporate the introduction of a strong promoter element for the overexpression of the cytochrome P450 80B1 gene within the engineered host cell. In some cases, the CYP80B1 gene may be codon optimized for expression in *Saccharomyces cerevisiae*. The cytochrome P450 80B1 gene may be derived from *P. somniferum, E. californica, T. flavum*, or another species. In some examples, the P450 80B1 gene may be 77% similar to the naturally occurring gene.

[FOL2] In some examples, the engineered host cell may modify the expression of the enzyme GTP cyclohydrolase. GTP cyclohydrolase is encoded by the FOL2 gene. In some examples, GTP cyclohydrolase catalyzes the reaction of GTP→dihydroneopterin triphosphate, as referenced in FIG. 1. The engineered host cell may be modified to include constitutive overexpression of the FOL2 gene in the engineered host cell. The engineered host cell may also be modified to include native regulation. Additionally or alternatively, the engineered host cell may be modified to synthetically regulate the expression of the FOL2 gene in the engineered host cell. In examples, the engineered host cell may be modified to incorporate a copy, copies, or additional copies, of the FOL2 gene. Additionally or alternatively, the engineered host cell may be modified to incorporate the introduction of a strong promoter element for the overexpression of the FOL2 gene within the engineered host cell. The FOL2 gene may be derived from *Saccharomyces cerevisiae, Homo sapiens, Mus musculus*, or another species. In some examples, the FOL2 gene may be 100% similar to the naturally occurring gene.

[PTPS] In some examples, the engineered host cell may modify the expression of the enzyme 6-pyruvoyl tetrahydrobiopterin (PTP) synthase. Pyruvoyl tetrahydrobiopterin synthase is encoded by the PTPS gene. In some examples, 6-pyruvoyl tetrahydrobiopterin synthase catalyzes the reaction of dihydroneopterin triphosphate→PTP, as referenced in FIG. 1. The engineered host cell may be modified to include constitutive expression of the PTPS gene in the engineered host cell. Additionally or alternatively, the engineered host cell may be modified to synthetically regulate the expression of the PTPS gene in the engineered host cell. In examples, the engineered host cell may be modified to incorporate a copy, copies, or additional copies, of the PTPS gene. Additionally or alternatively, the engineered host cell may be modified to incorporate the introduction of a strong promoter element for the overexpression of the PTPS gene within the engineered host cell. In some cases, the PTPS gene may be codon optimized for expression in *Saccharomyces cerevisiae*. The PTPS gene may be derived from *Rattus norvegicus, Homo sapiens, Mus musculus*, or another species. In some examples, the PTPS gene may be 80% similar to the naturally occurring gene.

[SepR] In some examples, the engineered host cell may modify the expression of the enzyme sepiapterin reductase. Sepiapterin reductase is encoded by the SepR gene. In some examples, sepiapterin reductase catalyzes the reaction of PTP→$BH_4$, as referenced in FIG. 1. The engineered host cell may be modified to include constitutive expression of the SepR gene in the engineered host cell. Additionally or alternatively, the engineered host cell may be modified to synthetically regulate the expression of the SepR gene in the engineered host cell. In examples, the engineered host cell may be modified to incorporate a copy, copies, or additional copies, of the SepR gene. Additionally or alternatively, the engineered host cell may be modified to incorporate the introduction of a strong promoter element for the overexpression of the SepR gene within the engineered host cell. In some cases, the SepR gene may be codon optimized for expression in *Saccharomyces cerevisiae*. The SepR gene may be derived from *Rattus norvegicus, Homo sapiens, Mus musculus*, or another species. In some examples, the SepR gene may be 72% similar to the naturally occurring gene.

[PCD] In some examples, the engineered host cell may modify the expression of the enzyme 4a-hydroxytetrahydrobiopterin (pterin-4α-carbinolamine) dehydratase. 4a-hydroxytetrahydrobiopterin dehydratase is encoded by the PCD gene. In some examples, 4a-hydroxytetrahydrobiopterin dehydratase catalyzes the reaction of 4a-hydroxytetrahydrobiopterin→$H_2O$+quinonoid dihydropteridine, as referenced in FIG. 1. The engineered host cell may be modified to include constitutive expression of the PCD gene in the engineered host cell. Additionally or alternatively, the engineered host cell may be modified to synthetically regulate the expression of the PCD gene in the engineered host cell. In examples, the engineered host cell may be modified to incorporate a copy, copies, or additional copies, of the PCD gene. Additionally or alternatively, the engineered host cell may be modified to incorporate the introduction of a strong promoter element for the overexpression of the PCD gene within the engineered host cell. In some cases, the PCD gene may be codon optimized for expression in *Saccharomyces cerevisiae*. The PCD gene may be derived from *Rattus norvegicus, Homo sapiens, Mus musculus*, or another species. In some examples, the PCD gene may be 79% similar to the naturally occurring gene.

[QDHPR] In some examples, the engineered host cell may modify the expression of the enzyme quinonoid dihydropteridine reductase. Quinonoid dihydropteridine reductase is encoded by the QDHPR gene. In some examples, quinonoid dihydropteridine reductase catalyzes the reaction of quinonoid dihydropteridine→$BH_4$, as referenced in FIG. 1. The engineered host cell may be modified to include constitutive expression of the QDHPR gene in the engineered host cell. Additionally or alternatively, the engineered host cell may be modified to synthetically regulate the expression of the QDHPR gene in the engineered host cell. In examples, the engineered host cell may be modified to incorporate a copy, copies, or additional copies, of the QDHPR gene. Additionally or alternatively, the engineered host cell may be modified to incorporate the introduction of a strong promoter element for the overexpression of the QDHPR gene within the engineered host cell. In some cases, the QDHPR gene may be codon optimized for expression in *Saccharomyces cerevisiae*. The QDHPR gene may be derived from *Rattus norvegicus, Homo sapiens, Mus musculus*, or another species. In some examples, the QDHPR gene may be 75% similar to the naturally occurring gene.

[DHFR] In some examples, the engineered host cell may modify the expression of the enzyme dihydrofolate reductase. Dihydrofolate reductase is encoded by the DHFR gene. In some examples, dihydrofolate reductase catalyzes the reaction of 7,8-dihydrobiopterin ($BH_2$)→5,6,7,8-tetrahydrobiopterin ($BH_4$), as referenced in FIG. 1. This reaction may be useful in recovering $BH_4$ as a co-substrate for the converstion of tyrosine to L-DOPA, as illustrated in FIG. 5. The engineered host cell may be modified to include constitutive expression of the DHFR gene in the engineered host cell. Additionally or alternatively, the engineered host cell may be modified to synthetically regulate the expression of the DHFR gene in the engineered host cell. In examples, the engineered host cell may be modified to incorporate a copy, copies, or additional copies, of the DHFR gene. Additionally or alternatively, the engineered host cell may be modified to incorporate the introduction of a strong promoter element for the overexpression of the DHFR gene within the engineered host cell. In some cases, the DHFR gene may be codon optimized for expression in *Saccharomyces cerevisiae*. The DHFR gene may be derived from *Rattus norvegicus, Homo sapiens*, or another species. In some examples, the DHFR gene may be 77% similar to the naturally occurring gene.

Figure 7:
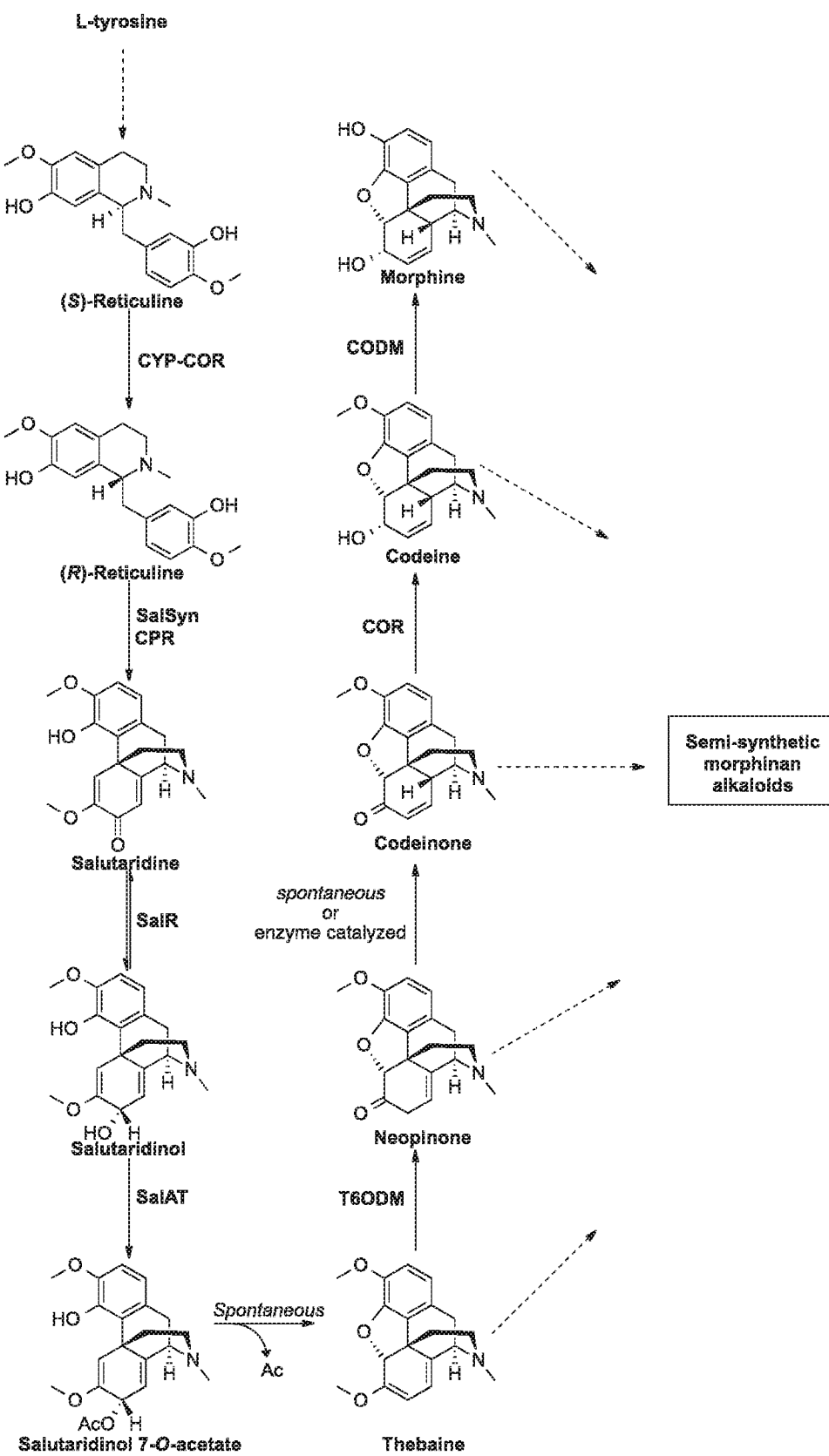
FIG. 7 illustrates a biosynthetic scheme for conversion of L-tyrosine to morphinan alkaloids, in accordance with embodiments of the invention.

[CYP-COR] As discussed above with regard to epimerizing 1-BIAs, the engineered host cell may modify the expression of a BIA epimerase. The BIA epimerase is encoded by the CYP-COR gene (e.g., CYP82Y2-COR gene). In some examples, CYP-COR may also be referred to as DRS-DRR. In some examples, the BIA epimerase catalyzes the conversion of (S)-1-BIA→(R)-1-BIA, as referenced in FIG. 7. In particular, FIG. 7 illustrates a biosynthetic scheme for conversion of L-tyrosine to morphinan alkaloids, in accordance with embodiments of the invention. FIG. 7 provides the use of the enzymes CPR, cytochrome P450 reductase; CYP-COR, cytochrome P450 CYP82Y1-like codeinone reductase-like fusion; SalSyn, salutaridine synthase; SalR, salutaridine reductase; SalAT, salutaridinol 7-O-acetyltransferase; T6ODM, thebaine 6-O-demethylase; COR, codeinone reductase; and CODM, codeine-O-demethylase.

The engineered host cell may be modified to include constitutive expression of the CYP-COR gene in the engineered host cell. Additionally or alternatively, the engineered host cell may be modified to synthetically regulate the expression of the CYP-COR gene in the engineered host cell. In examples, the engineered host cell may be modified to incorporate a copy, copies, or additional copies, of the CYP-COR gene. Additionally or alternatively, the engineered host cell may be modified to incorporate the introduction of a strong promoter element for the overexpression of the CYP-COR gene within the engineered host cell. The CYP-COR gene may be derived from *Papaver bracteatum, Papaver somniferum, Papaver setigerum, Chelidonium*

*majus*, or another species. In some examples, the CYP-COR gene may be 77% similar to the naturally occurring gene.

[CPR] In some examples, the engineered host cell may modify the expression of the enzyme cytochrome P450 reductase. The cytochrome P450 reductase is encoded by the CPR gene. In some examples, the cytochrome P450 reductase catalyzes the reaction of (R)-reticuline→salutaridine, as referenced in FIG. 7. Additionally, the cytochrome P450 reductase catalyzes other reactions such as those described in FIGs. throughout the application. The engineered host cell may be modified to include constitutive expression of the CPR gene in the engineered host cell. Additionally or alternatively, the engineered host cell may be modified to synthetically regulate the expression of the CPR gene in the engineered host cell. In examples, the engineered host cell may be modified to incorporate a copy, copies, or additional copies, of the CPR gene. Additionally or alternatively, the engineered host cell may be modified to incorporate the introduction of a strong promoter element for the overexpression of the CPR gene within the engineered host cell. The CPR gene may be derived from *E. californica, P. somniferum, H. sapiens, S. cerevisiae, A. thaliana*, or another species. In some examples, the CPR gene may be 100% similar to the naturally occurring gene.

[SalSyn] In some examples, the engineered host cell may modify the expression of the enzyme salutaridine synthase. The salutaridine synthase is encoded by the SalSyn gene. In some examples, the salutaridine synthase catalyzes the reaction of (R)-reticuline→salutaridine, as referenced in FIG. 7. The engineered host cell may be modified to include constitutive expression of the SalSyn gene in the engineered host cell. Additionally or alternatively, the engineered host cell may be modified to synthetically regulate the expression of the SalSyn gene in the engineered host cell. In examples, the engineered host cell may be modified to incorporate a copy, copies, or additional copies, of the SalSyn gene. Additionally or alternatively, the engineered host cell may be modified to incorporate the introduction of a strong promoter element for the overexpression of the SalSyn gene within the engineered host cell. In some cases, the SalSyn gene may be codon optimized for expression in *Saccharomyces cerevisiae*. In some examples the SalSyn may be modified at the N-terminus. The SalSyn gene may be derived from *Papaver somniferum, Papaver* spp, *Chelidonium majus*, or another species. In some examples, the SalSyn gene may be 78% similar to the naturally occurring gene.

[SalR] In some examples, the engineered host cell may modify the expression of the enzyme salutaridine reductase. Salutaridine reductase is encoded by the SalR gene. In some examples, salutaridine reductase reversibly catalyzes the reaction of salutaridinol→salutaridine, as referenced in FIG. 7. The engineered host cell may be modified to include constitutive expression of the SalR gene in the engineered host cell. Additionally or alternatively, the engineered host cell may be modified to synthetically regulate the expression of the SalR gene in the engineered host cell. In examples, the engineered host cell may be modified to incorporate a copy, copies, or additional copies, of the SalR gene. Additionally or alternatively, the engineered host cell may be modified to incorporate the introduction of a strong promoter element for the overexpression of the SalR gene within the engineered host cell. In some cases, the SalR gene may be codon optimized for expression in *Saccharomyces cerevisiae*. The SalR gene may be derived from *Papaver somniferum, Papaver bracteatum, Papaver* spp., *Chelidonium majus*, or another species. In some examples, the SalR gene may be 80-100% similar to the naturally occurring gene.

[SalAT] In some examples, the engineered host cell may modify the expression of the enzyme acetyl-CoA:salutaridinol 7-O-acetyltransferase. Acetyl-CoA:salutaridinol 7-O-acetyltransferase is encoded by the SalAT gene. In some examples, acetyl-CoA:salutaridinol 7-O-acetyltransferase catalyzes the reaction of acetyl-CoA+salutaridinol→CoA+7-O-acetylsalutaridinol, as referenced in FIG. 7. The engineered host cell may be modified to include constitutive expression of the SalAT gene in the engineered host cell. Additionally or alternatively, the engineered host cell may be modified to synthetically regulate the expression of the SalAT gene in the engineered host cell. In examples, the engineered host cell may be modified to incorporate a copy, copies, or additional copies, of the SalAT gene. Additionally or alternatively, the engineered host cell may be modified to incorporate the introduction of a strong promoter element for the overexpression of the SalAT gene within the engineered host cell. In some cases, the SalAT gene may be codon optimized for expression in *Saccharomyces cerevisiae*. The SalAT gene may be derived from *Papaver somniferum, Papaver bracteatum, Papaver orientate, Papaver* spp., or another species. In some examples, the SalAT gene may be 77-80% similar to the naturally occurring gene.

[T6ODM] In some examples, the engineered host cell may modify the expression of the enzyme thebaine 6-O-demethylase. Thebaine 6-0 demethylase is encoded by the T6ODM gene. In some examples, thebaine 6-O-demethylase catalyzes the reaction of thebaine→neopinone, as referenced in FIG. 7. Once the neopinone has been produced, the neopinone may be converted to codeinone. The conversion of neopinone→codeinone may occur spontaneously. Alternatively, the conversion of neopinone→codeinone may occur as a result of a catalyzed reaction. In other examples, the T6ODM enzyme may catalyze the O-demethylation of substrates other than thebaine. For example, T6ODM may O-demethylate oripavine to produce morphinone. Alternatively, T6ODM may catalyze the O-demethylation of BIAs within the 1-benzylisoquinoline, protoberberine, or protopine classes such as papaverine, canadine, and allocryptopine, respectively. The engineered host cell may be modified to include constitutive expression of the T6ODM gene in the engineered host cell. Additionally or alternatively, the engineered host cell may be modified to synthetically regulate the expression of the T6ODM gene in the engineered host cell. In examples, the engineered host cell may be modified to incorporate a copy, copies, or additional copies, of the T6ODM gene. Additionally or alternatively, the engineered host cell may be modified to incorporate the introduction of a strong promoter element for the overexpression of the T6ODM gene within the engineered host cell. In some cases, the T6ODM gene may be codon optimized for expression in *Saccharomyces cerevisiae*. The T6ODM gene may be derived from *Papaver somniferum*, or another species. In some examples, the T6ODM gene may be 76.2% similar to the naturally occurring gene.

[COR] In some examples, the engineered host cell may modify the expression of the enzyme codeinone reductase. Codeinone reductase is encoded by the COR gene. In some examples, codeinone reductase catalyzes the reaction of codeinone to codeine, as referenced in FIG. 7. In some cases, codeinone reductase can catalyze the reaction of neopinone to neopine. In other examples, COR can catalyze the reduction of other morphinans including hydrocodone→dihydrocodeine, 14-hydroxycodeinone→14-hydroxycodeine, and hydromorphone→dihydromorphine. The engineered host cell may be modified to include constitutive expression of the COR gene in the engineered host cell. Additionally or alternatively, the engineered host cell may be modified to synthetically regulate the expression of the COR gene in the engineered host cell. In examples, the engineered host cell may be modified to incorporate a copy, copies, or additional copies, of the COR gene. Additionally or alternatively, the engineered host cell may be modified to incorporate the introduction of a strong promoter element for the overexpression of the COR gene within the engineered host cell. In some cases, the COR gene may be codon optimized for expression in *Saccharomyces cerevisiae*. Additionally or alternatively, the COR gene may be modified with the addition of targeting sequences for mitochondria, vacuole, endoplasmic reticulum, or a combination thereof. The COR gene may be derived from *Papaver somniferum*, or another species. In some examples, the COR gene may be 76-78% similar to the naturally occurring gene. In examples, the COR gene may be 76.8%, 77.0%, 77.3%, or 77.7% similar to the naturally occurring gene.

[CODM] In some examples, the engineered host cell may modify the expression of the enzyme codeine O-demethylase. Codeine O-demethylase is encoded by the CODM gene. In some examples, codeine O-demethylase catalyzes the reaction of codeine to morphine, as referenced in FIG. 7. Codeine O-demethylase can also catalyze the reaction of neopine to neomorphine. Codeine O-demethylase can also catalyze the reaction of thebaine to oripavine. In other examples, CODM may catalyze the O-demethylation of BIAs within the 1-benzylisoquinoline, aporphine, and protoberberine classes such as reticuline, isocorydine, and scoulerine, respectively. In other examples, the CODM enzyme may catalyze an O,O-demethylenation reaction to cleave the methylenedioxy bridge structures in protopines. The engineered host cell may be modified to include constitutive expression of the CODM gene in the engineered host cell. Additionally or alternatively, the engineered host cell may be modified to synthetically regulate the expression of the CODM gene in the engineered host cell. In examples, the engineered host cell may be modified to incorporate a copy, copies, or additional copies, of the CODM gene. Additionally or alternatively, the engineered host cell may be modified to incorporate the introduction of a strong promoter element for the overexpression of the CODM gene within the engineered host cell. In some cases, the CODM gene may be codon optimized for expression in *Saccharomyces cerevisiae*. Additionally or alternatively, the CODM gene may be modified with the addition of targeting sequences for mitochondria. The CODM gene may be derived from *Papaver somniferum, Papaver* spp., or another species. In some examples, the CODM gene may be 75% similar to the naturally occurring gene. In examples, the CODM gene may be 75.2% similar to the naturally occurring gene.

Figure 8:
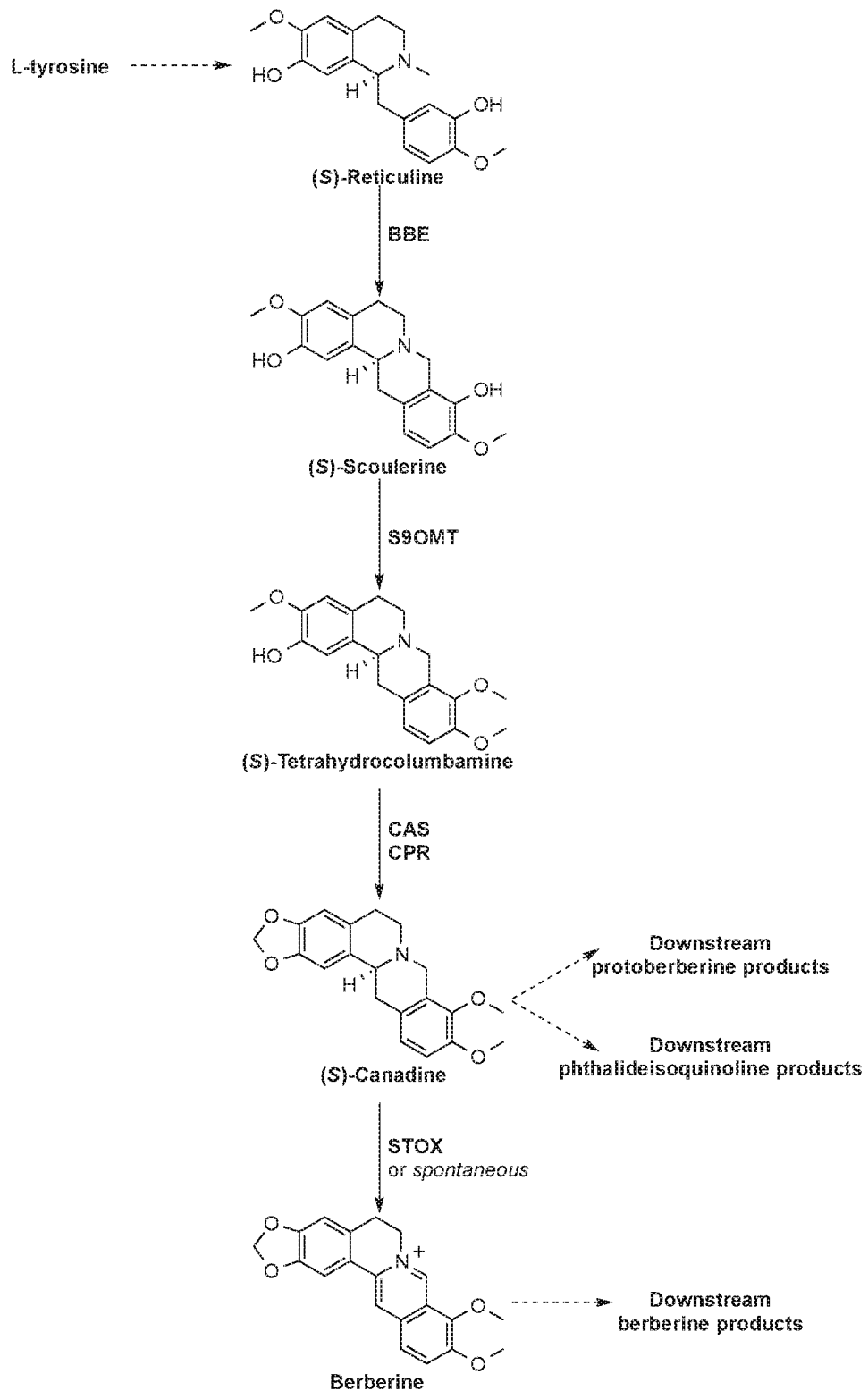
FIG. 8 illustrates a biosynthetic scheme for conversion of L-tyrosine to protoberberine, phthalideisoquinoline, and berberine alkaloid products, in accordance with embodiments of the invention.

[BBE] In some examples, the engineered host cell may modify the expression of the enzyme berberine bridge enzyme. The berberine bridge enzyme is encoded by the BBE gene. In some examples, berberine bridge enzyme catalyzes the reaction of (S)-reticuline→(S)-scoulerine, as referenced in FIG. 8. FIG. 8 illustrates a biosynthetic scheme for conversion of L-tyrosine to protoberberine alkaloids, in accordance with embodiments of the invention. In particular, FIG. 8 provides the use of the enzymes BBE, berberine bridge enzyme; S9OMT, scoulerine 9-O-methyltransferase; CAS, canadine synthase; CPR, cytochrome P450 reductase; and STOX, tetrahydroprotoberberine oxidase. The engineered host cell may be modified to include constitutive expression of the BBE gene in the engineered host cell. Additionally or alternatively, the engineered host cell may be modified to synthetically regulate the expression of the BBE gene in the engineered host cell. In examples, the engineered host cell may be modified to incorporate a copy, copies, or additional copies, of the BBE gene. Additionally or alternatively, the engineered host cell may be modified to incorporate the introduction of a strong promoter element for the overexpression of the BBE gene within the engineered host cell. The BBE gene may be derived from *Papaver somniferum, Argemone mexicana, Eschscholzia californica, Berberis stolonifera, Thalictrum flavum* subsp. *glaucum, Coptis japonica, Papaver* spp., or another species. In some examples, the BBE gene may be 99% similar to the naturally occurring gene.

[S9OMT] In some examples, the engineered host cell may modify the expression of the enzyme S-adenosyl-L-methionine:(S)-scoulerine 9-O-methyltransferase. S-adenosyl-L-methionine:(S)-scoulerine 9-O-methyltransferase is encoded by the S9OMT gene. In some examples, S-adenosyl-L-methionine:(S)-scoulerine 9-O-methyltransferase catalyzes the reaction of S-adenosyl-L-methionine+(S)-scoulerine 4 S-adenosyl-L-homocysteine+(S)-tetrahydrocolumbamine, as referenced in FIG. 8. The engineered host cell may be modified to include constitutive expression of the S9OMT gene in the engineered host cell. Additionally or alternatively, the engineered host cell may be modified to synthetically regulate the expression of the S9OMT gene in the engineered host cell. In examples, the engineered host cell may be modified to incorporate a copy, copies, or additional copies, of the S9OMT gene. Additionally or alternatively, the engineered host cell may be modified to incorporate the introduction of a strong promoter element for the overexpression of the S9OMT gene within the engineered host cell. In some cases, the S9OMT gene may be codon optimized for expression in *Saccharomyces cerevisiae*. The S9OMT gene may be derived from *Thalictrum flavum* subsp. *glaucum, Coptis japonica, Coptis chinensis, Papaver somniferum, Thalictrum* spp., *Coptis* spp., *Papaver* spp., or another species. In some examples, the S9OMT gene may be 100% similar to the naturally occurring gene. In examples, the S9OMT gene may be 80% similar to the naturally occurring gene.

[CAS] In some examples, the engineered host cell may modify the expression of the enzyme (S)-canadine synthase. (S)-canadine synthase is encoded by the CAS gene. In some examples, (S)-canadine synthase catalyzes the reaction of (S)-tetrahydrocolumbamine→(S)-canadine, as referenced in FIG. 8. The engineered host cell may be modified to express the CAS gene in the engineered host cell. The engineered host cell may be modified to include constitutive expression of the CAS gene in the engineered host cell. Additionally or alternatively, the engineered host cell may be modified to synthetically regulate the expression of the CAS gene in the engineered host cell. In examples, the engineered host cell may be modified to incorporate a copy, copies, or additional copies, of the CAS gene. Additionally or alternatively, the engineered host cell may be modified to incorporate the introduction of a strong promoter element for the overexpression of the CAS gene within the engineered host cell. The CAS gene may be derived from *Thalictrum flavum* subsp. *glaucum, Coptis japonica, Thalictrum* spp., *Coptis* spp., or another species. In some examples, the CAS gene may be 100% similar to the naturally occurring gene.

[STOX] In some examples, the engineered host cell may modify the expression of the enzyme (S)-tetrahydroprotoberberine oxidase. (S)-tetrahydroprotoberberine oxidase is encoded by the STOX gene. In some examples, (S)-tetrahydroprotoberberine oxidase catalyzes the reaction of (S)-tetrahydroberberine+2O$_2$→berberine+2H$_2$O$_2$, as referenced in FIG. 8. The engineered host cell may be modified to include constitutive expression of the STOX gene in the engineered host cell. Additionally or alternatively, the engineered host cell may be modified to synthetically regulate the expression of the STOX gene in the engineered host cell. In examples, the engineered host cell may be modified to incorporate a copy, copies, or additional copies, of the STOX gene. Additionally or alternatively, the engineered host cell may be modified to incorporate the introduction of a strong promoter element for the overexpression of the STOX gene within the engineered host cell. In some examples the STOX may be modified at the N-terminus. In some cases, the STOX gene may be codon optimized for expression in *Saccharomyces cerevisiae*. The STOX gene may be derived from *Berberis wilsonae, Coptis japonica, Berberis* spp., *Coptis* spp., or another species. In some examples, the STOX gene may be 78% similar to the naturally occurring gene.

Figure 9:
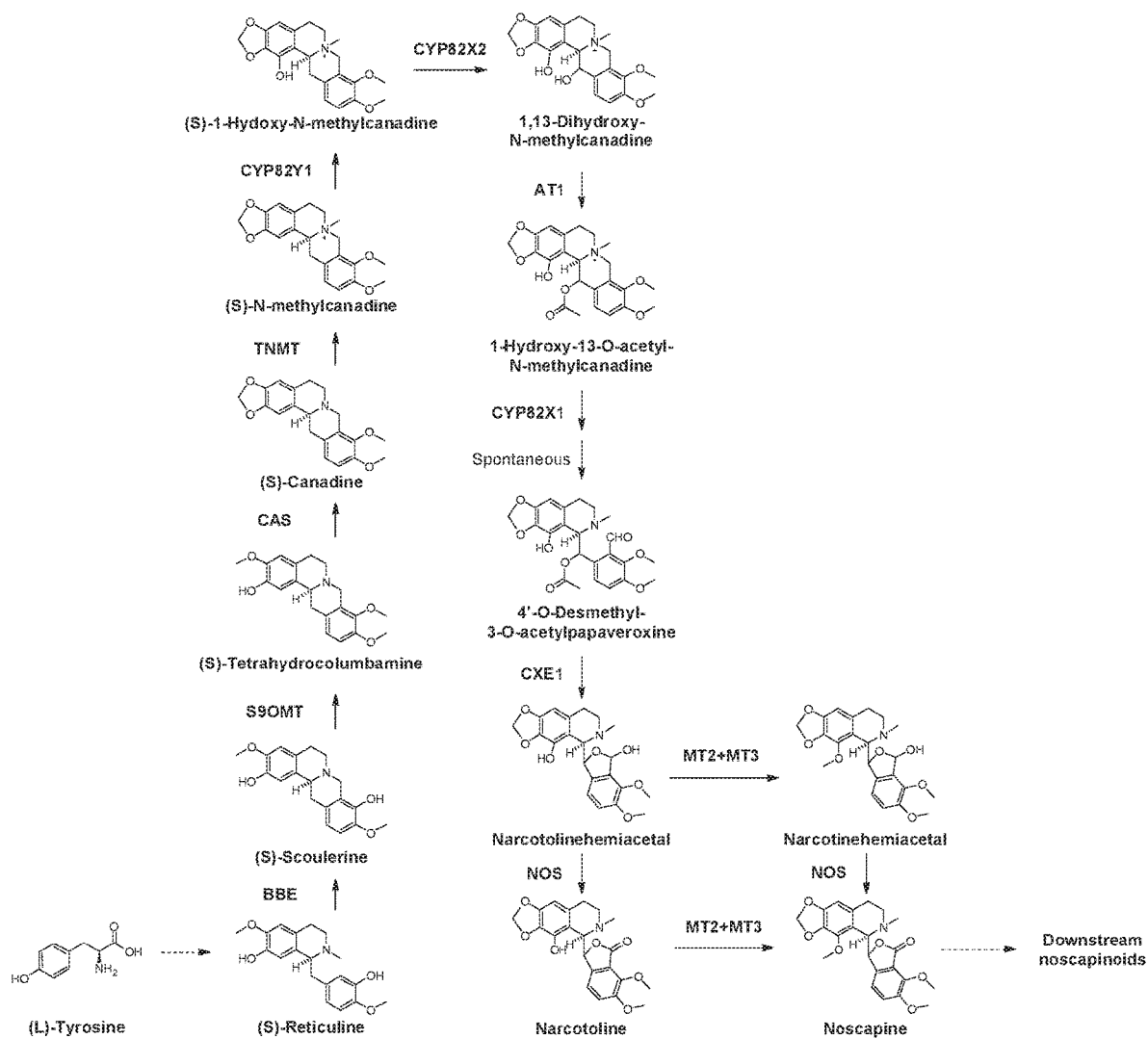
FIG. 9 illustrates a biosynthetic scheme for conversion of L-tyrosine to noscapine, noscapinoid, and phthalideisoquinoline alkaloid products, in accordance with embodiments of the invention.

[TNMT] In some examples, the engineered host cell may modify the expression of the enzyme tetrahydroprotoberberine-N-methyltransferase. Tetrahydroprotoberberine-N-methyltransferase is encoded by the TNMT gene. In some examples, tetrahydroprotoberberine-N-methyltransferase catalyzes the reaction of canadine→N-methylcanadine, as referenced in FIG. 9. FIG. 9 illustrates a biosynthetic scheme for conversion of L-tyrosine to noscapine, noscapinoid, and phthalideisoquinoline, in accordance with embodiments of the invention. In particular, FIG. 9 provides the use of the enzymes BBE, berberine bridge enzyme; S9OMT, scoulerine 9-O-methyltransferase; CAS, canadine synthase; CPR, cytochrome P450 reductase; TNMT, tetrahydroprotoberberine cis-N-methyltransferase; CYP82Y1, N-methylcanadine 1-hydroxylase; CYP82X2, 1-hydroxy-N-methylcanadine 13-hydroxylase; AT1, 1,13-dihydroxy-N-methylcandine 13-O-acetyltransferase; CYP82X1, 4'-O-desmethyl-3-O-acetylpapaveroxine synthase; CXE1, narcotine hemiacetal synthase; NOS (or SDR1), noscapine synthase; MT2, narcotoline-4'-O-methyltrasnferase 1; MT3, narcotoline-4'-O-methyltransferase 2; and 6OMT, 6-O-methyltransferase.

Figure 10:
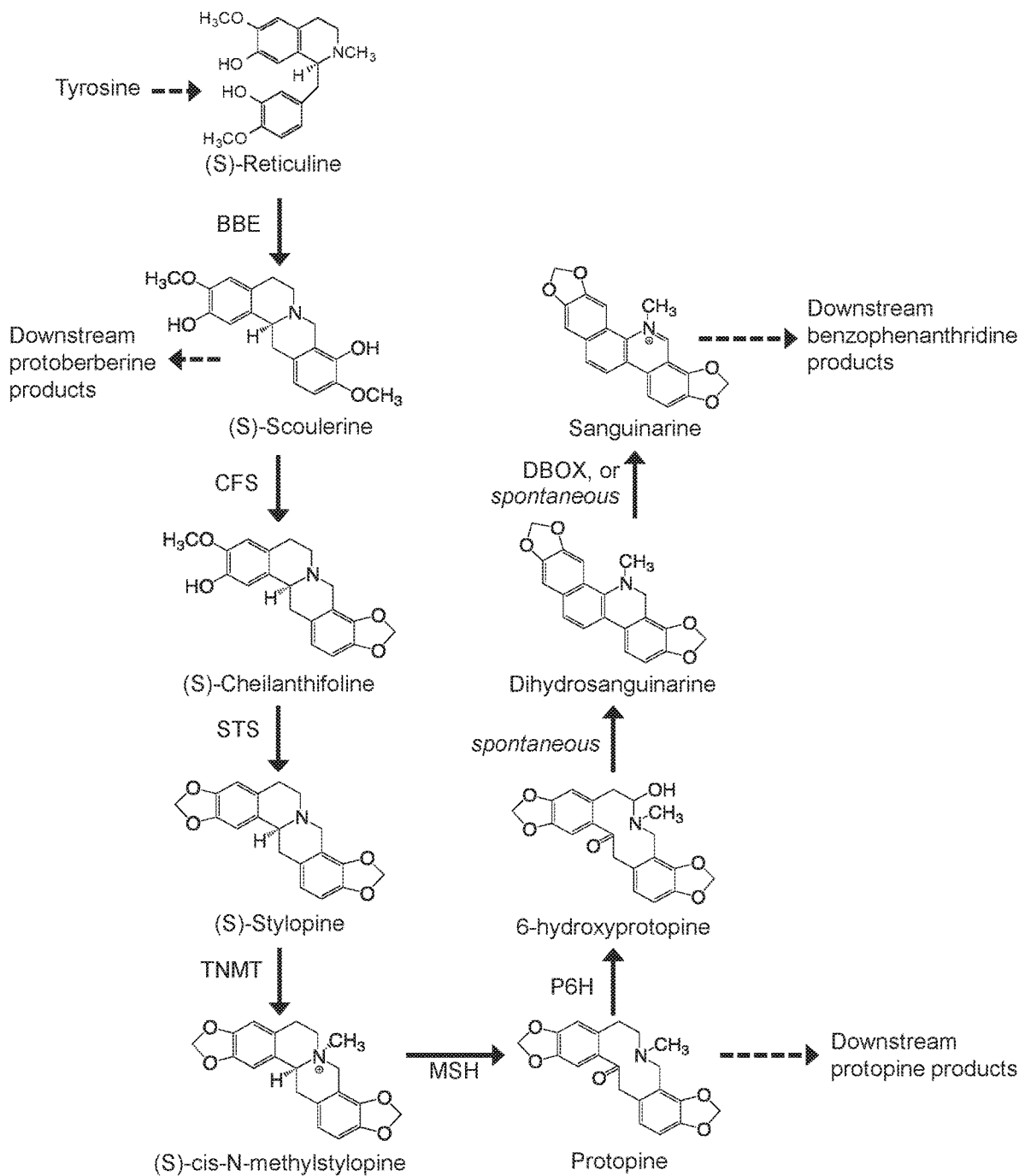
FIG. 10 illustrates a biosynthetic scheme for conversion of L-tyrosine to sanguinarine and benzophenanthridine alkaloids, in accordance with embodiments of the invention.

In other examples, tetrahydroprotoberberine-N-methyltransferase catalyzes the reaction of stylopine→cis-N-methylstylopine, as referenced in FIG. 10. FIG. 10 illustrates a biosynthetic scheme for conversion of L-tyrosine to sanguinarine and benzophenanthridine alkaloids, in accordance with embodiments of the invention. In particular, FIG. 10 provides the use of the enzymes BBE, berberine bridge enzyme; CFS, cheilanthifoline synthase; STS, stylopine synthase; TNMT, tetrahydroberberine N-methyltransferase; MSH, cis-N-methylstylopine 14-hydroxylase; P6H, protopine 6-hydroxylase; and DB OX, dihydrobenzophenanthride oxidase. The engineered host cell may be modified to include constitutive expression of the TNMT gene in the engineered host cell. Additionally or alternatively, the engineered host cell may be modified to synthetically regulate the expression of the TNMT gene in the engineered host cell. In examples, the engineered host cell may be modified to incorporate a copy, copies, or additional copies, of the TNMT gene. Additionally or alternatively, the engineered host cell may be modified to incorporate the introduction of a strong promoter element for the overexpression of the TNMT gene within the engineered host cell. In some cases, the TNMT gene may be codon optimized for expression in *Saccharomyces cerevisiae*. The TNMT gene may be derived from *Papaver somniferum, Eschscholzia californica, Papaver bracteatum, Argemone mexicana*, or another species. In some examples, the TNMT gene may be 100% similar to the naturally occurring gene. In examples, the TNMT gene may be 81% similar to the naturally occurring gene.

[CYP82Y1] In some examples, the engineered host cell may modify the expression of the enzyme N-methylcanadine 1-hydroxylase. N-methylcanadine 1-hydroxylase is encoded by the CYP82Y1 gene. In some examples, N-methylcanadine 1-hydroxylase catalyzes the reaction of N-methylcanadine→1-hydroxy-N-methylcanadine, as referenced in FIG. 9. The engineered host cell may be modified to include constitutive expression of the CYP82Y1 gene in the engineered host cell. Additionally or alternatively, the engineered host cell may be modified to synthetically regulate the expression of the CYP82Y1 gene in the engineered host cell. In examples, the engineered host cell may be modified to incorporate a copy, copies, or additional copies, of the CYP82Y1 gene. Additionally or alternatively, the engineered host cell may be modified to incorporate the introduction of a strong promoter element for the overexpression of the CYP82Y1 gene within the engineered host cell. In some cases, the CYP82Y1 gene may be codon optimized for expression in *Saccharomyces cerevisiae*. In some examples the CYP82Y1 may be modified at the N-terminus. The CYP82Y1 gene may be derived from *Papaver somniferum, Papaver* spp., *Plantago arenaria, Rauwolfia heterophylla, Adlumia fungosa, Hydrastis canadensis, Stylomecon heterophylla, Hypecoum*, or another species. In some examples, the CYP82Y1 gene may be 70-78% similar to the naturally occurring gene.

[CYP82X2] In some examples, the engineered host cell may modify the expression of the enzyme 1-hydroxy-N-methylcanadine 13-hydroxylase. 1-hydroxy-N-methylcanadine 13-hydroxylase is encoded by the CYP82X2 gene. In some examples, 1-hydroxy-N-methylcanadine 13-hydroxylase catalyzes the reaction of 1-hydroxy-N-methylcanadine→1-hydroxy-N-methylophiocarpine (i.e. 1,13-dihydroxy-N-methylcanadine), as referenced in FIG. 9. The engineered host cell may be modified to include constitutive expression of the CYP82X2 gene in the engineered host cell. Additionally or alternatively, the engineered host cell may be modified to synthetically regulate the expression of the CYP82X2 gene in the engineered host cell. In examples, the engineered host cell may be modified to incorporate a copy, copies, or additional copies, of the CYP82X2 gene. Additionally or alternatively, the engineered host cell may be modified to incorporate the introduction of a strong promoter element for the overexpression of the CYP82X2 gene within the engineered host cell. In some cases, the CYP82X2 gene may be codon optimized for expression in *Saccharomyces cerevisiae*. In some examples the CYP82X2 may be modified at the N-terminus. The CYP82X2 gene may be derived from *P. somniferum, Papaver* spp, *Plantago arenaria, Rauwolfia heterophylla, Adlumia fungosa, Hydrastis Canadensis, Stylomecon heterophylla, Dactylicapnos torulosa, Glaucium flavum, Berberis laurina, B. Vulgaris, Corydalis* spp, *Fumaria* spp, *Dactylicapnos* spp., or another species. In some examples, the CYP82X2 gene may be 70-77% similar to the naturally occurring gene. In other examples, the CYP82X2 gene may undergo N-terminus engineering. In examples, N-terminus engineering may include N-terminal truncation.

[CYP82X1] In some examples, the engineered host cell may modify the expression of the enzyme 4'-O-desmethyl-3-O-acetylpapaveroxine synthase. 4'-O-desmethyl-3-O-acetylpapaveroxine synthase is encoded by the CYP82X1 gene. In some examples, 4'-O-desmethyl-3-O-acetylpapaveroxine synthase catalyzes the reaction of 1-hydroxy-13-O-acetyl-N-methylcanadine→4'-O-desmethyl-3-O-acetylpapaveroxine, as referenced in FIG. 9. Additionally, CYP82X1 catalyzes the reaction of 1-hydroxy-N-methylcanadine→4'-O-desmethylmacrantaldehyde. The engineered host cell may be modified to include constitutive expression of the CYP82X1 gene in the engineered host cell. Additionally or alternatively, the engineered host cell may be modified to synthetically regulate the expression of the CYP82X1 gene in the engineered host cell. In examples, the engineered host cell may be modified to incorporate a copy, copies, or additional copies, of the CYP82X1 gene. Additionally or alternatively, the engineered host cell may be modified to incorporate the introduction of a strong promoter element for the overexpression of the CYP82X1 gene within the engineered host cell. In some cases, the CYP82X1 gene may be codon optimized for expression in *Saccharomyces cerevisiae*. In some examples the CYP82X1 may be modified at the N-terminus. The CYP82X1 gene may be derived from *Papaver somniferum, Papaver* spp., *Plantago arenaria, Rauwolfia heterophylla, Adlumia fungosa, Hydrastis canadensis, Stylomecon heterophylla, Hypecoum*, or another species. In some examples, the CYP82X1 gene may be 71-77% similar to the naturally occurring gene. In other examples, the CYP82X1 gene may undergo N-terminus engineering. In examples, N-terminus engineering may include N-terminal truncation.

[CFS] In some examples, the engineered host cell may modify the expression of the enzyme cheilanthifoline synthase. Cheilanthifoline synthase is encoded by the CFS gene. In examples, cheilanthifoline synthase catalyzes the reaction of scoulerine→cheilanthifoline, as referenced in FIG. 10. An engineered host cell may be modified to include constitutive expression of the CFS gene in the engineered host cell. Additionally or alternatively, the engineered host cell may be modified to synthetically regulate the expression of the CFS gene in the engineered host cell. In examples, the engineered host cell may be modified to incorporate a copy, copies, or additional copies, of the CFS gene. Additionally or alternatively, the engineered host cell may be modified to incorporate the introduction of a strong promotor element for the overexpression of the CFS gene within the engineered host cell. The CFS gene may be derived from *P. somniferum, E. californica, A. mexicana*, or another species. In some examples, the CFS gene may be 77%, 78%, or 79% similar to the naturally occurring gene. Additionally, the CFS gene may be codon optimized for expression in *Saccharomyces cerevisiae*.

[STS] In some examples, the engineered host cell may modify the expression of the enzyme stylopine synthase. Stylopine synthase is encoded by the STS gene. In examples, stylopine synthase catalyzes the reaction of cheilanthifoline→stylopine, as referenced in FIG. 10. An engineered host cell may be modified to include constitutive expression of the STS gene in the engineered host cell. Additionally or alternatively, the engineered host cell may be modified to synthetically regulate the expression of the STS gene in the engineered host cell. In examples, the engineered host cell may be modified to incorporate a copy, copies, or additional copies, of the STS gene. Additionally or alternatively, the engineered host cell may be modified to incorporate the introduction of a strong promoter element for the overexpression of the STS gene within the engineered host cell. The STS gene may be derived from *P. somniferum, E. californica, A. mexicana*, or another species. In some examples, the STS gene may be 76%, 78%, or 79% similar to the naturally occurring gene. Additionally, the STS gene may be codon optimized for expression in *Saccharomyces cerevisiae*.

[MSH] In some examples, the engineered host cell may modify the expression of the enzyme cis-N-methylstylopine 14-hydroxylase. Cis-N-methylstylopine 14-hydroxylase is encoded by the MSH gene. In examples, cis-N-methylstylopine 14-hydroxylase catalyzes the reaction of cis-N-methylstylopine→protopine, as referenced in FIG. 10. An engineered host cell may be modified to include constitutive expression of the MSH gene in the engineered host cell. Additionally or alternatively, the engineered host cell may be modified to synthetically regulate the expression of the MSH gene in the engineered host cell. In examples, the engineered host cell may be modified to incorporate a copy, copies, or additional copies, of the MSH gene. Additionally or alternatively, the engineered host cell may be modified to incorporate the introduction of a strong promotor element for the overexpression of the MSH gene within the engineered host cell. The MSH gene may be derived from *P. somniferum* or another species. In some examples, the MSH gene may be 79% similar to the naturally occurring gene. Additionally, the MSH gene may be codon optimized for expression in *Saccharomyces cerevisiae*.

[P6H] In some examples, the engineered host cell may modify the expression of the enzyme protopine-6-hydroxylase. Protopine-6-hydroxylase is encoded by the P6H gene. In examples, protopine-6-hydroxylase catalyzes the reaction of Protopine→6-hydroxyprotopine, as referenced in FIG. 10. An engineered host cell may be modified to include constitutive expression of the P6H gene in the engineered host cell. Additionally or alternatively, the engineered host cell may be modified to synthetically regulate the expression of the P6H gene in the engineered host cell. In examples, the engineered host cell may be modified to incorporate a copy, copies, or additional copies, of the P6H gene. Additionally or alternatively, the engineered host cell may be modified to incorporate the introduction of a strong promoter element for the overexpression of the CFS gene within the engineered host cell. The P6H gene may be derived from *P. somniferum, E. californica*, or another species. In some examples, the P6H gene may be 79% similar to the naturally occurring gene. Additionally, the P6H gene may be codon optimized for expression in *Saccharomyces cerevisiae*.

[DBOX] In some examples, the engineered host cell may modify the expression of the enzyme dihydrobenzophenanthridine oxidase. Dihydrobenzophenanthridine oxidase is encoded by the DBOX gene. In examples, dihydrobenzophenanthridine oxidase catalyzes the reaction of dihydrosanguinarine→sanguinarine, as referenced in FIG. 10. An engineered host cell may be modified to include constitutive expression of the DBOX gene in the engineered host cell. Additionally or alternatively, the engineered host cell may be modified to synthetically regulate the expression of the DBOX gene in the engineered host cell. In examples, the engineered host cell may be modified to incorporate a copy, copies, or additional copies, of the DBOX gene. Additionally or alternatively, the engineered host cell may be modified to incorporate the introduction of a strong promotor element for the overexpression of the DBOX gene within the engineered host cell. The DBOX gene may be derived from *P. somniferum* or another species. In some examples, the DBOX gene may be 100% similar to the naturally occurring gene. Additionally, the DBOX gene may be codon optimized for expression in *Saccharomyces cerevisiae*.

Figure 11A:
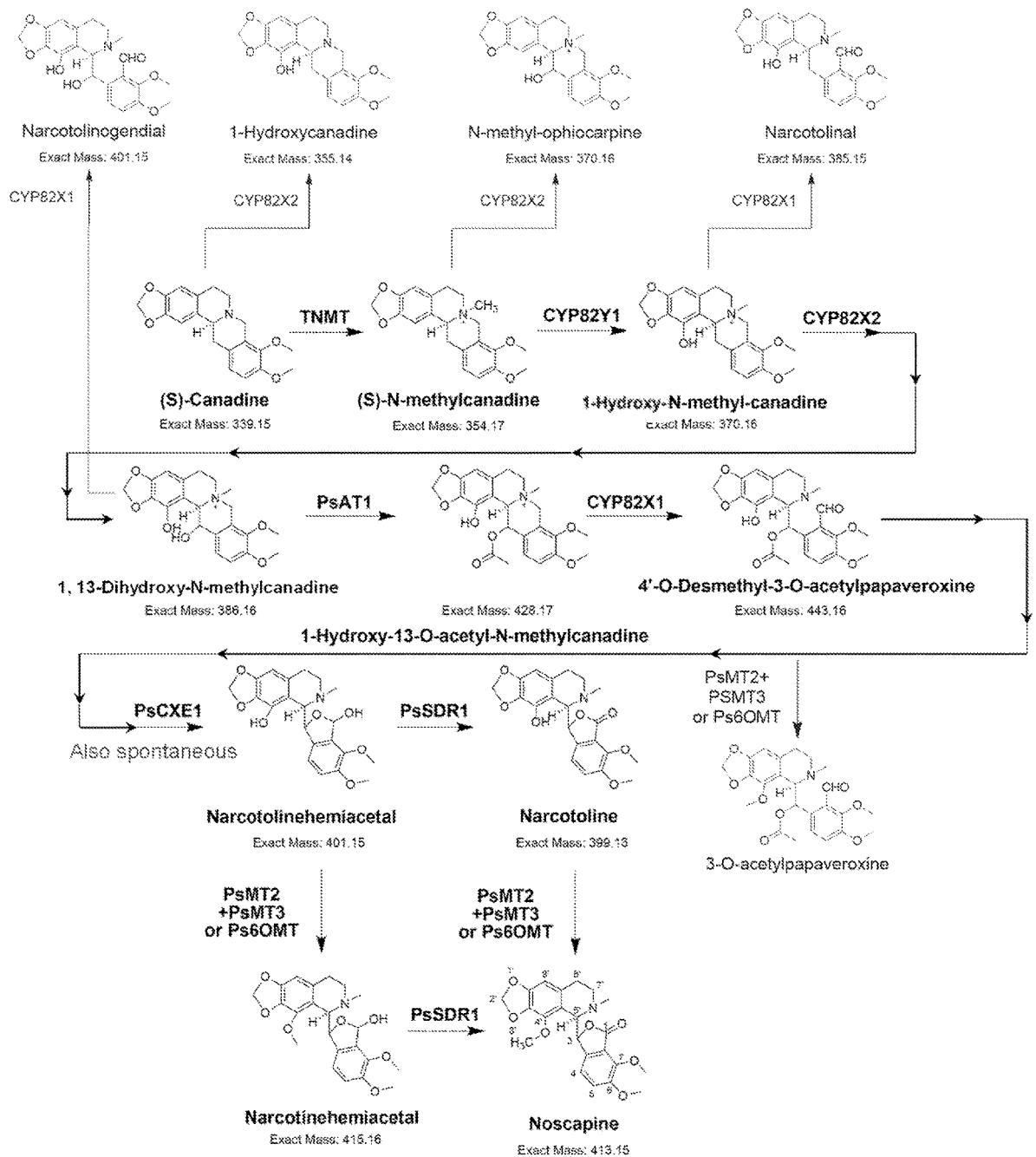
FIG. 11A illustrates a biosynthetic scheme for conversion of canadine to noscapine, in accordance with embodiments of the invention.

[AT1] In some examples, the engineered host cell may modify the expression of the enzyme 1, 13-dihydroxy-N-methylcanadine 13-O acetyl transferase. 1, 13-dihydroxy-N-methylcanadine 13-O acetyltransferase is encoded by the AT1 gene. In some examples, 1, 13-dihydroxy-N-methylcanadine 13-O acetyltransferase catalyzes the reaction of 1, 13-dihydroxy-N-methylcanadine→1-hydroxy-13-O-acetyl-N-methylcanadine, as referenced in FIG. 11A. FIG. 11A illustrates a biosynthetic scheme for conversion of canadine to noscapine, in accordance with embodiments of the invention. The engineered host cell may be modified to include constitutive expression of the AT1 gene in the engineered host cell. Additionally or alternatively, the engineered host cell may be modified to synthetically regulate the expression of the AT1 gene in the engineered host cell. In examples, the engineered host cell may be modified to incorporate a copy, copies, or additional copies, of the AT1 gene. Additionally or alternatively, the engineered host cell may be modified to incorporate the introduction of a strong promoter element for the overexpression of the AT1 gene within the engineered host cell. In some cases, the AT1 gene may be codon optimized for expression in *Saccharomyces cerevisiae*. The AT1 gene may be derived from *P. somniferum*, *Papaver* spp, *Plantago arenaria*, *Rauwolfia heterophylla*, *Adlumia fungosa*, *Hydrastis Canadensis*, *Stylomecon heterophylla*, *Hypecoum leptocarpum*, *Dactylicapnos torulosa*, *Glaucium flavum*, *Berberis laurina*, *B. Vulgaris*, *Corydalis* spp, *Fumaria* spp, *Dactylicapnos* spp, or another species. In some examples, the AT1 gene may be 81% similar to the naturally occurring gene.

[CXE1 or CXE2] In some examples, the engineered host cell may modify the expression of the enzyme narcotinehemiacetal synthase. Narcotinehemiacetal synthase is encoded by the CXE1 gene. The enzyme encoded by the CXE2 gene can also function as a narcotinehemiacetal synthase. In some examples, narcotinehemiacetal synthase catalyzes the reaction of 4'-O-desmethyl-3-O-acetylpapaveroxine→narcotolinehemiacetal and 3-O-acetylpapaveroxine→narcotinehemiacetal, as referenced in FIG. 11A. The engineered host cell may be modified to include constitutive expression of the CXE1 or CXE2 gene in the engineered host cell. Additionally or alternatively, the engineered host cell may be modified to synthetically regulate the expression of the CXE1 or CXE2 gene in the engineered host cell. In examples, the engineered host cell may be modified to incorporate a copy, copies, or additional copies, of the CXE1 or CXE2 gene. Additionally or alternatively, the engineered host cell may be modified to incorporate the introduction of a strong promoter element for the overexpression of the CXE1 or CXE2 gene within the engineered host cell. In some cases, the CXE1 or CXE2 gene may be codon optimized for expression in *Saccharomyces cerevisiae*. The CXE1 or CXE2 gene may be derived from *P. somniferum*, *Papaver* spp, *Plantago arenaria*, *Rauwolfia heterophylla*, *Adlumia fungosa*, *Hydrastis Canadensis*, *Stylomecon heterophylla*, *Hypecoum leptocarpum*, *Dactylicapnos torulosa*, *Glaucium flavum*, *Berberis laurina*, *B. Vulgaris*, *Corydalis* spp, *Fumaria* spp, *Dactylicapnos* spp, or another species. In some examples, the CXE1 gene or CXE2 gene may be 78% similar to the naturally occurring gene.

[SDR1] In some examples, the engineered host cell may modify the expression of the enzyme noscapine synthase. Noscapine synthase is encoded by the SDR1 gene. In some examples, noscapine synthase catalyzes the reaction of narcotolinehemiacetal→narcotoline, as referenced in FIG. 11A. Additionally, noscapine synthase catalyzes the reaction of narcotinehemiacetal→noscapine. The engineered host cell may be modified to include constitutive expression of the SDR1 gene in the engineered host cell. Additionally or alternatively, the engineered host cell may be modified to synthetically regulate the expression of the SDR1 gene in the engineered host cell. In examples, the engineered host cell may be modified to incorporate a copy, copies, or additional copies, of the SDR1 gene. Additionally or alternatively, the engineered host cell may be modified to incorporate the introduction of a strong promoter element for the overexpression of the SDR1 gene within the engineered host cell. In some cases, the SDR1 gene may be codon optimized for expression in *Saccharomyces cerevisiae*. The SDR1 gene may be derived from *P. somniferum*, *Papaver* spp, *Plantago arenaria*, *Rauwolfia heterophylla*, *Adlumia fungosa*, *Hydrastis Canadensis*, *Stylomecon heterophylla*, *Hypecoum leptocarpum*, *Dactylicapnos torulosa*, *Glaucium flavum*, *Berberis laurina*, *B. Vulgaris*, *Corydalis* spp, *Fumaria* spp, *Dactylicapnos* spp, or another species. In some examples, the SDR1 gene may be 79% similar to the naturally occurring gene.

[MT2 and MT3] In some examples, the engineered host cell may modify the expression of the enzyme narcotoline 4'-O-methylase. Narcotoline 4'-O-methylase is a heterodimer formed by the O-methyltransferase monomer encoded by the MT2 and MT3 genes. In some examples, narcotoline 4'-O-methylase catalyzes the reaction of narcotoline→noscapine, as referenced in FIG. 11A. Additionally, narcotoline 4'-O-methylase catalyzes the reaction of narcotolinenehemiacetal→narcotinehemiacetal and 4'-O-desmethyl-3-O-acetylpapaveroxine→3-O-acetylpapaveroxine.

The engineered host cell may be modified to include constitutive expression of the MT2 and MT3 genes in the engineered host cell. Additionally or alternatively, the engineered host cell may be modified to synthetically regulate the expression of the MT2 and MT3 genes in the engineered host cell. In examples, the engineered host cell may be modified to incorporate a copy, copies, or additional copies, of the MT2 and MT3 genes. Additionally or alternatively, the engineered host cell may be modified to incorporate the introduction of a strong promoter element for the overexpression of the MT2 and MT3 genes within the engineered host cell. In some cases, the MT2 and MT3 genes may be codon optimized for expression in *Saccharomyces cerevisiae*. The MT2 and MT3 genes may be derived from *P. somniferum*, *Papaver* spp, *Fumaria parviflora*, *Plantago arenaria*, *Rauwolfia heterophylla*, or another species. In some examples, the MT2 and MT3 genes may be 80% and 79% similar, respectively, to the naturally occurring genes.

Figure 11B:
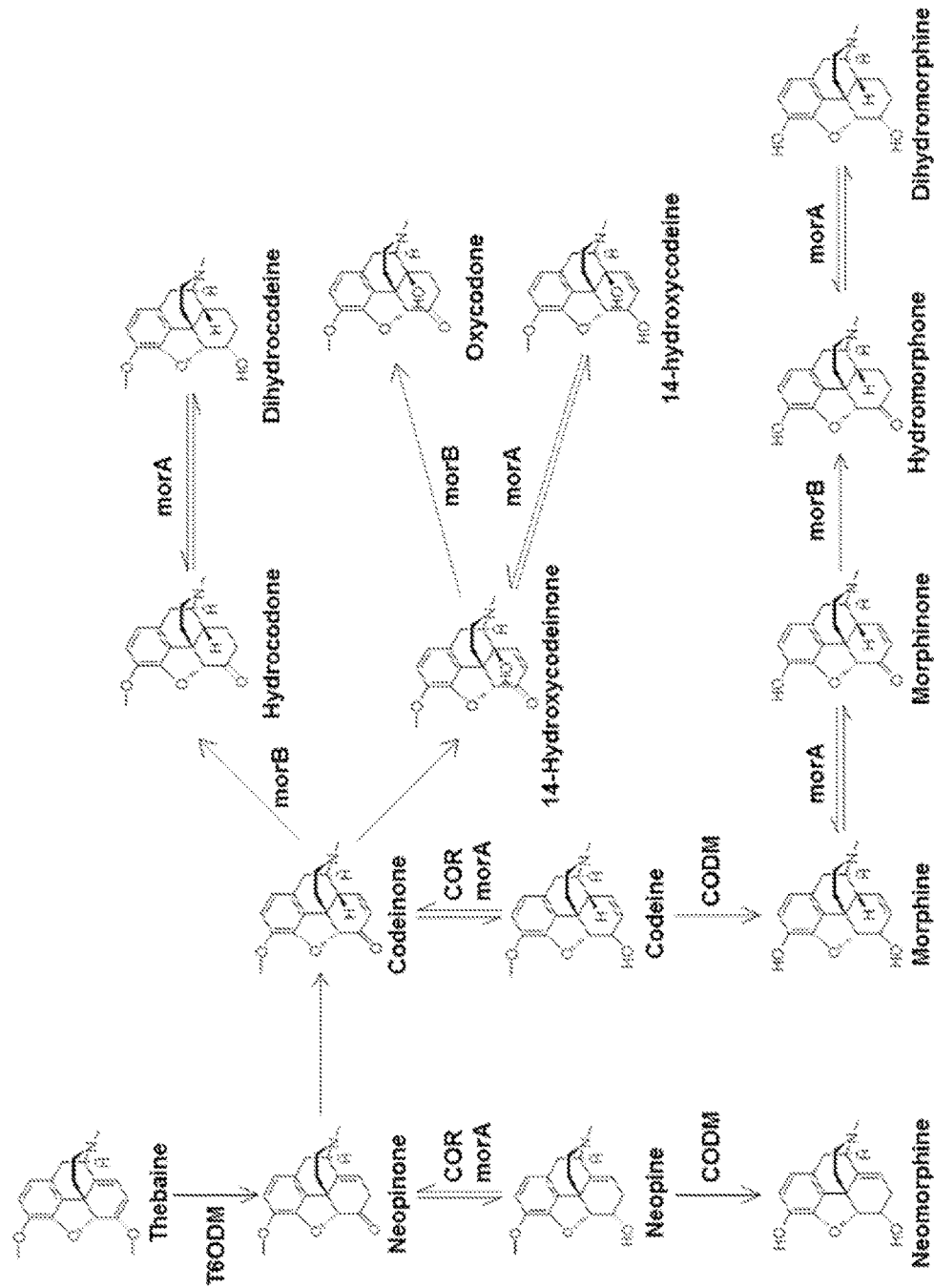
FIG. 11B illustrates a biosynthetic scheme for production of semi-synthetic opioids, in accordance with embodiments of the invention.

[morA] In some examples, the engineered host cell may modify the expression of the enzyme morphine dehydrogenase. Morphine dehydrogenase is encoded by the morA gene. In some examples, morphine dehydrogenase catalyzes the reaction of morphine→morphinone, as referenced in FIG. 11B. In other examples, morphine dehydrogenase catalyzes the reaction of codeinone→codeine, also as referenced in FIG. 11B. FIG. 11B illustrates a biosynthetic scheme for production of semi-synthetic opiods, in accordance with embodiments of the invention. In particular, FIG. 11B illustrates extended transformations of thebaine in yeast by incorporating morA, morphine dehydrogenase; and morB, morphine reductase.

The engineered host cell may be modified to include constitutive expression of the morA gene in the engineered host cell. Additionally or alternatively, the engineered host cell may be modified to synthetically regulate the expression of the morA gene in the engineered host cell. In examples, the engineered host cell may be modified to incorporate a copy, copies, or additional copies, of the morA gene. Additionally or alternatively, the engineered host cell may be modified to incorporate the introduction of a strong promoter element for the overexpression of the morA gene within the engineered host cell. In some cases, the morA gene may be codon optimized for expression in *Saccharomyces cerevisiae*. The morA gene may be derived from *Pseudomonas putida* or another species. In some examples, the morA gene may be 73.7% similar to the naturally occurring gene.

[morB] In some examples, the engineered host cell may modify the expression of the enzyme morphinone reductase. Morphinone reductase is encoded by the morB gene. In some examples, morphinone reductase catalyzes the reaction of codeinone→hydrocodone, as referenced in FIG. 11B. In other examples, morphinone reductase catalyzes the reaction of morphinone hydromorphone, also as referenced in FIG. 11B. In other examples, morphinone reductase catalyzes the reaction 14-hydroxycodeinone→oxycodone. The engineered host cell may be modified to include constitutive expression of the morB gene in the engineered host cell. Additionally or alternatively, the engineered host cell may be modified to synthetically regulate the expression of the morB gene in the engineered host cell. In examples, the engineered host cell may be modified to incorporate a copy, copies, or additional copies, of the morB gene. Additionally or alternatively, the engineered host cell may be modified to incorporate the introduction of a strong promoter element for the overexpression of the morB gene within the engineered host cell. In some cases, the morB gene may be codon optimized for expression in *Saccharomyces cerevisiae*. The morB gene may be derived from *Pseudomonas putida* or another species. In some examples, the morB gene may be 67.2% similar to the naturally occurring gene.

[CYP80A1] In some examples, the engineered host cell may express the enzyme berbamunine synthase. Berbamunine synthase is encoded by the gene for cytochrome P450 enzyme 80A1 (CYP80A1). In some examples, CYP80A1 catalyzes the reaction (S)—N-methylcoclaurine+(R)—N-methylcoclaurine berbamunine. In other examples, CYP80A1 catalyzes the reaction (R)—N-methylcoclaurine+(R)—N-methylcoclaurine→guattegaumerine. In other examples, CYP80A1 catalyzes the reaction (R)—N-methylcoclaurine+(S)-coclaurine→2'norberbamunine. The engineered host cell may be modified to include constitutive expression of the CYP80A1 gene in the engineered host cell. Additionally or alternatively, the engineered host cell may be modified to synthetically regulate the expression of the CYP80A1 gene in the engineered host cell. In examples, the engineered host cell may be modified to incorporate a copy, copies, or additional copies, of the CYP80A1 gene. Additionally or alternatively, the engineered host cell may be modified to incorporate the introduction of a strong promoter element for the overexpression of the CYP80A1 gene within the engineered host cell. In some cases, the CYP80A1 gene may be codon optimized for expression in *Saccharomyces cerevisiae*. The CYP80A1 gene may be derived from *Berberis stolonifera* or another species. In some examples, the CYP80A1 gene may be 76% similar to the naturally occurring gene.

[PODA] In some example, the engineered host cell may express the enzyme protopine O-dealkylase. Protopine O-dealkylase is encoded by the gene PODA. In some examples, PODA catalyzes the O,O-demethylenation of protoberberines and protopines such as canadine, stylopine, berberine, cryptopine, allocryptopine, and protopine. In some examples, PODA catalyzes the O-demethylation of BIAs including tetrahydropapaverine, tetrahydropalmatine, and cryptopine. The engineered host cell may be modified to include constitutive expression of the PODA gene in the engineered host cell. Additionally or alternatively, the engineered host cell may be modified to synthetically regulate the expression of the PODA gene in the engineered host cell. In examples, the engineered host cell may be modified to incorporate a copy, copies, or additional copies, of the PODA gene. Additionally or alternatively, the engineered host cell may be modified to incorporate the introduction of a strong promoter element for the overexpression of the PODA gene within the engineered host cell. In some cases, the PODA gene may be codon optimized for expression in *Saccharomyces cerevisiae*. The PODA gene may be derived from *Papaver somniferum* or other species. In some examples, the PODA gene may be 70-100% similar to the naturally occurring gene.

Examples of the aforementioned genes can be expressed from a number of different platforms in the host cell, including plasmid (2µ, ARS/CEN), YAC, or genome. In addition, examples of the aforementioned gene sequences can either be native or codon optimized for expression in the desired heterologous host (e.g., *Saccharomyces cerevisiae*).

EXAMPLES

The following examples are given for the purpose of illustrating various embodiments of the invention and are not meant to limit the invention in any fashion. Where indicated, expression constructs are understood to incorporate a suitable promoter, gene, and terminator, even if the exact terminator sequence used is not specified. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Figure 12:
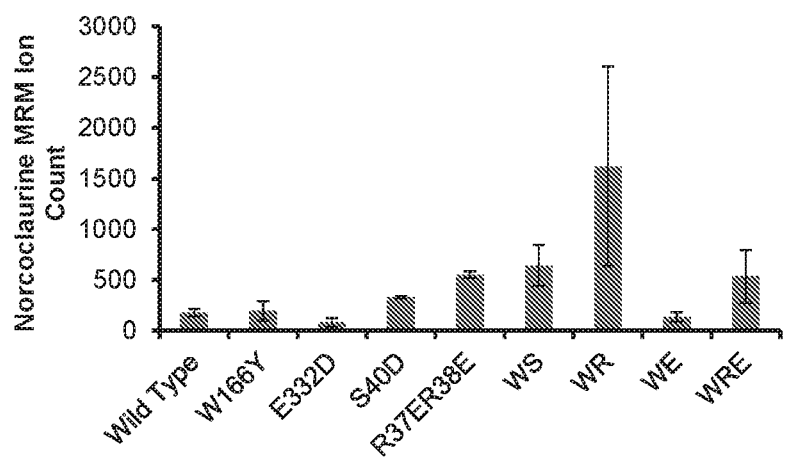
FIG. 12 illustrates tyrosine hydroxylase mutants that improve norcoclaurine production from sugar in engineered yeast strains, in accordance with embodiments of the invention.

Example 1: Tyrosine Hydroxylase Mutants Improve Norcoclaurine Production in Engineered Yeast Strains Tyrosine hydroxylase from *R. norvegicus* was yeast codon optimized, synthesized, and cloned into a low-copy plasmid. Single mutants (W166Y, E332D, S40D and R37ER38E), double mutants (W166Y and E332D, W166Y and 540D, W166Y and R37ER38E), and one triple mutant (W166Y, R37ER38E, and E332D) were generated through site-directed mutagenesis. Each TyrH mutant was expressed from a low-copy plasmid with the GPD promoter in a yeast strain containing the following mutations to central metabolism (as described in U.S. Provisional Patent Application Ser. No. 61/899,496): ARO4$^{FBR}$, ΔZWF1, and GPD-TKL1 promoter replacement. In addition, the strain expressed a chromosomally integrated copy of DOPA decarboxylase (DODC) from *P. putida*, four chromosomally integrated genes from *R. norvegicus* that generate the cosubstrate tetrahydrobiopterin (pyruvoyl tetrahydropterin synthase, PTPS; sepiapterin reductase, SepR; pterin 4a-carbinolamine dehydratase, PCD; dihydropteridine reductase, QDHPR) and norcoclaurine synthase (NCS) from *C. japonica* expressed from a low-copy plasmid with a GPD promoter. The strains harboring TyrH mutants were grown in selective defined media (YNB) lacking tyrosine with 2% dextrose for 96 hours, and the production of norcoclaurine was measured in the media via LC-MS/MS in MRM mode with the transition 272 m/z to 107 m/z. FIG. 12 shows the results of this assay and demonstrates that TyrH mutants can improve norcoclaurine production by as much as 9-fold when compared to wild-type TyrH. As such, FIG. 12 illustrates tyrosine hydroxylase mutants that improve norcoclaurine production from sugar in engineered yeast strains, in accordance with embodiments of the invention.

Figure 13:
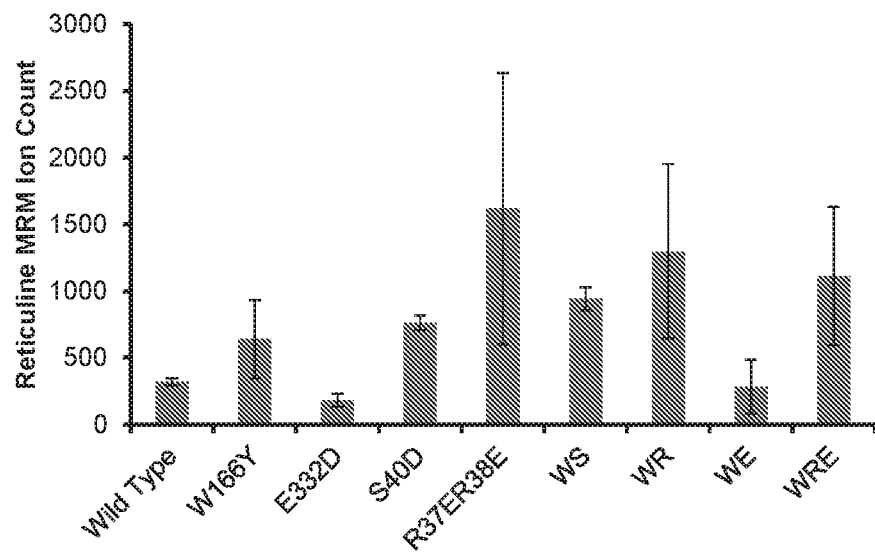
FIG. 13 illustrates tyrosine hydroxylase mutants that improve reticuline production from sugar in engineered yeast strains, in accordance with embodiments of the invention.

Example 2: Tyrosine Hydroxylase Mutants Improve Reticuline Production in Engineered Yeast Strains Tyrosine hydroxylase from *R. norvegicus* was yeast codon optimized, synthesized, and cloned into a low-copy plasmid. Single mutants (W166Y, E332D, S40D and R37ER38E), double mutants (W166Y and E332D, W166Y and S40D, W166Y and R37ER38E), and one triple mutant (W166Y, R37ER38E, and E332D) were generated through site-directed mutagenesis. Each TyrH mutant was expressed from a low-copy plasmid with the GPD promoter in a yeast strain containing the following mutations to central metabolism (as described in U.S. Provisional Patent Application Ser. No. 61/899,496): ARO4$^{FBR}$, ΔZWF1, and GPD-TKL1 promoter replacement. In addition, the strain expressed a chromosomally integrated copy of DOPA decarboxylase (DODC) from *P. putida*, four chromosomally integrated genes from *R. norvegicus* that generate the cosubstrate tetrahydrobiopterin (pyruvoyl tetrahydropterin synthase, PTPS; sepiapterin reductase, SepR; pterin 4a-carbinolamine dehydratase, PCD; dihydropteridine reductase, QDHPR), norcoclaurine synthase (NCS) from *C. japonica* expressed from a low-copy plasmid with a GPD promoter, and five genes for the biosynthesis of reticuline from norcoclaurine (*P. somniferum* 6-O-methyltransferase, Ps6OMT; *P. somniferum* coclaurine N-methyltransferase, PsCNMT; *E. californica* cytochrome P450 80B1, EcCYP80B1; *P. somniferum* cytochrome P450 NADPH reductase, PsCPR; and *P. somniferum* 3'hydroxy-N-methylcoclaurine 4'-O-methyltransferase, Ps4'OMT). The strains harboring TyrH mutants were grown in selective defined media (YNB) lacking tyrosine with 2% dextrose for 96 hours, and the production of reticuline was measured in the media via LC-MS/MS in MRM mode with the transition 330 m/z to 137 m/z. FIG. 13 shows the results of this assay and demonstrates that TyrH mutants can improve reticuline production by as much as 5-fold when compared to wild-type TyrH. As such, FIG. 13 illustrates tyrosine hydroxylase mutants that improve reticuline production from sugar in engineered yeast strains, in accordance with embodiments of the invention.

Figure 14:
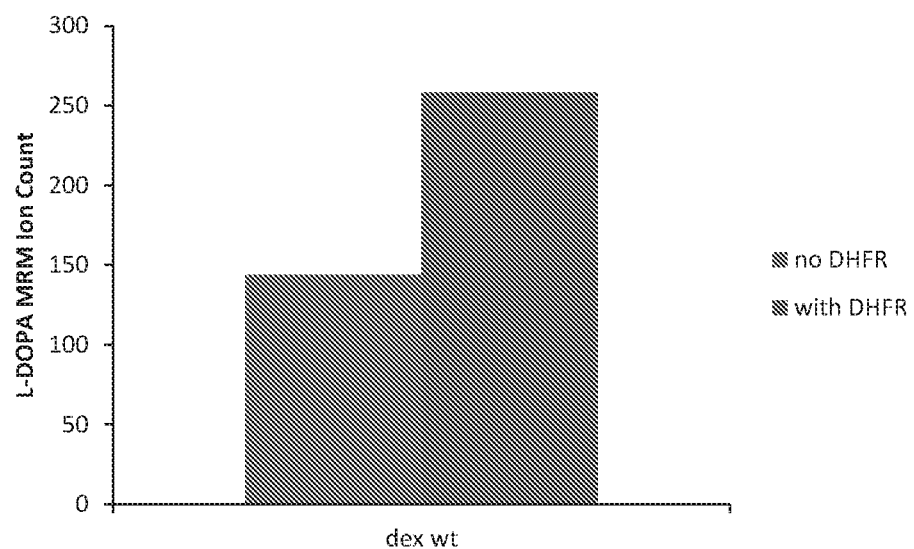
FIG. 14 illustrates coexpression of dihydrofolate reductase (DHFR) that improves L-DOPA production by tyrosine hydroxylase in engineered yeast strains, in accordance with embodiments of the invention.

Example 3: Expression of DHFR Improves Tyrosine Hydroxylase Activity in Engineered Yeast Strains Dihydrofolate reductase (DHFR) from *R. norvegicus* was yeast codon optimized, synthesized, and cloned into a low-copy plasmid under the control of a GPD promoter. DHFR was coexpressed with wild-type RnTyrH (low-copy plasmid with a GPD promoter) in a yeast strain containing the following mutations to central metabolism (as described in U.S. Provisional Patent Application Ser. No. 61/899,496): ARO4$^{FBR}$, ΔZWF1, and GPD-TKL1 promoter replacement. In addition, the strain expressed four chromosomally integrated genes from *R. norvegicus* that generate the cosubstrate tetrahydrobiopterin (pyruvoyl tetrahydropterin synthase, PTPS; sepiapterin reductase, SepR; pterin 4a-carbinolamine dehydratase, PCD; dihydropteridine reductase, QDHPR). The strains expressing DHFR and wild-type RnTyrH were grown in selective defined media (YNB) lacking tyrosine with 2% dextrose for 96 hours, and the production of L-DOPA was measured in the media via LC-MS/MS in MRM mode with the transition 198 m/z to 152 m/z. Expression of DHFR with wild-type RnTyrH increases L-DOPA production by 1.8-fold, as illustrated in FIG. 14. As such, FIG. 14 illustrates coexpression of dihydrofolate reductase (DHFR) that improves L-DOPA production by tyrosine hydroxylase in engineered yeast strains, in accordance with embodiments of the invention.

Example 4: Addition of Antioxidants to Growth Media Improve Tyrosine Hydroxylase Activity in Engineered Yeast Strains A yeast strain containing the following mutations to central metabolism (as described in U.S. Provisional Patent Application Ser. No. 61/899,496):ARO4$^{FBR}$, ΔZWF1, and GPD-TKL1 promoter replacement and expressing four chromosomally integrated genes from *R. norvegicus* that generate the cosubstrate tetrahydrobiopterin (pyruvoyl tetrahydropterin synthase, PTPS; sepiapterin reductase, SepR; pterin 4a-carbinolamine dehydratase, PCD; dihydropteridine reductase, QDHPR) as well as wild-type RnTyrH from a low-copy plasmid under the control of the GPD promoter was grown in selective defined media (YNB) lacking tyrosine with 2% galactose and 2 mM ascorbic acid for 96 hours.

The production of L-DOPA was measured in the media via LC-MS/MS in MRM mode with the transition 198 m/z to 152 m/z. The addition of 2 mM ascorbic acid improves L-DOPA production with wild-type RnTyrH by 1.8-fold. In addition, the concentration BH$_4$ intermediates were measured with LC-MS/MS in MRM mode with the following transitions: B, 238 m/z to 178 m/z; BH2, 240 m/z to 165 m/z and BH4, 242 m/z to 166 m/z. The addition of ascorbic acid also increases BH$_4$ in the media, which indicates the oxidation of BH$_4$ to BH$_2$ is prevented.

Figure 15:
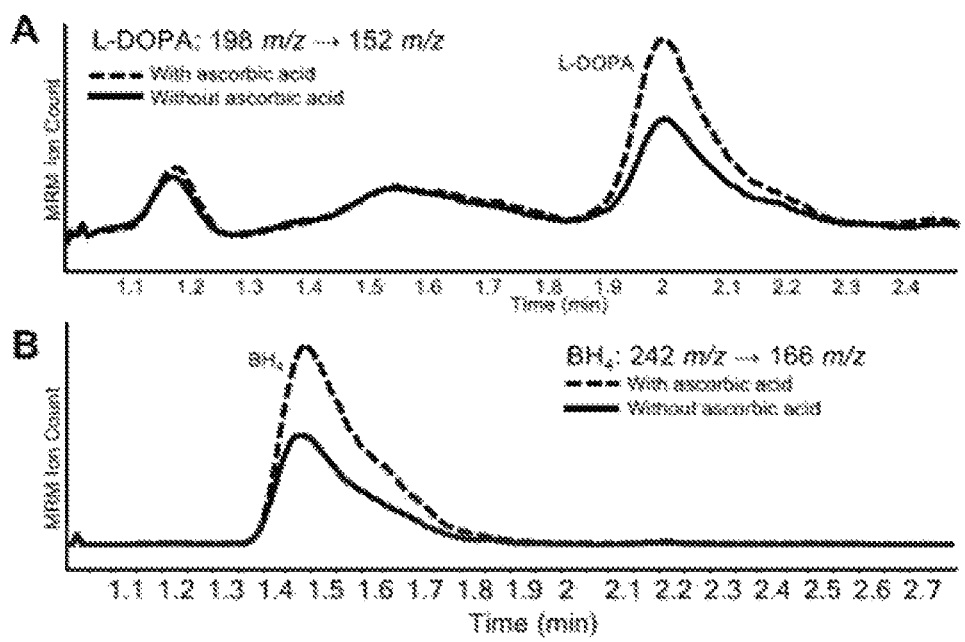
FIG. 15 illustrates (A) the addition of antioxidants to culture media that improves L-DOPA production by tyrosine hydroxylase in engineered yeast strains and (B) the addition of antioxidants to culture media that increase $BH_4$ levels, in accordance with embodiments of the invention.

Accordingly, FIG. 15 illustrates (A) addition of antioxidants to culture media that improves L-DOPA production by tyrosine hydroxylase in engineered yeast strains and (B) addition of antioxidants to culture media that increase BH$_4$ levels, in accordance with embodiments of the invention. In particular, FIG. 15A illustrate a wild-type RnTyrH (expressed from a low-copy plasmid under the control of a GPD promoter) was expressed in a yeast strain containing the following mutations to central metabolism (as described in U.S. Provisional Patent Application Ser. No. 61/899,496): ARO4$^{FBR}$, ΔZWF1, and GPD-TKL1 promoter replacement. In addition, the strain expressed four chromosomally integrated genes from *R. norvegicus* that generate the cosubstrate tetrahydrobiopterin (pyruvoyl tetrahydropterin synthase, PTPS; sepiapterin reductase, SepR; pterin 4a-carbinolamine dehydratase, PCD; dihydropteridine reductase, QDHPR). The strains expressing wild-type RnTyrH was grown in selective defined media (YNB) lacking tyrosine with 2% dextrose, with and without 2 mM ascorbic acid (aa) for 96 hours. The production of L-DOPA was measured in the media via LC-MS/MS in MRM mode with the transition 198 m/z to 152 m/z. Additionally, FIG. 15B illustrates, in the same strain described in FIG. 15A, the concentration of the BH$_4$ intermediate was measured in the media of strains grown with and without 2 mM ascorbic acid (aa) with LC-MS/MS in MRM mode with the following transition: BH$_4$, 242 m/z to 166 m/z.

Example 5: Yeast Strains Engineered to Produce the bisBIA Berbamunine

FIG. 16 illustrates (A) a biosynthetic scheme for conversion of L-tyrosine to bisBlAs and (B) yeast strains engineered to biosynthesize bisBIAs, in accordance with embodiments of the invention. In particular, FIG. 16 illustrates (A) a pathway that is used to produce bisBIAs berbamunine and guattegaumerine. FIG. 16 provides the use of the enzymes ARO9, aromatic aminotransferase; ARO10, phenylpyruvate decarboxlase; TyrH, tyrosine hydroxylase; DODC, DOPA decarboxylase; NCS, norcoclaurine synthase; 6OMT, 6-O-methyltransferase; CNMT, coclaurine N-methyltransferase; CYP80A1, cytochrome P450 80A1; CPR, cytochrome P450 NADPH reductase. Of the metabolites provided in FIG. 16, 4-HPA, 4-HPP, and L-tyrosine are naturally synthesized in yeast. Other metabolites that are shown in FIG. 16 are not naturally produced in yeast.

In examples of the invention, a bisBIA-producing yeast strain, that produces bisBIAs such as those generated using the pathway illustrated in (A), is engineered by integration of a single construct into locus YDR514C. Additionally, FIG. 16 provides (B) example yeast strains engineered to synthesize bisBIAs. Ps6OMT, PsCNMT, PsCPR, and BsCYP80A1 were integrated into the yeast genome at a single locus (YDR514C). Each enzyme was expressed from a constitutive promoter. The arrangement and orientation of gene expression cassettes is indicated by arrows in the schematic. These strains convert (R)- and (S)-norcoclaurine to coclaurine and then to N-methylcoclaurine. In one example, the strains may then conjugate one molecule of (R)—N-methylcoclaurine and one molecule of (S)—N-methylcoclaurine to form berbamunine. In another example, the strains may conjugate two molecules of (R)—N-methylcoclaurine to form guattegaumerine. In another example, the strains may conjugate one molecule of (R)—N-methylcoclaurine and one molecule of (S)-coclaurine to form 2'-norberbamunine. In another embodiment, the strain may be engineered to supply the precursors (R)- and (S)-norcoclaurine from L-tyrosine, as provided in FIG. 5.

The construct includes expression cassettes for *P. somniferum* enzymes 6OMT and CNMT expressed as their native plant nucleotide sequences. A third enzyme from *P. somniferum*, CPR, is codon optimized for expression in yeast. The PsCPR supports the activity of a fourth enzyme, *Berberis stolonifera* CYP80A1, also codon optimized for expression in yeast. The expression cassettes each include unique yeast constitutive promoters and terminators. Finally, the integration construct includes a LEU2 selection marker flanked by loxP sites for excision by Cre recombinase.

A yeast strain expressing Ps6OMT, PsCNMT, BsCYP80A1, and PsCPR is cultured in selective medium for 16 hours at 30° C. with shaking. Cells are harvested by centrifugation and resuspended in 400 µL breaking buffer (100 mM Tris-HCl, pH 7.0, 10% glycerol, 14 mM 2-mercaptoethanol, protease inhibitor cocktail). Cells are physically disrupted by the addition of glass beads and vortexing. The liquid is removed and the following substrates and cofactors are added to start the reaction: 1 mM (R,S)-norcoclaurine, 10 mM S-adenosyl methionine, 25 mM NADPH. The crude cell lysate is incubated at 30° C. for 4 hours and then quenched by the 1:1 addition of ethanol acidified with 0.1% acetic acid. The reaction is centrifuged and the supernatant analyzed by liquid chromatography mass spectrometry (LC-MS) to detect bisBIA products berbamunine, guattegaumerine, and 2'-norberbamunine by their retention and mass/charge.

Example 6: Identification of an Epimerase Enzyme

Figure 17:
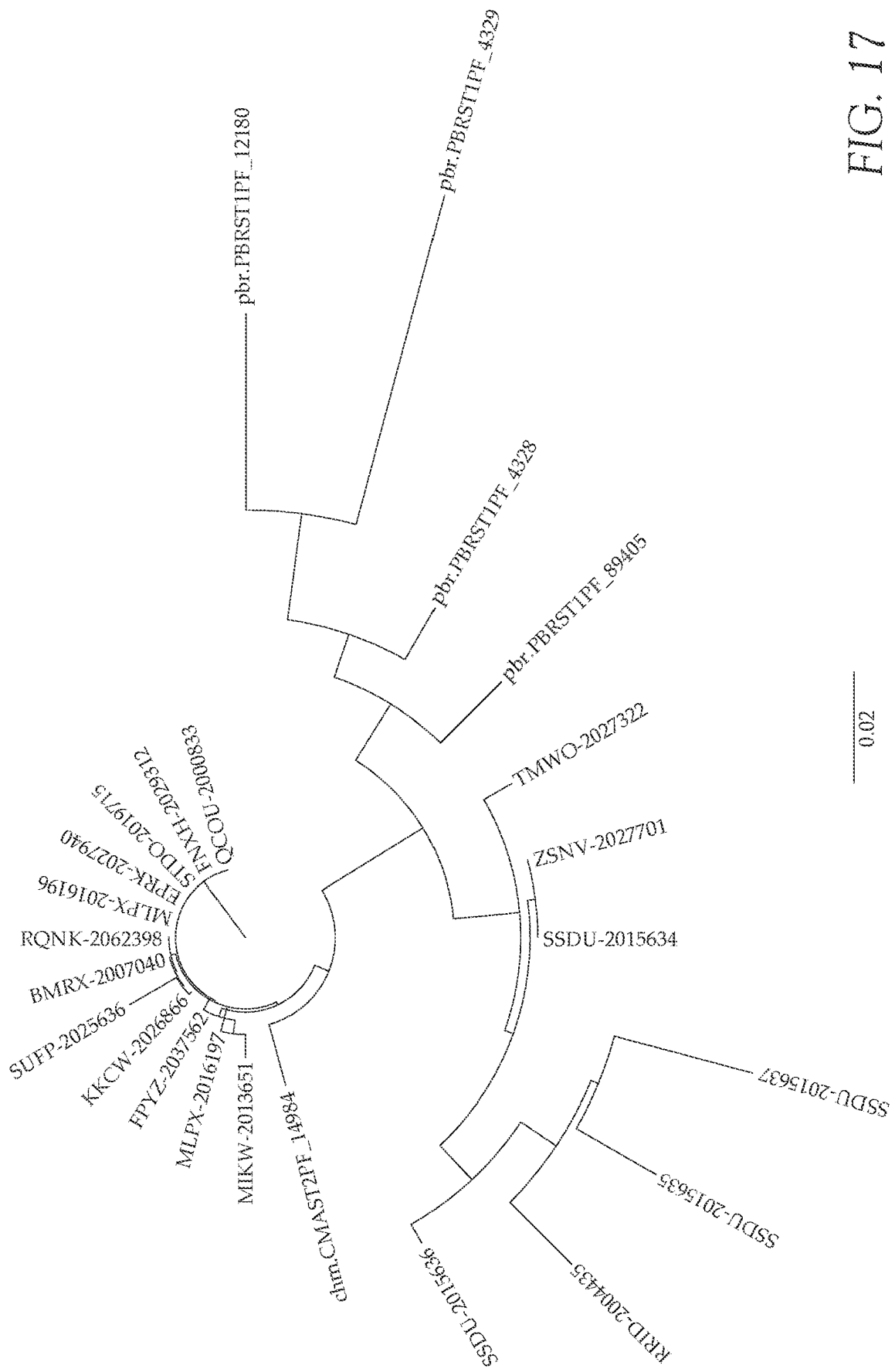
FIG. 17 illustrates a phylogenetic tree of cytochrome P450 oxidase-codeinone reductase-like (CYP-COR) fusions, in accordance with embodiments of the invention.

To identify an epimerase enzyme suitable for performing the epimerization reactions of the methods disclosed herein, a cytochrome P450 oxidase 82Y1-like domain and a codeinone reductase-like domain were identified in a single open reading frame (CYP-COR) in publically available plant transcriptomes. The CYP-COR fusions were identified from a BLAST search of the 1000 Plants Project (Matasci, et al. 2014. Gigascience. 3: 17) and PhytoMetaSyn (Facchini, et al. 2012. Trends Biotechnol. 30: 127-31; Xiao, et al. 2013. J. Biotechnol. 166: 122-34) transcriptomes using blastn with the query being the sequence of a previously published COR-silencing VIGS construct that resulted in reticuline accumulation (Wijekoon and Facchini. 2012. Plant J. 69: 1052-63). Once one CYP-COR fusion sequence was observed as a hit, that sequence was translated and the amino acid sequence was used as the query for a second search of both databases with tblastn. A phylogenetic tree of the CYP-COR fusion enzymes identified from the databases is provided in FIG. 17. The sequences were identified from The 1000 Plants Project and PhytoMetaSyn transcriptome databases based on a bioinformatic search. Additionally, an example amino acid sequence is provided in FIG. 4, as discussed above. Additionally, Table 1 lists various examples of amino acid sequences identified for this CYP-COR enzyme, which come from various plants including *Papaver somniferum* (opium poppy), *Papaver setigerum* (poppy of Troy), *Papaver bracteatum* (Iranian poppy), and *Chelidonium majus* (greater celandine).

Example 7: Epimerization of (S)-Reticuline to (R)-Reticuline in an Engineered Non-Plant Host Cell Non-plant host cells were engineered to heterologously express enzymes described herein. For instance, yeast strains (*Saccharomyces cerevisiae*) were engineered to heterologously express the identified epimerases described in Example 6 and to verify their function in the context of this microbial host. The yeast-codon optimized DNA coding sequences for the partial amino acid sequences pbr.PBRST1PF_4328 and pbr.PBRST1PF_89405 were synthesized in-frame with the yeast-codon optimized coding sequence for amino acids 1-40 of SSDU-2015634 (Table 1) to generate CYP-COR_4328 and CYP-COR_89405, respectively. These CYP-COR coding sequences were cloned into a low-copy plasmid harboring a URA3 selection marker and expressed from the TDH3 promoter. The plasmids were transformed into yeast strains that harbored an expression cassette for a cytochrome P450 reductase ($P_{TEF1}$-ATR1 or $P_{TEF1}$-PsCPRv2) integrated into the chromosome. These yeast strains harboring the two plasmids were grown in synthetic complete media with the appropriated drop out solution (-Ura-Trp). The yeast strains were fed (S)-reticuline and BIA metabolites were analyzed after 72 hours of growth by LC-MS/MS analysis.

Figure 18:
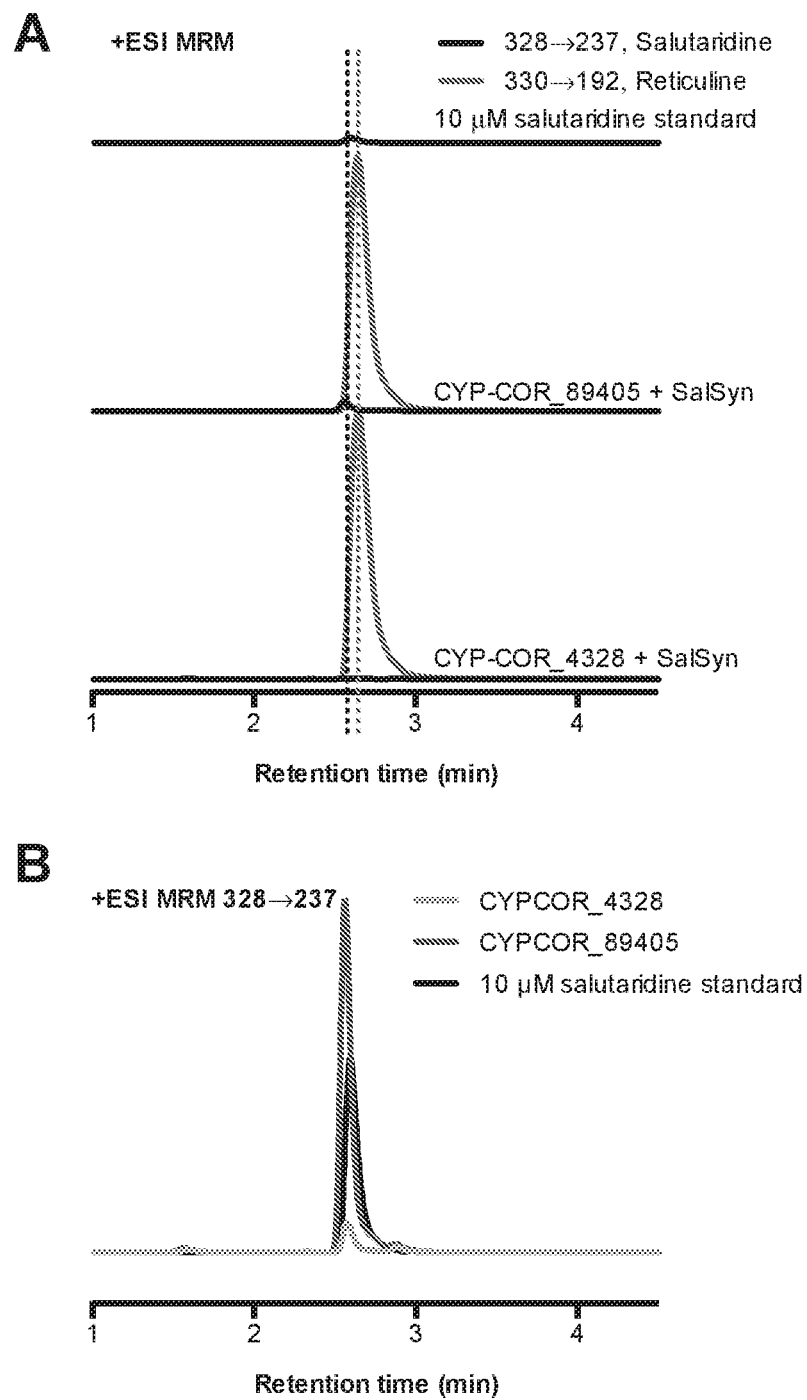
FIGS. 18(A) and 18(B) illustrate an LC-MS/MS analysis of yeast strains engineered to convert (S)-reticuline to salutaridine, in accordance with embodiments of the invention.

Example 8: Production of Salutaridine from (S)-Reticuline in an Engineered Yeast Cell Yeast strains (*Saccharomyces cerevisiae*) were engineered to heterologously express the identified epimerases described in Example 6 and to verify their function in the context of this microbial host. The yeast-codon optimized DNA coding sequences for the partial amino acid sequences pbr.PBRST1PF_4328 and pbr.PBRST1PF_89405 were synthesized in-frame with the yeast-codon optimized coding sequence for amino acids 1-40 of SSDU-2015634 (Table 1) to generate CYP-COR_4328 and CYP-COR_89405, respectively. These CYP-COR coding sequences were cloned into a low-copy plasmid harboring a URA3 selection marker and expressed from the TDH3 promoter. The salutaridine synthase (SalSyn) coding sequence was cloned into a low-copy plasmid harboring a TRP1 selection marker and expressed from the TDH3 promoter. The plasmids were transformed into yeast strains that harbored an expression cassette for a cytochrome P450 reductase ($P_{TEF1}$-ATR1 or $P_{TEF1}$-PsCPRv2) integrated into the chromosome. These yeast strains harboring the two plasmids were grown in synthetic complete media with the appropriated drop out solution (-Ura-Trp). The yeast strains were fed (S)-reticuline and BIA metabolites were analyzed after 72 hours of growth by LC-MS/MS analysis. The analysis indicated that the engineered yeast cells were able to convert (S)-reticuline to (R)-reticuline, which was then acted on by salutaridine synthase to form salutaridine, a 4-ring promorphinan alkaloid (FIG. 7, FIG. 18). Salutaridine synthase has been previously shown to act on (R)-reticuline and have no observable activity on (S)-reticuline (Gesell, et al. 2009. J. Biol. Chem. 284: 24432-42).

As shown in FIG. 7, CYP-COR catalyzes the conversion of (S)-reticuline to (R)-reticuline, which is then acted on by salutaridine synthase to make the promorphinan alkaloid salutaridine. FIG. 18 illustrates (A) chromatogram traces showing reticuline and salutaridine for two epimerase variants (CYP-COR_89405, CYP-COR_4328) and a standard. FIG. 18 also illustrates (B) the same chromatogram traces for salutaridine in (A) as replotted to demonstrate co-elution with the standard. In this experiment, the yeast contains two low-copy CEN/ARS plasmids with URA3 and TRP1 selective markers, TDH3 promoters, and the CYP-COR and SalSyn coding sequences. Yeast were grown from freshly transformed colonies in 3 mL selective media overnight, back-diluted into 3.5 mL media to OD 0.8, grown 7 hours, pelleted, and then resuspended into pH 7.4 HEPES buffer with 100 µM (S)-reticuline (Specs). After 16 hours on a spinner at 30° C., the yeast were pelleted and the buffer supernatant was analyzed by LC-MS/MS. Each trace is from a single sample representative of 2. Peaks are normalized such that the largest peak in all chromatograms is 100%.

Figure 19:
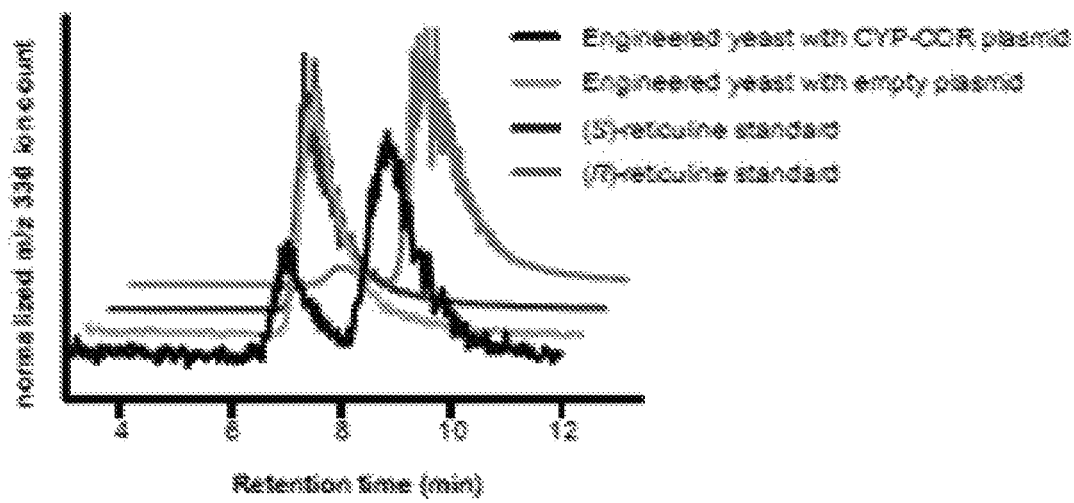
FIG. 19 illustrates a chiral LC-MS/MS analysis of yeast strains engineered to convert racemic norlaudanosoline to (R)-reticuline, in accordance with embodiments of the invention.

Example 9: Production of (R)-Reticuline from Racemic Norlaudanosoline in an Engineered Non Plant Host Cell Yeast strains (*Saccharomyces cerevisiae*) were engineered to heterologously express the identified epimerases described in Example 6 and to verify their function in the context of this microbial host. The yeast-codon optimized DNA coding sequence CYP-COR_89405 described in Example 7 was cloned into a low-copy plasmid harboring a URA3 selection marker and expressed from the TDH3 promoter. This plasmid was transformed into yeast strains that harbored expression cassettes for a cytochrome P450 reductase ($P_{TEF1}$-ATR1 or $P_{TEF1}$-PsCPRv2) and three methyltransferases (*Papaver somniferum* norcoclaurine-6-O-methyltransferase, coclaurine N-methyltransferase, and 3'-hydroxy-N-methylcoclaurine 4'-O-methyltransferase, all expressed from $P_{TEF1}$) integrated into the chromosome. This yeast strain harboring the plasmid was grown in synthetic complete media with the appropriated drop out solution (-Ura). The yeast strain was fed racemic norlaudanosoline and BIA metabolites were analyzed after 72 hours of growth by LC-MS/MS analysis. For chiral characterization, reticuline was concentrated from yeast media by pelleting 5 mL yeast culture and adding 120 mg XAD-4 resin to 4 mL supernatant, incubating on rotator overnight at room temperature, and eluting with 0.5 mL methanol. The concentrate was fractionated by reverse-phase HPLC (Pursuit XRs-C18, 5 µm, 50 mm×10 mm) with isocratic 15% methanol with 0.1% formic acid over 6.5 min with a flow rate of 5 mL/min and injection volume of 40-50 µL. Peak-based fractions were collected at approximately 4.5 min. Fractions were pooled, freeze-dried, and resuspended in 0.5 mL isopropanol. Depending on concentration, 0.5-5 µL were injected onto a chiral column (Phenomenex Lux cellulose-1, 3 µm, 150 mm×2 mm) and separated with isocratic 72% N-hexane, 28% isopropanol, 0.1% diethylamine with a flow rate of 0.3 mL/min and detection by MS and 250 nm UV. MS detection was performed with an Agilent 6320 Ion Trap mass spectrometer with ESI source gas temperature 350° C., gas flow of 10 L/min, nebulizer pressure 40 PSI and isolation of m/z 330.1 with width 1.0. The retention time of reticuline peaks was compared to that of authentic (S)-reticuline and (R)-reticuline standards. The analysis indicated that the engineered yeast cells containing the CYP-COR plasmid were able to convert racemic norlaudanosoline to (R)-reticuline, while engineered yeast cells with an empty plasmid produced exclusively (S)-reticuline (FIG. 19).

Figure 20:
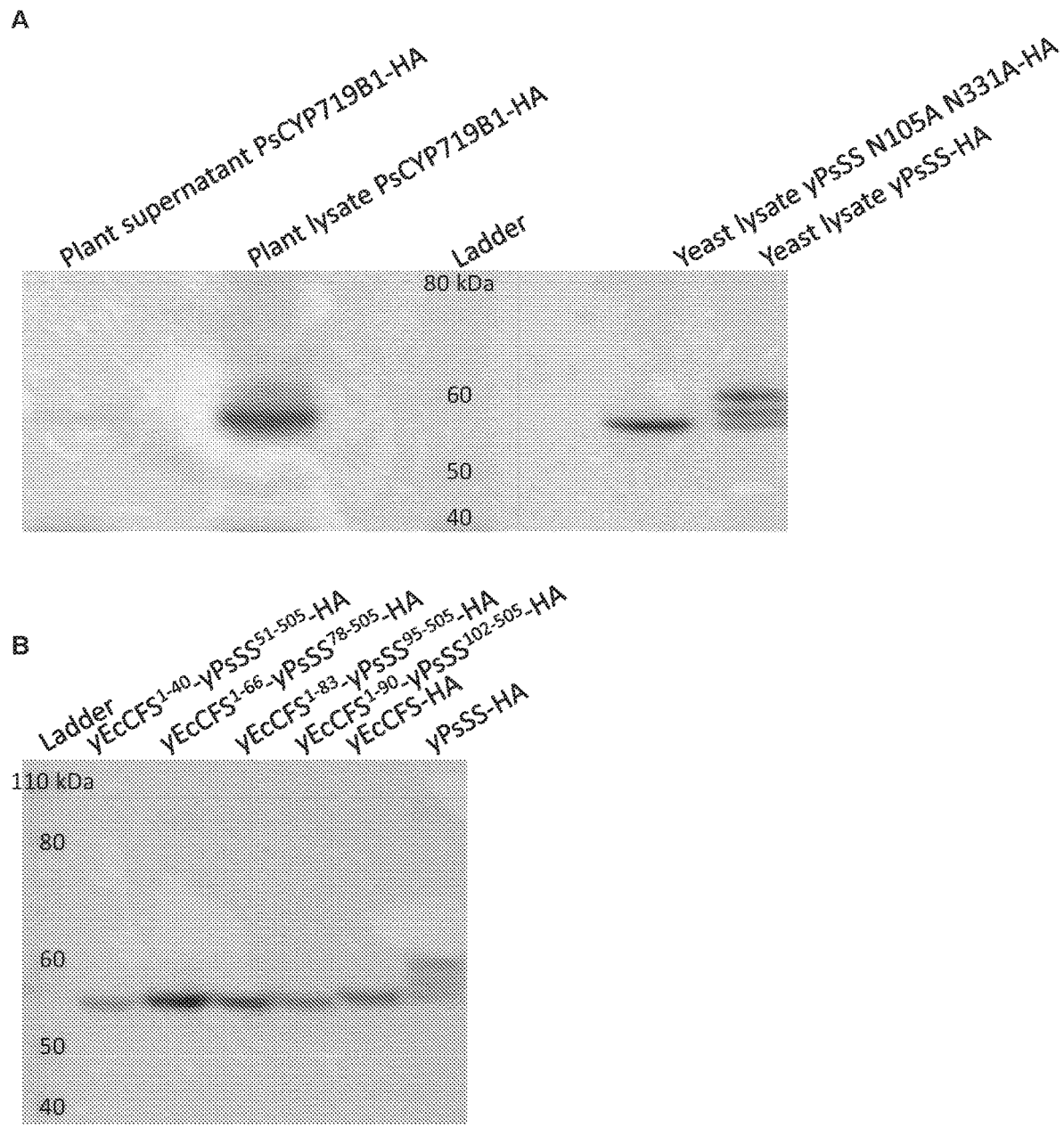
FIGS. 20(A) and 20(B) illustrate engineered fusions of salutaridine synthase that eliminates N-linked glycosylation of the protein observed when heterologously expressed in yeast but not plants, in accordance with embodiments of the invention

Example 10: Protein Engineering of Salutaridine Synthase to Improve its Processing and Activity when Expressed in a Microbial Host Heterologous proteins may be incorrectly processed when expressed in a recombinant host, for example, plant proteins such as cytochrome P450 enzymes expressed in microbial production hosts. For example, salutaridine synthase, which converts (R)-reticuline to salutaridine, undergoes N-linked glycosylation when heterologously expressed in yeast (FIG. 20). The observed N-linked glycosylation pattern on salutaridine synthase is not observed when the enzyme is expressed in plants and is indicative of incorrect N-terminal sorting of the nascent SalSyn transcript, which reduces the activity of the enzyme in the heterologous microbial host. Thus, protein engineering directed at correcting N-terminal sorting of the nascent transcript and thereby removing the N-linked glycosylation pattern will result in improved activity of the salutaridine synthase enzyme in the recombinant production host.

Figure 21A:
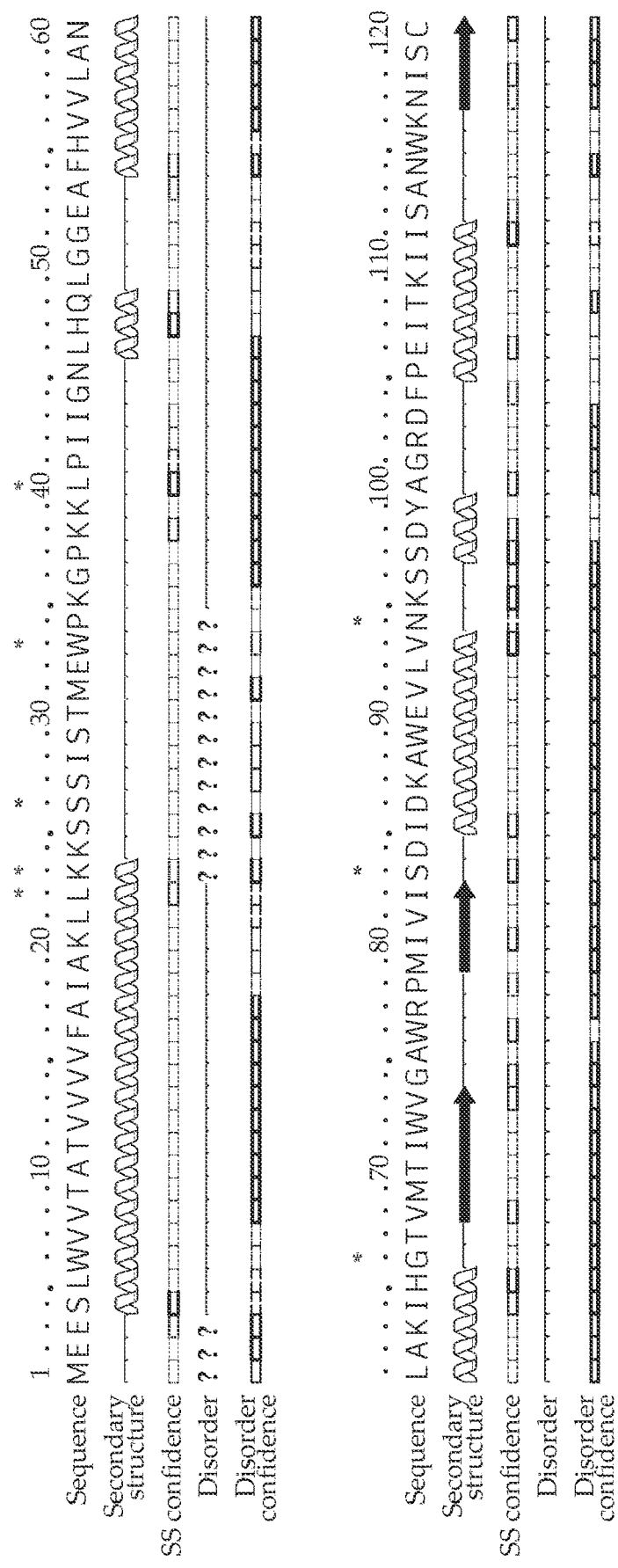
FIGS. 21(A) and 21(B) illustrate cheilanthifoline synthase-salutaridine synthase fusion designs, in accordance with embodiments of the invention.
Figure 21B:
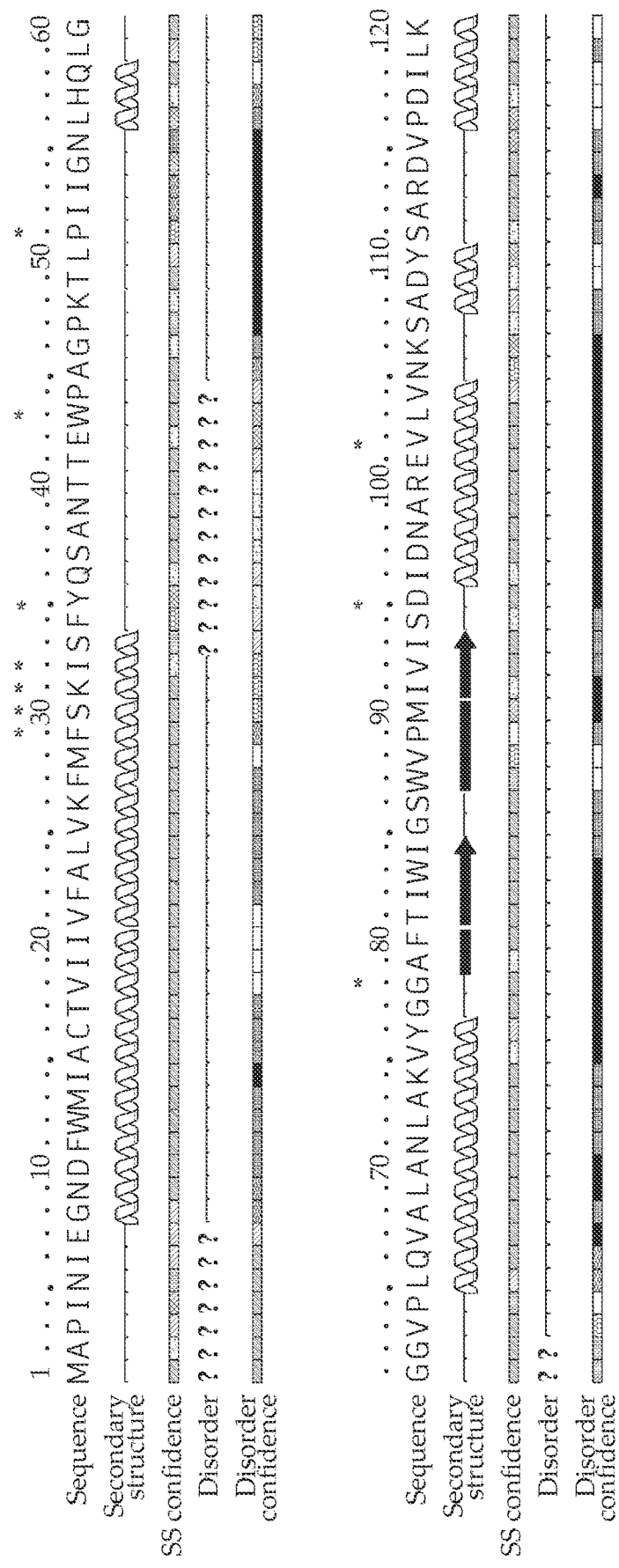

For example, N-terminal alpha-helices from cheilanthifoline synthase (CFS) were used to replace N-terminal alpha-helices from salutaridine synthase (SalSyn, FIG. 21). Junction points for these fusions were selected based on secondary structure motifs of CFS and SalSyn or based on amino acid alignments of CFS and SalSyn. The fusions were cloned by amplifying the N-terminal fragment from CFS and C-terminal fragment from SalSyn with 15-40 nucleotides of overlap with the other fragment, and then assembled with each other and a vector backbone by Gibson assembly to form the complete fusion open reading frame (Gibson, et al. 2009. Nat Methods. 6: 343-5).

As another example, the coding sequence for the cytochrome P450 domain from salutaridine synthase was placed directly into the P450 encoding region of other stably expressed cytochrome P450s such as the BM3 enzyme. For example, the conserved cytochrome P450 domain of the salutaridine synthase and the cytochrome P450 domain from an engineered variant of the *Bacillus megaterium* P450 monooxygenase CYP102A1 (BM3, (Michener and Smolke. 2012. Metab. Eng. 14: 306-16)) were identified by NCBI conserved domain search. Primers were designed to fuse the coding sequence of the first few amino acids of the BM3 to the coding sequence for the P450 domain of the salutaridine synthase, followed by the coding sequence for BM3 domains C-terminal to the P450 domain. As before, this construct was assembled via Gibson assembly.

The engineered salutaridine synthase protein fusions were analyzed by Western Blot analysis to confirm full-length expression and modification to or elimination of N-linked glycosylation patterns in yeast (FIG. 20). The salutaridine synthase enzyme and protein fusions were C-terminally tagged with the human influenza hemagglutinin (HA) epitope and cloned into expression plasmids appropriate for yeast and plant expression. For yeast, the enzyme coding sequences were cloned into a low-copy yeast/*E. coli* shuttle vector harboring a URA3 selection marker and expressed from the TDH3 promoter. For plants, the sequences were cloned into an *E. coli/Agrobacterium tumefaciens* shuttle vector with kanamycin resistance and the Cauliflower mosaic virus (CaMV) 35S promoter with flanking 5' and 3'-untranslated regions from Cowpea mosaic virus RNA-2 for transient plant expression via *Agrobacterium tumefaciens*-infiltration. Yeast engineered to express salutaridine synthase exhibited a banding pattern indicative of N-linked glycosylation. We confirmed that this pattern was due to N-linked glycosylation by performing site-directed mutagenesis on the glycosylation site. In contrast, plant expression of this enzyme did not result in a banding pattern indicative of N-linked glycosylation, as seen in (A) of FIG. 20. Although the N-linked glycosylation sites were unmodified, the engineered salutaridine synthase protein fusions were not N-glycosylated when expressed in yeast, as seen in (B) of FIG. 20. By Western blot, we demonstrated that the yeast-expressed fusion enzymes were present as a single band, similar to the expression observed for the plant-expressed parent enzyme, indicating that the mis-processing of the nascent protein in yeast that resulted in N-linked glycosylation was repaired by the engineered fusions.

The engineered salutaridine synthase protein fusions were analyzed for improved enzyme activity when heterologously expressed in yeast. Coding sequences for salutaridine synthase and the engineered fusions were cloned into a low-copy plasmid harboring a URA3 selection marker and expressed from the TDH3 promoter. The yeast have $P_{TEF1}$-PsCPRv2 integrated into the TRP1 locus and contain a single low-copy plasmid with the URA3 selective marker and the salutaridine synthase coding sequence with the TDH3 promoter. Yeast were grown from freshly transformed colonies in 1 mL selective media (-Ura) overnight and back-diluted 1:20 into 0.5 mL selective media in 96-well plates with 10 μM (R)-reticuline (Toronto Research Chemicals). After 72-96 hours in the shaking incubator, the yeast were pelleted and the media supernatant was analyzed by LC-MS/MS. The analysis indicated that the engineered salutaridine synthase enzymes exhibited improved activity relative to that of the wild-type sequence when heterologously expressed in yeast (FIG. 22).

Figure 22:
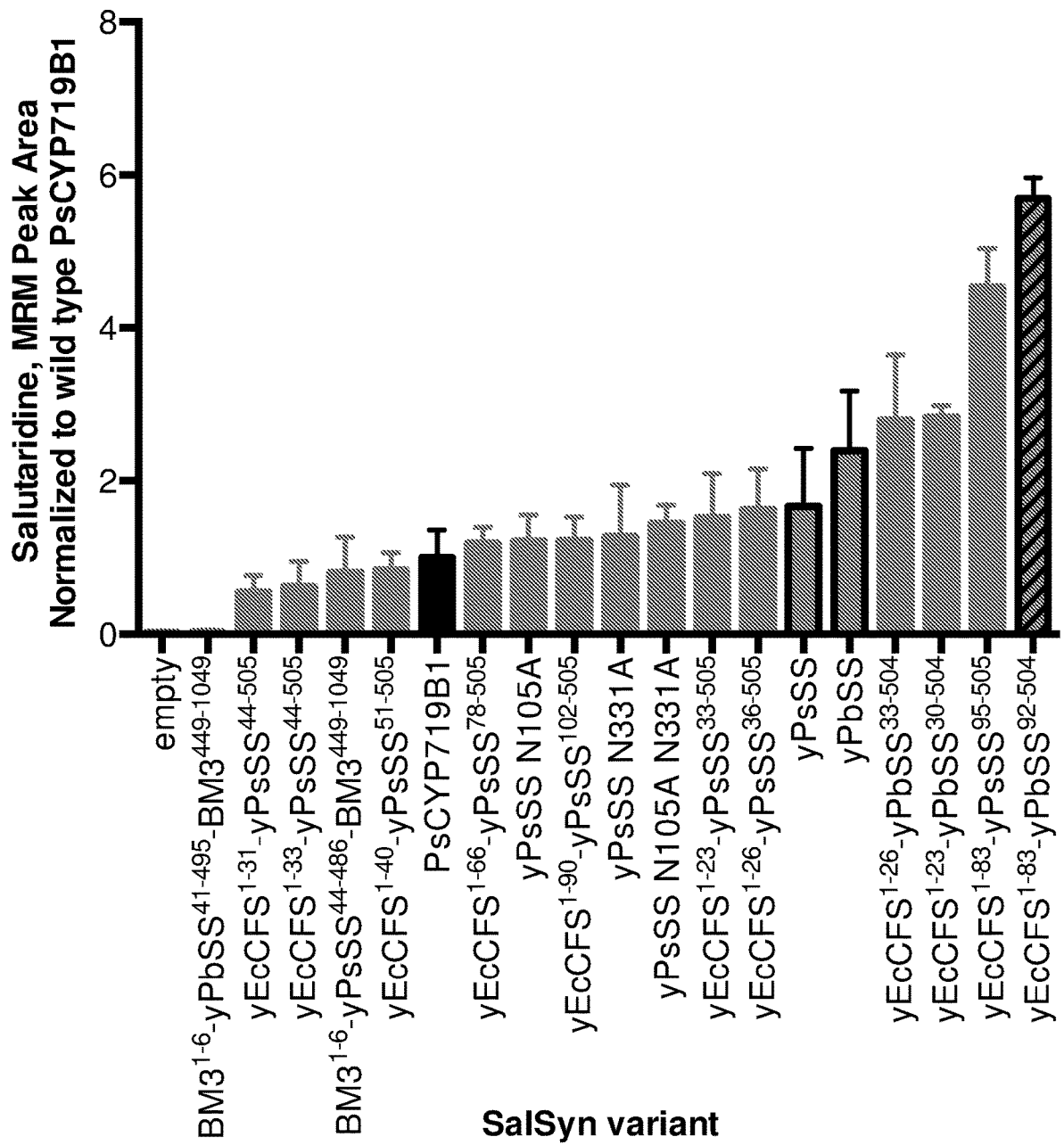
FIG. 22 illustrates salutaridine synthase codon-optimization and engineered fusions that improve activity in yeast, in accordance with embodiments of the invention.

FIG. 22 illustrates salutaridine synthase codon-optimization and engineered fusions that improve activity in yeast, in accordance with embodiments of the invention. As seen in FIG. 22, a black bar indicates a native wild-type sequence for salutaridine synthase, PsCYP719B1. Grey bars with black borders are yeast codon-optimized variants from *Papaver somniferum* and a newly identified sequence from *Papaver bracteatum*. The diagonally patterned bar indicates the most improved engineered fusion, which is based on the *P. bracteatum* sequence. Error bars indicate the range of at least two biological replicates. Natural, synthetic codon-optimized, and/or protein engineered variants of salutaridine synthase from *P. bracteatum*, *P. somniferum*, or *P. setigerum* (or related plant) may be used in these engineered strains.

The engineered salutaridine synthase protein fusions can be used in the context of a biosynthetic pathway to increase production of downstream benzylisoquinoline alkaloid products. In one example, yeast were engineered to heterologously express yeast codon optimized genes encoding an engineered salutaridine synthase fusion, *P. bracteatum* salutaridine reductase, and *P. somniferum* salutaridinol 7-O-acetyltransferase. The three expression cassettes ($P_{TDH3}$D94yPsSS, $P_{TP11}$-yPbSalR, $P_{TEF1}$-yPsSalAT) were assembled into a yeast artificial chromosome (YAC) with a TRP1 section marker. The YAC was placed into yeast that harbored an expression cassette for a cytochrome P450 reductase ($P_{TEF1}$-ATR1 or $P_{TEF1}$-yPsCPRv2) integrated into the chromosome. The yeast strains were grown in synthetic complete media with the appropriated drop out solution (-Trp) and fed (R)-reticuline. BIA metabolites were analyzed after 96 hours of growth through LC-MS/MS analysis. The analysis indicates that yeast strains engineered with the engineered salutaridine synthase enzymes and other pathway enzymes produce the morphinan alkaloid thebaine, as illustrated in (A) of FIG. 23.

Figure 23:
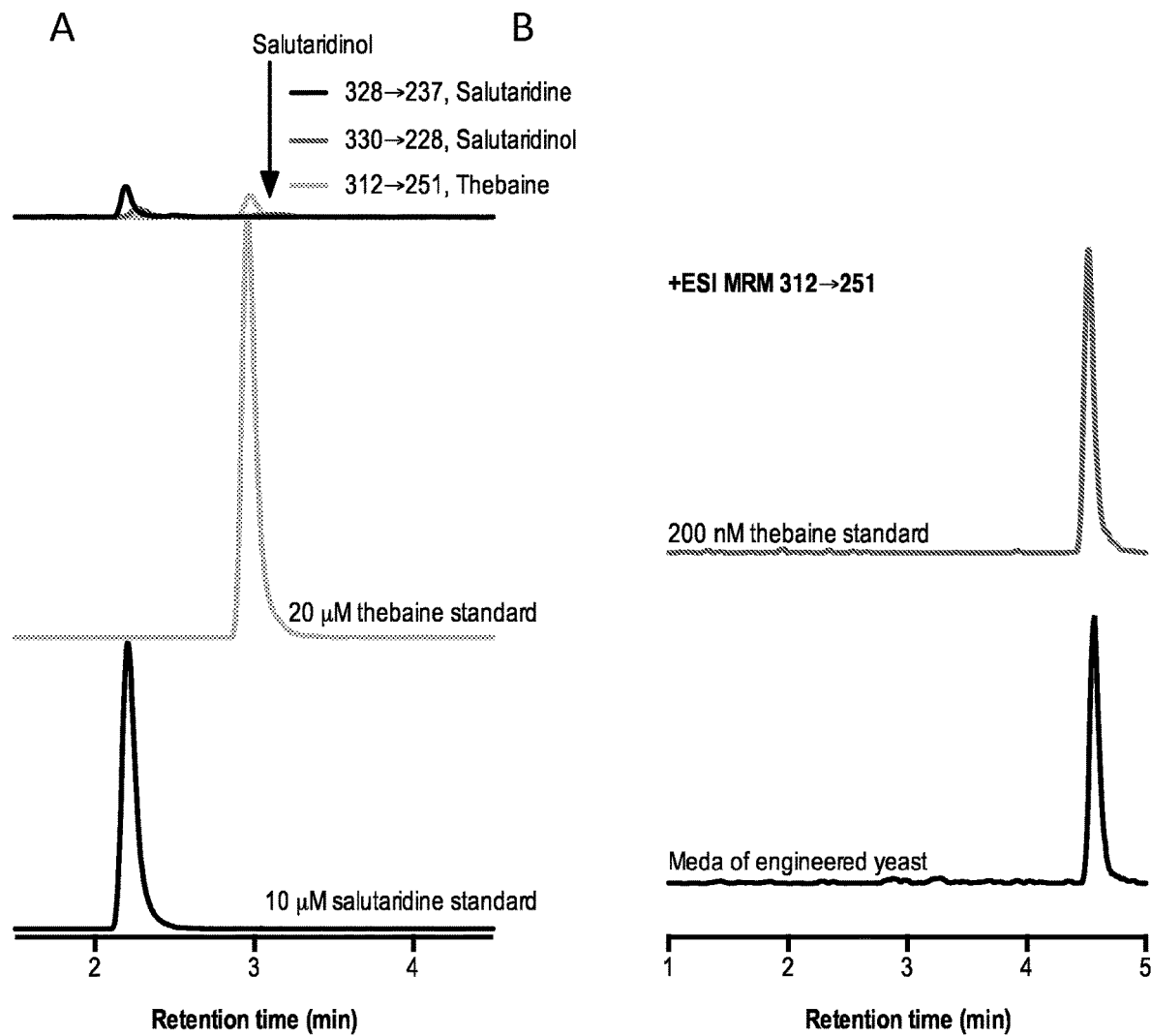
FIGS. 23(A) and 23(B) illustrate an LC-MS/MS analysis of small scale batch fermentation in which engineered yeast catalyze the conversion of (R)-reticuline to thebaine and the conversion of rac-norlaudanosoline to thebaine, in accordance with embodiments of the invention.

Accordingly, FIG. 23 illustrates (A) an LC-MS/MS analysis of small scale batch fermentation in which engineered yeast catalyze the conversion of (R)-reticuline to thebaine, in accordance with embodiments of the invention. As provided in (A) of FIG. 23, yeast strains are engineered to have a $P_{TEF1}$-ATR1 expression cassette integrated into the TRP1 locus and contain a single yeast artificial chromosome with the TRP1 selective marker and three expression cassettes: $P_{TDH3}$-yEcCFS$^{1-83}$-yPsSS$^{95-505}$, $P_{TP11}$-yPbSalR, and $P_{TEF1}$-yPsSa1AT. Yeast were grown from freshly transformed colonies in 3 mL selective media overnight and back-diluted 1:20 into 0.5 mL selective media (-Trp) in culture tubes with 100 μM (R)-reticuline (Toronto Research Chemicals). After 72 hours in the shaking incubator, the yeast were pelleted and the media supernatant was analyzed by LC-MS/MS. Chromatogram traces show thebaine produced by this strain and salutaridinol and salutaridine accumulated, along with standards. These traces are representative of two samples.

Example 11: Protein Engineering of Enzymes in the Downstream Morphinan Branch to Improve Production of Morphinan Products from a Heterologous Microbial Host In one embodiment of the invention, pathway enzymes are engineered to exhibit increased activity to increase production of the BIA of interest. In this example, mutations were introduced into the open reading frame of a particular pathway enzyme by amplification with Mutazyme II (see Table 6). Sufficient template DNA was included in the amplification reaction to result in a mutation rate of 1-4 nucleotide substitutions per gene. The mutagenized library was cloned into the pYES1L vector by gap repair directly in yeast. In several instances, yeast strains selected for library expression contained integrated copies of genes that generate the substrate of the mutagenized enzyme. For example, a library of CODM variants was transformed into a strain with integrated copies of T6ODM and COR1.3 and fed thebaine in the culture medium. Expression of T6ODM and COR1.3 in these strains ensured that codeine and neopine would be available as substrates for each introduced CODM variant. Individual colonies were inoculated into 96-well plates and cultured 96 hours then assayed for production of their product by liquid chromatograph mass spectrometry (LC-MS). In the example of the CODM library, the products screened for were morphine and neomorphine. In each screen, variants with enhanced BIA production were sequenced and re-cloned for validation. Table 6 includes a summary of mutated enzyme variants identified through the screens that resulted in increased BIA production in yeast.

Figure 24:
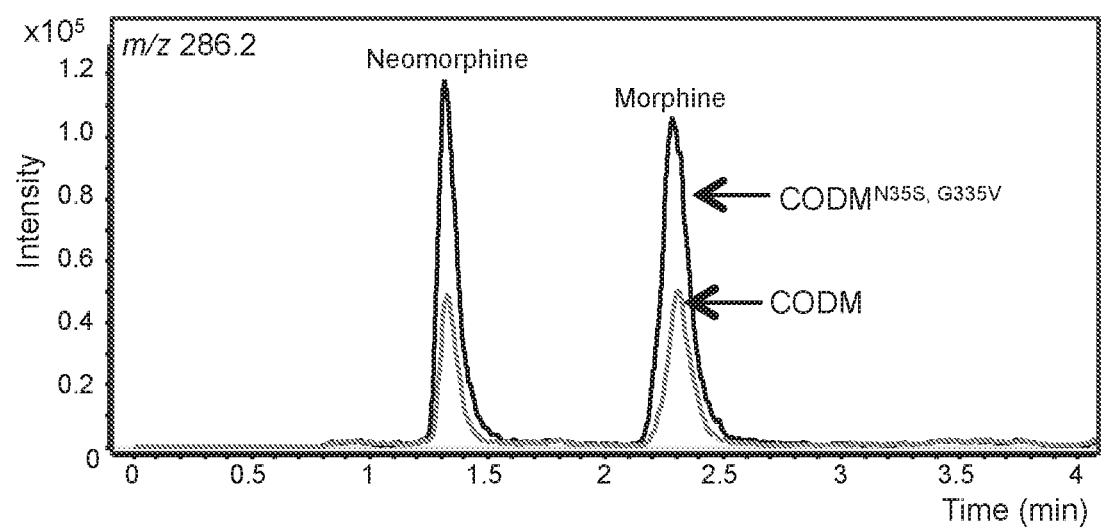
FIG. 24 illustrates generation of a CODM enzyme variant exhibiting enhanced activity in yeast through random mutagenesis and screening, in accordance embodiments of the invention.

FIG. 24 shows data of the validated enhanced activity of one of these mutants. In particular, FIG. 24 illustrates generation of a CODM enzyme variant exhibiting enhanced activity in yeast through random mutagenesis and screening, in accordance with embodiments of the invention. A library of CODM variants was generated by mutagenizing the coding region by error-prone PCR. A variant identified by screening of this library, CODM$^{N35S,G335V}$, was re-cloned and expressed in a yeast strain harboring integrated copies of T6ODM and COR1.3. This strain and another control strain expressing wild-type CODM were cultured in liquid medium with 1 mM thebaine. After 96 hours the culture medium was analyzed for CODM activity by LC-MS. Variant CODM$^{N35S,G335V}$ produced 1.4× more morphine and 2.6× more neomorphine than a strain expressing wild-type CODM.

Example 12: Optimization of Expression and Growth Conditions to Improve Benzylisoquinoline Alkaloid Production from a Heterologous Microbial Host Bezylisoquinoline alkaloid production from an engineered microbial host can be further improved by optimizing the expression of pathway enzymes and growth conditions. In one example, the expression of salutaridinol 7-O-acetyltransferase was altered in yeast by expressing the enzyme from a series of different promoters. The yeast were engineered to heterologously express yeast codon-optimized genes encoding *P. somniferum* salutaridinol 7-O-acetyltransferase from different promoters (as provided in (A) of FIG. 25). Two expression cassettes (P$_{TP11}$-yPbSalR, P$_X$-yPsSalAT) were assembled into a yeast artificial chromosome (YAC) with a TRP1 section marker. The YAC was placed into yeast and cells were grown in synthetic complete media with the appropriated drop out solution (-Trp) and fed salutaridine. BIA metabolites were analyzed after 72 hours of growth by LC-MS/MS analysis. The optimization of pathway enzyme expression level can result in increased production of the morphinan alkaloid thebaine (as provided in (A) of FIG. 25).

Optimization of strain cultivation conditions, including but not limited to sugar source, growth temperature, and pH, can be used to increase production of benzylisoquinoline alkaloids from engineered yeast strains (as provided in (B) and (C) of FIG. 25). In one example, pH was varied to increase thebaine production from engineered yeast strains. Two expression cassettes (P$_{TP11}$-yPbSalR, P$_{TEF1}$-yPsSalAT) were assembled into a yeast artificial chromosome (YAC) with a TRP1 section marker. The YAC was placed into yeast and cells were grown in synthetic complete media with the appropriated drop out solution (-Trp), resuspended in buffer at pH 5.7-9, and fed salutaridine. BIA metabolites were analyzed after 16 hours of incubation by LC-MS/MS analysis. Levels of the 4-ring promorphinan alkaloid salutaridinol and the 5-ring morphinan alkaloid thebaine increased as a function of increasing pH (as provided in (B) of FIG. 25).

In another example, temperature, sugar, and media buffer content were varied to increase thebaine production from engineered yeast strains. Three expression cassettes (P$_{TDH3}$-D94yPsSS, P$_{TP11}$-yPbSalR, P$_{TEF1}$-yPsSa1AT) were assembled into a yeast artificial chromosome (YAC) with a TRP1 section marker. The YAC was placed into yeast that harbored an expression cassette for a cytochrome P450 reductase (P$_{TEF1}$-ATR1 or P$_{TEF1}$-yPsCPRv2) integrated into the chromosome. The yeast strains were grown in synthetic complete media with the appropriated drop out solution (-Trp) and fed (R)-reticuline. BIA metabolites were analyzed after 72 hours of growth by LC-MS/MS analysis. The analysis indicates the microbial production of the morphinan alkaloid thebaine increases under certain cultivation conditions (buffered media with dextrose at 30° C., as provided in (C) of FIG. 25).

Accordingly, FIG. 25 illustrates fermentation optimization for conversion of (R)-reticuline to thebaine by engineered yeast, in accordance with embodiments of the invention. LC-MS/MS analysis of whole cell buffered assay of (A) SalAT promoter variants, (B) SalR and SalAT strain grown under different pH conditions, and (C) optimization of sugar source, growth temperature, and media buffer content. (A) Yeast strains engineered to contain a single yeast artificial chromosome with the TRP1 selective marker and two expression cassettes: P$_{TP11}$-yPbSalR and P$_X$-yPsSalAT with varied SalAT promoters. Yeast were grown from freshly transformed colonies in 3 mL selective media overnight and back-diluted 1:20 into 0.5 mL media in culture tubes with 100 µM salutaridine (Specs). After 72 hours in the shaking incubator, the yeast were pelleted and the media supernatant was analyzed by LC-MS/MS. (B) Yeast strains engineered to contain a single yeast artificial chromosome with the TRP1 selective marker and two expression cassettes: P$_{TP11}$-yPbSa1R and P$_{TEF1}$-yPsSalAT. Yeast were grown from freshly transformed colonies in 3 mL selective media overnight, back-diluted into 3.5 mL media to OD 0.8, grown 7 hours, pelleted, and then resuspended into pH 5.7 MOPS, or pH 7, 8, or 9 Tris buffer with 10 µM salutaridine (Specs). After 16 hours on a spinner at 30° C., the yeast were pelleted and the buffer supernatant was analyzed by LC-MS/MS. Error bars represent the range of two samples. (C) Optimization of sugar source, growth temperature, and media buffer content. In this experiment, the yeast strains are engineered to have P$_{TEF1}$-ATR1 integrated into the TRP1 locus and contain a single yeast artificial chromosome with the TRP1 selective marker and three expression cassettes: P$_{TDH3}$ yEcCFS$^{1-83}$-yPsSS$^{95-505}$, P$_{TP11}$-yPbSa1R, and P$_{TEF1}$-yPsSalAT. Yeast were grown from freshly transformed colonies in 3 mL selective media overnight and back-diluted 1:20 into 0.5 mL media in culture tubes with 100 µM (R)-reticuline (Toronto Research Chemicals). After 72 hours in the shaking incubator, the yeast were pelleted and the media supernatant was analyzed by LC-MS/MS.

Example 13: Yeast Engineered for the Production of thebaine from an Early 1-Benzylisoquinoline Alkaloid Scaffold Yeast strains can be engineered for the production of the morphinan alkaloid thebaine, or morphinan alkaloids derived from thebaine, from early 1-benzylisoquinoline alkaloids. As an example, the engineered yeast strains can produce the morphinan alkaloid products from racemic or (S)-norcoclaurine or racemic or (S)-norlaudanosoline (FIGS. 5, 6, 7, and (B) of 23). Yeast strains are engineered to produce (S)-reticuline from (S)-norcoclaurine or racemic or (S)-norlaudanosoline by the integration of three or five expression cassettes into the yeast genome. To produce (S)-reticuline from racemic or (S)-norlaudanosoline, the integrated expression cassettes encode *Papaver somniferum* norcoclaurine 6-O-methyltransferase (Ps6OMT, EC 2.1.1.128), 4'-O-methyltransferase (Ps4'OMT, EC 2.1.1.116), and coclaurine-N-methyltransferase (CNMT, EC 2.1.1.140), each with a TEF1 promoter (Hawkins and Smolke. 2008. Nat. Chem. Biol. 4: 564-73). To produce (S)-reticuline from racemic or (S)-norcoclaurine, the strain further harbors integrated expression cassettes for yeast codon-optimized *Eschscholzia californica* N-methylcoclaurine 3'-hydroxylase (yEcCYP80B1, EC 1.14.13.71) and ATR1 or yPsCPRv2 cytochrome P450 reductase expressed from the TDH3 or TEF1 promoter (CPR, EC 1.6.2.4). These strains are further engineered to incorporate epimerization-catalyzing enzymes (e.g., CYP-COR), salutaridine synthase, salutaridine reductase, and salutaridinol acetyltransferase to convert racemic or (S)-norcoclaurine or racemic or (S)-norlaudanosoline to the morphinan alkaloid thebaine, or morphinan alkaloids derived from thebaine (FIG. 7). As an alternative to expression of an epimerization-catalyzing enzyme, 6OMT, 4'OMT, CNMT, and/or CYP80B1 may be engineered such that rac-reticuline is produced from rac-norcoclaurine or rac-norlaudanosoline.

In one example, a yeast strain was engineered to convert rac-norlaudanosoline to thebaine. The yeast strain harbors integrated expression cassettes encoding Ps6OMT, Ps4'OMT, CNMT, and yPsCPRv2, each with a TEF1 promoter. Four expression cassettes ($P_{TDH3}$-yEcCFS$^{1-83}$-yPsSS$^{95-505}$, $P_{TP11}$-yPbSalR, $P_{TEF1}$-yPsSa1AT, $P_{HXT7}$-CYP-COR_89405) were assembled into a yeast artificial chromosome (YAC) with a TRP1 selective marker in this strain. The yeast strain harboring the YAC and integrated cassettes was grown in synthetic complete media with the appropriated drop out solution (-Trp) and 1 mM rac-norlaudanosoline substrate. After 96 hours of growth, the media was analyzed for BIA metabolites by LC-MS/MS analysis. Nearly 200 nM thebaine was detected ((B) of FIG. 23). Other engineered salutaridine synthase variants may also be used in this strain (FIG. 22, Example 10).

Example 14: Platform Yeast Strains Engineered for the Production of Reticuline from L-Tyrosine A platform yeast strain that produces the key branch point BIA intermediate (S)-reticuline from L-tyrosine was constructed (FIG. 5). Specifically, four multi-gene expression constructs were integrated into the genome of a yeast strain. The composition of the four constructs is indicated in FIG. 26. Each construct is comprised of 4 or 5 genes expressed from strong constitutive promoters. Genes are positioned at each locus as complete expression cassettes comprising a promoter, gene open reading frame, and terminator as specified in the annotations above the schematic. The schematic shows the orientation of each expression cassette by the direction of the arrow representing a given gene. Selectable markers are italicized in the annotation and represented by grey arrows in the schematic. Each selection marker is flanked by loxP sites to allow removal of the marker from the locus. Additionally, each construct has a selectable marker flanked by loxP sites so that it can be removed by Cre recombinase.

In the first integration construct, four heterologous genes from *Rattus norvegicus* are integrated into the YBR197C locus together with a G418 selection marker (KanMX). RnPTPS, RnSepR, RnPCD, and RnQDHPR are required to synthesize and regenerate tetrahydrobiopterin ($BH_4$) from the yeast endogenous folate synthesis pathway. Each gene is codon optimized for expression in yeast.

In the second integration construct, four heterologous genes are integrated into the HIS3 locus together with the HIS5 selection marker. *Rattus norvegicus* tyrosine hydroxylase (RnTyrH) converts tyrosine to L-DOPA using the cosubstrate $BH_4$ generated by the preceding integration construct. The RnTyrH gene can be any of the wild-type or improved mutants which confer enhanced activity (e.g., W166Y, R37E, and R38E, Example 2). A second *Rattus norvegicus* gene, RnDHFR, encodes an enzyme that reduces dihydrobiopterin (an oxidation product of $BH_4$) to $BH_4$, in this way increasing the availability of this cosubstrate. Also included in the third construct is PpDODC from *Pseudomonas putida*, an enzyme that converts L-DOPA to dopamine. The fourth enzyme is CjNCS from *Coptis japonica*, which condenses 4-HPA and dopamine to make norcoclaurine. Each gene is codon optimized for expression in yeast.

In the third integration construct, five heterologous genes from plants and the LEU2 selection marker are integrated into the locus YDR514C. Ps6OMT, Ps4'OMT, and PsCNMT are methyltransferases from *Papaver somniferum* and are expressed as native plant nucleotide sequences. A fourth *P. somniferum* gene, yPsCPRv2, is codon optimized for yeast and encodes a reductase that supports the activity of a cytochrome P450 from *Eschscholzia californica*, EcCYP80A1. EcCYP80A1 is expressed as its native plant nucleotide sequence. The enzymes encoded in this construct perform two O-methylations, an N-methylation, and a hydroxylation to produce reticuline from the norcoclaurine produced by the preceding integration construct.

In the final integration construct, additional copies of *Saccharomyces cerevisiae* endogenous genes ARO4$^{Q166K}$, ARO7$^{T226I}$, TKL1, and ARO10 are integrated into the ARO4 locus together with a hygromycin resistance selection marker. ARO4$^{Q166K}$ and ARO7$^{T226I}$ are feedback-resistant mutants of ARO4 and ARO10 which each encode a single base pair substitution relative to the wild-type sequence. TKL1 and ARO10 are identical to the native yeast genes, but are expressed behind strong promoters. Aro4p and Aro7p are enzymes in the biosynthesis of aromatic amino acids including tyrosine. Removing feedback inhibition from these enzymes results in upregulation of endogenous tyrosine biosynthesis. Overexpression of Tk11p upregulates the pentose phosphate pathway resulting in enhanced supply of erythrose 4-phosphate (E4P), a precursor for tyrosine. Overexpression of Aro10p increases the production of 4-HPA.

Platform yeast strains can be constructed with any number of the four expression cassettes. Specifically, platform yeast strains were constructed with integration constructs 1-4 and integration constructs 1-3. In the latter strain in which the tyrosine over-production construct (construct 4) is excluded, additional tyrosine may be supplied in the culture medium to support the biosynthesis of reticuline. Additional genetic modifications may be incorporated into the platform strains to support production of downstream BIAs and increased flux to BIA biosynthesis.

The yeast strains were grown in synthetic complete media with the appropriated amino acid drop out solution at 25 and 30° C. BIA metabolites in the media supernatant were analyzed after 48 and 96 hours of growth by LC-MS/MS analysis.

Example 15: Yeast Engineered for the Production of Thebaine and Other Morphinan Alkaloids from L-Tyrosine Yeast strains can be engineered for the production of the morphinan alkaloid thebaine, or morphinan alkaloids derived from thebaine, from early precursors such as tyrosine. As an example, the platform yeast strains described in Example 14 can be further engineered to produce the morphinan alkaloid products from L-tyrosine (FIG. 7).

The platform yeast strain producing (S)-reticuline from L-tyrosine (see description in Example 14) was further engineered to incorporate epimerization-catalyzing enzymes, such as the newly identified CYP-COR, salutaridine synthase, salutaridine reductase, and salutaridinol acetyltransferase to convert the biosynthesized (S)-reticuline to the morphinan alkaloid thebaine, or morphinan alkaloids derived from thebaine (FIG. 7). Three expression cassettes ($P_{TDH3}$-yEcCFS$^{1-26}$-yPbSS$^{33-504}$, $P_{TP11}$-yPbSalR, $P_{TEF1}$-yPsSalAT) were assembled into a yeast artificial chromosome (YAC) with a TRP1 selective marker directly in the platform yeast strain. Other engineered salutaridine synthase variants may also be incorporated into the YAC (FIG. 22, Example 10). The resulting yeast strain was also transformed with a low-copy CEN/ARS plasmid with a URA3 selective marker, TDH3 promoter, and a CYP-COR coding sequence.

The yeast strains harboring the YAC, low-copy plasmid, and integrated cassettes were grown in synthetic complete media with the appropriated drop out solution (-Ura-Trp) at 25 and 30° C. After 96 hours of growth, the media was analyzed for BIA metabolites by LC-MS/MS analysis. Further culture optimization with respect to temperature, carbon source, pH condition, and media composition was performed to improve BIA production.

Additional genetic modifications can be introduced into the yeast strains to produce morphinan alkaloids derived from thebaine (FIG. 7). In one example, the expression cassettes $P_{ADH1}$-T6ODM-$T_{ADH1}$, $P_{HXT7}$-COR-$T_{PGK1}$, and $P_{TEF1}$-CODM-$T_{CYC1}$ were directly assembled and integrated into the trp1 locus of the thebaine-producing yeast strain (Thodey et al., 2014). In another example, these yeast strains can be further engineered to produce additional morphine alkaloids by directly assembling the expression cassettes $P_{GPD}$-morA-$T_{CYC1}$, $P_{PGK1}$-morB-$T_{PHO5}$ and integrating this construct into the ura3 locus on the chromosome (Thodey et al., 2014).

Example 16: Yeast Engineered for the Production of Berberine and Other Protoberberine Alkaloids from L-Tyrosine Yeast strains can be engineered for the production of the alkaloid berberine, and of protoberberine, phthalideisoquinoline, and berberine alkaloids derived from berberine or the intermediates involved in forming berberine, from L-tyrosine (FIGS. 5, 8). For example, three or four expression cassettes ($P_{PGK1}$-PsBBE-$T_{PHO5}$, $P_{TEF1}$-yPsS9OMT-$T_{CYC1}$, $P_{TDH3}$-yCjCAS-$T_{ADH1}$, with or without $P_{TP11}$-yBwSTOX-$T_{STE2}$) were assembled into a yeast artificial chromosome (YAC) with a TRP1 section marker. The YAC was placed into a platform yeast strain that produce (S)-reticuline from L-tyrosine (see Example 14) and additionally harbors an expression cassette for a cytochrome P450 reductase ($P_{TEF1}$-ATR1 or $P_{TEF1}$-PsCPRv2) integrated into the chromosome. An additional high-copy plasmid containing the $P_{TEF1}$-S9OMT-$T_{CYC1}$ expression cassette was transformed into this strain to improve flux to downstream products.

The yeast strains were grown in synthetic complete media with the appropriated amino acid drop out solution (-Trp) at 25 and 30° C. BIA metabolites in the media supernatant were analyzed after 48 and 96 hours of growth by LC-MS/MS analysis.

Example 17: Yeast Engineered for the Production of Noscapine and Other Noscapinoid Alkaloids from L-Tyrosine Yeast strains can be engineered for the production of phthalideisoquinoline alkaloids such as narcotoline and noscapine, the intermediates involved in forming noscapine, or derivatives thereof from L-tyrosine (FIGS. 5, 9).

For example, the expression cassettes $P_{ADH1}$-CAS-$T_{ADH1}$, $P_{HXT7}$-CYP82Y1-$T_{PGK1}$, $P_{TEF1}$-S9OMT-$T_{CYC1}$, and $P_{PGK1}$-BBE-$T_{PHO5}$ were directly assembled and integrated into the trp1 locus of a platform yeast strain that produces (S)-reticuline from L-tyrosine (see Example 14) and additionally harbors an expression cassette for a cytochrome P450 reductase ($P_{TEF1}$-ATR1 or $P_{TEF1}$-PsCPRv2) integrated into the chromosome. Then, the expression cassettes $P_{GPD}$-TNMT-$T_{CYC1}$, $P_{PGK1}$-PsMT2-$T_{PHO5}$, $P_{ADH1}$-CYP82X1-$T_{GAP1}$, and $P_{PYK1}$-PsCXE1-$T_{Mf1}$ were directly assembled and integrated into the ura3 locus of the yeast strain. Then, the expression cassettes $P_{HXT7}$-CYP82X2-$T_{CYC1}$, $P_{GPD}$-PsAT1-$T_{ADH1}$, $P_{TP11}$-PsSDR1-$T_{Ste2}$, and $P_{PGK1}$-PsMT3-$T_{PHO5}$ were directly assembled and integrated into the leu2 locus of the yeast strain. An additional high-copy plasmid containing the $P_{TEF1}$-S9OMT-$T_{CYC1}$ expression cassette and an additional low-copy plasmid containing the $P_{HXT7}$-CYP82X2-$T_{CYC1}$ expression cassette were transformed into this yeast strain to improve flux to downstream products.

The yeast strains were grown in synthetic complete media with the appropriated amino acid drop out solution (-Trp, Ura) at 25 and 30° C. BIA metabolites in the media supernatant were analyzed after 48 and 96 hours of growth by LC-MS/MS analysis.

Example 18: Yeast Engineered for the Production of Sanguinarine and Other Benzophenanthridine Alkaloids from L-Tyrosine Yeast strains can be engineered for the production of protoberberine, protopine, and benzophenanthridine alkaloids such as the end-product sanguinarine, the intermediates involved in forming sanguinarine, or derivatives thereof from L-tyrosine (FIGS. 5, 10).

For example, the expression cassettes $P_{ADH1}$-TNMT-$T_{ADH1}$, $P_{HXT7}$-EcSTS-$T_{PGK1}$, $P_{GPD}$-EcCFS-$T_{CYC1}$, and $P_{PGK1}$-BBE-$T_{PHO5}$ were directly assembled and integrated into the trp1 locus of a platform yeast strain that produces (S)-reticuline from L-tyrosine (see Example 14) and additionally harbors an expression cassette for a cytochrome P450 reductase ($P_{TEF1}$-ATR1 or $P_{TEF1}$-PsCPRv2) integrated into the chromosome. Then, the expression cassettes $P_{GPD}$-PsMSH-$T_{CYC1}$, $P_{PGK1}$-PsP6H-$T_{PHO5}$ were directly assembled and integrated into the ura3 locus of the yeast strain.

The yeast strains were grown in synthetic complete media with the appropriated amino acid drop out solution at 25 and 30° C. BIA metabolites in the media supernatant were analyzed after 48 and 96 hours of growth by LC-MS/MS analysis.

Example 19: Yeast Engineered for the Production of Hydrocodone and Other Morphinan Alkaloids from L-Tyrosine Yeast strains can be engineered for the production of hydrocodone. As an example, the thebaine-producing yeast strain described in Example 15 can be further engineered to produce the active pharmaceutical ingredient hydrocodone. FIG. 27 illustrates thebaine and hydrocodone production in engineered yeast strains, in accordance with embodiments of the invention. In FIG. 27A, multi-gene constructs were incorporated into engineered yeast strains containing constructs 1-4 (FIG. 26). In FIG. 27B, the integration of construct 5 increased reticuline titers relative to the strain containing constructs 1-4. In FIG. 27C, the integration of construct 6 leads to thebaine production from sugar. Thebaine produced by the engineered strain was identified in the culture medium by LC-MS/MS analysis and compared to a commercial reference standard. In FIG. 27D, the introduction of construct 7 on a YAC leads to hydrocodone production from sugar. Hydrocodone produced by the engineered strain was identified in the culture medium by LC-MS/MS analysis and compared to a commercial reference standard.

In one example, the yeast strain that produces reticuline from L-tyrosine (see description in Example 14) was further engineered to increase reticuline production, then modified further to incorporate the thebaine-producing enzymes described in Example 15, and then modified further to incorporate thebaine demethylase and morphinone reductase to convert the biosynthesized thebaine to hydrocodone. Three multi-gene expression constructs were incorporated into the reticuline-producing yeast strain described in Example 14; two as chromosomal integrations, and a third as an episomal YAC construct.

In the first construct, genes were incorporated to increase biosynthesis of (S)-reticuline from the strain described in Example 14. To increase (S)-reticuline production, additional copies of CjNCS (to increase incorporation of dopamine into norcoclaurine) and Ps4'OMT (to increase incorporation of 3'-hydroxy-N-methylcoclaurine into (S)-reticuline) were incorporated into the strain. An additional copy of RnTyrH was also included to increase entry of tyrosine into the heterologous pathway for reticuline biosynthesis. The three expression cassettes ($P_{PGK1}$-yCjNCS-$T_{PHO5}$, $P_{TEF1}$-Ps4'OMT-$T_{CYC1}$, and $P_{GPD}$-RnTyrH$^{WR}$-$T_{ADH1}$) were integrated into locus YPL250C together with the ble selection marker for phleomycin resistance (FIG. 27A). The resulting yeast strain exhibited a 4-fold increase in reticuline accumulation (FIG. 27B).

In the second construct, genes were incorporated to produce thebaine from biosynthesized (S)-reticuline. Four enzymes for thebaine production described in Example 15 were assembled as four expression cassettes ($P_{HXT7}$-yPbCYP-COR-$T_{CYC1}$, $P_{GPD}$-yEcCFS$^{1-83}$-yPbSalSyn$^{92-504}$-$T_{ADH1}$, $P_{TP11}$-yPbSalR-$T_{STE2}$, and $P_{PGK1}$-yPsSa1AT-$T_{PHO5}$) and integrated into locus TRP1 with selection marker KlURA3 (FIG. 27A). The resulting yeast strain produced thebaine when cultured in standard yeast culture medium (FIG. 27C).

In the third construct, genes were incorporated to produce hydrocodone from biosynthesized thebaine. In this example, thebaine demethylase activity was incorporated as the T6ODM enzyme from *P. somniferum* to convert thebaine to neopinone, and morphinone reductase activity was incorporated as the morB enzyme from *P. putida* to convert codeinone to hydrocodone. In this example, the intervening conversion of neopinone to codeinone occurred spontaneously. In another example, an isomerase enzyme is included to enzymatically convert neopinone to codeinone. The T6ODM and morB genes were codon optimized for yeast and included as two expression cassettes ($P_{GPD}$-yT6ODM-$T_{ADH1}$ and $P_{PGK1}$-yPbmorB-$T_{PHO5}$) assembled into a YAC with TRP1 selection marker (FIG. 27A). In this example, the yeast strain is cultured in medium supplemented with 50 mM 2-oxoglutarate to support the activity of T6ODM, a 2-oxoglutarate-dependent dioxygenase. In another example, the yeast host cell is engineered to accumulate 2-oxoglutarate at levels sufficient to support T6ODM activity. The yeast strain harboring the described multi-gene constructs and cultured in the described culture medium biosynthesized hydrocodone from glucose (FIG. 27D).

Example 20: Increasing Gene Copy Number to Overcome Bottlenecks in Pathway Flux

In some instances yeast strains can be optimized to enhance the production of benzylisoquinoline alkaloids by increasing the gene copy number for enzymes whose activity is limiting.

In one example, reticuline production in a reticuline-producing strain as described in Example 19 was optimized by addition of a third gene copy of NCS (FIG. 28). In this example, the parent strain had one copy of NCS integrated at the YMR206W locus and another at the YPL250C locus, each expressed from the PGK1 promoter. A third copy of NCS (expressed from a TDH3 promoter) was integrated at the BUD9 locus and this modification resulted in a 2-fold increase in reticuline titers. In another example, additional copies of other enzymes in the pathway are incorporated into the strain to further increase reticuline titers.

TABLE 2

Enzyme List

| Enzyme | Abbrev | Catalyzed Reactions | Source organisms | Similarity to naturally occurring gene | Modifications* | Genbank # |
| --- | --- | --- | --- | --- | --- | --- |
| Transketolase | TKL1 | fructose-6-phosphate + glyceraldehyde-3-phosphate ↔ xylulose-5-phosphate + erythrose-4-phosphate (EC 2.2.1.1) | Saccharomyces cerevisiae | 100% | constitutive overexpression, synthetic regulation | NP_015399.1 |
| Glucose-6-phosphate dehydrogenase | ZWF1 | glucose-6-phosphate → 6-phosphogluconolactone (EC 1.1.1.49) | Saccharomyces cerevisiae | | full deletion of coding region | CAA96146.1 |
| 3-deoxy-d-arabinose-heptulosonate-7-phosphate synthase | ARO4, DAHP synthase | erythrose-4-phosphate + PEP → DAHP (EC 2.5.1.54) | Saccharomyces cerevisiae | 100% | Feedback inhibition resistant mutation, K229L, Q166K | CAA85212.1 |
| Chorismate mutase | ARO7 | chorismate → prephenate (EC 5.4.99.5) | Saccharomyces cerevisiae | 100% | Feedback inhibition resistant mutation, T226I | NP_015385.1 |
| Phenylpyruvate decarboxylase | ARO10 | hydroxyphenylpyruvate → 4HPA (EC 4.1.1.80) | Saccharomyces cerevisiae | 100% | constitutive overexpression, synthetic regulation | NP_010668.3 |
| Alcohol dehydrogenase | ADH2-7, SFA1 | 4HPA → tyrosol (EC 1.1.1.90) | Saccharomyces cerevisiae | | full deletion of coding region | NP_014032.1, AAT93007.1, NP_011258.2, NP_009703.3, NP_014051.3, NP_010030.1, NP_010113.1 |
| Aldehyde oxidase | ALD2-6 | 4HPA → hydroxyphenylacetic acid (EC 1.2.1.39) | Saccharomyces cerevisiae | | full deletion of coding region | NP_013893.1, NP_013892.1, NP_015019.1, NP_010996.2, NP_015264.1 |
| Aromatic aminotransferase | ARO9 | hydroxyphenylpyruvate + glutamate → tyrosine + alpha-ketogluterate (EC 2.6.1.57) | Saccharomyces cerevisiae | 100% | constitutive overexpression, synthetic regulation | AEC14313.1 |
| Tyrosinase | TYR | tyrosine → L-DOPA, L-DOPA → dopaquinone (EC 1.14.18.1) | Ralstonia solanacearum, Agaricus bisporus | 100% | constitutive expression, synthetic regulation | NP_518458.1, AJ223816, |
| Tyrosine hydroxylase | TyH | tyrosine → L-DOPA (EC 1.14.16.2) | Homo sapiens, Rattus norvegicus, Mus musculus | 100% | constitutive expression, synthetic regulation | NM_012740, NM_000240 |
| L-DOPA decarboxylase | DODC | L-DOPA → dopamine (EC 4.1.1.28) | Pseudomonas putida, Rattus norvegicus | 100% | constitutive expression, synthetic regulation | AE015451.1, NP_001257782.1 |
| Tyrosine/DOPA decarboxylase | TYDC | L-DOPA → dopamine (EC 4.1.1.28) tyrosine → tyramine (EC 4.1.1.25) | Papaver somniferum | 100% | constitutive expression, synthetic regulation | AAA97535 |
| Monoamine oxidase | MAO | dopamine → 3,4-DHPA (EC 1.4.3.4) | Escherichia coli, Homo sapiens, Micrococcus luteus | 77% | constitutive expression, synthetic regulation; codon optimized for expression in Saccharomyces cerevisiae | J03792, D2367, AB010716.1 |
| Norcoclaurine synthase | NCS | 4HPA + dopamine → S-norcoclaurine (EC 4.2.1.78) 3,4-DHPA + dopamine → S-norlaudanosoline | Coptis japonica, Papaver somniferum, Papaver bracteatum, Thalictium flavum, Corydalis saxicola | 80% | constitutive expression, synthetic regulation; N-terminal truncation; codon optimized for expression in Saccharomyces cerevisiae | BAF45337.1, AB267399.2, ACI45396.1, ACO90258.1, ACO90247.1, AEB71889.1 |

TABLE 2-continued

Enzyme List

| Enzyme | Abbrev | Catalyzed Reactions | Source organisms | Similarity to naturally occurring gene | Modifications* | Genbank # |
|---|---|---|---|---|---|---|
| Norcoclaurine 6-O-methyltransferase | 6OMT | Norcoclaurine → coclaurine Norlaudanosoline → 3'hydroxycoclaurine (EC 2.1.1.128) | *P. somniferum* *T. flavum* *Coptis japonica** | 100% 100% 100% | constitutive expression, synthetic regulation | AY268894 AY610507 D29811 |
| Coclaurine-N-methyltransferase | CNMT | Coclaurine → N-methylcoclaurine 3'hydroxycoclaurine → 3'-hydroxy-N-methylcoclaurine (EC 2.1.1.140) | *P. somniferum* *T. flavum* *Coptis japonica** | 100% 100% | constitutive expression, synthetic regulation | AY217336 AY610508 AB061863 |
| 4'-O-methyltransferase | 4'OMT | 3'-hydroxy-N-methylcoclaurine → Reticuline (EC 2.1.1.116) | *P. somniferum* *T. flavum* *Coptis japonica** | 100% 100% 100% | constitutive expression, synthetic regulation | AY217333, AY217334 AY610510 D29812 |
| Cytochrome P450 80B1 | CYP80B1 | N-methylcoclaurine → 3'-hydroxy-N-methylcoclaurine | *P. somniferum*, *E. californica*, *T. flavum* | 77% | constitutive expression, synthetic regulation; codon optimized for expression in *Saccharomyces cerevisiae* | AAF61400.1 AAC39453.1 AAU20767.1 |
| GTP cyclohydrolase | FOL2 | GTP → dihydroneopterin triphosphate (EC 3.5.4.16) | *Saccharomyces cerevisiae*, *Homo sapiens*, *Mus musculus* | 100% | native regulation, constitutive overexpression, synthetic regulation | CAA97297.1, NP_001019195.1, NP_032128.1 |
| 6-pyruvoyl tetrahydrobiopterin (PTP) synthase | PTPS | dihydroneopterin triphosphate → PTP (EC 4.2.3.12) | *Rattus norvegicus*, *Homo sapiens*, *Mus musculus* | 80% | constitutive expression, synthetic regulation; codon optimized for expression in *Saccharomyces cerevisiae* | AAH59140.1, BAA04224.1, AAH29013.1 |
| Sepiapterin reductase | SepR | PTP → BH4 (EC 1.1.1.153) | *Rattus norvegicus*, *Homo sapiens*, *Mus musculus* | 72% | constitutive expression, synthetic regulation; codon optimized for expression in *Saccharomyces cerevisiae* | NP_062054.1, NP_003115.1, NP_035597.2 |
| 4a-hydroxytetrahydro biopterin (pterin-4α-carbinolamine) | PCD | 4a-hydroxytetrahydrobiopterin → H2O + quinoid dihydropteridine (EC 4.2.1.96) | *Rattus norvegicus*, *Homo sapiens*, *Mus musculus* | 79% | constitutive expression, synthetic regulation; codon optimized for expression in *Saccharomyces cerevisiae* | NP_001007602.1, AAB25581.1, NP_079549.1 |
| Quinoid dihydropteridine reductase | QDHPR | quinoid dihydropteridine → BH4 (EC 1.5.1.34) | *Rattus norvegicus*, *Homo sapiens*, *Mus musculus* | 75% | constitutive expression, synthetic regulation; codon optimized for expression in *Saccharomyces cerevisiae* | AAH72536.1, NP_000311.2, AAH02107.1 |
| Dihydrofolate reductase | DHFR | 7,8-Dihydrobiopterin → 5,6,7,8-Tetrahydrobiopterin (BH4) (EC 1.5.1.3) | *Rattus norvegicus*, *Homo sapiens* | 77% | constitutive expression, synthetic regulation; codon optimized for expression in *Saccharomyces cerevisiae* | AF318150.1 |
| 1-benzylisoquinoline alkaloid epimerase (cytochrome P450 82Y2-codeinone reductase) | CYP-COR | (S)-reticuline -> (R)-reticuline (S)-1-benzylisoquinoline->(R)-1-benzylisoquinoline (EC 1.5.1.27) | *Papaver bracteatum*, *Papaver somniferum*, *Papaver setigerum*, *Chelidonium majus* | 77% | constitutive expression, synthetic regulation; Isolated from transcriptome data set and codon optimized for expression in *Saccharomyces cerevisiae* | amino acid sequences listed in Table 1 |
| SalSyn (R)-reticuline, NADPH:oxygen oxidoreductase (C-C phenol-coupling), also known as | SalSyn | (R)-reticuline → salutaridine (EC 1.14.21.4) | *Papaver somniferum*, *Papaver spp* *Chelidonium majus* | 78% | Codon-optimized by DNA2.0 for expression in *Saccharomyces cerevisiae*; | EF451150 (Farrow, et al. 2012. |

TABLE 2-continued

Enzyme List

| Enzyme | Abbrev | Catalyzed Reactions | Source organisms | Similarity to naturally occurring gene | Modifications* | Genbank # |
|---|---|---|---|---|---|---|
| salutaridine synthase |  |  |  |  | N-terminus engineering | Phytochemistry. 77: 79-88) |
| salutaridinol:NADP + 7-oxidoreductase, also known as salutaridine reductase | SalR | salutaridinol ↔ salutaridine (EC 1.1.1.248) | Papaver somniferum, Papaver bracteatum, Papaver spp Chelidonium majus | 80-100% | constitutive expression, synthetic regulation; Codon-optimized by DNA2.0 for expression in Saccharomyces cerevisiae; site-directed mutants | DQ316261, EF184229 (Farrow, et al. 2012. Phytochemistry. 77: 79-88) |
| acetyl-CoA:salutaridinol 7-O-acetyltransferase | SalAT | acetyl-CoA + salutaridinol → CoA + 7-O-acetylsalutaridinol (EC 2.3.1.150) | Papaver somniferum, Papaver bracteatum, Papaver orientale, Papaver spp | 77-80% | constitutive expression, synthetic regulation; Codon-optimized by Life Technologies or DNA2.0 for expression in Saccharomyces cerevisiae | AF339913, FJ200355, FJ200358, FJ200356, JQ659008 |
| Thebaine 6-O demethylase | T6ODM | thebaine → neopinone (EC 1.14.11.31) | Papaver somniferum, Papaver spp. | 76.2% | constitutive expression, synthetic regulation; Codon optimized for expression in Saccharomyces cerevisiae | GQ500139.1 |
| Codeinone reductase | COR | codeinone→ codeine (EC 1.1.1.247), neopinone→ neopine | Papaver somniferum, Papaver spp. | 77.7% 76.8% 77.3% 77.0% | constitutive expression, synthetic regulation; Codon optimized for expression in Saccharomyces cerevisiae; addition of targeting sequences for mitochondria, vacuole, ER. | AF108432.1 AF108433.1 AF108434.1 AF108435.1 |
| Codeine O-demethylase | CODM | codeine→ morphine (EC 1.14.11.32), neopine→ neomorphine | Papaver somniferum, Papaver spp. | 75.2% | constitutive expression, synthetic regulation; Codon optimized for expression in Saccharomyces cerevisiae; addition of targeting sequence for mitochondria | GQ500141.1 |
| (S)-reticuline:oxygen oxidoreductase (methylene-bridge-forming), also known as berberine bridge enzyme | BBE | (S)-reticuline → (S)-scoulerine (EC 1.21.3.3) | Papaver somniferum, Argemone mexicana, Eschscholzia californica, Berberis stolonifera, Thalictrum flavum subsp. glaucum, Coptis japonica, Papaver spp, Eschscholzia spp, Berberis spp, Thalictrum spp. Coptis spp | 99% | constitutive expression, synthetic regulation | AF025430, EU881889, EU881890, S65550 AF005655, AF049347, AY610511, AB747097 |
| S-adenosyl-L-methionine:(S)-scoulerine 9-O-methyltransferase | S9OMT | S-adenosyl-L-methionine + (S)-scoulerine → S-adenosyl-L-homocysteine + (S)-tetrahydrocolumbamine (EC 2.1.1.117) | Thalictrum flavum subsp. glaucum, Papaver somniferum, Coptis japonica, Coptis chinensis, Thalictrum spp, Coptis spp, Papaver spp | 100% 80% | constitutive expression, synthetic regulation; codon-optimized by Life Technologies for expression in Saccharomyces cerevisiae | AY610512, D29809, EU980450, JN185323 |

TABLE 2-continued

Enzyme List

| Enzyme | Abbrev | Catalyzed Reactions | Source organisms | Similarity to naturally occurring gene | Modifications* | Genbank # |
|---|---|---|---|---|---|---|
| (S5)-tetrahydrocolumbamine,NADPH: oxygen oxidoreductase (methylenedioxy-bridge-forming), also known as (S)-canadine synthase | CAS | (S)-tetrahydrocolumbamine → (S)-canadine (EC 1.14.21.5) | *Thalictrum flavum* subsp. *glaucum*, *Coptis japonica*, *Thalictrum* spp. *Coptis* spp | 100% | constitutive expression, synthetic regulation | AY610513, AB026122, AB374407, AB374408 |
| (S)-tetrahydroprotoberberine oxidase | STOX | (S)-tetrahydroberberine + 2 O$_2$ → berberine + 2 H$_2$O$_2$ (EC 1.3.3.8) | *Berberis wilsonae*, *Coptis japonica*, *Berberis* spp, *Coptis* spp | 78% | constitutive expression, synthetic regulation; Codon-optimized by GeneArt for expression in *Saccharomyces cerevisiae* | HQ116697, AB564543 |
| Tetrahydroprotoberberine-N-methyltransferase | TNMT | Stylopine → cis-N-methylstylopine (EC 2.1.1.122) Canadine → N-methylcanadine | *P. somniferum*, *E. californica*, *P. bracteatum*, *A. mexicana* | 100% 81% | constitutive expression, synthetic regulation; codon-optimized by Life Technologies for expression in *Saccharomyces cerevisiae* | DQ028579 EU882977 EU882994 HQ116698 |
| N-methylcanadine 14-hydroxylase | CYP82Y1 | N-methylcanadine → 1-hydroxy-N-methylcanadine | *P. somniferum*, *Papaver* spp, *Plantago arenaria*, *Rauwolfia heterophylla*, *Adlumia fungosa*, *Hydrastis Canadensis*, *Stylomecon heterophylla*, *Hypecoum leptocarpum*, *Dactylicapnos torulosa*, *Glaucium flavum*, *Berberis laurina*, *B. Vulgaris*, *Corydalis* spp, *Fumaria* spp, *Dactylicapnos* spp | 70 (N-terminus engineering)-78% | constitutive expression, synthetic regulation; Codon-optimized by Life Technologies for expression in *Saccharomyces cerevisiae*; N-terminus engineering | JQ659006S1 |
| 1-hydroxy-N-methylcanadine 13-hydroxylase | CYP82X2 | 1-hydroxy-N-methylcanadine → 1,13-dihydroxy-N-methylcanadine | *P. somniferum*, *Papaver* spp, *Plantago arenaria*, *Rauwolfia heterophylla*, *Adlumia fungosa*, *Hydrastis Canadensis*, *Stylomecon heterophylla*, *Dactylicapnos torulosa*, *Glaucium flavum*, *Berberis laurina*, *B. Vulgaris*, *Corydalis* spp, *Fumaria* spp, *Dactylicapnos* spp | 70 (N-terminus engineering)-77% | constitutive expression, synthetic regulation; Codon-optimized by Life Technologies for expression in *Saccharomyces cerevisiae*; N-terminus engineering | JQ659004.1 |
| 4'-O-Desmethyl-3-O-acetylpapaveroxine synthase | CYP82X1 | 1-Hydroxy-13-O-acetyl-N-methylcanadine → 4'-O-Desmethyl-3-O-acetylpapaveroxine 1-hydroxy-N-methylcanadine → 4'-O-desmethylmacrantaldehyde | *P. somniferum*, *Papaver* spp, *Plantago arenaria*, *Rauwolfia heterophylla*, *Adlumia fungosa*, *Hydrastis* | 71 (N-terminus engineering)-77% | constitutive expression, synthetic regulation; Codon-optimized by Life Technologies for expression in *Saccharomyces cerevisiae*; | JQ659002.1 |

TABLE 2-continued

Enzyme List

| Enzyme | Abbrev | Catalyzed Reactions | Source organisms | Similarity to naturally occurring gene | Modifications* | Genbank # |
|---|---|---|---|---|---|---|
| | | | *Canadensis, Stylomecon heterophylla, Hypecoum leptocarpum, Dactylicapnos torulosa, Glaucium flavum, Berberis laurina, B. Vulgaris, Corydalis spp, Fumaria spp, Dactylicapnos spp* | | N-terminus engineering | |
| Cheilanthifoline synthase | CFS | Scoulerine → cheilanthifoline (EC 1.14.21.2) | *P. somniferum E. californica A. mexicana* | 79% 77% 78% | constitutive expression, synthetic regulation; Codon optimized for expression in *Saccharomyces cerevisiae* | GU325749 AB434654 EF451152 |
| Stylopine synthase | STS | Cheilanthifoline → stylopine (EC 1.14.21.1) | *P. somniferum E. californica A. mexicana* | 79% 78% 76% | constitutive expression, synthetic regulation; Codon optimized for expression in *Saccharomyces cerevisiae* | GU325750 AB126257 EF451151 |
| Cis-N-methylstylopine 14-hydroxylase | MSH | cis-N-methylstylopine → protopine (EC 1.14.13.37) | *P. somniferum* | 79% | constitutive expression, synthetic regulation; Codon optimized for expression in *Saccharomyces cerevisiae* | KC154003 |
| Protopine-6-hydroxylase | P6H | Protopine → 6-hydroxyprotopine (EC 1.14.13.55) | *E. californica P. somniferum* | 79% | constitutive expression, synthetic regulation; Codon optimized for expression in *Saccharomyces cerevisiae* | AB598834 AGC92397 |
| Dihydrobenzophenanthridine oxidase | DBOX | Dihydrosanguinarine → sanguinarine (EC 1.5.3.12) | *P. somniferum* | 100% | constitutive expression, synthetic regulation; Codon optimized for expression in *Saccharomyces cerevisiae* | [not in genbank] |
| Narcotoline 14-O-methylase I | MT2 | Narcotoline → Noscapine Narcotolinehemiacetal → Narcotinehemiacetal 4'-O-desmethyl-3-O-acetylpapaveroxine → 3-O-acetylpapveroxine | *P. somniferum, Papaver spp, Fumaria parviflora, Plantago arenaria, Rauwolfia heterophylla* | 80% | constitutive expression, synthetic regulation; Codon-optimized by Life Technologies for expression in *Saccharomyces cerevisiae* | JQ659000.1 |
| 1,13-dihydroxy-N-methylcanadine 13-O acetyl transferase | AT1 | 1,13-dihydroxy-N-methylcanadine → 1-hydroxy-13-O-acetyl-N-methycanadine | *P. somniferum, Papaver spp, Plantago arenaria, Rauwolfia heterophylla, Adlumia fungosa, Hydrastis Canadensis, Stylomecon heterophylla, Hypecoum leptocarpum, Dactylicapnos torulosa, Glaucium flavum, Berberis laurina, B. Vulgaris, Corydalis spp, Fumaria spp, Dactylicapnos spp* | 81% | constitutive expression, synthetic regulation; Codon-optimized by Life Technologies for expression in *Saccharomyces cerevisiae* | JQ659008.1 |

TABLE 2-continued

Enzyme List

| Enzyme | Abbrev | Catalyzed Reactions | Source organisms | Similarity to naturally occurring gene | Modifications* | Genbank # |
|---|---|---|---|---|---|---|
| Narcotinehemiacetal synthase | CXE1 | 4'-O-desmethyl-3-O-acetylpapaveroxine → Narcotinehemiacetal<br>Papaveroxine → Narcotinehemiacetal | P. somniferum, Papaver spp, Plantago arenaria, Rauwolfia heterophylla, Adlumia fungosa, Hydrastis Canadensis, Stylomecon heterophylla, Hypecoum leptocarpum, Dactylicapnos torulosa, Glaucium flavum, Berberis laurina, B. Vulgaris, Corydalis spp, Fumaria spp, Dactylicapnos spp | 78% | constitutive expression, synthetic regulation; Codon-optimized by Life Technologies for expression in Saccharomyces cerevisiae | JQ659006.1 |
| Narcotinehemiacetal synthase | CXE2 | 4'-O-desmethyl-3-O-acetylpapaveroxine → Narcotinehemiacetal<br>Papaveroxine → Narcotinehemiacetal | P. somniferum, Papaver spp, Plantago arenaria, Rauwolfia heterophylla, Adlumia fungosa, Hydrastis Canadensis, Stylomecon heterophylla, Hypecoum leptocarpum, Dactylicapnos torulosa, Glaucium flavum, Berberis laurina, B. Vulgaris, Corydalis spp, Fumaria spp, Dactylicapnos spp | 78% | constitutive expression, synthetic regulation; Codon-optimized by Life Technologies for expression in Saccharomyces cerevisiae | KJ890443.1 |
| Noscapine synthase | SDR1 | Narcotinehemiacetal → Narcotoline<br>Narcotinehemiacetal → Noscapine | P. somniferum, Papaver spp, Plantago arenaria, Rauwolfia heterophylla, Adlumia fungosa, Hydrastis Canadensis, Stylomecon heterophylla, Hypecoum leptocarpum, Dactylicapnos torulosa, Glaucium flavum, Berberis laurina, B. Vulgaris, Corydalis spp, Fumaria spp, Dactylicapnos spp | 79% | constitutive expression, synthetic regulation; Codon-optimized by Life Technologies for expression in Saccharomyces cerevisiae | JQ659007.1 |
| Narcotoline 14-O-methylase II | MT3 | Narcotoline → Noscapine<br>Narcotinehemiacetal → Narcotinehemiacetal<br>4'-O-desmethyl-3-O-acetylpapaveroxine → 3-O-acetylpapveroxine | P. somniferum, Papaver spp, Fumaria parviflora, Plantago arenaria, Rauwolfia heterophylla | 79% | constitutive expression, synthetic regulation; Codon-optimized by Life Technologies for expression in Saccharomyces cerevisiae | JQ659001.1 |

TABLE 2-continued

Enzyme List

| Enzyme | Abbrev | Catalyzed Reactions | Source organisms | Similarity to naturally occurring gene | Modifications* | Genbank # |
|---|---|---|---|---|---|---|
| Morphine dehydrogenase | morA | morphine → morphinone (EC 1.1.1.218), codeinone → codeine (EC 1.1.1.247) | Pseudomonas putida | 73.7% | constitutive expression, synthetic regulation; Codon optimized for expression in Saccharomyces cerevisiae; introduced mutation morAC81S | M94775.1 |
| Morphinone reductase | morB | codeinone → hydrocodone morphinone → hydromorphone (EC 1.3.1.) | Pseudomonas putida | 67.2% | constitutive expression, synthetic regulation; Codon optimized for expression in Saccharomyces cerevisiae; introduced mutation morBE160G | U37350.1 |
| NADPH:hemoprotein oxidoreductase, also known as cytochrome P450 reductase | ATR1, CPR | NADPH + H+ + n oxidized hemoprotein → NADP+ + n reduced hemoprotein (EC 1.6.2.4) | Arabidopsis thaliana, all plants (e.g., P. somniferum, E. californica), yeast (e.g., S. cerevisiae), H. sapiens | 100% | constitutive expression, synthetic regulation at various promoter strengths | NM118585, many others (Jensen and Moller. 2010. Phytochemistry. 71: 132-41) |
| Cytochrome P450, family 2, subfamily D, polypeptide 6 | CYP2D6 | Promiscuous oxidase, can perform (R)-reticuline → salutaridine, among other reactions (EC 1.14.14.1) | Homo sapiens | 73% | constitutive expression, synthetic regulation; Codon-optimized by DNA2.0 for expression in Saccharomyces cerevisiae | BC067432 |
| Berbamunine synthase Cytochrome P450 80A1 | CYP80A1 | (S)-N-methylcoclaurine + (R)-N-methylcoclaurine → berbamunine (EC 1.14.21.3) | Berberis stolonifera | 76% | constitutive over expression, synthetic regulation; codon-optimized for expression in Saccharomyces cerevisiae | UO9610.1 |
| Protopine O-dealkylase | PODA | O,O-demethylenation of canadine, stylopine and berberine | P. somniferum, Papaver spp. | 70-100% | Constitutive overexpression, synthetic regulation; codon-optimized for expression in Saccharomyces cerevisiae | GQ500140.1 |

TABLE 3

Tailoring enzymes

| Reaction Catalyzed | Enzyme | Species |
|---|---|---|
| Carbon-carbon coupling | Berberine bridge enzyme (BBE) | Ps, Ec, Cj, Bs, Tf |
| | Salutaridine synthase (SalSyn) | Ps |
| | Corytuberine synthase (CorSyn) | Cj |
| Oxidation | Tetrahydroprotoberberine oxidase (STOX) | Cj, Am, Bw |
| | Dihydrobenzophenanthridine oxidase (DBOX) | Ps |
| | Methylstylopine hydroxylase (MSH) | Ps |
| | Protopine 6-hydroxylase (P6H) | Ps, Ec |
| Methylenedioxy bridge formation | Stylopine synthase (StySyn) | Ps, Ec, Am |
| | Cheilanthifoline synthase (CheSyn) | Ps, Ec, Am |
| | Canadine synthase (CAS) | Tf, Cc |
| O-methylation | Norcoclaurine 6-O-methyltransferase (6OMT) | Ps, Tf, Cj, Pb |
| | 3'hydroxy-N-methylcoclaurine 4'-O-methyltransferase (4'OMT) | Ps, Tf, Cj, Cc |
| | Reticuline 7-O-methyltransferase (7OMT) | Ps, Ec |
| | Scoulerine 9-O-methyltransferase (9OMT) | Ps, Tf, Cj, Cc |
| N-methylation | Coclaurine N-methyltransferase (CNMT) | Ps, Tf, Cj |
| | Tetrahydroprotoberberine N-methyltransferase (TMNT) | Ps, Ec, Pb |
| O-demethylation | Thebaine demethylase (T6ODM) | Ps |
| | Codeine demethylase (CODM) | Ps, Ga |
| Reduction | Salutaridine reductase (SalR) | Ps, Pb, Ga |
| | Codeinone reductase (COR) | Ps |
| | Sanguinarine reductase (SanR) | Ec |
| Acetylation | Salutaridine acetyltransferase (SalAT) | Ps |

TABLE 4

Comparison of impurities that may be present in concentrate of poppy straw (or opium) and clarified yeast culture medium.

| | Impurities: | Concentrate of Poppy Straw | Clarified Yeast Culture Medium |
|---|---|---|---|
| Inorganic | Sodium | ✓ | ✓ |
| | Magnesium | ✓ | ✓ |
| | Silicon | ✓ | x (not in culure medium) |
| | Phosphorus | ✓ | ✓ |
| | Sulfur | ✓ | ✓ |
| | Chloride | ✓ | ✓ |
| | Potassium | ✓ | ✓ |
| | Calcium | ✓ | ✓ |
| | Copper | ✓ | ✓ |
| | Zinc | ✓ | ✓ |
| | Molybdenum | ✓ | ✓ (sodium molybdenum in medium) |
| | Iron | ✓ | ✓ |
| | Manganese | ✓ | ✓ |
| | Ammonium | ✓ | ✓ |
| | Boron | ✓ | ✓ |
| Organic | Polysaccharides (starch, cellulose, xylan) | ✓ | x (yeast fed simple organic) |
| | Lignin (p-coumaryl, coniferyl, sinapyl alcohols) | ✓ | x |
| | Pigments (chlorophyll, anthocyanins, carotenoids) | ✓ | x |
| | Flavonoids | ✓ | x |
| | Phenanthreoids | ✓ | x |
| | Latex, gum, and wax | ✓ | x |
| | Rubisco | ✓ | x |
| | Meconic acid | ✓ | x |
| | Pseudomorphine | ✓ | x |
| | Narceine | ✓ | x |
| | Thebaol | ✓ | x |
| Other | Pesticides, Fungicides, Herbicides | ✓ | x |
| | Pollen | ✓ | x |

TABLE 5

Distinct groups of molecules present in clarified yeast culture medium (CYCM). Unlike concentrate of poppy straw (CPS) or opium, yeast host strains may be engineered to produce molecules of a predetermined class of alkaloids (i.e., only one biosynthesis pathway per strain) such that other classes of alkaloids are not present. Therefore, the CYCM may contain molecules within a single biosynthesis pathway including a subset of molecules spanning one or two columns, whereas the CPS may contain a subset of molecules across many columns.

| 1-Benzylisoquinoline | Protoberberine and Phthalldeisoquinoline | Morphinan | Isopavine | Aporphine | BisBIA |
|---|---|---|---|---|---|
| Tetrahydropapaverine | Scoulerine | Salutaridine | Pavine | Magneflorine | Dauricine |
| Dihydropapaverine | Chelarithifoline | Salutaridinol | Caryachine | Corytuberine | Barbamunine |
| Papaverine | Stylopine | Salutaridine-7-O-acetate | Bisnorargemonine | Apomorphine | Ligensinine |
| | Cis-N-methylstylopine | Thebaine | Isonoraremonine | Boldine | Fangchinoline |
| | Protopine | Codeinone | | | Tetrandrine |
| | Dihydrosanguinarine | Oripavine | | | Curine |
| | Sanguinarine | Morphinone | | | Capharanthine |
| | Tetrahydrocolumbamine | Neopinone | | | Berbamine |
| | Canadine | Neopine | | | |
| | N-methylcanadine | Codeine | | | |
| | Noscapine | Morphine | | | |
| | Berberine | Neomorphine | | | |
| | Nancotaline | Hydrocodone | | | |
| | Narcotinehemiacetal | Oxycodone | | | |
| | Narcoteinehemiacetal | 14-hydroxycodeinone | | | |
| | | 14-hydroxycodeine | | | |
| | | Dihydromorphine | | | |
| | | Dihydrocodeine | | | |
| | | Oxymorphone | | | |
| | | Hydromorphone | | | |

TABLE 6

Beneficial mutations of various enzymes identified by mutagenesis screening.

| Gene | GenBank ID# | Substrate(s) | Products(s) | Mutations |
|---|---|---|---|---|
| PsCODM | ADD85331.1 | Codeine, Neopine | Morphine, Neomorphine | N35S, G335V (FIG. 21) |
| PsT6ODM | ADD85329.1 | Thebaine, Cripavine | Neopinone, Murphinone | M151T, A202V, P229S, D96H, L158M |
| PsCOR1.3 | AAF13738.1 | Codeinone, Neopinone | Codeine, Neopine | C220G |
| Ps6OMT | AAP45315.1 | Norcoclaurine | Coclaurine | D322N |

Notwithstanding the appended clauses, the disclosure is also defined by the following clauses:

1. An engineered non-plant cell having increased tyrosine hydroxylase activity relative to a non-engineered cell, the engineered non-plant cell having at least one modification selected from the group consisting of: a substrate inhibition alleviating mutation; a product inhibition alleviating mutation; and a cofactor recovery promoting mechanism.
2. The engineered non-plant cell of clause 1, wherein the at least one modification comprises a substrate inhibition alleviating mutation.
3. The engineered non-plant cell of clause 2, wherein the substrate inhibition alleviating mutation comprises a point mutation W166Y.
4. The engineered non-plant cell of clause 1, wherein the at least one modification comprises at least one product inhibition alleviating mutation that relieves competitive binding at a cosubstrate binding site.
5. The engineered non-plant cell of clause 4, wherein the at least one product inhibition alleviating mutation comprises a point mutation S40D.
6. The engineered non-plant cell of clause 4, wherein the at least one product inhibition alleviating mutation comprises joint mutations R37E and R38E.
7. The engineered non-plant cell of clause 6, wherein the joint mutations R37E and R38E improve tyrosine hydroxylase activity in the presence of dopamine.
8. The engineered non-plant cell of clause 1, wherein the at least one modification comprises a product inhibition alleviating mutation that relieves irreversible product inhibition.
9. The engineered non-plant cell of clause 8, wherein the product inhibition alleviating mutation comprises a point mutation E332D.
10. The engineered non-plant cell of clause 8, wherein the product inhibition alleviating mutation comprises a point mutation Y371F.
11. The engineered non-plant cell of clause 8, wherein the product inhibition alleviating mutation relieves irreversible binding of catecholamine to iron in an active site.
12. The engineered non-plant cell of clause 1, wherein the at least one modification comprises a cofactor recovery promoting mechanism.
13. The engineered non-plant cell of clause 12, wherein the cofactor recovery promoting mechanism comprises a heterologous coding sequence that encodes dihydrofolate reductase.
14. The engineered non-plant cell of clause 13, wherein dihydrofolate reductase produced by the engineered non-plant cell catalyzes conversion of dihydrobiopterin to tetrahydrobiopterin within the engineered non-plant cell.
15. A method for forming a product stream having a benzylisoquinoline alkaloid product, comprising:
  (a) providing engineered non-plant cells and a feedstock including nutrients and water to a batch reactor, which engineered non-plant cells have at least one modification selected from the group consisting of: a substrate inhibition alleviating mutation; a product inhibition alleviating mutation; and a cofactor recovery promoting mechanism
  (b) in said batch reactor, subjecting said engineered non-plant cells to fermentation by incubating said engineered non-plant cells for a time period of at least about 5 minutes to produce a solution comprising said benzylisoquinoline alkaloid product and cellular material; and
  (c) using at least one separation unit to separate said benzylisoquinoline alkaloid product from said cellular material to provide said product stream comprising said benzylisoquinoline alkaloid product.
16. The method of clause 15, wherein at least one process parameter of the batch reactor is modifiable to alter a resultant benzylisoquinoline alkaloid product composition.
17. The method of clause 16, wherein the at least one process parameter that is modifiable comprises at least one of dissolved oxygen, pH, stirring speed, aeration rate, and cell density.
18. The method of clause 15, wherein the benzylisoquinoline alkaloid product comprises a benzylisoquinoline alkaloid precursor.
19. The method of clause 18, wherein the benzylisoquinoline alkaloid precursor is selected from the group of norcoclaurine, norlaudanosoline, tyrosine, tyramine, 4-hydroxyphenylacetaldehyde, 4-hydroxyphenylpyruvic acid, L-3,4-dihydroxyphenylalanine, 3,4-dihydroxyphenylacetaldehyde, and dopamine.
20. The method of clause 15, wherein the benzylisoquinoline alkaloid product comprises a benzylisoquinoline alkaloid.
21. The method of clause 20, wherein the benzylisoquinoline alkaloid has a structural class that is selected from the group of benzylisoquinolines, protoberberines, protopines, benzophenanthridines, promorphinans, morphinans, secoberberines, phthalideisoquinolines, aporphines, and bisbenzylisoquinolines.
22. The method of clause 21, wherein the benzylisoquinoline alkaloid is a benzylisoquinoline that is selected from the group of coclaurine, 3'-hydroxycoclaurine, 4'-O-methylnorlaudanosoline, 4'-O-methyl-laudanosoline, N-methylnorcoclaurine, laudanosoline, N-methylcoclaurine, 3'-hydroxy-N-methylcoclaurine, reticuline, norreticuline, papaverine, laudanine, laudanosine, tetrahydropapaverine, 1,2-dihydropapaverine, and orientaline.

23. The method of clause 21, wherein the benzylisoquinoline alkaloid is a protoberberine that is selected from the group of scoulerine, cheilanthifoline, stylopine, nandinine, jatrorrhizine, stepholidine, discretamine, cis-N-methylstylopine, tetrahydrocolumbamine, palmatine, tetrahydropalmatine, columbamine, canadine, N-methylcanadine, 1-hydroxycanadine, berberine, N-methyl-ophiocarpine, 1,13-dihydroxy-N-methylcanadine, and 1-hydroxy-10-O-acetyl-N-methylcanadine.

24. The method of clause 21, wherein the benzylisoquinoline alkaloid is a protopine that is selected from the group of protopine, 6-hydroxyprotopine, allocryptopine, cryptopine, muramine, and thalictricine.

25. The method of clause 21, wherein the benzylisoquinoline alkaloid is a benzophenanthridine that is selected from the group of dihydrosanguinarine, sanguinarine, dihydrocheilirubine, cheilirubine, dihydromarcapine, marcapine, and chelerythrine.

26. The method of clause 21, wherein the benzylisoquinoline alkaloid is a promorphinan that is selected from the group of salutaridine, salutaridinol, and salutaridinol-7-O-acetate.

27. The method of clause 21, wherein the benzylisoquinoline alkaloid is a morphinan that is selected from the group of thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydroetorphine, ethylmorphine, etorphine, metopon, buprenorphine, pholcodine, heterocodeine, and oxymorphone.

28. The method of clause 21, wherein the benzylisoquinoline alkaloid is a secoberberine that is selected from the group of 4'-O-desmethylmacrantaldehyde, 4'-O-desmethylpapaveroxine, 4'-O-desmethyl-3-O-acetylpapaveroxine, and 3-O-aceteylpapaveroxine.

29. The method of clause 21, wherein the benzylisoquinoline alkaloid is a phthalideisoquinoline that is selected from the group of narcotolinehemiacetal, narcotinehemiacetal, narcotoline, and noscapine.

30. The method of clause 21, wherein the benzylisoquinoline alkaloid is an aporphine that is selected from the group of magnoflorine, corytuberine, apomorphine, boldine, isoboldine, isothebaine, isocorytuberine, and glaufine.

31. The method of clause 21, wherein the benzylisoquinoline alkaloid is a bisbenzylisoquinoline that is selected from the group of berbamunine, guattgaumerine, dauricine, and liensinine.

32. A method for forming a product stream having a benzylisoquinoline alkaloid product, comprising:
(a) providing engineered non-plant cells having increased tyrosine hydroxylase activity relative to a cell that expresses wild-type tyrosine hydroxylase without mutations that increase tyrosine hydroxylase activity, a feedstock including nutrients, and water to a reactor;
(b) in said reactor, subjecting said engineered non-plant cells to fermentation by incubating said engineered non-plant cells for a time period of at least about 5 minutes to produce a solution comprising cellular material and said benzylisoquinoline alkaloid product, wherein said solution comprises not more than one class of molecule selected from the group of protoberberine, morphinan, isopavine, aporphine, and bisbenzylisoquinoline; and
(c) using at least one separation unit to separate said benzylisoquinoline alkaloid product from said cellular material to provide said product stream comprising said benzylisoquinoline alkaloid product.

33. The method of clause 32, wherein the product stream does not contain more than 5 ppm of a molecule selected from the group of lignin, flavonoids, phenanthreoids, latex, rubisco, meconic acid, pseudomorphine, narceine, thebaol, and pollen.

34. The method of clause 33, wherein the product stream does not contain more than 5 ppm of meconic acid.

35. The method of clause 32, wherein the product stream does not contain a detectable amount of a substance selected from the group consisting of pesticides, fungicides, or herbicides.

36. The method of clause 32, wherein the benzylisoquinoline alkaloid product is recovered from said product stream using at least liquid-liquid extraction.

37. The method of clause 36, wherein the benzylisoquinoline alkaloid product is recovered immediately after a fermentation process has been completed.

38. A method of epimerizing an (S)-1-benzylisoquinoline alkaloid to an (R)-1-benzylisoquinoline alkaloid, comprising:
contacting the (S)-1-benzylisoquinoline alkaloid with at least one enzyme,
wherein contacting the (S)-1-benzylisoquinoline alkaloid with the at least one enzyme converts the (S)-1-benzylisoquinoline alkaloid to an (R)-1-benzylisoquinoline alkaloid.

39. The method of clause 38, wherein the at least one enzyme is produced by culturing an engineered non-plant cell having a coding sequence for encoding the at least one enzyme.

40. The method of clause 39, further comprising:
adding an (S)-1-benzylisoquinoline alkaloid to the cell culture.

41. The method of clause 40, further comprising:
recovering the (R)-1-benzylisoquinoline alkaloid, or a derivative thereof, from the cell culture.

42. The method of any one of clauses 38-41, wherein the at least one enzyme comprises an oxidase.

43. The method of any one of clauses 38-42, wherein the at least one enzyme comprises a reductase.

44. The method of any one of clauses 38-43, wherein the at least one enzyme comprises an epimerase.

45. The method of clause 44, wherein the epimerase comprises an amino acid sequence selected from the group consisting of: SEQ ID NOs: 1, 2, 3, 4, 5, 6, 7, 8, 9, 10, 11, 12, 13, 14, and 15.

46. The method of clause 44 or 45, wherein the epimerase comprises an oxidase domain and a reductase domain.

47. The method of clause 46, wherein the oxidase domain is a cytochrome P450 oxidase-like domain 48. The method of clause 46, wherein the reductase domain is a codeinone reductase-like domain 49. The method of any one of clauses 38-48, wherein the (S)-1-benzylisoquinoline alkaloid is (S)-reticuline.

50. The method of any one of clauses 38-49, wherein the (R)-1-benzylisoquinoline alkaloid is (R)-reticuline.

51. The method of any one of clauses 38-50, further comprising:
converting the (R)-1-benzylisoquinoline alkaloid to a 4-ring promorphinan alkaloid.

52. The method of clause 51, wherein the 4-ring promorphinan alkaloid is salutaridine.
53. The method of any one of clauses 38-50, further comprising:
    converting the (R)-1-benzylisoquinoline alkaloid to a 5-ring morphinan alkaloid.
54. The method of any one of clauses 38-53, wherein the (S)-1-benzylisoquinoline alkaloid present within the engineered non-plant cell is produced within an engineered microbial cell.
55. The method of any one of clauses 38-54, wherein the (S)-1-benzylisoquinoline alkaloid is produced within the engineered non-plant cell by a metabolic pathway starting with L-tyrosine.
56. The method of any one of clauses 38-54, wherein the (S)-1-benzylisoquinoline alkaloid is produced within the engineered non-plant cell by a metabolic pathway starting with a carbohydrate and nitrogen source.
57. The method of any one of clauses 38-56, wherein the (S)-1-benzylisoquinoline alkaloid is selected from the group consisting of: (S)-norreticuline; (S)-reticuline; (S)-tetrahydropapaverine; (S)-norcoclaurine; (S)-coclaurine; (S)—N-methylcoclaurine; (S)-3'-hydroxy-N-methylcoclaurine; (S)-norisoorientaline; (S)-orientaline; (S)-isoorientaline; (S)-norprotosinomenine; (S)-protosinomenine; (S)-norlaudanosoline; (S)-laudanosoline; (S)-4'-O-methyllaudanosoline; (S)-6-O-methylnorlaudanosoline; and (S)-4'-O-methylnorlaudanosoline.
58. The method of any one of clauses 38-57, wherein the (S)-1-benzylisoquinoline alkaloid is a compound of Formula I:

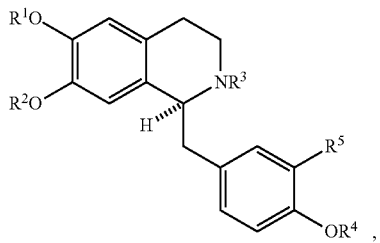

Formula I wherein:
    $R^1$, $R^2$, $R^3$, and $R^4$ are independently hydrogen or methyl; and
    $R^5$ is hydrogen, hydroxy, or methoxy.
59. An engineered non-plant cell that produces an (R)-1-benzylisoquinoline alkaloid from an (S)-1-benzylisoquinoline alkaloid present within the engineered non-plant cell, comprising a heterologous coding sequence encoding an epimerase, wherein the epimerase converts the (S)-1-benzylisoquinoline alkaloid to the (R)-1-benzylisoquinoline alkaloid.
60. The engineered non-plant cell of clause 59, further comprising a heterologous coding sequence encoding salutaridine synthase.
61. The engineered non-plant cell of clause 60, wherein the salutaridine synthase converts the (R)-1-benzylisoquinoline alkaloid to salutaridine.
62. An engineered non-plant cell that produces an epimerase that converts (S)-1-benzylisoquinoline alkaloid to (R)-1-benzylisoquinoline alkaloid, wherein the epimerase comprises an amino acid sequence selected from the group consisting of: SEQ ID NOs: 1, 2, 3, 4, 5, 6, 7, 8, 9, 10, 11, 12, 13, 14, and 15.
63. A process for converting an (S)-1-benzylisoquinoline alkaloid to an (R)-1-benzylisoquinoline alkaloid comprising contacting the (S)-1-benzylisoquinoline alkaloid with an epimerase in an amount sufficient to convert the (S)-1-benzylisoquinoline alkaloid to (R)-1-benzylisoquinoline alkaloid.
64. The process of clause 63, wherein said epimerase comprises an amino acid sequence selected from the group consisting of: SEQ ID NOs: 1, 2, 3, 4, 5, 6, 7, 8, 9, 10, 11, 12, 13, 14, and 15.
65. The process of clause 63, wherein at least 5% of the (S)-1-benzylisoquinoline alkaloid is converted to (R)-1-benzylisoquinoline alkaloid.
66. A method of epimerizing a stereocenter of a 1-benzylisoquinoline alkaloid, comprising:
    contacting the 1-benzylisoquinoline alkaloid with at least one enzyme,
    wherein the contacting the 1-benzylisoquinoline alkaloid with the at least one enzyme inverts the stereochemistry of the stereocenter of the 1-benzylisoquinoline alkaloid to the opposite stereochemistry of the stereocenter of the 1-benzylisoquinoline alkaloid.
67. The method of clause 66, wherein the at least one enzyme is produced by culturing an engineered non-plant cell having a coding sequence for encoding the at least one enzyme.
68. The method of clause 67, further comprising:
    adding the 1-benzylisoquinoline alkaloid to the cell culture.
69. The method of clause 66, wherein the 1-benzylisoquinoline alkaloid is present as a single stereoisomer of the 1-benzylisoquinoline alkaloid.
70. The method of clause 66, wherein the 1-benzylisoquinoline alkaloid is present as a mixture of stereoisomers of the 1-benzylisoquinoline alkaloid.
71. The method of clause 70, wherein the mixture of stereoisomers of the 1-benzylisoquinoline alkaloid is a racemic mixture of enantiomers of the 1-benzylisoquinoline alkaloid.
72. The method of clause 67, further comprising:
    recovering a stereoisomer of the 1-benzylisoquinoline alkaloid, or a derivative thereof, from the cell culture.
73. The method of clause 72, wherein the recovered 1-benzylisoquinoline alkaloid has an enantiomeric excess of at least about 80%.
74. The method of clause 72, wherein the recovered 1-benzylisoquinoline alkaloid has an enantiomeric excess of at least about 98%.
75. The method of any one of clauses 66-74, wherein the at least one enzyme comprises an oxidase.
76. The method of any one of clauses 66-75, wherein the at least one enzyme comprises a reductase.
77. The method of any one of clauses 66-74, wherein the at least one enzyme comprises an epimerase.
78. The method of clause 77, wherein the epimerase comprises an amino acid sequence selected from the group consisting of: SEQ ID NOs: 1, 2, 3, 4, 5, 6, 7, 8, 9, 10, 11, 12, 13, 14, and 15.
79. The method of clause 77, wherein the epimerase comprises an amino acid sequence that is at least 75% identical to any of the SEQ ID NOs: 1, 2, 3, 4, 5, 6, 7, 8, 9, 10, 11, 12, 13, 14, and 15.
80. The method of clause 77, wherein the epimerase comprises an amino acid sequence that is at least 80% identical to any of the SEQ ID NOs: 1, 2, 3, 4, 5, 6, 7, 8, 9, 10, 11, 12, 13, 14, and 15.
81. The method of clause 77, wherein the epimerase comprises an amino acid sequence that is at least 85% identical to any of the SEQ ID NOs: 1, 2, 3, 4, 5, 6, 7, 8, 9, 10, 11, 12, 13, 14, and 15.
82. The method of clause 77, wherein the epimerase comprises an amino acid sequence that is at least 90% identical to any of the SEQ ID NOs: 1, 2, 3, 4, 5, 6, 7, 8, 9, 10, 11, 12, 13, 14, and 15.
83. The method of clause 77, wherein the epimerase comprises an amino acid sequence that is at least 95% identical to any of the SEQ ID NOs: 1, 2, 3, 4, 5, 6, 7, 8, 9, 10, 11, 12, 13, 14, and 15.
84. The method of clause 77, wherein the epimerase comprises an amino acid sequence that is at least 98% identical to any of the SEQ ID NOs: 1, 2, 3, 4, 5, 6, 7, 8, 9, 10, 11, 12, 13, 14, and 15.
85. The method of any of clauses 77-84, wherein the epimerase comprises an oxidase domain and a reductase domain
86. The method of clause 85, wherein the oxidase domain is a cytochrome P450 oxidase-like domain.
87. The method of clause 85, wherein the reductase domain is a codeinone reductase-like domain.
88. An engineered non-plant cell that produces a bisbenzylisoquinoline alkaloid from two benzylisoquinoline alkaloid monomers that are present within the engineered non-plant cell, comprising:
a heterologous coding sequence encoding at least one coupling enzyme,
wherein the at least one coupling enzyme dimerizes the two benzylisoquinoline alkaloid monomers, thereby forming the bisbenzylisoquinoline alkaloid.
89. The engineered non-plant cell of clause 88, wherein the at least one coupling enzyme dimerizes the two benzylisoquinoline alkaloid monomers by forming one or more covalent bonds.
90. The engineered non-plant cell of clause 88, wherein the at least one coupling enzyme dimerizes the two benzylisoquinoline alkaloid monomers by forming one or more carbon-carbon bonds.
91. The engineered non-plant cell of clause 88, wherein the at least one coupling enzyme dimerizes the two benzylisoquinoline alkaloid monomers by forming one or more carbon-oxygen bonds.
92. The engineered non-plant cell of clause 88, wherein the at least one coupling enzyme dimerizes identical benzylisoquinoline alkaloid monomers, thereby forming a homodimer.
93. The engineered non-plant cell of clause 88, wherein the at least one coupling enzyme dimerizes distinct benzylisoquinoline alkaloid monomers, thereby forming a heterodimer.
94. The engineered non-plant cell of clause 88, wherein the two benzylisoquinoline alkaloid monomers are stereoisomers of each other.
95. The engineered non-plant cell of clause 88, wherein a first benzylisoquinoline alkaloid monomer of the two benzylisoquinoline alkaloid monomers is selected from the group of: coclaurine, N-methylcoclaurine, laudanine, norcoclaurine, norlaudanosoline, 6-O-methyl-norlaudanosoline, 3'-hydroxy-N-methylcoclaurine 3'-hydroxycoclaurine, reticuline, norreticuline, norlaudanine.
96. The engineered non-plant cell of clause 95, wherein a second benzylisoquinoline alkaloid monomer of the two benzylisoquinoline alkaloid monomers is selected from the group of: coclaurine, N-methylcoclaurine, laudanine, norcoclaurine, norlaudanosoline, 6-O-methyl-norlaudanosoline, 3'-hydroxy-N-methylcoclaurine, 3'-hydroxycoclaurine, reticuline, norreticuline, norlaudanine.
97. The engineered non-plant cell of clause 88, wherein at least one of the two benzylisoquinoline alkaloid monomers is produced within the engineered non-plant cell.
98. The engineered non-plant cell of clause 88, wherein at least one of the two benzylisoquinoline alkaloid monomers is produced outside the engineered non-plant cell.
99. An engineered non-plant cell that produces a bisbenzylisoquinoline alkaloid using a coupling enzyme that is present within the engineered non-plant cell, comprising:
at least one heterologous coding sequence encoding at least one enzyme used in the production of at least one benzylisoquinoline alkaloid monomer within the engineered non-plant cell,
wherein the at least one coupling enzyme dimerizes two benzylisoquinoline alkaloid monomers within the engineered non-plant cell, thereby forming the bisbenzylisoquinoline alkaloid.
100. The engineered non-plant cell of clause 99, wherein the at least one coupling enzyme dimerizes the two benzylisoquinoline alkaloid monomers by forming one or more covalent bonds.
101. The engineered non-plant cell of clause 99, wherein the at least one coupling enzyme dimerizes the two benzylisoquinoline alkaloid monomers by forming one or more carbon-carbon bonds.
102. The engineered non-plant cell of clause 99, wherein the at least one coupling enzyme dimerizes the two benzylisoquinoline alkaloid monomers by forming one or more carbon-oxygen bonds.
103. The engineered non-plant cell of clause 99, wherein the at least one coupling enzyme dimerizes identical benzylisoquinoline alkaloid monomers, thereby forming a homodimer.
104. The engineered non-plant cell of clause 99, wherein the at least one coupling enzyme dimerizes distinct benzylisoquinoline alkaloid monomers, thereby forming a heterodimer.
105. The engineered non-plant cell of clause 99, wherein the two benzylisoquinoline alkaloid monomers are stereoisomers of each other.
106. The engineered non-plant cell of clause 99, wherein a first benzylisoquinoline alkaloid monomer of the two benzylisoquinoline alkaloid monomers is selected from the group of: coclaurine, N-methylcoclaurine, laudanine, norcoclaurine, norlaudanosoline, 6-O-methyl-norlaudanosoline, 3'-hydroxy-N-methylcoclaurine, 3'-hydroxycoclaurine, reticuline, norreticuline, norlaudanine.
107. The engineered non-plant cell of clause 106, wherein a second benzylisoquinoline alkaloid monomer of the two benzylisoquinoline alkaloid monomers is selected from the group of: coclaurine, N-methylcoclaurine, laudanine, norcoclaurine, norlaudanosoline, 6-O-methyl-norlaudanosoline, 3'-hydroxy-N-methylcoclaurine, 3'-hydroxycoclaurine, reticuline, norreticuline, norlaudanine.
108. The engineered non-plant cell of clause 99, wherein the coupling enzyme is produced within the engineered non-plant cell.

109. The engineered non-plant cell of clause 99, wherein the coupling enzyme is produced outside the engineered non-plant cell.
110. A method for forming a product stream having a bisbenzylisoquinoline alkaloid product, comprising:
(a) providing engineered non-plant cells and a feedstock including nutrients and water to a batch reactor, which engineered non-plant cells comprise at least one heterologous coding sequence encoding at least one coupling enzyme, wherein the engineered non-plant cells further comprise at least one heterologous coding sequence encoding at least one enzyme used in the production of at least one benzylisoquinoline alkaloid monomer;
(b) in said batch reactor, subjecting said engineered non-plant cells to fermentation by incubating said engineered non-plant cells for a time period of at least about 5 minutes to produce a solution comprising said bisbenzylisoquinoline alkaloid product and cellular material; and
(c) using at least one separation unit to separate said bisbenzylisoquinoline alkaloid product from said cellular material to provide said product stream comprising said bisbenzylisoquinoline alkaloid product.
111. The method of clause 108, wherein at least one process parameter of the batch reactor is modifiable to alter a resultant bisbenzylisoquinoline alkaloid product composition.
112. The method of clause 109, wherein the at least one process parameter that is modifiable comprises at least one of dissolved oxygen, pH, stirring speed, aeration rate, and cell density.
113. The method of clause 108, wherein the at least one benzylisoquinoline alkaloid monomer comprises at least one of coclaurine, N-methylcoclaurine, laudanine, norcoclaurine, norlaudanosoline, 6-O-methyl-norlaudanosoline, 3'-hydroxy-N-methylcoclaurine, 3'-hydroxycoclaurine, reticuline, norreticuline, norlaudanine.
114. An engineered non-plant cell that converts a carbohydrate source to a benzylisoquinoline alkaloid product that is derived from (S)-reticuline.
115. The engineered non-plant cell of clause 114, wherein the engineered non-plant cell comprises a plurality of multigene expression constructs having a plurality of heterologous coding sequences that encode one or more enzymes used to convert guanosine triphosphate to tetrahydrobiopterin.
116. The engineered non-plant cell of clause 115, wherein the plurality of heterologous coding sequences encode at least one of pyruvoyl tetrahydropterin synthase, sepiapterin reductase, pterin 4a-carbinolamine dehydratase, and dihydropteridine reductase.
117. The engineered non-plant cell of clause 115, wherein the engineered non-plant cell further comprises one or more heterologous coding sequences that encode one or more enzymes used to convert tyrosine to L-DOPA.
118. The engineered non-plant cell of clause 117, wherein one or more heterologous coding sequences encode at least one of tyrosine hydroxylase.
119. The engineered non-plant cell of clause 114, wherein the engineered non-plant cell comprises a plurality of multigene expression constructs having a plurality of heterologous coding sequences that encode one or more enzymes used to convert L-DOPA to (S)-reticuline.
120. The engineered non-plant cell of clause 119, wherein the plurality of heterologous coding sequences encode at least one of L-DOPA decarboxylase, norcoclaurine synthase, norcoclaurine-6-O-methyltransferase, coclaurine-N-methyltransferase, cytochrome P450 80B1, cytochrome P450 reductase, and 4'-O-methyltransferase.
121. The engineered non-plant cell of clause 119, wherein the plurality of heterologous coding sequences encode at least one of L-DOPA decarboxylase, monoamine oxidase, norcoclaurine synthase, norcoclaurine-6-O-methyltransferase, coclaurine-N-methyltransferase, and 4'-O-methyltransferase.
122. The engineered non-plant cell of clause 114, wherein the engineered non-plant cell comprises a plurality of multigene expression constructs having a plurality of heterologous coding sequences that encode one or more enzymes used to convert (S)-reticuline to morphinan alkaloids.
123. The engineered non-plant cell of clause 122, wherein the plurality of heterologous coding sequences encode at least one of a 1-benzylisoquinoline alkaloid epimerase, salutaridine synthase, cytochrome P450 reductase, salutaridine reductase, and salutaridinol 7-O-acetyltransferase.
124. The engineered non-plant cell of clause 123, wherein the plurality of heterologous coding sequences additionally encode at least one of thebaine-6-O-demethylase, codeinone reductase, and codeine demethylase.
125. The engineered non-plant cell of clause 122, wherein the one or more enzymes are used to convert (S)-reticuline to promorphinan alkaloids.
126. The engineered non-plant cell of clause 122, wherein the one or more enzymes are used to convert (S)-reticuline to semi-synthetic morphinan alkaloids.
127. The engineered non-plant cell of clause 114, wherein the engineered non-plant cell comprises a plurality of multigene expression constructs having a plurality of heterologous coding sequences that encode one or more enzymes used to convert (S)-reticuline to canadine.
128. The engineered non-plant cell of clause 127, wherein the plurality of heterologous coding sequences encode at least one of berberine bridge enzyme, scoulerine-9-O-methyltransferase, canadine synthase, and cytochrome P450 reductase.
129. The engineered non-plant cell of clause 128, wherein the plurality of heterologous coding sequences additionally encode one or more enzymes to convert canadine to protoberberine products.
130. The engineered non-plant cell of clause 128, wherein the plurality of heterologous coding sequences additionally encode one or more enzymes to convert canadine to phthalideisoquinnoline products.
131. The engineered non-plant cell of clause 128, wherein the plurality of heterologous coding sequences additionally encode one or more enzymes to convert canadine to noscapinoid products.
132. The engineered non-plant cell of clause 114, wherein the engineered non-plant cell comprises a plurality of multigene expression constructs having a plurality of heterologous coding sequences that encode one or more enzymes used to convert (S)-reticuline to berberine.
133. The engineered non-plant cell of clause 132, wherein the plurality of heterologous coding sequences encode at least one of berberine bridge enzyme, scoulerine-9-O-methyltransferase, canadine synthase, cytochrome P450 reductase, and tetrahydroprotoberberine oxidase.
134. The engineered non-plant cell of clause 133, wherein the plurality of heterologous coding sequences additionally encode one or more enzymes to convert berberine to berberine products.
135. The engineered non-plant cell of clause 114, wherein the engineered non-plant cell comprises a plurality of multigene expression constructs having a plurality of heterologous coding sequences that encode one or more enzymes used to convert (S)-reticuline to protoberberine products.
136. The engineered non-plant cell of clause 138, wherein the plurality of heterologous coding sequences encode berberine bridge enzyme.
137. The engineered non-plant cell of clause 114, wherein the engineered non-plant cell comprises a plurality of multigene expression constructs having a plurality of heterologous coding sequences that encode one or more enzymes used to convert (S)-reticuline to protopine.
138. The engineered non-plant cell of clause 137, wherein the plurality of heterologous coding sequences encode at least one of berberine bridge enzyme, cheilanthifoline synthase, stylopine synthase, cytochrome P450 reductase, tetrahydroprotoberberine-N-methyltransferase, and cis-N-methylstylopine 14-hydroxylase.
139. The engineered non-plant cell of clause 138, wherein the plurality of heterologous coding sequences additionally encode one or more enzymes to convert protopine to protopine products.
140. The engineered non-plant cell of clause 138, wherein the plurality of heterologous coding sequences additionally encode one or more enzymes to convert protopine to benzophenanthridine products.
141. The engineered non-plant cell of clause 140, wherein the plurality of heterologous coding sequences additionally encode protopine-6-hydroxylase.
142. A method for forming a product stream having a benzylisoquinoline alkaloid product, comprising:
(a) providing engineered non-plant cells and a feedstock including nutrients and water to a batch reactor;
(b) in said batch reactor, contacting the engineered non-plant cells with a carbohydrate source and a nitrogen source, and subjecting said engineered non-plant cells to fermentation by incubating said engineered non-plant cells for a time period of at least about 5 minutes to produce a solution comprising said benzylisoquinoline alkaloid product and cellular material, wherein said benzylisoquinoline alkaloid product is derived from reticuline; and
(c) using at least one separation unit to separate said benzylisoquinoline alkaloid product from said cellular material to provide said product stream comprising said benzylisoquinoline alkaloid product.
143. The method of clause 139, wherein at least one process parameter of the batch reactor is modifiable to alter a resultant benzylisoquinoline alkaloid product composition.
144. The method of clause 140, wherein the at least one process parameter that is modifiable comprises at least one of dissolved oxygen, pH, stirring speed, aeration rate, and cell density.
145. The method of clause 139, wherein the benzylisoquinoline alkaloid product comprises a benzylisoquinoline alkaloid.
146. The method of clause 142, wherein the benzylisoquinoline alkaloid has a structural class that is selected from the group of benzylisoquinolines, protoberberines, protopines, benzophenanthridines, promorphinans, morphinans, secoberberines, phthalideisoquinolines, aporphines, and bisbenzylisoquinolines.
147. The method of clause 143, wherein the benzylisoquinoline alkaloid is a benzylisoquinoline that is selected from the group of papaverine, tetrahydropapaverine, 1,2-dihydropapaverine, and orientaline.
148. The method of clause 143, wherein the benzylisoquinoline alkaloid is a protoberberine that is selected from the group of scoulerine, cheilanthifoline, stylopine, nandinine, jatrorrhizine, stepholidine, discretamine, cis-N-methylstylopine, tetrahydrocolumbamine, palmatine, tetrahydropalmatine, columbamine, canadine, N-methylcanadine, 1-hydroxycanadine, berberine, N-methyl-ophiocarpine, 1,13-dihydroxy-N-methylcanadine, and 1-hydroxy-10-O-acetyl-N-methylcanadine.
149. The method of clause 143, wherein the benzylisoquinoline alkaloid is a protopine that is selected from the group of protopine, 6-hydroxyprotopine, allocryptopine, cryptopine, muramine, and thalictricine.
150. The method of clause 143, wherein the benzylisoquinoline alkaloid is a benzophenanthridine that is selected from the group of dihydrosanguinarine, sanguinarine, dihydrocheilirubine, cheilirubine, dihydromarcapine, marcapine, and chelerythrine.
151. The method of clause 143, wherein the benzylisoquinoline alkaloid is a promorphinan that is selected from the group of salutaridine, salutaridinol, and salutaridinol-7-O-acetate.
152. The method of clause 143, wherein the benzylisoquinoline alkaloid is a morphinan that is selected from the group of thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydroetorphine, ethylmorphine, etorphine, metopon, buprenorphine, pholcodine, heterocodeine, and oxymorphone.
153. The method of clause 143, wherein the benzylisoquinoline alkaloid is a secoberberine that is selected from the group of 4'-O-desmethylmacrantaldehyde, 4'-O-desmethylpapaveroxine, 4'-O-desmethyl-3-O-acetylpapaveroxine, and 3-O-aceteylpapaveroxine.
154. The method of clause 143, wherein the benzylisoquinoline alkaloid is a phthalideisoquinoline that is selected from the group of narcotolinehemiacetal, narcotinehemiacetal, narcotoline, and noscapine.
155. The method of clause 143, wherein the benzylisoquinoline alkaloid is an aporphine that is selected from the group of magnoflorine, corytuberine, apomorphine, boldine, isoboldine, isothebaine, isocorytuberine, and glaufine.
156. The method of clause 143, wherein the benzylisoquinoline alkaloid is a bisbenzylisoquinoline that is selected from the group of berbamunine, guattgaumerine, dauricine, and liensinine.
157. A method for forming a product stream having a benzylisoquinoline alkaloid product, comprising:
(a) providing engineered non-plant cells and a feedstock including nutrients and water to a reactor;
(b) in said reactor, contacting the engineered non-plant cells with a carbohydrate source and a nitrogen source, thereby producing a solution comprising cellular material and said benzylisoquinoline alkaloid product, wherein said benzylisoquinoline alkaloid product is derived from reticuline, wherein said solution comprises not more than one class of molecule selected from the group of protoberberine, morphinan, isopavine, aporphine, and bisbenzylisoquinoline; and (c) using at least one separation unit to separate said benzylisoquinoline alkaloid product from said cellular material to provide said product stream comprising said benzylisoquinoline alkaloid product.

158. The method of clause 154, wherein the product stream does not contain more than 5 ppm of a molecule selected from the group of lignin, flavonoids, phenanthreoids, latex, rubisco, meconic acid, pseudomorphine, narceine, thebaol, and pollen.

159. The method of clause 155, wherein the product stream does not contain more than 5 ppm of meconic acid.

160. The method of clause 154, wherein the product stream does not contain a detectable amount of a substance selected from the group consisting of pesticides, fungicides, or herbicides.

161. The method of clause 154, wherein the benzylisoquinoline alkaloid product is recovered from said product stream using at least liquid-liquid extraction.

162. The method of clause 158, wherein the benzylisoquinoline alkaloid product is recovered immediately after a fermentation process has been completed.

163. The method of any of the previous clauses, wherein the engineered non-plant cell comprises two or more heterologous coding sequences, wherein the two or more heterologous coding sequences encode at least a first enzyme and a second enzyme that are involved in a metabolic pathway that converts a substrate to the benzylisoquinoline alkaloid product, wherein the first enzyme and the second enzyme are operably connected along the metabolic pathway.

164. The method of any of the previous clauses, wherein the engineered non-plant cell comprises three heterologous coding sequences, wherein the three heterologous coding sequences encode at least a first enzyme, a second enzyme, and a third enzyme that are involved in a metabolic pathway that converts a substrate to the benzylisoquinoline alkaloid product, wherein the first enzyme, the second enzyme, and the third enzyme are operably connected along the metabolic pathway.

165. The method of clause 163, wherein each of the first and second enzymes involved in the metabolic pathway that produces the benzylisoquinoline alkaloid product is selected from the group consisting of 4'-O-methyltransferase, berberine bridge enzyme, cheilanthifoline synthase, stylopine synthase, tetrahydroprotoberberine-N-methyltransferase, scoulerine 9-O-methyltransferase, canadine synthase, tetrahydroprotoberberine oxidase, protopine O-dealkylase, and cytochrome P450 reductase.

166. The method of clause 164, wherein each of the first, second, and third enzymes involved in the metabolic pathway that produces the benzylisoquinoline alkaloid product is selected from the group consisting of 4'-O-methyltransferase, berberine bridge enzyme, cheilanthifoline synthase, stylopine synthase, tetrahydroprotoberberine-N-methyltransferase, scoulerine 9-O-methyltransferase, canadine synthase, tetrahydroprotoberberine oxidase, protopine O-dealkylase, and cytochrome P450 reductase.

167. The method of clause 165 or 166, wherein the benzylisoquinoline alkaloid product is a protoberberine product.

168. The method of clause 163, wherein each of the first and second enzymes involved in the metabolic pathway that produces the benzylisoquinoline alkaloid product is selected from the group consisting of berberine bridge enzyme, cheilanthifoline synthase, stylopine synthase, tetrahydroprotoberberine-N-methyltransferase, cis-N-methylstylopine 14-hydroxylase, protopine-6-hydroxylase, protopine O-dealkylase, and cytochrome P450 reductase.

169. The method of clause 164, wherein each of the first, second, and third enzymes involved in the metabolic pathway that produces the benzylisoquinoline alkaloid product is selected from the group consisting of berberine bridge enzyme, cheilanthifoline synthase, stylopine synthase, tetrahydroprotoberberine-N-methyltransferase, cis-N-methylstylopine 14-hydroxylase, protopine-6-hydroxylase, protopine O-dealkylase, and cytochrome P450 reductase.

170. The method of clause 168 or 169, wherein the benzylisoquinoline alkaloid product is a protopine product.

171. The method of clause 163, wherein each of the first and second enzymes involved in the metabolic pathway that produces the benzylisoquinoline alkaloid product is selected from the group consisting of berberine bridge enzyme, cheilanthifoline synthase, stylopine synthase, tetrahydroprotoberberine-N-methyltransferase, cis-N-methylstylopine 14-hydroxylase, protopine-6-hydroxylase, dihydrobenzophenanthridine oxidase, and cytochrome P450 reductase.

172. The method of clause 164, wherein each of the first, second, and third enzymes involved in the metabolic pathway that produces the benzylisoquinoline alkaloid product is selected from the group consisting of berberine bridge enzyme, cheilanthifoline synthase, stylopine synthase, tetrahydroprotoberberine-N-methyltransferase, cis-N-methylstylopine 14-hydroxylase, protopine-6-hydroxylase, dihydrobenzophenanthridine oxidase, and cytochrome P450 reductase.

173. The method of clause 171 or 172, wherein the benzylisoquinoline alkaloid product is a benzophenanthridine product.

174. The method of clause 163, wherein each of the first and second enzymes involved in the metabolic pathway that produces the benzylisoquinoline alkaloid product is selected from the group consisting of 4'-O-methyltransferase, BIA epimerase, salutaridine synthase, salutaridine reductase, salutaridinol 7-O-acetyltransferase, and cytochrome P450 reductase.

175. The method of clause 164, wherein each of the first, second, and third enzymes involved in the metabolic pathway that produces the benzylisoquinoline alkaloid product is selected from the group consisting of 4'-O-methyltransferase, BIA epimerase, salutaridine synthase, salutaridine reductase, salutaridinol 7-O-acetyltransferase, and cytochrome P450 reductase.

176. The method of clause 174 or 175, wherein the benzylisoquinoline alkaloid product is a promorphinan product.

177. The method of clause 163, wherein each of the first and second enzymes involved in the metabolic pathway that produces the benzylisoquinoline alkaloid product is selected from the group consisting of BIA epimerase, salutaridine synthase, salutaridine reductase, salutaridinol 7-O-acetyltransferase, thebaine 6-O-demethylase, codeinone reductase, codeine O-demethylase, morphine dehydrogenase, morphinone reductase, and cytochrome P450 reductase.

178. The method of clause 164, wherein each of the first, second, and third enzymes involved in the metabolic pathway that produces the benzylisoquinoline alkaloid product is selected from the group consisting of BIA epimerase, salutaridine synthase, salutaridine reductase, salutaridinol 7-O-acetyltransferase, thebaine 6-O-demethylase, codeinone reductase, codeine O-demethylase, morphine dehydrogenase, morphinone reductase, and cytochrome P450 reductase.

179. The method of clause 177 or 178, wherein the benzylisoquinoline alkaloid product is a morphinan product.

180. The method of clause 163, wherein each of the first and second enzymes involved in the metabolic pathway that produces the benzylisoquinoline alkaloid product is selected from the group consisting of berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, and cytochrome P450 reductase.

181. The method of clause 164, wherein each of the first, second, and third enzymes involved in the metabolic pathway that produces the benzylisoquinoline alkaloid product is selected from the group consisting of berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, and cytochrome P450 reductase.

182. The method of clause 180 or 181, wherein the benzylisoquinoline alkaloid product is a secoberberine product.

183. The method of clause 163, wherein each of the first and second enzymes involved in the metabolic pathway that produces the benzylisoquinoline alkaloid product is selected from the group consisting of berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, narcotinehemiacetal synthase, noscapine synthase, narcotoline 4'-O-methylase, and cytochrome P450 reductase.

184. The method of clause 164, wherein each of the first, second, and third enzymes involved in the metabolic pathway that produces the benzylisoquinoline alkaloid product is selected from the group consisting of berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, narcotinehemiacetal synthase, noscapine synthase, narcotoline 4'-O-methylase, and cytochrome P450 reductase.

185. The method of clause 183 or 184, wherein the benzylisoquinoline alkaloid product is a phthalideisoquinoline product.

186. The method of clause 163, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, and berbamunine synthase.

187. The method of clause 164, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, and berbamunine synthase.

188. The method of clause 186 or 187, wherein the benzylisoquinoline alkaloid product is a bisbenzylisoquinoline product.

189. The method of clause 163, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

190. The method of clause 164, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

191. The method of clause 189 or 190, wherein the benzylisoquinoline alkaloid product is a benzylisoquinoline product.

192. The method of any of clauses 165-191, wherein the engineered non-plant cell comprises two or more additional heterologous coding sequences, wherein the two or more additional heterologous coding sequences encode at least a first additional enzyme and a second additional enzyme that are involved in a metabolic pathway that converts a substrate to the benzylisoquinoline alkaloid product, wherein the first additional enzyme and the second additional enzyme are operably connected along the metabolic pathway, and wherein each of the first additional and second additional enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

193. The method of any of clauses 165-191, wherein the engineered non-plant cell comprises three additional heterologous coding sequences, wherein the three heterologous coding sequences encode at least a first additional enzyme, a second additional enzyme, and a third additional enzyme that are involved in a metabolic pathway that converts a substrate to the benzylisoquinoline alkaloid product, wherein the first additional enzyme, the second additional enzyme, and the third additional enzyme are operably connected along the metabolic pathway, and wherein each of the first additional, second additional, and third additional enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

194. The engineered non-plant cell of any of the previous clauses, wherein the engineered non-plant cell comprises two or more heterologous coding sequences, wherein the two or more heterologous coding sequences encode at least a first enzyme and a second enzyme that are involved in a metabolic pathway that converts a substrate to the benzylisoquinoline alkaloid product, wherein the first enzyme and the second enzyme are operably connected along the metabolic pathway.

195. The engineered non-plant cell of any of the previous clauses, wherein the engineered non-plant cell comprises three heterologous coding sequences, wherein the three heterologous coding sequences encode at least a first enzyme, a second enzyme, and a third enzyme that are involved in a metabolic pathway that converts a substrate to the benzylisoquinoline alkaloid product, wherein the first enzyme, the second enzyme, and the third enzyme are operably connected along the metabolic pathway.

196. The engineered non-plant cell of clause 194, wherein each of the first and second enzymes involved in the metabolic pathway that produces the benzylisoquinoline alkaloid product is selected from the group consisting of 4'-O-methyltransferase, berberine bridge enzyme, cheilanthifoline synthase, stylopine synthase, tetrahydroprotoberberine-N-methyltransferase, scoulerine 9-O-methyltransferase, canadine synthase, tetrahydroprotoberberine oxidase, protopine O-dealkylase, and cytochrome P450 reductase.

197. The engineered non-plant cell of clause 195, wherein each of the first, second, and third enzymes involved in the metabolic pathway that produces the benzylisoquinoline alkaloid product is selected from the group consisting of 4'-O-methyltransferase, berberine bridge enzyme, cheilanthifoline synthase, stylopine synthase, tetrahydroprotoberberine-N-methyltransferase, scoulerine 9-O-methyltransferase, canadine synthase, tetrahydroprotoberberine oxidase, protopine O-dealkylase, and cytochrome P450 reductase.

198. The engineered non-plant cell of clause 196 or 197, wherein the benzylisoquinoline alkaloid product is a protoberberine product.

199. The engineered non-plant cell of clause 194, wherein each of the first and second enzymes involved in the metabolic pathway that produces the benzylisoquinoline alkaloid product is selected from the group consisting of berberine bridge enzyme, cheilanthifoline synthase, stylopine synthase, tetrahydroprotoberberine-N-methyltransferase, cis-N-methylstylopine 14-hydroxylase, protopine-6-hydroxylase, protopine O-dealkylase, and cytochrome P450 reductase.

200. The engineered non-plant cell of clause 195, wherein each of the first, second, and third enzymes involved in the metabolic pathway that produces the benzylisoquinoline alkaloid product is selected from the group consisting of berberine bridge enzyme, cheilanthifoline synthase, stylopine synthase, tetrahydroprotoberberine-N-methyltransferase, cis-N-methylstylopine 14-hydroxylase, protopine-6-hydroxylase, protopine O-dealkylase, and cytochrome P450 reductase.

201. The engineered non-plant cell of clause 199 or 200, wherein the benzylisoquinoline alkaloid product is a protopine product.

202. The engineered non-plant cell of clause 194, whereineach of the first and second enzymes involved in the metabolic pathway that produces the benzylisoquinoline alkaloid product is selected from the group consisting of berberine bridge enzyme, cheilanthifoline synthase, stylopine synthase, tetrahydroprotoberberine-N-methyltransferase, cis-N-methylstylopine 14-hydroxylase, protopine-6-hydroxylase, dihydrobenzophenanthridine oxidase, and cytochrome P450 reductase.

203. The engineered non-plant cell of clause 195, wherein each of the first, second, and third enzymes involved in the metabolic pathway that produces the benzylisoquinoline alkaloid product is selected from the group consisting of berberine bridge enzyme, cheilanthifoline synthase, stylopine synthase, tetrahydroprotoberberine-N-methyltransferase, cis-N-methylstylopine 14-hydroxylase, protopine-6-hydroxylase, dihydrobenzophenanthridine oxidase, and cytochrome P450 reductase.

204. The engineered non-plant cell of clause 202 or 203, wherein the benzylisoquinoline alkaloid product is a benzophenanthridine product.

205. The engineered non-plant cell of clause 194, wherein each of the first and second enzymes involved in the metabolic pathway that produces the benzylisoquinoline alkaloid product is selected from the group consisting of 4'-O-methyltransferase, BIA epimerase, salutaridine synthase, salutaridine reductase, salutaridinol 7-O-acetyltransferase, and cytochrome P450 reductase.

206. The engineered non-plant cell of clause 195, wherein each of the first, second, and third enzymes involved in the metabolic pathway that produces the benzylisoquinoline alkaloid product is selected from the group consisting of 4'-O-methyltransferase, BIA epimerase, salutaridine synthase, salutaridine reductase, salutaridinol 7-O-acetyltransferase, and cytochrome P450 reductase.

207. The engineered non-plant cell of clause 205 or 206, wherein the benzylisoquinoline alkaloid product is a promorphinan product.

208. The engineered non-plant cell of clause 194, wherein each of the first and second enzymes involved in the metabolic pathway that produces the benzylisoquinoline alkaloid product is selected from the group consisting of BIA epimerase, salutaridine synthase, salutaridine reductase, salutaridinol 7-O-acetyltransferase, thebaine 6-O-demethylase, codeinone reductase, codeine O-demethylase, morphine dehydrogenase, morphinone reductase, and cytochrome P450 reductase.

209. The engineered non-plant cell of clause 195, wherein each of the first, second, and third enzymes involved in the metabolic pathway that produces the benzylisoquinoline alkaloid product is selected from the group consisting of BIA epimerase, salutaridine synthase, salutaridine reductase, salutaridinol 7-O-acetyltransferase, thebaine 6-O-demethylase, codeinone reductase, codeine O-demethylase, morphine dehydrogenase, morphinone reductase, and cytochrome P450 reductase.

210. The engineered non-plant cell of clause 208 or 209, wherein the benzylisoquinoline alkaloid product is a morphinan product.

211. The engineered non-plant cell of clause 194, wherein each of the first and second enzymes involved in the metabolic pathway that produces the benzylisoquinoline alkaloid product is selected from the group consisting of berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, and cytochrome P450 reductase.

212. The engineered non-plant cell of clause 195, wherein each of the first, second, and third enzymes involved in the metabolic pathway that produces the benzylisoquinoline alkaloid product is selected from the group consisting of berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, and cytochrome P450 reductase.

213. The engineered non-plant cell of clause 211 or 212, wherein the benzylisoquinoline alkaloid product is a secoberberine product.

214. The engineered non-plant cell of clause 194, wherein each of the first and second enzymes involved in the metabolic pathway that produces the benzylisoquinoline alkaloid product is selected from the group consisting of berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, narcotinehemiacetal synthase, noscapine synthase, narcotoline 4'-O-methylase, and cytochrome P450 reductase.

215. The engineered non-plant cell of clause 195, wherein each of the first, second, and third enzymes involved in the metabolic pathway that produces the benzylisoquinoline alkaloid product is selected from the group consisting of berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, narcotinehemiacetal synthase, noscapine synthase, narcotoline 4'-O-methylase, and cytochrome P450 reductase.

216. The engineered non-plant cell of clause 214 or 215, wherein the benzylisoquinoline alkaloid product is a phthalideisoquinoline product.

217. The engineered non-plant cell of clause 194, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, and berbamunine synthase.

218. The engineered non-plant cell of clause 195, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, and berbamunine synthase.

219. The engineered non-plant cell of clause 217 or 218, wherein the benzylisoquinoline alkaloid product is a bisbenzylisoquinoline product.

220. The engineered non-plant cell of clause 194, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

221. The engineered non-plant cell of clause 195, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

222. The engineered non-plant cell of clause 220 or 221, wherein the benzylisoquinoline alkaloid product is a benzylisoquinoline product.

223. The engineered non-plant cell of any of clauses 196-222, wherein the engineered non-plant cell comprises two or more additional heterologous coding sequences, wherein the two or more additional heterologous coding sequences encode at least a first additional enzyme and a second additional enzyme that are involved in a metabolic pathway that converts a substrate to the benzylisoquinoline alkaloid product, wherein the first additional enzyme and the second additional enzyme are operably connected along the metabolic pathway, and wherein each of the first additional and second additional enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

224. The engineered non-plant cell of any of clauses 196-222, wherein the engineered non-plant cell comprises three additional heterologous coding sequences, wherein the three heterologous coding sequences encode at least a first additional enzyme, a second additional enzyme, and a third additional enzyme that are involved in a metabolic pathway that converts a substrate to the benzylisoquinoline alkaloid product, wherein the first additional enzyme, the second additional enzyme, and the third additional enzyme are operably connected along the metabolic pathway, and wherein each of the first additional, second additional, and third additional enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

225. The method of clause 163, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, 4'-O-methyltransferase, berberine bridge enzyme, cheilanthifoline synthase, stylopine synthase, tetrahydroprotoberberine-N-methyltransferase, scoulerine 9-O-methyltransferase, canadine synthase, tetrahydroprotoberberine oxidase, and protopine O-dealkylase.

226. The method of clause 164, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, 4'-O-methyltransferase, berberine bridge enzyme, cheilanthifoline synthase, stylopine synthase, tetrahydroprotoberberine-N-methyltransferase, scoulerine 9-O-methyltransferase, canadine synthase, tetrahydroprotoberberine oxidase, and protopine O-dealkylase.

227. The method of clause 225 or 226, wherein the benzylisoquinoline alkaloid product is a protoberberine product.

228. The method of clause 163, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, cheilanthifoline synthase, stylopine synthase, tetrahydroprotoberberine-N-methyltransferase, cis-N-methylstylopine 14-hydroxylase, protopine-6-hydroxylase, and protopine O-dealkylase.

229. The method of clause 164, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, cheilanthifoline synthase, stylopine synthase, tetrahydroprotoberberine-N-methyltransferase, cis-N-methylstylopine 14-hydroxylase, protopine-6-hydroxylase, and protopine O-dealkylase.

230. The method of clause 228 or 229, wherein the benzylisoquinoline alkaloid product is a protopine product.

231. The method of clause 163, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, cheilanthifoline synthase, stylopine synthase, tetrahydroprotoberberine-N-methyltransferase, cis-N-methylstylopine 14-hydroxylase, protopine-6-hydroxylase, and dihydrobenzophenanthridine oxidase.

232. The method of clause 164, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, cheilanthifoline synthase, stylopine synthase, tetrahydroprotoberberine-N-methyltransferase, cis-N-methylstylopine 14-hydroxylase, protopine-6-hydroxylase, and dihydrobenzophenanthridine oxidase.

233. The method of clause 231 or 232, wherein the benzylisoquinoline alkaloid product is a benzophenanthridine product.

234. The method of clause 163, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, 4'-O-methyltransferase, BIA epimerase, salutaridine synthase, salutaridine reductase, and salutaridinol 7-O-acetyltransferase.

235. The method of clause 164, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, 4'-O-methyltransferase, BIA epimerase, salutaridine synthase, salutaridine reductase, and salutaridinol 7-O-acetyltransferase.

236. The method of clause 234 or 235, wherein the benzylisoquinoline alkaloid product is a promorphinan product.

237. The method of clause 163, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, salutaridine synthase, salutaridine reductase, salutaridinol 7-O-acetyltransferase, thebaine 6-O-demethylase, codeinone reductase, codeine O-demethylase, morphine dehydrogenase, and morphinone reductase.

238. The method of clause 164, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, salutaridine synthase, salutaridine reductase, salutaridinol 7-O-acetyltransferase, thebaine 6-O-demethylase, codeinone reductase, codeine O-demethylase, morphine dehydrogenase, and morphinone reductase.

239. The method of clause 237 or 238, wherein the benzylisoquinoline alkaloid product is a morphinan product.

240. The method of clause 163, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, and 1, 13-dihydroxy-N-methylcanadine 13-O acetyl transferase.

241. The method of clause 164, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, and 1, 13-dihydroxy-N-methylcanadine 13-O acetyl transferase.

242. The method of clause 240 or 241, wherein the benzylisoquinoline alkaloid product is a secoberberine product.

243. The method of clause 163, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, narcotinehemiacetal synthase, noscapine synthase, and narcotoline 4'-O-methylase.

244. The method of clause 164, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, narcotinehemiacetal synthase, noscapine synthase, and narcotoline 4'-O-methylase.

245. The method of clause 243 or 244, wherein the benzylisoquinoline alkaloid product is a phthalideisoquinoline product.

246. The method of clause 163, wherein each of the first and second enzymes involved in the metabolic pathway that produces the benzylisoquinoline alkaloid product is selected from the group consisting of tyrosine hydroxylase, dopa decarboxylase, tyrosine/dopa decarboxylase, monoamine oxidase, tyrosinase, norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, and berbamunine synthase.

247. The method of clause 164, wherein each of the first, second, and third enzymes involved in the metabolic pathway that produces the benzylisoquinoline alkaloid product is selected from the group consisting of tyrosine hydroxylase, dopa decarboxylase, tyrosine/dopa decarboxylase, monoamine oxidase, tyrosinase, norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, and berbamunine synthase.

248. The method of clause 246 or 247, wherein the benzylisoquinoline alkaloid product is a bisbenzylisoquinoline product.

249. The method of clause 163, wherein each of the first and second enzymes involved in the metabolic pathway that produces the benzylisoquinoline alkaloid product is selected from the group consisting of tyrosine hydroxylase, dopa decarboxylase, tyrosine/dopa decarboxylase, monoamine oxidase, tyrosinase, norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

250. The method of clause 164, wherein each of the first, second, and third enzymes involved in the metabolic pathway that produces the benzylisoquinoline alkaloid product is selected from the group consisting of tyrosine hydroxylase, dopa decarboxylase, tyrosine/dopa decarboxylase, monoamine oxidase, tyrosinase, norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

251. The method of clause 249 or 250, wherein the benzylisoquinoline alkaloid product is a benzylisoquinoline product.

252. The method of any of clauses 225-251, wherein the engineered non-plant cell comprises two or more additional heterologous coding sequences, wherein the two or more additional heterologous coding sequences encode at least a first additional enzyme and a second additional enzyme that are involved in a metabolic pathway that converts a substrate to the benzylisoquinoline alkaloid product, wherein the first additional enzyme and the second additional enzyme are operably connected along the metabolic pathway, and wherein each of the first additional and second additional enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

253. The method of any of clauses 225-251, wherein the engineered non-plant cell comprises three additional heterologous coding sequences, wherein the three heterologous coding sequences encode at least a first additional enzyme, a second additional enzyme, and a third additional enzyme that are involved in a metabolic pathway that converts a substrate to the benzylisoquinoline alkaloid product, wherein the first additional enzyme, the second additional enzyme, and the third additional enzyme are operably connected along the metabolic pathway, and wherein each of the first additional, second additional, and third additional enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

254. The engineered non-plant cell of clause 194, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, 4'-O-methyltransferase, berberine bridge enzyme, cheilanthifoline synthase, stylopine synthase, tetrahydroprotoberberine-N-methyltransferase, scoulerine 9-O-methyltransferase, canadine synthase, tetrahydroprotoberberine oxidase, and protopine O-dealkylase.

255. The engineered non-plant cell of clause 195, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, 4'-O-methyltransferase, berberine bridge enzyme, cheilanthifoline synthase, stylopine synthase, tetrahydroprotoberberine-N-methyltransferase, scoulerine 9-O-methyltransferase, canadine synthase, tetrahydroprotoberberine oxidase, and protopine O-dealkylase.

256. The engineered non-plant cell of clause 254 or 255, wherein the benzylisoquinoline alkaloid product is a protoberberine product.

257. The engineered non-plant cell of clause 194, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, cheilanthifoline synthase, stylopine synthase, tetrahydroprotoberberine-N-methyltransferase, cis-N-methylstylopine 14-hydroxylase, protopine-6-hydroxylase, and protopine O-dealkylase.

258. The engineered non-plant cell of clause 195, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, cheilanthifoline synthase, stylopine synthase, tetrahydroprotoberberine-N-methyltransferase, cis-N-methylstylopine 14-hydroxylase, protopine-6-hydroxylase, and protopine O-dealkylase.

259. The engineered non-plant cell of clause 257 or 258, wherein the benzylisoquinoline alkaloid product is a protopine product.

260. The engineered non-plant cell of clause 194, whereineach of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, cheilanthifoline synthase, stylopine synthase, tetrahydroprotoberberine-N-methyltransferase, cis-N-methylstylopine 14-hydroxylase, protopine-6-hydroxylase, and dihydrobenzophenanthridine oxidase.

261. The engineered non-plant cell of clause 195, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, cheilanthifoline synthase, stylopine synthase, tetrahydroprotoberberine-N-methyltransferase, cis-N-methylstylopine 14-hydroxylase, protopine-6-hydroxylase, and dihydrobenzophenanthridine oxidase.

262. The engineered non-plant cell of clause 260 or 261, wherein the benzylisoquinoline alkaloid product is a benzophenanthridine product.

263. The engineered non-plant cell of clause 194, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, 4'-O-methyltransferase, BIA epimerase, salutaridine synthase, salutaridine reductase, and salutaridinol 7-O-acetyltransferase.

264. The engineered non-plant cell of clause 195, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, 4'-O-methyltransferase, BIA epimerase, salutaridine synthase, salutaridine reductase, and salutaridinol 7-O-acetyltransferase.

265. The engineered non-plant cell of clause 263 or 264, wherein the benzylisoquinoline alkaloid product is a promorphinan product.

266. The engineered non-plant cell of clause 194, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, salutaridine synthase, salutaridine reductase, salutaridinol 7-O-acetyltransferase, thebaine 6-O-demethylase, codeinone reductase, codeine O-demethylase, morphine dehydrogenase, and morphinone reductase.

267. The engineered non-plant cell of clause 195, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, salutaridine synthase, salutaridine reductase, salutaridinol 7-O-acetyltransferase, thebaine 6-O-demethylase, codeinone reductase, codeine O-demethylase, morphine dehydrogenase, and morphinone reductase.
268. The engineered non-plant cell of clause 266 or 267, wherein the benzylisoquinoline alkaloid product is a morphinan product.
269. The engineered non-plant cell of clause 194, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, and 1, 13-dihydroxy-N-methylcanadine 13-O acetyl transferase.
270. The engineered non-plant cell of clause 195, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, and 1, 13-dihydroxy-N-methylcanadine 13-O acetyl transferase.
271. The engineered non-plant cell of clause 269 or 270, wherein the benzylisoquinoline alkaloid product is a secoberberine product.
272. The engineered non-plant cell of clause 194, wherein each of the first and second enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, narcotinehemiacetal synthase, noscapine synthase, and narcotoline 4'-O-methylase.
273. The engineered non-plant cell of clause 195, wherein each of the first, second, and third enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, berberine bridge enzyme, scoulerine 9-O-methyltransferase, canadine synthase, tetrahydroprotoberberine-N-methyltransferase, N-methylcanadine 1-hydroxylase, 1-hydroxy-N-methylcanadine 13-hydroxylase, 4'-O-desmethyl-3-O-acetylpapaveroxine synthase, 1, 13-dihydroxy-N-methylcanadine 13-O acetyl transferase, narcotinehemiacetal synthase, noscapine synthase, and narcotoline 4'-O-methylase.
274. The engineered non-plant cell of clause 272 or 273, wherein the benzylisoquinoline alkaloid product is a phthalideisoquinoline product.
275. The engineered non-plant cell of clause 194, wherein each of the first and second enzymes involved in the metabolic pathway that produces the benzylisoquinoline alkaloid product is selected from the group consisting of tyrosine hydroxylase, dopa decarboxylase, tyrosine/dopa decarboxylase, monoamine oxidase, tyrosinase, norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, and berbamunine synthase.
276. The engineered non-plant cell of clause 195, wherein each of the first, second, and third enzymes involved in the metabolic pathway that produces the benzylisoquinoline alkaloid product is selected from the group consisting of tyrosine hydroxylase, dopa decarboxylase, tyrosine/dopa decarboxylase, monoamine oxidase, tyrosinase, norcoclaurine synthase, norcoclaurine 6-O-methyltransferase, coclaurine-N-methyltransferase, 4'-O-methyltransferase, cytochrome P450 80B1, cytochrome P450 reductase, BIA epimerase, and berbamunine synthase.
277. The engineered non-plant cell of clause 275 or 276, wherein the benzylisoquinoline alkaloid product is a bisbenzylisoquinoline product.
278. The engineered non-plant cell of clause 194, wherein each of the first and second enzymes involved in the metabolic pathway that produces the benzylisoquinoline alkaloid product is selected from the group consisting of tyrosine hydroxylase, dopa decarboxylase, tyrosine/dopa decarboxylase, monoamine oxidase, tyrosinase, norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.
279. The engineered non-plant cell of clause 195, wherein each of the first, second, and third enzymes involved in the metabolic pathway that produces the benzylisoquinoline alkaloid product is selected from the group consisting of tyrosine hydroxylase, dopa decarboxylase, tyrosine/dopa decarboxylase, monoamine oxidase, tyrosinase, norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.
280. The engineered non-plant cell of clause 220 or 221, wherein the benzylisoquinoline alkaloid product is a benzylisoquinoline product.
281. The engineered non-plant cell of any of clauses 196-222, wherein the engineered non-plant cell comprises two or more additional heterologous coding sequences, wherein the two or more additional heterologous coding sequences encode at least a first additional enzyme and a second additional enzyme that are involved in a metabolic pathway that converts a substrate to the benzylisoquinoline alkaloid product, wherein the first additional enzyme and the second additional enzyme are operably connected along the metabolic pathway, and wherein each of the first additional and second additional enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

282. The engineered non-plant cell of any of clauses 196-222, wherein the engineered non-plant cell comprises three additional heterologous coding sequences, wherein the three heterologous coding sequences encode at least a first additional enzyme, a second additional enzyme, and a third additional enzyme that are involved in a metabolic pathway that converts a substrate to the benzylisoquinoline alkaloid product, wherein the first additional enzyme, the second additional enzyme, and the third additional enzyme are operably connected along the metabolic pathway, and wherein each of the first additional, second additional, and third additional enzymes involved in the metabolic pathway that produces the benzylisoquinoline alkaloid product is selected from the group consisting of norcoclaurine synthase, norcoclaurine 6-O-methyltransferase, coclaurine-N-methyltransferase, 4'-O-methyltransferase, cytochrome P450 80B1, cytochrome P450 reductase, and BIA epimerase.

283. The engineered non-plant cell of any of the previous clauses, wherein the engineered non-plant cell is an engineered yeast cell.

284. The method of any of the previous clauses, wherein the engineered non-plant cell is an engineered yeast cell.

285. The engineered non-plant cell of any of clauses 1-282, wherein the engineered non-plant cell is an engineered bacteria cell.

286. The method of any of clauses 1-282, wherein the engineered non-plant cell is an engineered bacteria cell.

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of producing an (R)-1-benzylisoquinoline alkaloid, the method comprising:
   (a) culturing an engineered non-plant cell in a cell culture comprising a feedstock, wherein the engineered non-plant cell stably expresses a plurality of heterologous enzymes within the same engineered non-plant-cell for the production of an (S)-1-benzylisoquinoline alkaloid wherein the plurality of heterologous enzymes comprise tyrosine hydroxylase (TyrH), L-DOPA decarboxylase (DODC), norcoclaurine synthase (NCS), norcoclaurine 6-O-methyltransferase (6OMT), coclaurine N-methyltransferase (CNMT), cytochrome P450 80B1 (CYP80B1), and 4'-O-methyltransferase (4'OMT),
   (b) producing an (S)-1-benzylisoquinoline alkaloid within the same engineered non-plant cell,
   (c) contacting, within the same engineered non-plant cell, the (S)-1-benzylisoquinoline alkaloid that is produced within the engineered non-plant cell with at least one heterologous, fused enzyme expressed within the same engineered non-plant cell that converts the (S)-1-benzylisoquinoline alkaloid to an (R)-1-benzylisoquinoline alkaloid within the engineered non-plant cell, and
   (d) producing the (R)-1-benzylisoquinoline alkaloid within the engineered non-plant cell.

2. The method of claim 1, wherein the at least one enzyme that converts the (S)-1-benzylisoquinoline alkaloid to the (R)-1-benzylisoquinoline alkaloid is encoded by at least one coding sequence within a chromosome of the engineered non-plant cell.

3. The method of claim 2, further comprising: adding an (S)-1-benzylisoquinoline alkaloid to the cell culture.

4. The method of claim 2, further comprising: recovering the (R)-1-benzylisoquinoline alkaloid, or a derivative thereof, from the cell culture.

5. The method of claim 1, wherein the at least one enzyme that converts the (S)-1-benzylisoquinoline alkaloid to the (R)-1-benzylisoquinoline alkaloid comprises an epimerase.

6. The method of claim 5, wherein the epimerase comprises an amino acid sequence having at least 80% sequence identity to an amino acid sequence selected from the group consisting of SEQ ID NOs: 1, 2, 3, 4, 5, 6, 7, 8, 9, 10, 11, 12, 13, 14, and 15.

7. The method of claim 5, wherein the epimerase comprises an oxidase domain and a reductase domain.

8. The method of claim 7, wherein the oxidase domain is a cytochrome P450 oxidase-like domain.

9. The method of claim 7, wherein the reductase domain is a codeinone reductase-like domain.

10. The method of claim 1, wherein the engineered non-plant cell is an engineered yeast cell or an engineered bacteria cell.

11. The method of claim 1, wherein the (S)-1-benzylisoquinoline alkaloid is (S)-reticuline.

12. The method of claim 1, wherein the (S)-1-benzylisoquinoline alkaloid is produced within the engineered non-plant cell by a metabolic pathway starting with L-tyrosine.

13. The method of claim 1, wherein the at least one enzyme that converts the (S)-1-benzylisoquinoline alkaloid to the (R)-1-benzylisoquinoline alkaloid comprises a first enzyme having an oxidase domain and a second enzyme having a reductase domain, wherein the first enzyme is separate from the second enzyme.

14. The method of claim 5, wherein the epimerase comprises an amino acid sequence having at least 85% sequence identity to an amino acid sequence selected from the group consisting of SEQ ID NOs: 1, 2, 3, 4, 5, 6, 7, 8, 9, 10, 11, 12, 13, 14, and 15.

15. The method of claim 5, wherein the epimerase comprises an amino acid sequence having at least 90% sequence identity to an amino acid sequence selected from the group consisting of SEQ ID NOs: 1, 2, 3, 4, 5, 6, 7, 8, 9, 10, 11, 12, 13, 14, and 15.

16. The method of claim 5, wherein the epimerase comprises an amino acid sequence having at least 95% sequence identity to an amino acid sequence selected from the group consisting of SEQ ID NOs: 1, 2, 3, 4, 5, 6, 7, 8, 9, 10, 11, 12, 13, 14, and 15.

17. The method of claim 5, wherein the activity of the epimerase is encoded in a single polypeptide.

18. The method of claim 5, wherein the activity of the epimerase is encoded across multiple polypeptides.

19. The method of claim 18, wherein the activity of the epimerase is encoded across two polypeptides.

20. A method of producing an (R)-1-benzylisoquinoline alkaloid, the method comprising:
   (a) culturing an engineered non-plant cell in a cell culture comprising a feedstock, wherein the engineered non-plant cell stably expresses a plurality of heterologous enzymes within the same engineered non-plant-cell for the production of an (S)-1-benzylisoquinoline alkaloid wherein the plurality of heterologous enzymes comprise tyrosine hydroxylase (TyrH), L-DOPA decarboxylase (DODC), monoamine oxidase (MAO), norcoclaurine synthase (NCS), norcoclaurine 6-O-methyltransferase (6OMT), coclaurine N-methyltransferase (CNMT), and 4'-O-methyltransferase (4'OMT), (b) producing an (S)-1-benzylisoquinoline alkaloid within the same engineered non-plant cell, (c) contacting, within the same engineered non-plant cell, the (S)-1-benzylisoquinoline alkaloid that is produced within the engineered non-plant cell with at least one heterologous, fused enzyme expressed within the same engineered non-plant cell that converts the (S)-1-benzylisoquinoline alkaloid to an (R)-1-benzylisoquinoline alkaloid within the engineered non-plant cell, and (d) producing the (R)-1-benzylisoquinoline alkaloid within the engineered non-plant cell.

21. The method of claim 5, wherein the epimerase comprises an amino acid sequence having 100% sequence identity to an amino acid sequence selected from the group consisting of SEQ ID NOs: 1, 2, 3, 4, 5, 6, 7, 8, 9, 10, 11, 12, 13, 14, and 15.

22. The method of claim 5, wherein the epimerase comprises the amino acid sequence of SEQ ID NO: 8.

23. The method of claim 20, wherein the epimerase comprises an amino acid sequence having 100% sequence identity to an amino acid sequence selected from the group consisting of SEQ ID NOs: 1, 2, 3, 4, 5, 6, 7, 8, 9, 10, 11, 12, 13, 14, and 15.

24. The method of claim 20, wherein the epimerase comprises the amino acid sequence of SEQ ID NO: 8.

* * * * *

SEQUENCE LISTING

```
<160> NUMBER OF SEQ ID NOS: 15

<210> SEQ ID NO 1
<211> LENGTH: 901
<212> TYPE: PRT
<213> ORGANISM: Papaver somniferum

<400> SEQUENCE: 1

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

Arg Lys Thr Phe Leu Asn Asn Tyr Ser Ser Ser Pro Ala Ser Ser Thr
        35                  40                  45

Lys Thr Ala Val Leu Ser His Gln Arg Gln Gln Ser Cys Ala Leu Pro
    50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
            100                 105                 110

Lys Glu Cys Phe Thr Gly Asn Asn Asp Thr Ala Phe Ser Asn Arg Pro
        115                 120                 125

Ile Pro Leu Ala Phe Lys Thr Ile Phe Tyr Ala Cys Gly Gly Ile Asp
    130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
```

```
            180                 185                 190
Tyr Glu Leu Cys Lys Asn Ser Glu Asp Asn His Gly Asn Tyr Thr Thr
            195                 200                 205

Thr Thr Thr Thr Ala Ala Gly Met Val Arg Ile Asp Asp Trp Leu Ala
210                 215                 220

Glu Leu Ser Phe Asn Val Ile Gly Arg Ile Val Cys Gly Phe Gln Ser
225                 230                 235                 240

Gly Pro Lys Thr Gly Ala Pro Ser Arg Val Glu Gln Phe Lys Glu Ala
                245                 250                 255

Ile Asn Glu Ala Ser Tyr Phe Met Ser Thr Ser Pro Val Ser Asp Asn
                260                 265                 270

Val Pro Met Leu Gly Trp Ile Asp Gln Leu Thr Gly Leu Thr Arg Asn
                275                 280                 285

Met Lys His Cys Gly Lys Lys Leu Asp Leu Val Glu Ser Ile Ile
            290                 295                 300

Asn Asp His Arg Gln Lys Arg Arg Phe Ser Arg Thr Lys Gly Gly Asp
305                 310                 315                 320

Glu Lys Asp Asp Glu Gln Asp Asp Phe Ile Asp Ile Cys Leu Ser Ile
                325                 330                 335

Met Glu Gln Pro Gln Leu Pro Gly Asn Asn Asn Pro Ser Gln Ile Pro
                340                 345                 350

Ile Lys Ser Ile Val Leu Asp Met Ile Gly Gly Thr Asp Thr Thr
            355                 360                 365

Lys Leu Thr Thr Ile Trp Thr Leu Ser Leu Leu Leu Asn Asn Pro His
            370                 375                 380

Val Leu Asp Lys Ala Lys Gln Glu Val Asp Ala His Phe Arg Thr Lys
385                 390                 395                 400

Arg Arg Ser Thr Asn Asp Ala Ala Ala Val Val Asp Phe Asp Asp
                405                 410                 415

Ile Arg Asn Leu Val Tyr Ile Gln Ala Ile Ile Lys Glu Ser Met Arg
            420                 425                 430

Leu Tyr Pro Ala Ser Pro Val Val Glu Arg Leu Ser Gly Glu Asp Cys
            435                 440                 445

Val Val Gly Gly Phe His Val Pro Ala Gly Thr Arg Leu Trp Ala Asn
450                 455                 460

Val Trp Lys Met Gln Arg Asp Pro Lys Val Trp Asp Pro Leu Val
465                 470                 475                 480

Phe Arg Pro Asp Arg Phe Leu Ser Asp Glu Gln Lys Met Val Asp Val
                485                 490                 495

Arg Gly Gln Asn Tyr Glu Leu Leu Pro Phe Gly Ala Gly Arg Arg Val
                500                 505                 510

Cys Pro Gly Val Ser Phe Ser Leu Asp Leu Met Gln Leu Val Leu Thr
            515                 520                 525

Arg Leu Ile Leu Glu Phe Glu Met Lys Ser Pro Ser Gly Lys Val Asp
530                 535                 540

Met Thr Ala Thr Pro Gly Leu Met Ser Tyr Lys Val Ile Pro Leu Asp
545                 550                 555                 560

Ile Leu Leu Thr His Arg Arg Ile Lys Pro Cys Val Gln Ser Ala Ala
                565                 570                 575

Ser Glu Arg Asp Met Glu Ser Ser Gly Val Pro Val Ile Thr Leu Gly
                580                 585                 590

Ser Gly Lys Val Met Pro Val Leu Gly Met Gly Thr Phe Glu Lys Val
            595                 600                 605
```

```
Gly Lys Gly Ser Glu Arg Glu Arg Leu Ala Ile Leu Lys Ala Ile Glu
            610                 615                 620

Val Gly Tyr Arg Tyr Phe Asp Thr Ala Ala Tyr Glu Thr Glu Glu
625                 630                 635                 640

Val Leu Gly Glu Ala Ile Ala Glu Ala Leu Gln Leu Gly Leu Val Lys
                645                 650                 655

Ser Arg Asp Glu Leu Phe Ile Ser Ser Met Leu Trp Cys Thr Asp Ala
            660                 665                 670

His Ala Asp Arg Val Leu Leu Ala Leu Gln Asn Ser Leu Arg Asn Leu
            675                 680                 685

Lys Leu Glu Tyr Val Asp Leu Tyr Met Leu Pro Phe Pro Ala Ser Leu
            690                 695                 700

Lys Pro Gly Lys Ile Thr Met Asp Ile Pro Glu Glu Asp Ile Cys Arg
705                 710                 715                 720

Met Asp Tyr Arg Ser Val Trp Ala Ala Met Glu Glu Cys Gln Asn Leu
            725                 730                 735

Gly Phe Thr Lys Ser Ile Gly Val Ser Asn Phe Ser Cys Lys Lys Leu
            740                 745                 750

Gln Glu Leu Met Ala Thr Ala Asn Ile Pro Pro Ala Val Asn Gln Val
            755                 760                 765

Glu Met Ser Pro Ala Phe Gln Gln Lys Lys Leu Arg Glu Tyr Cys Asn
770                 775                 780

Ala Asn Asn Ile Leu Val Ser Ala Ile Ser Val Leu Gly Ser Asn Gly
785                 790                 795                 800

Thr Pro Trp Gly Ser Asn Ala Val Leu Gly Ser Glu Val Leu Lys Lys
            805                 810                 815

Ile Ala Met Ala Lys Gly Lys Ser Val Ala Gln Val Ser Met Arg Trp
            820                 825                 830

Val Tyr Glu Gln Gly Ala Ser Leu Val Val Lys Ser Phe Ser Glu Glu
            835                 840                 845

Arg Leu Arg Glu Asn Leu Asn Ile Phe Asp Trp Glu Leu Thr Lys Glu
            850                 855                 860

Asp His Glu Lys Ile Gly Glu Ile Pro Gln Cys Arg Ile Leu Ser Ala
865                 870                 875                 880

Tyr Phe Leu Val Ser Pro Asn Gly Pro Phe Lys Ser Gln Glu Glu Leu
            885                 890                 895

Trp Asp Asp Glu Ala
            900

<210> SEQ ID NO 2
<211> LENGTH: 919
<212> TYPE: PRT
<213> ORGANISM: Papaver somniferum
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid

<400> SEQUENCE: 2

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
                20                  25                  30
```

```
Arg Lys Thr Phe Leu Asn Asn Tyr Ser Ser Ser Pro Ala Ser Ser Thr
        35                  40                  45

Lys Thr Ala Val Leu Ser His Gln Arg Gln Gln Ser Cys Ala Leu Pro
 50                  55                  60

Ile Ser Gly Leu Leu His Ile Phe Met Asn Lys Asn Gly Leu Ile His
 65                  70                  75                  80

Val Thr Leu Gly Asn Met Ala Asp Lys Tyr Gly Pro Ile Phe Ser Phe
                 85                  90                  95

Pro Thr Gly Ser His Arg Thr Leu Val Val Ser Ser Trp Glu Met Val
            100                 105                 110

Lys Glu Cys Phe Thr Gly Asn Asn Asp Thr Ala Phe Ser Asn Arg Pro
            115                 120                 125

Ile Pro Leu Ala Phe Lys Thr Ile Phe Tyr Ala Cys Gly Gly Ile Asp
            130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn His Gly Asn Tyr Thr Thr
            195                 200                 205

Xaa Leu Leu Pro Gln Leu Ala Trp Arg Gln Pro Trp Lys Leu Tyr
    210                 215                 220

Tyr Xaa Thr Thr Thr Ala Ala Gly Met Val Arg Ile Asp Asp Trp
225                 230                 235                 240

Leu Ala Glu Leu Ser Phe Asn Val Ile Gly Arg Ile Val Cys Gly Phe
                245                 250                 255

Gln Ser Gly Pro Lys Thr Gly Ala Pro Ser Arg Val Glu Gln Phe Lys
            260                 265                 270

Glu Ala Ile Asn Glu Ala Ser Tyr Phe Met Ser Thr Ser Pro Val Ser
            275                 280                 285

Asp Asn Val Pro Met Leu Gly Trp Ile Asp Gln Leu Thr Gly Leu Thr
            290                 295                 300

Arg Asn Met Lys His Cys Gly Lys Lys Leu Asp Leu Val Val Glu Ser
305                 310                 315                 320

Ile Ile Asn Asp His Arg Gln Lys Arg Arg Phe Ser Arg Thr Lys Gly
                325                 330                 335

Gly Asp Glu Lys Asp Asp Glu Gln Asp Phe Ile Asp Ile Cys Leu
            340                 345                 350

Ser Ile Met Glu Gln Pro Gln Leu Pro Gly Asn Asn Pro Ser Gln
            355                 360                 365

Ile Pro Ile Lys Ser Ile Val Leu Asp Met Ile Gly Gly Thr Asp
370                 375                 380

Thr Thr Lys Leu Thr Thr Ile Trp Thr Leu Ser Leu Leu Asn Asn
385                 390                 395                 400

Pro His Val Leu Asp Lys Ala Lys Gln Glu Val Asp Ala His Phe Arg
            405                 410                 415

Thr Lys Arg Arg Ser Thr Asn Asp Ala Ala Ala Val Val Asp Phe
            420                 425                 430

Asp Asp Ile Arg Asn Leu Val Tyr Ile Gln Ala Ile Ile Lys Glu Ser
            435                 440                 445
```

```
Met Arg Leu Tyr Pro Ala Ser Pro Val Glu Arg Leu Ser Gly Glu
450                 455                 460

Asp Cys Val Val Gly Gly Phe His Val Pro Ala Gly Thr Arg Leu Trp
465                 470                 475                 480

Ala Asn Val Trp Lys Met Gln Arg Asp Pro Lys Val Trp Asp Pro
                485                 490                 495

Leu Val Phe Arg Pro Asp Arg Phe Leu Ser Asp Glu Gln Lys Met Val
            500                 505                 510

Asp Val Arg Gly Gln Asn Tyr Glu Leu Leu Pro Phe Gly Ala Gly Arg
        515                 520                 525

Arg Val Cys Pro Gly Val Ser Phe Ser Leu Asp Leu Met Gln Leu Val
530                 535                 540

Leu Thr Arg Leu Ile Leu Glu Phe Glu Met Lys Ser Pro Ser Gly Lys
545                 550                 555                 560

Val Asp Met Thr Ala Thr Pro Gly Leu Met Ser Tyr Lys Val Ile Pro
                565                 570                 575

Leu Asp Ile Leu Leu Thr His Arg Arg Ile Lys Pro Cys Val Gln Ser
            580                 585                 590

Ala Ala Ser Glu Arg Asp Met Glu Ser Ser Gly Val Pro Val Ile Thr
        595                 600                 605

Leu Gly Ser Gly Lys Val Met Pro Val Leu Gly Met Gly Thr Phe Glu
610                 615                 620

Lys Val Gly Lys Gly Ser Glu Arg Glu Arg Leu Ala Ile Leu Lys Ala
625                 630                 635                 640

Ile Glu Val Gly Tyr Arg Tyr Phe Asp Thr Ala Ala Ala Tyr Glu Thr
                645                 650                 655

Glu Glu Val Leu Gly Glu Ala Ile Ala Glu Ala Leu Gln Leu Gly Leu
            660                 665                 670

Val Lys Ser Arg Asp Glu Leu Phe Ile Ser Ser Met Leu Trp Cys Thr
        675                 680                 685

Asp Ala His Ala Asp Arg Val Leu Leu Ala Leu Gln Asn Ser Leu Arg
690                 695                 700

Asn Leu Lys Leu Glu Tyr Val Asp Leu Tyr Met Leu Pro Phe Pro Ala
705                 710                 715                 720

Ser Leu Lys Pro Gly Lys Ile Thr Met Asp Ile Pro Glu Glu Asp Ile
                725                 730                 735

Cys Arg Met Asp Tyr Arg Ser Val Trp Ala Ala Met Glu Glu Cys Gln
            740                 745                 750

Asn Leu Gly Phe Thr Lys Ser Ile Gly Val Ser Asn Phe Ser Cys Lys
        755                 760                 765

Lys Leu Gln Glu Leu Met Ala Thr Ala Asn Ile Pro Pro Ala Val Asn
770                 775                 780

Gln Val Glu Met Ser Pro Ala Phe Gln Gln Lys Lys Leu Arg Glu Tyr
785                 790                 795                 800

Cys Asn Ala Asn Asn Ile Leu Val Ser Ala Ile Ser Val Leu Gly Ser
                805                 810                 815

Asn Gly Thr Pro Trp Gly Ser Asn Ala Val Leu Gly Ser Glu Val Leu
            820                 825                 830

Lys Lys Ile Ala Met Ala Lys Gly Lys Ser Val Ala Gln Val Ser Met
        835                 840                 845

Arg Trp Val Tyr Glu Gln Gly Ala Ser Leu Val Val Lys Ser Phe Ser
850                 855                 860

Glu Glu Arg Leu Arg Glu Asn Leu Asn Ile Phe Asp Trp Glu Leu Thr
```

```
            865                 870                 875                 880
Lys Glu Asp His Glu Lys Ile Gly Glu Ile Pro Gln Cys Arg Ile Leu
                    885                 890                 895

Ser Ala Tyr Phe Leu Val Ser Pro Asn Gly Pro Phe Lys Ser Gln Glu
                900                 905                 910

Glu Leu Trp Asp Asp Glu Ala
        915

<210> SEQ ID NO 3
<211> LENGTH: 732
<212> TYPE: PRT
<213> ORGANISM: Papaver somniferum
<220> FEATURE:
<221> NAME/KEY: misc_feature
<222> LOCATION: (725)..(725)
<223> OTHER INFORMATION: Xaa can be any naturally occurring amino acid

<400> SEQUENCE: 3

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

Arg Lys Thr Phe Leu Asn Asn Tyr Ser Ser Pro Ala Ser Ser Thr
        35                  40                  45

Lys Thr Ala Val Leu Ser His Gln Arg Gln Ser Cys Ala Leu Pro
50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
            100                 105                 110

Lys Glu Cys Phe Thr Gly Asn Asn Asp Thr Ala Phe Ser Asn Arg Pro
        115                 120                 125

Ile Pro Leu Ala Phe Lys Thr Ile Phe Tyr Ala Cys Gly Gly Ile Asp
    130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn His Gly Asn Tyr Thr Thr
        195                 200                 205

Thr Thr Thr Thr Ala Ala Gly Met Val Arg Ile Asp Asp Trp Leu Ala
    210                 215                 220

Glu Leu Ser Phe Asn Val Ile Gly Arg Ile Val Cys Gly Phe Gln Ser
225                 230                 235                 240

Gly Pro Lys Thr Gly Ala Pro Ser Arg Val Glu Gln Phe Lys Glu Ala
                245                 250                 255

Ile Asn Glu Ala Ser Tyr Phe Met Ser Thr Ser Pro Val Ser Asp Asn
            260                 265                 270

Val Pro Met Leu Gly Trp Ile Asp Gln Leu Thr Gly Leu Thr Arg Asn
        275                 280                 285

Met Lys His Cys Gly Lys Lys Leu Asp Leu Val Val Glu Ser Ile Ile
    290                 295                 300
```

```
Asn Asp His Arg Gln Lys Arg Phe Ser Arg Thr Lys Gly Gly Asp
305                 310                 315                 320

Glu Lys Asp Asp Glu Gln Asp Asp Phe Ile Asp Ile Cys Leu Ser Ile
                    325                 330                 335

Met Glu Gln Pro Gln Leu Pro Gly Asn Asn Pro Ser Gln Ile Pro
            340                 345                 350

Ile Lys Ser Ile Val Leu Asp Met Ile Gly Gly Thr Asp Thr Thr
                355                 360                 365

Lys Leu Thr Thr Ile Trp Thr Leu Ser Leu Leu Asn Asn Pro His
370                 375                 380

Val Leu Asp Lys Ala Lys Gln Glu Val Asp Ala His Phe Arg Thr Lys
385                 390                 395                 400

Arg Arg Ser Thr Asn Asp Ala Ala Ala Val Val Asp Phe Asp Asp
                405                 410                 415

Ile Arg Asn Leu Val Tyr Ile Gln Ala Ile Ile Lys Glu Ser Met Arg
                420                 425                 430

Leu Tyr Pro Ala Ser Pro Val Val Glu Arg Leu Ser Gly Glu Asp Cys
            435                 440                 445

Val Val Gly Gly Phe His Val Pro Ala Gly Thr Arg Leu Trp Ala Asn
            450                 455                 460

Val Trp Lys Met Gln Arg Asp Pro Lys Val Trp Asp Pro Leu Val
465                 470                 475                 480

Phe Arg Pro Asp Arg Phe Leu Ser Asp Glu Gln Lys Met Val Asp Val
                485                 490                 495

Arg Gly Gln Asn Tyr Glu Leu Leu Pro Phe Gly Ala Gly Arg Arg Val
                500                 505                 510

Cys Pro Gly Val Ser Phe Ser Leu Asp Leu Met Gln Leu Val Leu Thr
            515                 520                 525

Arg Leu Ile Leu Glu Phe Glu Met Lys Ser Pro Ser Gly Lys Val Asp
530                 535                 540

Met Thr Ala Thr Pro Gly Leu Met Ser Tyr Lys Val Ile Pro Leu Asp
545                 550                 555                 560

Ile Leu Leu Thr His Arg Arg Ile Lys Pro Cys Val Gln Ser Ala Ala
                565                 570                 575

Ser Glu Arg Asp Met Glu Ser Ser Gly Val Pro Val Ile Thr Leu Gly
            580                 585                 590

Ser Gly Lys Val Met Pro Val Leu Gly Met Gly Thr Phe Glu Lys Val
            595                 600                 605

Gly Lys Gly Ser Glu Arg Glu Arg Leu Ala Ile Leu Lys Ala Ile Glu
            610                 615                 620

Val Gly Tyr Arg Tyr Phe Asp Thr Ala Ala Tyr Glu Thr Glu Glu
625                 630                 635                 640

Val Leu Gly Glu Ala Ile Ala Glu Ala Leu Gln Leu Gly Leu Val Lys
                645                 650                 655

Ser Arg Asp Glu Leu Phe Ile Ser Ser Met Leu Trp Cys Thr Asp Ala
            660                 665                 670

His Ala Asp Arg Val Leu Leu Ala Leu Gln Asn Ser Leu Arg Asn Leu
            675                 680                 685

Lys Leu Glu Tyr Val Asp Leu Tyr Met Leu Pro Phe Pro Ala Ser Leu
            690                 695                 700

Lys Pro Gly Lys Ile Thr Met Asp Ile Pro Glu Glu Asp Ile Cys Arg
705                 710                 715                 720
```

Met Asp Tyr Arg Xaa Val Ser Lys Pro Trp Leu His
            725                 730

<210> SEQ ID NO 4
<211> LENGTH: 764
<212> TYPE: PRT
<213> ORGANISM: Papaver somniferum
<220> FEATURE:
<221> NAME/KEY: misc_feature
<222> LOCATION: (6)..(6)
<223> OTHER INFORMATION: Xaa can be any naturally occurring amino acid

<400> SEQUENCE: 4

Met Arg Trp His Arg Xaa Ile Asp Ser Tyr Gly Leu Ser Ser Val Pro
1               5                   10                  15

Tyr Gly Lys Tyr Trp Arg Glu Leu Arg Lys Val Cys Val His Asn Leu
            20                  25                  30

Leu Ser Asn Gln Gln Leu Leu Lys Phe Arg His Leu Ile Ile Ser Gln
        35                  40                  45

Val Asp Thr Ser Phe Asn Lys Leu Tyr Glu Leu Cys Lys Asn Ser Glu
    50                  55                  60

Asp Asn Gln Gly Asn Tyr Pro Thr Thr Thr Ala Ala Gly Met Val
65                  70                  75                  80

Arg Ile Asp Asp Trp Leu Ala Glu Leu Ser Phe Asn Val Ile Gly Arg
                85                  90                  95

Ile Val Cys Gly Phe Gln Ser Gly Pro Lys Thr Gly Ala Pro Ser Arg
            100                 105                 110

Val Glu Gln Phe Lys Glu Ala Ile Asn Glu Ala Ser Tyr Phe Met Ser
        115                 120                 125

Thr Ser Pro Val Ser Asp Asn Val Pro Met Leu Gly Trp Ile Asp Gln
    130                 135                 140

Leu Thr Gly Leu Thr Arg Asn Met Lys His Cys Gly Lys Lys Leu Asp
145                 150                 155                 160

Leu Val Val Glu Ser Ile Ile Asn Asp His Arg Gln Lys Arg Arg Phe
                165                 170                 175

Ser Arg Thr Lys Gly Gly Asp Glu Lys Asp Asp Glu Gln Asp Asp Phe
            180                 185                 190

Ile Asp Ile Cys Leu Ser Ile Met Glu Gln Pro Gln Leu Pro Gly Asn
        195                 200                 205

Asn Asn Pro Ser Gln Ile Pro Ile Lys Ser Ile Val Leu Asp Met Ile
    210                 215                 220

Gly Gly Gly Thr Asp Thr Thr Lys Leu Thr Thr Ile Trp Thr Leu Ser
225                 230                 235                 240

Leu Leu Leu Asn Asn Pro His Val Leu Asp Lys Ala Lys Gln Glu Val
                245                 250                 255

Asp Ala His Phe Arg Thr Lys Arg Arg Ser Thr Asn Asp Ala Ala Ala
            260                 265                 270

Ala Val Val Asp Phe Asp Asp Ile Arg Asn Leu Val Tyr Ile Gln Ala
        275                 280                 285

Ile Ile Lys Glu Ser Met Arg Leu Tyr Pro Ala Ser Pro Val Val Glu
    290                 295                 300

Arg Leu Ser Gly Glu Asp Cys Val Val Gly Phe His Val Pro Ala
305                 310                 315                 320

Gly Thr Arg Leu Trp Ala Asn Val Trp Lys Met Gln Arg Asp Pro Lys
                325                 330                 335

Val Trp Asp Asp Pro Leu Val Phe Arg Pro Asp Arg Phe Leu Ser Asp

```
            340                 345                 350
Glu Gln Lys Met Val Asp Val Arg Gly Gln Asn Tyr Glu Leu Leu Pro
            355                 360                 365

Phe Gly Ala Gly Arg Arg Val Cys Pro Gly Val Ser Phe Ser Leu Asp
370                 375                 380

Leu Met Gln Leu Val Leu Thr Arg Leu Ile Leu Glu Phe Glu Met Lys
385                 390                 395                 400

Ser Pro Ser Gly Lys Val Asp Met Thr Ala Thr Pro Gly Leu Met Ser
                405                 410                 415

Tyr Lys Val Ile Pro Leu Asp Ile Leu Leu Thr His Arg Arg Ile Lys
                420                 425                 430

Pro Cys Val Gln Ser Ala Ala Ser Glu Arg Asp Met Glu Ser Ser Gly
                435                 440                 445

Val Pro Val Ile Thr Leu Gly Ser Gly Lys Val Met Pro Val Leu Gly
                450                 455                 460

Met Gly Thr Phe Glu Lys Val Gly Lys Gly Ser Glu Arg Glu Arg Leu
465                 470                 475                 480

Ala Ile Leu Lys Ala Ile Glu Val Gly Tyr Arg Tyr Phe Asp Thr Ala
                485                 490                 495

Ala Ala Tyr Glu Thr Glu Glu Val Leu Gly Glu Ala Ile Ala Glu Ala
                500                 505                 510

Leu Gln Leu Gly Leu Val Lys Ser Arg Asp Glu Leu Phe Ile Ser Ser
                515                 520                 525

Met Leu Trp Cys Thr Asp Ala His Ala Asp Arg Val Leu Leu Ala Leu
                530                 535                 540

Gln Asn Ser Leu Arg Asn Leu Lys Leu Glu Tyr Val Asp Leu Tyr Met
545                 550                 555                 560

Leu Pro Phe Pro Ala Ser Leu Lys Pro Gly Lys Ile Thr Met Asp Ile
                565                 570                 575

Pro Glu Glu Asp Ile Cys Arg Met Asp Tyr Arg Ser Val Trp Ala Ala
                580                 585                 590

Met Glu Glu Cys Gln Asn Leu Gly Phe Thr Lys Ser Ile Gly Val Ser
                595                 600                 605

Asn Phe Ser Cys Lys Lys Leu Gln Glu Leu Met Ala Thr Ala Asn Ile
                610                 615                 620

Pro Pro Ala Val Asn Gln Val Glu Met Ser Pro Ala Phe Gln Gln Lys
625                 630                 635                 640

Lys Leu Arg Glu Tyr Cys Asn Ala Asn Asn Ile Leu Val Ser Ala Ile
                645                 650                 655

Ser Val Leu Gly Ser Asn Gly Thr Pro Trp Gly Ser Asn Ala Val Leu
                660                 665                 670

Gly Ser Glu Val Leu Lys Lys Ile Ala Met Ala Lys Gly Lys Ser Val
                675                 680                 685

Ala Gln Val Ser Met Arg Trp Val Tyr Glu Gln Gly Ala Ser Leu Val
                690                 695                 700

Val Lys Ser Phe Ser Glu Glu Arg Leu Arg Glu Asn Leu Asn Ile Phe
705                 710                 715                 720

Asp Trp Glu Leu Thr Lys Glu Asp His Glu Lys Ile Gly Glu Ile Pro
                725                 730                 735

Gln Cys Arg Ile Leu Ser Ala Tyr Phe Leu Val Ser Pro Asn Gly Pro
                740                 745                 750

Phe Lys Ser Gln Glu Glu Leu Trp Asp Asp Glu Ala
                755                 760
```

<210> SEQ ID NO 5
<211> LENGTH: 900
<212> TYPE: PRT
<213> ORGANISM: Papaver setigerum

<400> SEQUENCE: 5

```
Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

Arg Lys Thr Phe Leu Asn Asn Tyr Ser Ser Ser Pro Ala Ser Ser Thr
        35                  40                  45

Lys Thr Ala Val Leu Ser His Gln Arg Gln Gln Ser Cys Ala Leu Pro
50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
            100                 105                 110

Lys Glu Cys Phe Thr Gly Asn Asn Asp Thr Ala Phe Ser Asn Arg Pro
        115                 120                 125

Ile Pro Leu Ala Phe Lys Thr Ile Phe Tyr Ala Cys Gly Gly Ile Asp
130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn Gly Asn Tyr Thr Thr
        195                 200                 205

Thr Thr Thr Ala Ala Gly Met Val Arg Ile Asp Asp Trp Leu Ala Glu
210                 215                 220

Leu Ser Phe Asn Val Ile Gly Arg Ile Val Cys Gly Phe Gln Ser Gly
225                 230                 235                 240

Pro Lys Thr Gly Ala Pro Ser Arg Val Glu Gln Phe Lys Glu Ala Ile
                245                 250                 255

Asn Glu Ala Ser Tyr Phe Met Ser Thr Ser Pro Val Ser Asp Asn Val
            260                 265                 270

Pro Met Leu Gly Trp Ile Asp Gln Leu Thr Gly Leu Thr Arg Asn Met
        275                 280                 285

Lys His Cys Gly Lys Lys Leu Asp Leu Val Val Glu Ser Ile Ile Asn
290                 295                 300

Asp His Arg Gln Lys Arg Phe Ser Arg Thr Lys Gly Gly Asp Glu
305                 310                 315                 320

Lys Asp Asp Glu Gln Asp Asp Phe Ile Asp Ile Cys Leu Ser Ile Met
                325                 330                 335

Glu Gln Pro Gln Leu Pro Gly Asn Asn Pro Ser Gln Ile Pro Ile
            340                 345                 350

Lys Ser Ile Val Leu Asp Met Ile Gly Gly Gly Thr Asp Thr Thr Lys
        355                 360                 365

Leu Thr Thr Ile Trp Thr Leu Ser Leu Leu Leu Asn Asn Pro His Val
```

-continued

```
           370                 375                 380
Leu Asp Lys Ala Lys Gln Glu Val Asp Ala His Phe Arg Thr Lys Arg
385                 390                 395                 400

Arg Ser Thr Asn Asp Ala Ala Ala Val Val Asp Phe Asp Asp Ile
                405                 410                 415

Arg Asn Leu Val Tyr Ile Gln Ala Ile Ile Lys Glu Ser Met Arg Leu
                420                 425                 430

Tyr Pro Ala Ser Pro Val Val Glu Arg Leu Ser Gly Glu Asp Cys Val
                435                 440                 445

Val Gly Gly Phe His Val Pro Ala Gly Thr Arg Leu Trp Ala Asn Val
450                 455                 460

Trp Lys Met Gln Arg Asp Pro Lys Val Trp Asp Pro Leu Val Phe
465                 470                 475                 480

Arg Pro Asp Arg Phe Leu Ser Asp Glu Gln Lys Met Val Asp Val Arg
                485                 490                 495

Gly Gln Asn Tyr Glu Leu Leu Pro Phe Gly Ala Gly Arg Arg Val Cys
                500                 505                 510

Pro Gly Val Ser Phe Ser Leu Asp Leu Met Gln Leu Val Leu Thr Arg
                515                 520                 525

Leu Ile Leu Glu Phe Glu Met Lys Ser Pro Ser Gly Lys Val Asp Met
530                 535                 540

Thr Ala Thr Pro Gly Leu Met Ser Tyr Lys Val Ile Pro Leu Asp Ile
545                 550                 555                 560

Leu Leu Thr His Arg Arg Ile Lys Pro Cys Val Gln Ser Ala Ala Ser
                565                 570                 575

Glu Arg Asp Met Glu Ser Ser Gly Val Pro Val Ile Thr Leu Gly Ser
                580                 585                 590

Gly Lys Val Met Pro Val Leu Gly Met Gly Thr Phe Glu Lys Val Gly
                595                 600                 605

Lys Gly Ser Glu Arg Glu Arg Leu Ala Ile Leu Lys Ala Ile Glu Val
                610                 615                 620

Gly Tyr Arg Tyr Phe Asp Thr Ala Ala Ala Tyr Glu Thr Glu Glu Val
625                 630                 635                 640

Leu Gly Glu Ala Ile Ala Glu Ala Leu Gln Leu Gly Leu Val Lys Ser
                645                 650                 655

Arg Asp Glu Leu Phe Ile Ser Ser Met Leu Trp Cys Thr Asp Ala His
                660                 665                 670

Ala Asp Arg Val Leu Leu Ala Leu Gln Asn Ser Leu Arg Asn Leu Lys
                675                 680                 685

Leu Glu Tyr Val Asp Leu Tyr Met Leu Pro Phe Pro Ala Ser Leu Lys
                690                 695                 700

Pro Gly Lys Ile Thr Met Asp Ile Pro Glu Asp Ile Cys Arg Met
705                 710                 715                 720

Asp Tyr Arg Ser Val Trp Ala Ala Met Glu Glu Cys Gln Asn Leu Gly
                725                 730                 735

Phe Thr Lys Ser Ile Gly Val Ser Asn Phe Ser Cys Lys Lys Leu Gln
                740                 745                 750

Glu Leu Met Ala Thr Ala Asn Ile Pro Pro Ala Val Asn Gln Val Glu
                755                 760                 765

Met Ser Pro Ala Phe Gln Gln Lys Lys Leu Arg Glu Tyr Cys Asn Ala
                770                 775                 780

Asn Asn Ile Leu Val Ser Ala Ile Ser Val Leu Gly Ser Asn Gly Thr
785                 790                 795                 800
```

-continued

Pro Trp Gly Ser Asn Ala Val Leu Gly Ser Glu Val Leu Lys Lys Ile
                805                 810                 815

Ala Met Ala Lys Gly Lys Ser Val Ala Gln Val Ser Met Arg Trp Val
                820                 825                 830

Tyr Glu Gln Gly Ala Ser Leu Val Val Lys Ser Phe Ser Glu Glu Arg
                835                 840                 845

Leu Arg Glu Asn Leu Asn Ile Phe Asp Trp Glu Leu Thr Lys Glu Asp
850                 855                 860

His Glu Lys Ile Gly Glu Ile Pro Gln Cys Arg Ile Leu Ser Ala Tyr
865                 870                 875                 880

Phe Leu Val Ser Pro Asn Gly Pro Phe Lys Ser Gln Glu Glu Leu Trp
                885                 890                 895

Asp Asp Glu Ala
            900

<210> SEQ ID NO 6
<211> LENGTH: 724
<212> TYPE: PRT
<213> ORGANISM: Papaver setigerum

<400> SEQUENCE: 6

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
                20                  25                  30

Arg Lys Thr Phe Leu Asn Asn Tyr Ser Ser Ser Pro Ala Ser Ser Thr
            35                  40                  45

Lys Thr Ala Val Leu Ser His Gln Arg Gln Gln Ser Cys Ala Leu Pro
    50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
            100                 105                 110

Lys Glu Cys Phe Thr Gly Asn Asn Asp Thr Ala Phe Ser Asn Arg Pro
        115                 120                 125

Ile Pro Leu Ala Phe Lys Thr Ile Phe Tyr Ala Cys Gly Gly Ile Asp
    130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn Gly Asn Tyr Thr Thr
        195                 200                 205

Thr Thr Thr Ala Ala Gly Met Val Arg Ile Asp Asp Trp Leu Ala Glu
    210                 215                 220

Leu Ser Phe Asn Val Ile Gly Arg Ile Val Cys Gly Phe Gln Ser Gly
225                 230                 235                 240

Pro Lys Thr Gly Ala Pro Ser Arg Val Glu Gln Phe Lys Glu Ala Ile
                245                 250                 255

Asn Glu Ala Ser Tyr Phe Met Ser Thr Ser Pro Val Ser Asp Asn Val

-continued

```
            260                 265                 270
Pro Met Leu Gly Trp Ile Asp Gln Leu Thr Gly Leu Thr Arg Asn Met
        275                 280                 285

Lys His Cys Gly Lys Lys Leu Asp Leu Val Val Glu Ser Ile Ile Asn
    290                 295                 300

Asp His Arg Gln Lys Arg Arg Phe Ser Arg Thr Lys Gly Gly Asp Glu
305                 310                 315                 320

Lys Asp Asp Glu Gln Asp Asp Phe Ile Asp Ile Cys Leu Ser Ile Met
                325                 330                 335

Glu Gln Pro Gln Leu Pro Gly Asn Asn Asn Pro Ser Gln Ile Pro Ile
            340                 345                 350

Lys Ser Ile Val Leu Asp Met Ile Gly Gly Thr Asp Thr Thr Lys
        355                 360                 365

Leu Thr Thr Ile Trp Thr Leu Ser Leu Leu Asn Asn Pro His Val
    370                 375                 380

Leu Asp Lys Ala Lys Gln Glu Val Asp Ala His Phe Arg Thr Lys Arg
385                 390                 395                 400

Arg Ser Thr Asn Asp Ala Ala Ala Val Val Asp Phe Asp Asp Ile
                405                 410                 415

Arg Asn Leu Val Tyr Ile Gln Ala Leu Tyr Pro Ala Ser Pro Val Val
            420                 425                 430

Glu Arg Leu Ser Gly Glu Asp Cys Val Val Gly Gly Phe His Val Pro
        435                 440                 445

Ala Gly Thr Arg Leu Trp Ala Asn Val Trp Lys Met Gln Arg Asp Pro
    450                 455                 460

Lys Val Trp Asp Asp Pro Leu Val Phe Arg Pro Asp Arg Phe Leu Ser
465                 470                 475                 480

Asp Glu Gln Lys Met Val Asp Val Arg Gly Gln Asn Tyr Glu Leu Leu
                485                 490                 495

Pro Phe Gly Ala Gly Arg Arg Val Cys Pro Gly Val Ser Phe Ser Leu
            500                 505                 510

Asp Leu Met Gln Leu Val Leu Thr Arg Leu Ile Leu Glu Phe Glu Met
        515                 520                 525

Lys Ser Pro Ser Gly Lys Val Asp Met Thr Ala Thr Pro Gly Leu Met
    530                 535                 540

Ser Tyr Lys Val Ile Pro Leu Asp Ile Leu Leu Thr His Arg Arg Ile
545                 550                 555                 560

Lys Pro Cys Val Gln Ser Ala Ala Ser Glu Arg Asp Met Glu Ser Ser
                565                 570                 575

Gly Val Pro Val Ile Thr Leu Gly Ser Gly Lys Val Met Pro Val Leu
            580                 585                 590

Gly Met Gly Thr Phe Glu Lys Val Gly Lys Gly Ser Glu Arg Glu Arg
        595                 600                 605

Leu Ala Ile Leu Lys Ala Ile Glu Val Gly Tyr Arg Tyr Phe Asp Thr
    610                 615                 620

Ala Ala Ala Tyr Glu Thr Glu Glu Val Leu Gly Glu Ala Ile Ala Glu
625                 630                 635                 640

Ala Leu Gln Leu Gly Leu Val Lys Ser Arg Asp Glu Leu Phe Ile Ser
                645                 650                 655

Ser Met Leu Trp Cys Thr Asp Ala His Ala Asp Arg Val Leu Leu Ala
            660                 665                 670

Leu Gln Asn Ser Leu Arg Asn Leu Lys Leu Glu Tyr Val Asp Leu Tyr
        675                 680                 685
```

```
Met Leu Pro Phe Pro Ala Ser Leu Lys Pro Gly Lys Ile Thr Met Asp
            690                 695                 700

Ile Pro Glu Glu Asp Ile Cys Arg Met Asp Tyr Arg Ser Val Trp Ala
705                 710                 715                 720

Ala Met Glu Glu

<210> SEQ ID NO 7
<211> LENGTH: 889
<212> TYPE: PRT
<213> ORGANISM: Papaver bracteatum

<400> SEQUENCE: 7

Met Glu Leu Gln Tyr Phe Ser Tyr Phe Gln Pro Thr Ser Ser Val Val
1                   5                   10                  15

Ala Leu Leu Leu Ala Leu Val Ser Ile Leu Phe Ser Val Val Val Leu
                20                  25                  30

Arg Lys Thr Phe Ser Asn Asn Tyr Ser Ser Pro Ala Ser Ser Thr Glu
            35                  40                  45

Thr Ala Val Leu Cys His Gln Arg Gln Gln Ser Cys Ala Leu Pro Ile
        50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
                245                 250                 255

Val Ser Asp Asn Val Pro Met Leu Gly Trp Ile Asp Gln Leu Thr Gly
            260                 265                 270

Leu Thr Arg Asn Met Lys His Cys Gly Lys Lys Leu Asp Leu Val Val
        275                 280                 285

Glu Ser Ile Ile Lys Asp His Arg Gln Lys Arg Phe Ser Arg Thr
    290                 295                 300

Lys Gly Gly Asp Glu Lys Asp Asp Glu Gln Asp Phe Ile Asp Ile
305                 310                 315                 320

Cys Leu Ser Ile Met Glu Gln Pro Gln Leu Pro Gly Asn Asn Ser Pro
                325                 330                 335
```

```
Pro Gln Ile Pro Ile Lys Ser Ile Val Leu Asp Met Ile Gly Gly
                340                 345                 350

Thr Asp Thr Thr Lys Leu Thr Thr Ile Trp Thr Leu Ser Leu Leu Leu
        355                 360                 365

Asn Asn Pro His Val Leu Asp Lys Ala Lys Gln Glu Val Asp Ala His
    370                 375                 380

Phe Arg Lys Lys Arg Arg Ser Thr Asp Ala Ala Ala Val Val
385                 390                 395                 400

Asp Phe Asp Asp Ile Arg Asn Leu Val Tyr Ile Gln Ala Ile Ile Lys
                405                 410                 415

Glu Ser Met Arg Leu Tyr Pro Ala Ser Pro Val Val Glu Arg Leu Ser
            420                 425                 430

Gly Glu Asp Cys Val Val Gly Gly Phe His Val Pro Ala Gly Thr Arg
                435                 440                 445

Leu Trp Ala Asn Val Trp Lys Met Gln Arg Asp Pro Lys Val Trp Asp
            450                 455                 460

Asp Pro Leu Val Phe Arg Pro Glu Arg Phe Leu Ser Asp Glu Gln Lys
465                 470                 475                 480

Met Val Asp Val Arg Gly Gln Asn Tyr Glu Leu Leu Pro Phe Gly Ala
                485                 490                 495

Gly Arg Arg Ile Cys Pro Gly Val Ser Phe Ser Leu Asp Leu Met Gln
            500                 505                 510

Leu Val Leu Thr Arg Leu Ile Leu Glu Phe Glu Met Lys Ser Pro Ser
        515                 520                 525

Gly Lys Val Asp Met Thr Ala Thr Pro Gly Leu Met Ser Tyr Lys Val
    530                 535                 540

Val Pro Leu Asp Ile Leu Leu Thr His Arg Arg Ile Lys Ser Cys Val
545                 550                 555                 560

Gln Leu Ala Ser Ser Glu Arg Asp Met Glu Ser Ser Gly Val Pro Val
                565                 570                 575

Ile Thr Leu Ser Ser Gly Lys Val Met Pro Val Leu Gly Met Gly Thr
            580                 585                 590

Phe Glu Lys Val Gly Lys Gly Ser Glu Arg Glu Arg Leu Ala Ile Leu
        595                 600                 605

Lys Ala Ile Glu Val Gly Tyr Arg Tyr Phe Asp Thr Ala Ala Ala Tyr
    610                 615                 620

Glu Thr Glu Glu Val Leu Gly Glu Ala Ile Ala Glu Ala Leu Gln Leu
625                 630                 635                 640

Gly Leu Ile Glu Ser Arg Asp Glu Leu Phe Ile Ser Ser Met Leu Trp
                645                 650                 655

Cys Thr Asp Ala His Pro Asp Arg Val Leu Leu Ala Leu Gln Asn Ser
            660                 665                 670

Leu Arg Asn Leu Lys Leu Glu Tyr Leu Asp Leu Tyr Met Leu Pro Phe
        675                 680                 685

Pro Ala Ser Leu Lys Pro Gly Lys Ile Thr Met Asp Ile Pro Glu Glu
    690                 695                 700

Asp Ile Cys Arg Met Asp Tyr Arg Ser Val Trp Ser Ala Met Glu Glu
705                 710                 715                 720

Cys Gln Asn Leu Gly Phe Thr Lys Ser Ile Gly Val Ser Asn Phe Ser
                725                 730                 735

Ser Lys Lys Leu Gln Glu Leu Met Ala Thr Ala Asn Ile Pro Pro Ala
            740                 745                 750
```

```
Val Asn Gln Val Glu Met Ser Pro Ala Phe Gln Gln Lys Lys Leu Arg
        755                 760                 765

Glu Tyr Cys Asn Ala Asn Asn Ile Leu Val Ser Ala Val Ser Ile Leu
    770                 775                 780

Gly Ser Asn Gly Thr Pro Trp Gly Ser Asn Ala Val Leu Gly Ser Glu
785                 790                 795                 800

Val Leu Lys Gln Ile Ala Met Ala Lys Gly Lys Ser Val Ala Gln Val
                805                 810                 815

Ser Met Arg Trp Val Tyr Glu Gln Gly Ala Ser Leu Val Val Lys Ser
            820                 825                 830

Phe Ser Glu Glu Arg Leu Arg Glu Asn Leu Asn Ile Phe Asp Trp Glu
        835                 840                 845

Leu Thr Lys Glu Asp Asn Glu Lys Ile Gly Glu Ile Pro Gln Cys Arg
    850                 855                 860

Ile Leu Thr Ala Tyr Phe Leu Val Ser Pro Asn Gly Pro Phe Lys Ser
865                 870                 875                 880

Gln Glu Glu Leu Trp Asp Asp Lys Ala
                885

<210> SEQ ID NO 8
<211> LENGTH: 889
<212> TYPE: PRT
<213> ORGANISM: Papaver bracteatum

<400> SEQUENCE: 8

Met Glu Leu Gln Tyr Phe Ser Tyr Phe Gln Pro Thr Ser Ser Val Val
1               5                   10                  15

Ala Leu Leu Leu Ala Leu Val Ser Ile Leu Phe Ser Val Val Val Leu
                20                  25                  30

Arg Lys Thr Phe Ser Asn Asn Tyr Ser Ser Pro Ala Ser Ser Thr Glu
            35                  40                  45

Thr Ala Val Leu Cys His Gln Arg Gln Gln Ser Cys Ala Leu Pro Ile
        50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240
```

-continued

Phe Lys Glu Val Ile Asn Glu Ala Ser Tyr Phe Met Ser Thr Ser Pro
                245                 250                 255
Val Ser Asp Asn Val Pro Met Leu Gly Trp Ile Asp Gln Leu Thr Gly
            260                 265                 270
Leu Thr Arg Asn Met Lys His Cys Gly Lys Lys Leu Asp Leu Val Val
        275                 280                 285
Glu Ser Ile Ile Lys Asp His Arg Gln Lys Arg Arg Phe Ser Arg Thr
    290                 295                 300
Lys Gly Gly Asp Glu Lys Asp Asp Glu Gln Asp Asp Phe Ile Asp Ile
305                 310                 315                 320
Cys Leu Ser Ile Met Glu Gln Pro Gln Leu Pro Gly Asn Asn Ser Pro
                325                 330                 335
Pro Gln Ile Pro Ile Lys Ser Ile Val Leu Asp Met Ile Gly Gly Gly
            340                 345                 350
Thr Asp Thr Thr Lys Leu Thr Thr Ile Trp Thr Leu Ser Leu Leu Leu
        355                 360                 365
Asn Asn Pro His Val Leu Asp Lys Ala Lys Gln Glu Val Asp Ala His
    370                 375                 380
Phe Arg Lys Lys Arg Ser Thr Asp Ala Ala Ala Val Val
385                 390                 395                 400
Asp Phe Asp Asp Ile Arg Asn Leu Val Tyr Ile Gln Ala Ile Ile Lys
                405                 410                 415
Glu Ser Met Arg Leu Tyr Pro Ala Ser Pro Val Val Glu Arg Leu Ser
            420                 425                 430
Gly Glu Asp Cys Val Val Gly Phe His Val Pro Ala Gly Thr Arg
        435                 440                 445
Leu Trp Ala Asn Val Trp Lys Met Gln Arg Asp Pro Lys Val Trp Asp
    450                 455                 460
Asp Pro Leu Val Phe Arg Pro Glu Arg Phe Leu Ser Asp Glu Gln Lys
465                 470                 475                 480
Met Val Asp Val Arg Gly Gln Asn Tyr Glu Leu Leu Pro Phe Gly Ala
                485                 490                 495
Gly Arg Arg Ile Cys Pro Gly Val Ser Phe Ser Leu Asp Leu Met Gln
            500                 505                 510
Leu Val Leu Thr Arg Leu Ile Leu Glu Phe Glu Met Lys Ser Pro Ser
        515                 520                 525
Gly Lys Val Asp Met Thr Ala Thr Pro Gly Leu Met Ser Tyr Lys Val
    530                 535                 540
Val Pro Leu Asp Ile Leu Leu Thr His Arg Arg Ile Lys Ser Cys Val
545                 550                 555                 560
Gln Leu Ala Ser Ser Glu Arg Asp Met Glu Ser Ser Gly Val Pro Val
                565                 570                 575
Ile Thr Leu Ser Ser Gly Lys Val Met Pro Val Leu Gly Met Gly Thr
            580                 585                 590
Phe Glu Lys Val Gly Lys Gly Ser Glu Arg Glu Arg Leu Ala Ile Leu
        595                 600                 605
Lys Ala Ile Glu Val Gly Tyr Arg Tyr Phe Asp Thr Ala Ala Ala Tyr
    610                 615                 620
Glu Thr Glu Glu Val Leu Gly Glu Ala Ile Ala Glu Ala Leu Gln Leu
625                 630                 635                 640
Gly Leu Ile Glu Ser Arg Asp Glu Leu Phe Ile Ser Ser Met Leu Trp
                645                 650                 655

```
Cys Thr Asp Ala His Pro Asp Arg Val Leu Leu Ala Leu Gln Asn Ser
            660                 665                 670

Leu Arg Asn Leu Lys Leu Glu Tyr Leu Asp Leu Tyr Met Leu Pro Phe
        675                 680                 685

Pro Ala Ser Leu Lys Pro Gly Lys Ile Thr Met Asp Ile Pro Glu Glu
    690                 695                 700

Asp Ile Cys Arg Met Asp Tyr Arg Ser Val Trp Ser Ala Met Glu Glu
705                 710                 715                 720

Cys Gln Asn Leu Gly Phe Thr Lys Ser Ile Gly Val Ser Asn Phe Ser
                725                 730                 735

Cys Lys Lys Leu Gln Glu Leu Met Ala Thr Asn Ile Pro Pro Ala
            740                 745                 750

Val Asn Gln Val Glu Met Ser Pro Ala Phe Gln Gln Lys Lys Leu Arg
        755                 760                 765

Glu Tyr Cys Asn Ala Asn Asn Ile Leu Val Ser Ala Val Ser Ile Leu
    770                 775                 780

Gly Ser Asn Gly Thr Pro Trp Gly Ser Asn Ala Val Leu Gly Ser Glu
785                 790                 795                 800

Val Leu Lys Gln Ile Ala Met Ala Lys Gly Lys Ser Val Ala Gln Val
                805                 810                 815

Ser Met Arg Trp Val Tyr Glu Gln Gly Ala Ser Leu Val Val Lys Ser
            820                 825                 830

Phe Ser Glu Glu Arg Leu Arg Glu Asn Leu Asn Ile Phe Asp Trp Glu
        835                 840                 845

Leu Thr Lys Glu Asp Asn Glu Lys Ile Gly Ile Pro Gln Cys Arg
    850                 855                 860

Ile Leu Thr Ala Tyr Phe Leu Val Ser Pro Asn Gly Pro Phe Lys Ser
865                 870                 875                 880

Gln Glu Glu Leu Trp Asp Asp Lys Ala
                885

<210> SEQ ID NO 9
<211> LENGTH: 848
<212> TYPE: PRT
<213> ORGANISM: Papaver bracteatum

<400> SEQUENCE: 9

Ser Ser Pro Ala Ser Ser Thr Glu Thr Ala Val Leu Cys His Gln Arg
1               5                   10                  15

Gln Gln Ser Cys Ala Leu Pro Ile Ser Gly Leu Leu His Ile Phe Met
            20                  25                  30

Asn Lys Asn Gly Leu Ile His Val Thr Leu Gly Asn Met Ala Asp Lys
        35                  40                  45

Tyr Gly Pro Ile Phe Ser Phe Pro Thr Gly Ser His Arg Ile Leu Val
    50                  55                  60

Val Ser Ser Trp Glu Met Val Lys Glu Cys Phe Thr Gly Asn Asn Asp
65                  70                  75                  80

Thr Ala Phe Ser Asn Arg Pro Ile Pro Leu Ala Phe Lys Thr Ile Phe
                85                  90                  95

Tyr Ala Cys Arg Gly Ile Asp Ser Tyr Gly Leu Ser Ser Val Pro Tyr
            100                 105                 110

Gly Lys Tyr Trp Arg Glu Leu Arg Lys Val Cys Val His Asn Leu Leu
        115                 120                 125

Ser Asn Gln Gln Leu Leu Lys Phe Arg His Leu Ile Ile Ser Gln Val
    130                 135                 140
```

```
Asp Thr Ser Phe Asn Lys Leu Tyr Glu Leu Cys Lys Asn Ser Glu Asp
145                 150                 155                 160

Asn Gln Gly Met Val Arg Met Asp Asp Trp Leu Ala Gln Leu Ser Phe
                165                 170                 175

Ser Val Ile Gly Arg Ile Val Cys Gly Phe Gln Ser Asp Pro Lys Thr
            180                 185                 190

Gly Ala Pro Ser Arg Val Glu Gln Phe Lys Glu Ala Ile Asn Glu Ala
        195                 200                 205

Ser Tyr Phe Met Ser Thr Ser Pro Val Ser Asp Asn Val Pro Met Leu
    210                 215                 220

Gly Trp Ile Asp Gln Leu Thr Gly Leu Thr Arg Asn Met Thr His Cys
225                 230                 235                 240

Gly Lys Lys Leu Asp Leu Val Val Glu Ser Ile Ile Asn Asp His Arg
                245                 250                 255

Gln Lys Arg Arg Phe Ser Arg Thr Lys Gly Gly Asp Glu Lys Asp Asp
            260                 265                 270

Glu Gln Asp Asp Phe Ile Asp Ile Cys Leu Ser Ile Met Glu Gln Pro
        275                 280                 285

Gln Leu Pro Gly Asn Asn Asn Pro Pro Lys Ile Pro Ile Lys Ser Ile
    290                 295                 300

Val Leu Asp Met Ile Gly Ala Gly Thr Asp Thr Thr Lys Leu Thr Ile
305                 310                 315                 320

Ile Trp Thr Leu Ser Leu Leu Leu Asn Asn Pro Asn Val Leu Ala Lys
                325                 330                 335

Ala Lys Gln Glu Val Asp Ala His Phe Glu Thr Lys Lys Arg Ser Thr
            340                 345                 350

Asn Glu Ala Ser Val Val Asp Phe Asp Asp Ile Gly Asn Leu Val
        355                 360                 365

Tyr Ile Gln Ala Ile Ile Lys Glu Ser Met Arg Leu Tyr Pro Val Ser
    370                 375                 380

Pro Val Val Glu Arg Leu Ser Ser Glu Asp Cys Val Val Gly Gly Phe
385                 390                 395                 400

His Val Pro Ala Gly Thr Arg Leu Trp Ala Asn Val Trp Lys Met Gln
                405                 410                 415

Arg Asp Pro Lys Val Trp Asp Asp Pro Leu Val Phe Arg Pro Glu Arg
            420                 425                 430

Phe Leu Ser Asp Glu Gln Lys Met Val Asp Val Arg Gly Gln Asn Tyr
        435                 440                 445

Glu Leu Leu Pro Phe Gly Ala Gly Arg Arg Ile Cys Pro Gly Val Ser
    450                 455                 460

Phe Ser Leu Asp Leu Met Gln Leu Val Leu Thr Arg Leu Ile Leu Glu
465                 470                 475                 480

Phe Glu Met Lys Ser Pro Ser Gly Lys Val Asp Met Thr Ala Thr Pro
                485                 490                 495

Gly Leu Met Ser Tyr Lys Val Val Pro Leu Asp Ile Leu Leu Thr His
            500                 505                 510

Arg Arg Ile Lys Ser Cys Val Gln Leu Ala Ser Ser Glu Arg Asp Met
        515                 520                 525

Glu Ser Ser Gly Val Pro Val Ile Thr Leu Arg Ser Gly Lys Val Met
    530                 535                 540

Pro Val Leu Gly Met Gly Thr Phe Glu Lys Ala Gly Lys Gly Ser Glu
545                 550                 555                 560
```

```
Arg Glu Arg Leu Ala Ile Leu Lys Ala Ile Glu Val Gly Tyr Arg Tyr
                565                 570                 575

Phe Asp Thr Ala Ala Ala Tyr Glu Thr Glu Glu Val Leu Gly Glu Ala
            580                 585                 590

Ile Ala Glu Ala Leu Gln Leu Gly Leu Ile Lys Ser Arg Asp Glu Leu
        595                 600                 605

Phe Ile Ser Ser Met Leu Trp Cys Thr Asp Ala His Pro Asp Arg Val
    610                 615                 620

Leu Leu Ala Leu Gln Asn Ser Leu Arg Asn Leu Lys Leu Glu Tyr Val
625                 630                 635                 640

Asp Leu Tyr Met Leu Pro Phe Pro Ala Ser Leu Lys Pro Gly Lys Ile
            645                 650                 655

Thr Met Asp Ile Pro Glu Glu Asp Ile Cys Pro Met Asp Tyr Arg Ser
            660                 665                 670

Val Trp Ser Ala Met Glu Glu Cys Gln Asn Leu Gly Leu Thr Lys Ser
            675                 680                 685

Ile Gly Val Ser Asn Phe Ser Cys Lys Lys Leu Glu Glu Leu Met Ala
            690                 695                 700

Thr Ala Asn Ile Pro Pro Ala Val Asn Gln Val Glu Met Ser Pro Ala
705                 710                 715                 720

Phe Gln Gln Lys Lys Leu Arg Glu Tyr Cys Asn Ala Asn Asn Ile Leu
            725                 730                 735

Val Ser Ala Val Ser Ile Leu Gly Ser Asn Gly Thr Pro Trp Gly Ser
            740                 745                 750

Asn Ala Val Leu Gly Ser Glu Val Leu Lys Lys Ile Ala Met Ala Lys
            755                 760                 765

Gly Lys Ser Val Ala Gln Val Ser Met Arg Trp Val Tyr Glu Gln Gly
            770                 775                 780

Ala Ser Leu Val Val Lys Ser Phe Ser Glu Glu Arg Leu Arg Glu Asn
785                 790                 795                 800

Leu Asn Ile Phe Asp Trp Gln Leu Thr Lys Glu Asp Asn Glu Lys Ile
            805                 810                 815

Gly Glu Ile Pro Gln Cys Arg Ile Leu Ser Ala Tyr Phe Leu Val Ser
            820                 825                 830

Pro Lys Gly Pro Phe Lys Ser Gln Glu Glu Leu Trp Asp Asp Lys Ala
            835                 840                 845

<210> SEQ ID NO 10
<211> LENGTH: 847
<212> TYPE: PRT
<213> ORGANISM: Papaver bracteatum

<400> SEQUENCE: 10

Ser Ser Pro Ala Ser Ser Thr Glu Thr Ala Val Leu Cys His Gln Arg
1               5                   10                  15

Gln Gln Ser Cys Ala Leu Pro Ile Ser Gly Leu Leu His Ile Phe Met
            20                  25                  30

Asn Lys Asn Gly Leu Ile His Val Thr Leu Gly Asn Met Ala Asp Lys
        35                  40                  45

Tyr Gly Pro Ile Phe Ser Phe Pro Thr Gly Ser His Arg Ile Leu Val
    50                  55                  60

Val Ser Ser Trp Glu Met Val Lys Glu Cys Phe Thr Gly Asn Asn Asp
65                  70                  75                  80

Thr Phe Phe Ser Asn Arg Pro Ile Pro Leu Ala Phe Lys Ile Ile Phe
            85                  90                  95
```

```
Tyr Ala Gly Gly Val Asp Ser Tyr Gly Leu Ala Leu Val Pro Tyr Gly
                100                 105                 110

Lys Tyr Trp Arg Glu Leu Arg Lys Ile Cys Val His Asn Leu Leu Ser
            115                 120                 125

Asn Gln Gln Leu Leu Lys Phe Arg His Leu Ile Ile Ser Gln Val Asp
        130                 135                 140

Thr Ser Phe Asn Lys Leu Tyr Glu Leu Cys Lys Asn Ser Glu Asp Asn
145                 150                 155                 160

Gln Gly Met Val Arg Met Asp Asp Trp Leu Ala Gln Leu Ser Phe Ser
                165                 170                 175

Val Ile Gly Arg Ile Val Cys Gly Phe Gln Ser Asp Pro Lys Thr Gly
            180                 185                 190

Ala Pro Ser Arg Val Glu Gln Phe Lys Glu Ala Ile Asn Glu Ala Ser
        195                 200                 205

Tyr Phe Met Ser Thr Ser Pro Val Ser Asp Asn Val Pro Met Leu Gly
210                 215                 220

Trp Ile Asp Gln Leu Thr Gly Leu Thr Arg Asn Met Thr His Cys Gly
225                 230                 235                 240

Lys Lys Leu Asp Leu Val Val Glu Ser Ile Ile Asn Asp His Arg Gln
                245                 250                 255

Lys Arg Arg Phe Ser Arg Thr Lys Gly Gly Asp Glu Lys Asp Asp Glu
            260                 265                 270

Gln Asp Asp Phe Ile Asp Ile Cys Leu Ser Ile Met Glu Gln Pro Gln
        275                 280                 285

Leu Pro Gly Asn Asn Pro Pro Lys Ile Pro Ile Lys Ser Ile Val
        290                 295                 300

Leu Asp Met Ile Gly Gly Thr Asp Thr Thr Lys Leu Thr Thr Ile
305                 310                 315                 320

Trp Thr Leu Ser Leu Leu Leu Asn Asn Pro His Val Leu Asp Lys Ala
                325                 330                 335

Lys Gln Glu Val Asp Ala His Phe Leu Thr Lys Arg Arg Ser Thr Asn
            340                 345                 350

Asp Ala Ala Val Val Asp Phe Asp Asp Ile Arg Asn Leu Val Tyr Ile
        355                 360                 365

Gln Ala Ile Ile Lys Glu Ser Met Arg Leu Tyr Pro Ala Ser Pro Val
370                 375                 380

Val Glu Arg Leu Ser Gly Glu Asp Cys Val Val Gly Gly Phe His Val
385                 390                 395                 400

Pro Ala Gly Thr Arg Leu Trp Val Asn Val Trp Lys Met Gln Arg Asp
                405                 410                 415

Pro Asn Val Trp Ala Asp Pro Met Val Phe Arg Pro Glu Arg Phe Leu
            420                 425                 430

Ser His Gly Gln Lys Lys Met Val Asp Val Arg Gly Lys Asn Tyr Glu
        435                 440                 445

Leu Leu Pro Phe Gly Ala Gly Arg Arg Ile Cys Pro Gly Ile Ser Phe
450                 455                 460

Ser Leu Asp Leu Met Gln Leu Val Leu Thr Arg Leu Ile Leu Glu Phe
465                 470                 475                 480

Glu Met Lys Ser Pro Ser Gly Lys Val Asp Met Thr Ala Thr Pro Gly
                485                 490                 495

Leu Met Ser Tyr Lys Val Val Pro Leu Asp Ile Leu Leu Thr His Arg
            500                 505                 510
```

```
Arg Ile Lys Ser Cys Val Gln Leu Ala Ser Ser Glu Arg Asp Met Glu
            515                 520                 525

Ser Ser Gly Val Pro Val Ile Thr Leu Arg Ser Gly Lys Val Met Pro
        530                 535                 540

Val Leu Gly Met Gly Thr Phe Glu Lys Ala Gly Lys Gly Ser Glu Arg
545                 550                 555                 560

Glu Arg Leu Ala Ile Leu Lys Ala Ile Glu Val Gly Tyr Arg Tyr Phe
                565                 570                 575

Asp Thr Ala Ala Ala Tyr Glu Thr Glu Glu Val Leu Gly Glu Ala Ile
            580                 585                 590

Ala Glu Ala Leu Gln Leu Gly Leu Ile Lys Ser Arg Asp Glu Leu Phe
        595                 600                 605

Ile Ser Ser Met Leu Trp Cys Thr Asp Ala His Pro Asp Arg Val Leu
    610                 615                 620

Leu Ala Leu Gln Asn Ser Leu Arg Asn Leu Lys Leu Glu Tyr Val Asp
625                 630                 635                 640

Leu Tyr Met Leu Pro Phe Pro Ala Ser Leu Lys Pro Gly Lys Ile Thr
                645                 650                 655

Met Asp Ile Pro Glu Glu Asp Ile Cys Pro Met Asp Tyr Arg Ser Val
            660                 665                 670

Trp Ser Ala Met Glu Glu Cys Gln Asn Leu Gly Leu Thr Lys Ser Ile
        675                 680                 685

Gly Val Ser Asn Phe Ser Cys Lys Lys Leu Glu Glu Leu Met Ala Thr
    690                 695                 700

Ala Asn Ile Pro Pro Ala Val Asn Gln Val Glu Met Ser Pro Ala Phe
705                 710                 715                 720

Gln Gln Lys Lys Leu Arg Glu Tyr Cys Asn Ala Asn Ile Leu Val
                725                 730                 735

Ser Ala Val Ser Ile Leu Gly Ser Asn Gly Thr Pro Trp Gly Ser Asn
            740                 745                 750

Ala Val Leu Gly Ser Glu Val Leu Lys Lys Ile Ala Met Ala Lys Gly
        755                 760                 765

Lys Ser Val Ala Gln Val Ser Met Arg Trp Val Tyr Glu Gln Gly Ala
    770                 775                 780

Ser Leu Val Val Lys Ser Phe Ser Glu Glu Arg Leu Arg Glu Asn Leu
785                 790                 795                 800

Asn Ile Phe Asp Trp Gln Leu Thr Lys Glu Asp Asn Glu Lys Ile Gly
                805                 810                 815

Glu Ile Pro Gln Cys Arg Ile Leu Ser Ala Tyr Phe Leu Val Ser Pro
            820                 825                 830

Lys Gly Pro Phe Lys Ser Gln Glu Glu Leu Trp Asp Asp Lys Ala
        835                 840                 845

<210> SEQ ID NO 11
<211> LENGTH: 845
<212> TYPE: PRT
<213> ORGANISM: Papaver bracteatum

<400> SEQUENCE: 11

Ser Ser Pro Ala Ser Ser Thr Glu Thr Ala Val Leu Cys His Gln Arg
1               5                   10                  15

Gln Gln Ser Cys Ala Leu Pro Ile Ser Gly Leu Leu His Ile Phe Met
            20                  25                  30

Asn Lys Asn Gly Leu Ile His Val Thr Leu Gly Asn Met Ala Asp Lys
        35                  40                  45
```

```
Tyr Gly Pro Ile Phe Ser Phe Pro Thr Gly Ser His Arg Ile Leu Val
 50                  55                  60

Val Ser Ser Trp Glu Met Val Lys Glu Cys Phe Thr Gly Asn Asn Asp
 65                  70                  75                  80

Thr Phe Phe Ser Asn Arg Pro Ile Pro Leu Ala Phe Lys Ile Ile Phe
                 85                  90                  95

Tyr Ala Gly Gly Val Asp Ser Tyr Gly Leu Ala Leu Val Pro Tyr Gly
                100                 105                 110

Lys Tyr Trp Arg Glu Leu Arg Lys Ile Cys Val His Asn Leu Leu Ser
                115                 120                 125

Asn Gln Gln Leu Leu Asn Phe Arg His Leu Ile Ile Ser Gln Val Asp
            130                 135                 140

Thr Ser Phe Asn Lys Leu Tyr Asp Leu Ser Asn Lys Lys Asn Thr
145                 150                 155                 160

Thr Thr Asp Ser Gly Thr Val Arg Met Asp Asp Trp Leu Ala Gln Leu
                165                 170                 175

Ser Phe Asn Val Ile Gly Arg Ile Val Cys Gly Phe Gln Thr His Thr
            180                 185                 190

Glu Thr Ser Ala Thr Ser Ser Val Glu Arg Phe Thr Glu Ala Ile Asp
            195                 200                 205

Glu Ala Ser Arg Phe Met Ser Ile Ala Thr Val Ser Asp Thr Phe Pro
210                 215                 220

Trp Leu Gly Trp Ile Asp Gln Leu Thr Gly Leu Thr Arg Lys Met Lys
225                 230                 235                 240

His Tyr Gly Lys Lys Leu Asp Leu Val Val Glu Ser Ile Ile Glu Asp
                245                 250                 255

His Arg Gln Asn Arg Arg Ile Ser Gly Thr Lys Gln Gly Asp Asp Phe
            260                 265                 270

Ile Asp Ile Cys Leu Ser Ile Met Glu Gln Pro Gln Ile Ile Pro Gly
            275                 280                 285

Asn Asn Asp Pro Pro Arg Gln Ile Pro Ile Lys Ser Ile Val Leu Asp
290                 295                 300

Met Ile Gly Gly Gly Thr Asp Thr Thr Lys Leu Thr Thr Thr Trp Thr
305                 310                 315                 320

Leu Ser Leu Leu Leu Asn Asn Pro His Val Leu Glu Lys Ala Arg Glu
                325                 330                 335

Glu Val Asp Ala His Phe Gly Thr Lys Arg Arg Pro Thr Asn Asp Asp
                340                 345                 350

Ala Val Met Val Glu Phe Asp Ile Arg Asn Leu Val Tyr Ile Gln
            355                 360                 365

Ala Ile Ile Lys Glu Ser Met Arg Leu Tyr Pro Ala Ser Pro Val Val
370                 375                 380

Glu Arg Leu Ser Gly Glu Asp Cys Val Val Gly Gly Phe His Val Pro
385                 390                 395                 400

Ala Gly Thr Arg Leu Trp Val Asn Val Trp Lys Met Gln Arg Asp Pro
                405                 410                 415

Asn Val Trp Ala Asp Pro Met Val Phe Arg Pro Glu Arg Phe Leu Ser
                420                 425                 430

Asp Glu Gln Lys Met Val Asp Val Arg Gly Gln Asn Tyr Glu Leu Leu
            435                 440                 445

Pro Phe Gly Ala Gly Arg Arg Ile Cys Pro Gly Val Ser Phe Ser Leu
450                 455                 460
```

```
Asp Leu Met Gln Leu Val Leu Thr Arg Leu Ile Leu Glu Phe Glu Met
465                 470                 475                 480

Lys Ser Pro Ser Gly Lys Val Asp Met Thr Ala Thr Pro Gly Leu Met
            485                 490                 495

Ser Tyr Lys Val Val Pro Leu Asp Ile Leu Leu Thr His Arg Arg Ile
        500                 505                 510

Lys Ser Cys Val Gln Leu Ala Ser Ser Glu Arg Asp Met Glu Ser Ser
    515                 520                 525

Gly Val Pro Val Ile Thr Leu Arg Ser Gly Lys Val Met Pro Val Leu
530                 535                 540

Gly Met Gly Thr Phe Glu Lys Ala Gly Lys Gly Ser Glu Arg Glu Arg
545                 550                 555                 560

Leu Ala Ile Leu Lys Ala Ile Glu Val Gly Tyr Arg Tyr Phe Asp Thr
                565                 570                 575

Ala Ala Ala Tyr Glu Thr Glu Glu Val Leu Gly Glu Ala Ile Ala Glu
            580                 585                 590

Ala Leu Gln Leu Gly Leu Ile Lys Ser Arg Asp Glu Leu Phe Ile Ser
        595                 600                 605

Ser Met Leu Trp Cys Thr Asp Ala His Pro Asp Arg Val Leu Leu Ala
610                 615                 620

Leu Gln Asn Ser Leu Arg Asn Leu Lys Leu Glu Tyr Val Asp Leu Tyr
625                 630                 635                 640

Met Leu Pro Phe Pro Ala Ser Leu Lys Pro Gly Lys Ile Thr Met Asp
                645                 650                 655

Ile Pro Glu Glu Asp Ile Cys Pro Met Asp Tyr Arg Ser Val Trp Ser
            660                 665                 670

Ala Met Glu Glu Cys Gln Asn Leu Gly Leu Thr Lys Ser Ile Gly Val
        675                 680                 685

Ser Asn Phe Ser Cys Lys Lys Leu Glu Glu Leu Met Ala Thr Ala Asn
690                 695                 700

Ile Pro Pro Ala Val Asn Gln Val Glu Met Ser Pro Ala Phe Gln Gln
705                 710                 715                 720

Lys Lys Leu Arg Glu Tyr Cys Asn Ala Asn Asn Ile Leu Val Ser Ala
                725                 730                 735

Val Ser Ile Leu Gly Ser Asn Gly Thr Pro Trp Gly Ser Asn Ala Val
            740                 745                 750

Leu Gly Ser Glu Val Leu Lys Lys Ile Ala Met Ala Lys Gly Lys Ser
        755                 760                 765

Val Ala Gln Val Ser Met Arg Trp Val Tyr Glu Gln Gly Ala Ser Leu
770                 775                 780

Val Val Lys Ser Phe Ser Glu Glu Arg Leu Arg Glu Asn Leu Asn Ile
785                 790                 795                 800

Phe Asp Trp Gln Leu Thr Lys Glu Asp Asn Glu Lys Ile Gly Glu Ile
                805                 810                 815

Pro Gln Cys Arg Ile Leu Ser Ala Tyr Phe Leu Val Ser Pro Lys Gly
            820                 825                 830

Pro Phe Lys Ser Gln Glu Glu Leu Trp Asp Asp Lys Ala
        835                 840                 845

<210> SEQ ID NO 12
<211> LENGTH: 869
<212> TYPE: PRT
<213> ORGANISM: Papaver bracteatum

<400> SEQUENCE: 12
```

Val Ala Leu Arg Lys Lys Ile Leu Lys Asn Tyr Tyr Ser Ser Ser
1               5                   10                  15

Ser Thr Ala Thr Ala Val Ser His Gln Trp Pro Lys Ala Ser Arg Ala
            20                  25                  30

Leu Pro Leu Ile Asp Leu Leu His Val Phe Phe Asn Lys Thr Asp Leu
            35                  40                  45

Met His Val Thr Leu Gly Asn Met Ala Asp Lys Phe Gly Pro Ile Phe
    50                  55                  60

Ser Phe Pro Thr Gly Ser His Arg Thr Leu Val Val Ser Ser Trp Glu
65                  70                  75                  80

Lys Ala Lys Glu Cys Phe Thr Gly Asn Asn Asp Ile Val Phe Ser Gly
                85                  90                  95

Arg Pro Leu Pro Leu Ala Phe Lys Leu Ile Phe Tyr Ala Gly Gly Ile
            100                 105                 110

Asp Ser Tyr Gly Ile Ser Gln Val Pro Tyr Gly Lys Lys Trp Arg Glu
            115                 120                 125

Leu Arg Asn Ile Cys Val His Asn Ile Leu Ser Asn Gln Gln Leu Leu
    130                 135                 140

Lys Phe Arg His Leu Met Ile Ser Gln Val Asp Asn Ser Phe Asn Lys
145                 150                 155                 160

Leu Tyr Glu Val Cys Asn Ser Asn Lys Asp Glu Gly Asp Ser Ala Thr
                165                 170                 175

Ser Thr Thr Ala Ala Gly Ile Val Arg Met Asp Asp Trp Leu Gly Lys
            180                 185                 190

Leu Ala Phe Asp Val Ile Ala Arg Ile Val Cys Gly Phe Gln Ser Gln
            195                 200                 205

Thr Glu Thr Ser Thr Thr Ser Ser Met Glu Arg Phe Thr Glu Ala Met
    210                 215                 220

Asp Glu Ala Ser Arg Phe Met Ser Val Thr Ala Val Ser Asp Thr Val
225                 230                 235                 240

Pro Trp Leu Gly Trp Ile Asp Gln Leu Thr Gly Leu Lys Arg Asn Met
                245                 250                 255

Lys His Cys Gly Lys Lys Leu Asn Leu Val Val Lys Ser Ile Ile Glu
            260                 265                 270

Asp His Arg Gln Lys Arg Arg Leu Ser Ser Thr Lys Lys Gly Asp Glu
            275                 280                 285

Asn Ile Ile Asp Glu Asp Glu Gln Asp Phe Ile Asp Ile Cys Leu
    290                 295                 300

Ser Ile Met Glu Gln Pro Gln Leu Pro Gly Asn Asn Asn Pro Pro Lys
305                 310                 315                 320

Ile Pro Ile Lys Ser Ile Val Leu Asp Met Ile Gly Gly Gly Thr Asp
                325                 330                 335

Thr Thr Lys Leu Thr Thr Ile Trp Thr Leu Ser Leu Leu Asn Asn
            340                 345                 350

Pro His Val Leu Asp Lys Ala Lys Gln Glu Val Asp Ala His Phe Leu
            355                 360                 365

Thr Lys Arg Arg Ser Thr Asn Asp Ala Ala Val Asp Phe Asp Asp
    370                 375                 380

Ile Arg Asn Leu Val Tyr Ile Gln Ala Ile Ile Lys Glu Ser Met Arg
385                 390                 395                 400

Leu Tyr Pro Ala Ser Pro Val Val Glu Arg Leu Ser Gly Glu Asp Cys
                405                 410                 415

-continued

Val Val Gly Gly Phe His Val Pro Ala Gly Thr Arg Leu Trp Val Asn
                420                 425                 430

Val Trp Lys Met Gln Arg Asp Pro Asn Val Trp Ala Asp Pro Met Val
            435                 440                 445

Phe Arg Pro Glu Arg Phe Leu Ser Asp Glu Gln Lys Met Val Asp Val
        450                 455                 460

Arg Gly Gln Asn Tyr Glu Leu Leu Pro Phe Gly Ala Gly Arg Arg Ile
465                 470                 475                 480

Cys Pro Gly Val Ser Phe Ser Leu Asp Leu Met Gln Leu Val Leu Thr
                485                 490                 495

Arg Leu Ile Leu Glu Phe Glu Met Lys Ser Pro Ser Gly Lys Val Asp
            500                 505                 510

Met Thr Ala Thr Pro Gly Leu Met Ser Tyr Lys Val Val Pro Leu Asp
        515                 520                 525

Ile Leu Leu Thr His Arg Arg Ile Lys Ser Cys Val Gln Leu Ala Ser
530                 535                 540

Ser Glu Arg Asp Met Glu Ser Ser Gly Val Pro Val Ile Thr Leu Arg
545                 550                 555                 560

Ser Gly Lys Val Met Pro Val Leu Gly Met Gly Thr Phe Glu Lys Ala
                565                 570                 575

Gly Lys Gly Ser Glu Arg Glu Arg Leu Ala Ile Leu Lys Ala Ile Glu
            580                 585                 590

Val Gly Tyr Arg Tyr Phe Asp Thr Ala Ala Ala Tyr Glu Thr Glu Glu
        595                 600                 605

Val Leu Gly Glu Ala Ile Ala Glu Ala Leu Gln Leu Gly Leu Ile Lys
        610                 615                 620

Ser Arg Asp Glu Leu Phe Ile Ser Ser Met Leu Trp Cys Thr Asp Ala
625                 630                 635                 640

His Pro Asp Arg Val Leu Leu Ala Leu Gln Asn Ser Leu Arg Asn Leu
                645                 650                 655

Lys Leu Glu Tyr Val Asp Leu Tyr Met Leu Pro Phe Pro Ala Ser Leu
            660                 665                 670

Lys Pro Gly Lys Ile Thr Met Asp Ile Pro Glu Glu Asp Ile Cys Pro
        675                 680                 685

Met Asp Tyr Arg Ser Val Trp Ser Ala Met Glu Glu Cys Gln Asn Leu
        690                 695                 700

Gly Leu Thr Lys Ser Ile Gly Val Ser Asn Phe Ser Cys Lys Lys Leu
705                 710                 715                 720

Glu Glu Leu Met Ala Thr Ala Asn Ile Pro Pro Ala Val Asn Gln Val
                725                 730                 735

Glu Met Ser Pro Ala Phe Gln Gln Lys Lys Leu Arg Glu Tyr Cys Asn
            740                 745                 750

Ala Asn Asn Ile Leu Val Ser Ala Val Ser Ile Leu Gly Ser Asn Gly
        755                 760                 765

Thr Pro Trp Gly Ser Asn Ala Val Leu Gly Ser Glu Val Leu Lys Lys
        770                 775                 780

Ile Ala Met Ala Lys Gly Lys Ser Val Ala Gln Val Ser Met Arg Trp
785                 790                 795                 800

Val Tyr Glu Gln Gly Ala Ser Leu Val Val Lys Ser Phe Ser Glu Glu
                805                 810                 815

Arg Leu Arg Glu Asn Leu Asn Ile Phe Asp Trp Gln Leu Thr Lys Glu
            820                 825                 830

Asp Asn Glu Lys Ile Gly Glu Ile Pro Gln Cys Arg Ile Leu Ser Ala

-continued

```
                835                 840                 845
Tyr Phe Leu Val Ser Pro Lys Gly Pro Phe Lys Ser Gln Glu Glu Leu
    850                 855                 860

Trp Asp Asp Lys Ala
865

<210> SEQ ID NO 13
<211> LENGTH: 858
<212> TYPE: PRT
<213> ORGANISM: Papaver bracteatum
<220> FEATURE:
<221> NAME/KEY: misc_feature
<222> LOCATION: (822)..(822)
<223> OTHER INFORMATION: Xaa can be any naturally occurring amino acid

<400> SEQUENCE: 13

Met Glu Leu Gln Tyr Phe Ser Tyr Phe Gln Pro Thr Ser Ser Val Val
1               5                   10                  15

Ala Leu Leu Ala Leu Val Ser Ile Leu Phe Ser Val Val Val Val Leu
            20                  25                  30

Arg Lys Thr Phe Ser Asn Asn Tyr Ser Ser Pro Ala Ser Ser Thr Glu
        35                  40                  45

Thr Ala Val Leu Cys His Gln Arg Gln Gln Ser Cys Ala Leu Pro Ile
    50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
                245                 250                 255

Val Ser Asp Asn Val Pro Met Leu Gly Trp Ile Asp Gln Leu Thr Gly
            260                 265                 270

Leu Thr Arg Asn Met Lys His Cys Gly Lys Leu Asp Leu Val Val
        275                 280                 285

Glu Ser Ile Ile Lys Asp His Arg Gln Lys Arg Phe Ser Arg Thr
    290                 295                 300

Lys Gly Gly Asp Glu Lys Asp Asp Glu Gln Asp Asp Phe Ile Asp Ile
305                 310                 315                 320
```

-continued

Cys Leu Ser Ile Met Glu Gln Pro Gln Leu Pro Gly Asn Asn Ser Pro
                325                 330                 335

Pro Gln Ile Pro Ile Lys Ser Ile Val Leu Asp Met Ile Gly Gly Gly
            340                 345                 350

Thr Asp Thr Thr Lys Leu Thr Thr Ile Trp Thr Leu Ser Leu Leu Leu
        355                 360                 365

Asn Asn Pro His Val Leu Asp Lys Ala Lys Gln Glu Val Asp Ala His
    370                 375                 380

Phe Arg Lys Lys Arg Arg Ser Thr Asp Ala Ala Ala Val Val
385                 390                 395                 400

Asp Phe Asp Asp Ile Arg Asn Leu Val Tyr Ile Gln Ala Ile Ile Lys
                405                 410                 415

Glu Ser Met Arg Leu Tyr Pro Ala Ser Pro Val Val Glu Arg Leu Ser
            420                 425                 430

Gly Glu Asp Cys Val Val Gly Phe His Val Pro Ala Gly Thr Arg
        435                 440                 445

Leu Trp Ala Asn Val Trp Lys Met Gln Arg Asp Pro Lys Val Trp Asp
    450                 455                 460

Asp Pro Leu Val Phe Arg Pro Glu Arg Phe Leu Ser Asp Glu Gln Lys
465                 470                 475                 480

Met Val Asp Val Arg Gly Gln Asn Tyr Glu Leu Leu Pro Phe Gly Ala
                485                 490                 495

Gly Arg Arg Ile Cys Pro Gly Val Ser Phe Ser Leu Asp Leu Met Gln
            500                 505                 510

Leu Val Leu Thr Arg Leu Ile Leu Glu Phe Glu Met Lys Ser Pro Ser
        515                 520                 525

Gly Lys Val Asp Met Thr Ala Thr Pro Gly Leu Met Ser Tyr Lys Val
    530                 535                 540

Val Pro Leu Asp Ile Leu Leu Thr His Arg Arg Ile Lys Ser Cys Val
545                 550                 555                 560

Gln Leu Ala Ser Ser Glu Arg Asp Met Glu Ser Ser Gly Val Pro Val
                565                 570                 575

Ile Thr Leu Ser Ser Gly Lys Val Met Pro Val Leu Gly Met Gly Thr
            580                 585                 590

Phe Glu Lys Val Gly Lys Gly Ser Glu Arg Glu Arg Leu Ala Ile Leu
        595                 600                 605

Lys Ala Ile Glu Val Gly Tyr Arg Tyr Phe Asp Thr Ala Ala Ala Tyr
    610                 615                 620

Glu Thr Glu Glu Val Leu Gly Glu Ala Ile Glu Ala Leu Gln Leu
625                 630                 635                 640

Gly Leu Ile Glu Ser Arg Asp Glu Leu Phe Ile Ser Ser Met Leu Trp
                645                 650                 655

Cys Thr Asp Ala His Pro Asp Arg Val Leu Leu Ala Leu Gln Asn Ser
            660                 665                 670

Leu Arg Asn Leu Lys Leu Glu Tyr Leu Asp Leu Tyr Met Leu Pro Phe
        675                 680                 685

Pro Ala Ser Leu Lys Pro Gly Lys Ile Thr Met Asp Ile Pro Glu Glu
    690                 695                 700

Asp Ile Cys Arg Met Asp Tyr Arg Ser Val Trp Ser Ala Met Glu Glu
705                 710                 715                 720

Cys Gln Asn Leu Gly Phe Thr Lys Ser Ile Gly Val Ser Asn Phe Ser
                725                 730                 735

```
Ser Lys Lys Leu Gln Glu Leu Met Ala Thr Ala Asn Ile Pro Pro Ala
        740                 745                 750

Val Asn Gln Val Glu Met Ser Pro Ala Phe Gln Gln Lys Lys Leu Arg
        755                 760                 765

Glu Tyr Cys Asn Ala Asn Asn Ile Leu Val Ser Ala Val Ser Ile Leu
        770                 775                 780

Gly Ser Asn Gly Thr Pro Trp Gly Ser Asn Ala Val Leu Gly Ser Glu
785                 790                 795                 800

Val Leu Lys Gln Ile Ala Met Ala Lys Gly Lys Ser Val Ala Gln Val
        805                 810                 815

Ser Met Arg Trp Val Xaa Lys Phe Ser Ala Tyr Ala Ile Val Trp Ser
        820                 825                 830

Leu Phe Phe Gly His Arg Ile Cys Ile Thr Leu Tyr Ser Phe Leu Ile
        835                 840                 845

Arg Asn Val Ala Tyr Ile Cys Ile Thr Tyr
        850                 855

<210> SEQ ID NO 14
<211> LENGTH: 716
<212> TYPE: PRT
<213> ORGANISM: Papaver bracteatum

<400> SEQUENCE: 14

Met Glu Leu Gln Tyr Phe Ser Tyr Phe Gln Pro Thr Ser Ser Val Val
1               5                   10                  15

Ala Leu Leu Leu Ala Leu Val Ser Ile Leu Phe Ser Val Val Val Leu
                20                  25                  30

Arg Lys Thr Phe Ser Asn Asn Tyr Ser Ser Pro Ala Ser Ser Thr Glu
            35                  40                  45

Thr Ala Val Leu Cys His Gln Arg Gln Gln Ser Cys Ala Leu Pro Ile
    50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
                245                 250                 255
```

```
Val Ser Asp Asn Val Pro Met Leu Gly Trp Ile Asp Gln Leu Thr Gly
            260                 265                 270

Leu Thr Arg Asn Met Lys His Cys Gly Lys Lys Leu Asp Leu Val Val
            275                 280                 285

Glu Ser Ile Ile Lys Asp His Arg Gln Lys Arg Phe Ser Arg Thr
290             295                 300

Lys Gly Gly Asp Glu Lys Asp Asp Gln Asp Asp Phe Ile Asp Ile
305                 310                 315                 320

Cys Leu Ser Ile Met Glu Gln Pro Gln Leu Pro Gly Asn Asn Ser Pro
                325                 330                 335

Pro Gln Ile Pro Ile Lys Ser Ile Val Leu Asp Met Ile Gly Gly
            340                 345                 350

Thr Asp Thr Thr Lys Leu Thr Thr Ile Trp Thr Leu Ser Leu Leu Leu
            355                 360                 365

Asn Asn Pro His Val Leu Asp Lys Ala Lys Gln Glu Val Asp Ala His
370                 375                 380

Phe Arg Lys Lys Arg Ser Thr Asp Asp Ala Ala Ala Val Val
385                 390                 395                 400

Asp Phe Asp Asp Ile Arg Asn Leu Val Tyr Ile Gln Ala Ile Ile Lys
                405                 410                 415

Glu Ser Met Arg Leu Tyr Pro Ala Ser Pro Val Val Glu Arg Leu Ser
            420                 425                 430

Gly Glu Asp Cys Val Val Gly Gly Phe His Val Pro Ala Gly Thr Arg
            435                 440                 445

Leu Trp Ala Asn Val Trp Lys Met Gln Arg Asp Pro Lys Val Trp Asp
450                 455                 460

Asp Pro Leu Val Phe Arg Pro Glu Arg Phe Leu Ser Asp Glu Gln Lys
465                 470                 475                 480

Met Val Asp Val Arg Gly Gln Asn Tyr Glu Leu Leu Pro Phe Gly Ala
                485                 490                 495

Gly Arg Arg Ile Cys Pro Gly Val Ser Phe Ser Leu Asp Leu Met Gln
            500                 505                 510

Leu Val Leu Thr Arg Leu Ile Leu Glu Phe Glu Met Lys Ser Pro Ser
            515                 520                 525

Gly Lys Val Asp Met Thr Ala Thr Pro Gly Leu Met Ser Tyr Lys Val
            530                 535                 540

Val Pro Leu Asp Ile Leu Leu Thr His Arg Arg Ile Lys Ser Cys Val
545                 550                 555                 560

Gln Leu Ala Ser Ser Glu Arg Asp Met Glu Ser Ser Gly Val Pro Val
                565                 570                 575

Ile Thr Leu Ser Ser Gly Lys Val Met Pro Val Leu Gly Met Gly Thr
            580                 585                 590

Phe Glu Lys Val Gly Lys Gly Ser Glu Arg Glu Arg Leu Ala Ile Leu
            595                 600                 605

Lys Ala Ile Glu Val Gly Tyr Arg Tyr Phe Asp Thr Ala Ala Ala Tyr
610                 615                 620

Glu Thr Glu Glu Val Leu Gly Glu Ala Ile Ala Glu Ala Leu Gln Leu
625                 630                 635                 640

Gly Leu Ile Glu Ser Arg Asp Glu Leu Phe Ile Ser Ser Met Leu Trp
                645                 650                 655

Cys Thr Asp Ala His Pro Asp Arg Val Leu Leu Ala Leu Gln Asn Ser
            660                 665                 670
```

Leu Arg Gln Val Phe Leu Met Gln Ile Arg Leu Ile Tyr Ile Cys Thr
            675                 680                 685

Tyr Gln Gln Val His Leu Asn Ile Tyr Phe Gln Ile Asn Glu Phe Val
            690                 695                 700

Leu Cys Asp Met Tyr Arg Asn Leu Lys Leu Glu Tyr
705                 710                 715

<210> SEQ ID NO 15
<211> LENGTH: 864
<212> TYPE: PRT
<213> ORGANISM: Conopodium majus

<400> SEQUENCE: 15

Leu Asn Asn Tyr Ser Ser Pro Ala Ser Thr Lys Thr Ala Val
1               5                   10                  15

Leu Ser His Gln Arg Gln Ser Cys Ala Leu Pro Ile Ser Gly Leu
            20                  25                  30

Leu His Ile Phe Met Asn Lys Asn Gly Leu Ile His Val Thr Leu Gly
            35                  40                  45

Asn Met Ala Asp Lys Tyr Gly Pro Ile Phe Ser Phe Pro Thr Gly Ser
50                  55                  60

His Arg Thr Leu Val Val Ser Ser Trp Glu Met Val Lys Glu Cys Phe
65                  70                  75                  80

Thr Gly Asn Asn Asp Thr Ala Phe Ser Asn Arg Pro Ile Pro Leu Ala
            85                  90                  95

Phe Lys Thr Ile Phe Tyr Ala Cys Gly Gly Ile Asp Ser Tyr Gly Leu
            100                 105                 110

Ser Ser Val Pro Tyr Gly Lys Tyr Trp Arg Glu Leu Arg Lys Val Cys
            115                 120                 125

Val His Asn Leu Leu Ser Asn Gln Gln Leu Leu Lys Phe Arg His Leu
130                 135                 140

Ile Ile Ser Gln Val Asp Thr Ser Phe Asn Lys Leu Tyr Glu Leu Cys
145                 150                 155                 160

Lys Asn Ser Glu Asp Asn Gln Gly Asn Tyr Pro Thr Thr Thr Ala
            165                 170                 175

Ala Gly Met Val Arg Ile Asp Asp Trp Leu Ala Glu Leu Ser Phe Asn
            180                 185                 190

Val Ile Gly Arg Ile Val Cys Gly Phe Gln Ser Gly Pro Lys Thr Gly
            195                 200                 205

Ala Pro Ser Arg Val Glu Gln Phe Lys Glu Ala Ile Asn Glu Ala Ser
210                 215                 220

Tyr Phe Met Ser Thr Ser Pro Val Ser Asp Asn Val Pro Met Leu Gly
225                 230                 235                 240

Trp Ile Asp Gln Leu Thr Gly Leu Thr Arg Asn Met Lys His Cys Gly
            245                 250                 255

Lys Lys Leu Asp Leu Val Val Glu Ser Ile Ile Asn Asp His Arg Gln
            260                 265                 270

Lys Arg Arg Phe Ser Arg Thr Lys Gly Gly Asp Glu Lys Asp Asp Glu
            275                 280                 285

Gln Asp Asp Phe Ile Asp Ile Cys Leu Ser Ile Met Glu Gln Pro Gln
290                 295                 300

Leu Pro Gly Asn Asn Asn Pro Ser Gln Ile Pro Ile Lys Ser Ile Val
305                 310                 315                 320

Leu Asp Met Ile Gly Gly Gly Thr Asp Thr Thr Lys Leu Thr Thr Ile
            325                 330                 335

```
Trp Thr Leu Ser Leu Leu Leu Asn Asn Pro His Val Leu Asp Lys Ala
            340                 345                 350

Lys Gln Glu Val Asp Ala His Phe Arg Thr Lys Arg Ser Thr Asn
        355                 360                 365

Asp Ala Ala Ala Val Val Asp Phe Asp Ile Arg Asn Leu Val
370                 375                 380

Tyr Ile Gln Ala Ile Ile Lys Glu Ser Met Arg Leu Tyr Pro Ala Ser
385                 390                 395                 400

Pro Val Val Glu Arg Leu Ser Gly Glu Asp Cys Val Val Gly Gly Phe
                405                 410                 415

His Val Pro Ala Gly Thr Arg Leu Trp Ala Asn Val Trp Lys Met Gln
            420                 425                 430

Arg Asp Pro Lys Val Trp Asp Pro Leu Val Phe Arg Pro Asp Arg
        435                 440                 445

Phe Leu Ser Asp Glu Gln Lys Met Val Asp Val Arg Gly Gln Asn Tyr
    450                 455                 460

Glu Leu Leu Pro Phe Gly Ala Gly Arg Arg Val Cys Pro Gly Val Ser
465                 470                 475                 480

Phe Ser Leu Asp Leu Met Gln Leu Val Leu Thr Arg Leu Ile Leu Glu
            485                 490                 495

Phe Glu Met Lys Ser Pro Ser Gly Lys Val Asp Met Thr Ala Thr Pro
        500                 505                 510

Gly Leu Met Ser Tyr Lys Val Ile Pro Leu Asp Ile Leu Leu Thr His
    515                 520                 525

Arg Arg Ile Lys Pro Cys Val Gln Ser Ala Ala Ser Glu Arg Asp Met
530                 535                 540

Glu Ser Ser Gly Val Pro Val Ile Thr Leu Gly Ser Gly Lys Val Met
545                 550                 555                 560

Pro Val Leu Gly Met Gly Thr Phe Glu Lys Val Gly Lys Gly Ser Glu
                565                 570                 575

Arg Glu Arg Leu Ala Phe Leu Lys Ala Ile Glu Val Gly Tyr Arg Tyr
            580                 585                 590

Phe Asp Thr Ala Ala Ala Tyr Glu Thr Glu Glu Phe Leu Gly Glu Ala
        595                 600                 605

Ile Ala Glu Ala Leu Gln Leu Gly Leu Ile Lys Ser Arg Asp Glu Leu
    610                 615                 620

Phe Ile Thr Ser Lys Leu Trp Pro Cys Asp Ala His Pro Asp Leu Val
625                 630                 635                 640

Val Pro Ala Leu Gln Asn Ser Leu Arg Asn Leu Lys Leu Glu Tyr Val
                645                 650                 655

Asp Leu Tyr Met Leu Pro Phe Pro Ala Ser Leu Lys Pro Gly Lys Ile
            660                 665                 670

Thr Met Asp Ile Pro Glu Glu Asp Ile Cys Arg Met Asp Tyr Arg Ser
        675                 680                 685

Val Trp Ala Ala Met Glu Glu Cys Gln Asn Leu Gly Phe Thr Lys Ser
    690                 695                 700

Ile Gly Val Ser Asn Phe Ser Cys Lys Lys Leu Gln Glu Leu Met Ala
705                 710                 715                 720

Thr Ala Asn Ile Pro Pro Ala Val Asn Gln Val Glu Met Ser Pro Ala
                725                 730                 735

Phe Gln Gln Lys Lys Leu Arg Glu Tyr Cys Asn Ala Asn Asn Ile Leu
            740                 745                 750
```

-continued

| | | | | | | | | | | | | | |
|---|---|---|---|---|---|---|---|---|---|---|---|---|---|
|Val|Ser|Ala|Ile|Ser|Val|Leu|Gly|Ser|Asn|Gly|Thr|Pro|Trp|Gly|Ser|
| | |755| | | |760| | | | |765| | | | |
|Asn|Ala|Val|Leu|Gly|Ser|Glu|Val|Leu|Lys|Lys|Ile|Ala|Met|Ala|Lys|
| |770| | | | |775| | | | |780| | | | |
|Gly|Lys|Ser|Val|Ala|Gln|Val|Ser|Met|Arg|Trp|Val|Tyr|Glu|Gln|Gly|
|785| | | | |790| | | | |795| | | | |800|
|Ala|Ser|Leu|Val|Val|Lys|Ser|Phe|Ser|Glu|Glu|Arg|Leu|Arg|Glu|Asn|
| | | | |805| | | | |810| | | | |815| |
|Leu|Asn|Ile|Phe|Asp|Trp|Glu|Leu|Thr|Lys|Glu|Asp|His|Glu|Lys|Ile|
| | | |820| | | | |825| | | | |830| | |
|Gly|Glu|Ile|Pro|Gln|Cys|Arg|Ile|Leu|Ser|Ala|Tyr|Phe|Leu|Val|Ser|
| | |835| | | | |840| | | | |845| | | |
|Pro|Asn|Gly|Pro|Phe|Lys|Ser|Gln|Glu|Glu|Leu|Trp|Asp|Asp|Glu|Ala|
| |850| | | | |855| | | | |860| | | | |